United States Patent
Lawrence

(10) Patent No.: US 7,759,459 B2
(45) Date of Patent: Jul. 20, 2010

(54) FLUORESCENT ASSAYS FOR PROTEIN KINASES

(75) Inventor: David S. Lawrence, Hartsdale, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 1620 days.

(21) Appl. No.: 10/755,086

(22) Filed: Jan. 9, 2004

(65) Prior Publication Data

US 2005/0054024 A1  Mar. 10, 2005

Related U.S. Application Data

(60) Provisional application No. 60/439,359, filed on Jan. 10, 2003, provisional application No. 60/505,097, filed on Sep. 22, 2003.

(51) Int. Cl.
*C07K 7/00* (2006.01)
*C12Q 1/48* (2006.01)
(52) U.S. Cl. ............... 530/300; 530/329; 435/15
(58) Field of Classification Search ........... 530/300, 530/329; 435/15
See application file for complete search history.

(56) References Cited

U.S. PATENT DOCUMENTS

| | | | |
|---|---|---|---|
| 5,252,743 A | 10/1993 | Barrett et al. | |
| 5,635,608 A * | 6/1997 | Haugland et al. | 536/1.11 |
| 5,981,200 A | 11/1999 | Tsien et al. | |
| 5,981,207 A | 11/1999 | Burbaum et al. | |
| 5,989,843 A | 11/1999 | Gallatin et al. | |
| 5,998,580 A | 12/1999 | Fay et al. | |
| 6,495,664 B1 | 12/2002 | Cubitt | |
| 6,670,144 B1 | 12/2003 | Craig et al. | |
| 6,803,188 B1 | 10/2004 | Tsien et al. | |
| 6,806,056 B2 | 10/2004 | Glickman et al. | |
| 6,900,304 B2 | 5/2005 | Tsien et al. | |
| 6,972,198 B2 | 12/2005 | Craig et al. | |
| 7,060,506 B2 | 6/2006 | Craig | |
| 7,176,037 B2 | 2/2007 | Hahn et al. | |
| 2002/0127623 A1 | 9/2002 | Minshull et al. | |
| 2002/0142347 A1 | 10/2002 | Knudsen et al. | |
| 2003/0044353 A1 | 3/2003 | Weissleder et al. | |
| 2004/0166553 A1* | 8/2004 | Nguyen et al. | 435/15 |
| 2004/0191926 A1 | 9/2004 | Zhang et al. | |
| 2005/0051706 A1 | 3/2005 | Witney et al. | |
| 2005/0148031 A1 | 7/2005 | Allbritton et al. | |
| 2005/0287518 A1 | 12/2005 | Hahn et al. | |
| 2006/0211075 A1 | 9/2006 | Lawrence et al. | |
| 2006/0240088 A1 | 10/2006 | Lawrence et al. | |
| 2007/0254312 A1 | 11/2007 | Lawrence | |
| 2008/0318246 A1 | 12/2008 | Lawrence et al. | |

OTHER PUBLICATIONS

Khalil-Rizvi S et al (1997) Structures and characteristics of novel siderophores from plant deleterious *Pseudomonas fluorescens* A225 and *Pseudomonas putida* ATCC 39167. Biochemistry, vol. 36, pp. 4163-4171.*
Shults, Melissa D., et al., entitled "Versatile Fluorescence Probes of Protein Kinase Activity," J Am Chem Soc. Nov. 26, 2003;125(47): 14248-9, wtih 12 pages of Supporting Information. Published on Web Nov. 4, 2003.
Yeh, Ren-Hwa, et al., entitled "Real Time Visualization of Protein Kinase Activity in Living Cells," The Journal of Biological Chemistry, vol. 277, No. 13, Issue of Mar. 29, pp. 11527-11532, 2002. Published. JBC Papers in Press, Jan. 14, 2002.
Chen, Chien-An, et al., entitled "Design and Synthesis of a Fluorescent Reporter of Protein Kinase Activity," J Am Chem Soc. 2002, 124, 3840-3841, with 10 pages of Supporting Information. Published on Web Mar. 22, 2002.
Veldhuyzen, Willem F., et al., entitled "A Light-Activated Probe of Intracellular Protein Kinase Activity," J Am Chem Soc 2003, 125, 13358-13359, with 7 pages of Supporting Information. Published on Web Oct. 11, 2003.
Zhang, Jin et al., entitled "Genetically encoded reporters of protein kinase A activity reveal impact of substrate tethering," PNAS, Dec. 18, 2001, vol. 98, No. 26, pp. 14997-15002.
Ting, Alice Y., et al., entitled "Genetically encoded fluorescent reporters of protein tyrosine kinase activites in living cells," PNAS, Dec. 18, 2001, vol. 98, No. 26. pp. 15003-15008.
Nagai, Yasuo, et al. entitled "A fluorescent indicator for visualizing cAMP-induced phosphorylation in vivo," Nature Biotechnology, vol. 18, Mar. 2000, pp. 313-316.
Ng, Tony, et al., entitled "Imaging Protein Kinase C-alpha Activation in Cells," Science, vol. 283, Mar. 26, 1999, pp. 2085-2089.
Blake et al., entitled "SU6656, a selective src family kinase inhibitor, used to probe growth factor signaling," Molecular and Cellular Biology, vol. 20 (23), pp. 9018-9027, Dec. 2000.
Vazquez M E et al., Fluorescent caged phosphoserine peptides as probes to investigate phosphorylation-dependent protein associations; J Am Chem Soc. 125: 10150-1, 2003, published on Web Jul. 30, 2003.
Walker J W et al., entitled "Signaling pathways underlying eosinophil cell motility revealed by using caged peptides," Proc. Natl. Acad. Sci., Feb. 1998, vol. 95, pp. 1568-1573.
Ross H et al., entitled "A non-radioactive method for the assay of many serine/threonine-specific protein kinases," Biochem J., 2002, 366, pp. 977-981.

* cited by examiner

*Primary Examiner*—Chih-Min Kam
(74) *Attorney, Agent, or Firm*—Amster, Rothstein & Ebenstein LLP

(57) ABSTRACT

This invention provides fluorescently-labeled peptide substrates for protein kinases; methods using the substrates for identifying compounds that inhibit protein kinases, for determining if particular protein kinases are active in cells, for diagnosing diseases, and for preparing compositions; and compositions comprising the substrates.

66 Claims, 9 Drawing Sheets

SEQUENCE LISTING

<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: Enzyme substrate

<400> SEQUENCE: 1

Ser Phe Arg Arg Arg Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Enzyme Substrate

<400> SEQUENCE: 2

Ser Phe Arg Arg Arg Arg Lys
1               5

<210> SEQ ID NO 3
<211> LENGTH: 7
<212> TYPE: PRT
<213> ORGANISM: Artificial Sequence
<220> FEATURE:
<223> OTHER INFORMATION: Enzyme Substrate
<220> FEATURE:
<221> NAME/KEY: MISC_FEATURE
<222> LOCATION: (1)..(1)
<223> OTHER INFORMATION: x is serine, threonine, or tyrosine

<400> SEQUENCE: 3

Xaa Phe Arg Arg Arg Arg Lys
1               5

FLUORESCENT ASSAYS FOR PROTEIN KINASES

PRIORITY CLAIM

This application claims the benefit of U.S. Provisional Application No. 60/439,359, filed Jan. 10, 2003, and of U.S. Provisional Application No. 60/505,097, filed Sep. 22, 2003, the contents of both of which are hereby incorporated by reference in their entirety into the subject application.

STATEMENT OF GOVERNMENT SUPPORT

The invention disclosed herein was made with U.S. Government support under grant number GM45989 from the National Institutes of Health, U.S. Department of Health and Human Services. Accordingly, the U.S. Government has certain rights in this invention.

FIELD OF THE INVENTION

The present invention relates to fluorescently-labeled peptide substrates for protein kinases and their uses in assays for protein kinases.

BACKGROUND OF THE INVENTION

Throughout this application various publications are referred to in parenthesis or by reference number. Citations for these references may be found at the end of the specification immediately preceding the claims. The disclosures of these publications are hereby incorporated by reference in their entireties into the subject application to more fully describe the art to which the subject application pertains.

Cells recognize and respond to environmental stimuli via activation of intracellular biochemical pathways primarily comprised of protein kinases. These enzymes catalyze the phosphorylation of serine, threonine, and/or tyrosine residues on protein substrates. More specifically, protein kinases catalyze the transfer of the γ-phosphoryl group of adenosine triphosphate (ATP) to the hydroxyl moieties of serine, threonine, and tyrosine. This deceptively modest reaction serves as a cornerstone for the extraordinarily complex phenomenon known as signal transduction, the biochemical process by which information is transmitted from the cell membrane to the cytoplasm and cell nucleus.[62] For example, the binding event between growth factor and its receptor on the cell surface is signaled to the nucleus via protein kinase-mediated pathways. In response to this signal, genes are transcribed and the cell prepares itself for division.[36] Mitosis is subsequently driven by a fine choreography of temporally- and spatially-regulated signaling pathways that ensure the myriad of biochemical processes required for replication occur in their proper chronological order. In short, signal transduction serves as a biochemical mechanism that drives an extraordinary array of biological phenomena. However, it would be simplistic to view signaling pathways as the molecular equivalent of the interstate highway system. The latter is fixed both in time and space. By contrast, kinase-mediated pathways not only evolved to rapidly form in response to some environmental stimulus, but their role in cellular homeostasis is dependent upon their rapid disassembly once the environmental signal has been acknowledged. Furthermore, the nature of the cellular response is dependent upon when and/or where a specific pathway is activated as well as by what other pathways may be simultaneously operating.

Protein kinases participate in the pathways that drive a variety of other important processes including apoptosis[37]. Members of this large enzyme family have been the objects of intense scientific scrutiny due to their role in disease onset and progression. The potential number of protein kinases encoded by the mammalian genome has been estimated to exceed 1,000.[63] The protein kinase C (PKC) family of enzymes has been implicated in a wide variety of processes, including control of gene expression,[72] mitotic progression,[26-30,78] angiogenesis, carcinogenesis, metastasis, and insulin action.[73] Cyclic guanosine monophosphate (cGMP)-dependent protein kinase (PKG) plays a key role in the signaling pathways responsible for memory and learning.[54,55] Protein kinases, and the signal transduction pathways in which they participate, are now recognized to be medicinally attractive targets of opportunity.[1-4,74-76] Inhibitors of the protein kinase family not only hold great promise as therapeutic agents, but are also of profound utility in the characterization of signaling pathways.[5] Consequently, there has been widespread interest in developing sensors of protein kinase activity, species that could furnish a visual readout of both where and when specific intracellular kinases are activated in response to a stimulus.

The substrate specificity of any given protein kinase is typically defined as the preferred amino acid sequence that envelops the serine, threonine, or tyrosine residue phosphorylated by the enzyme (consensus recognition sequences).[53] In addition, protein kinases are typically divided into two families on the basis of their active site specificity: those that phosphorylate the aromatic phenol of tyrosine and those that catalyze the phosphorylation of the aliphatic alcohols of serine and threonine. PKC, PKG, and cyclic adenosine monophosphate (cAMP)-dependent protein kinase (PKA) share a strong sequence homology, and all three comprise what is commonly referred to as the "ACG" subfamily of protein kinases. Not surprising, these enzymes display overlapping sequence specificities with respect to both substrate and inhibitor peptides. However, their active site specificities are remarkably different.[48,56] For example, whereas PKA is unable to phosphorylate alcohol-bearing residues that possess an α-stereocenter corresponding to that present in D-amino acids, both PKC and PKG readily phosphorylate residues containing this configuration.[48,56,57] Furthermore, the differences in active site specificity between these otherwise closely related protein kinases are not just limited to stereochemical biases. For example, PKC phosphorylates meta- and para-substituted phenols, whereas PKA and PKG do not.[22] Protein microarrays have been used to investigate essentially all of the protein kinases encoded by the yeast genome.[77]

A variety of approaches have been described to assess protein kinase activity, including using phosphorylation-specific antibodies[6,65,66] and cytoplasmic sampling with capillary electrophoresis.[38] Ng et al. reported the detection of phosphorylated (activated) PKCα via fluorescence resonance energy transfer (FRET) using cyanine-labeled anti-phospho-PKCα and antiphosphoThr[250] antibodies in fixed cells.[6] In this particular case, the activity of PKCα activity is not directly measured, but is inferred by detecting a functional state of the enzyme. Nagai et al. described the imaging of PKA activity in cells expressing a protein composed of two green fluorescent protein (GFP) variants tethered by a PKA phosphorylation site.[7] Phosphorylation of this protein generates a 23% decrease in FRET between the two GFPs. More recently, changes in FRET of 20-35% and 25-50% have been reported using genetically encoded reporters of protein tyrosine kinase[69] and PKA[68] activities, respectively.

Other studies have used peptide substrates that possess an appended fluorophore positioned near the site of phosphorylation[8-10,51,70,71] The phosphorylation-induced change in fluorescence intensity in these systems is modest (<20%)[8-10] and, as a consequence, the use of these substrates has often been limited to in vitro experiments with purified kinases. Nonetheless, peptide substrates possess a number of inherent advantages, including ready synthetic availability, straightforward modification with the wide array of commercially available fluorophores, and the potential for complete temporal and spatial control over both when and where the substrate is phosphorylated.[11-17] Accordingly, there has been a need for fluorescently-labeled peptide substrates for protein kinases which undergo large changes in fluorescent intensity upon phosphorylation and which are suitable for in vitro and in vivo applications.

SUMMARY OF THE INVENTION

The present application describes peptide-based reporters of protein kinase activity and uses thereof. The kinase peptide substrate comprises a fluorophore that is positioned on the same amino acid that undergoes phosphorylation. This allows the fluorophore to be placed within angstroms of the phosphorylatable moiety. Consequently, fluorophore-tagged peptides can be produced which display a phosphorylation-induced change in fluorescence that is an order of magnitude greater than previously described fluorophore-bearing peptide/protein substrates of protein kinases. These substrates serve as the basis of highly sensitive assays of protein kinases which have utility for high-throughput screening of chemical libraries for drug discovery, as well as for a variety of applications in fields such as enzymology, cell biology, structural biology and immunology. These substrates serve as effective fluorescent sensors of protein kinase activity in cell lysates and living cells, as well as for purified protein kinases.

The present invention provides a method for identifying a chemical compound that inhibits a protein kinase, which comprises separately contacting the protein kinase with both the chemical compound and a fluorescently-labeled substrate for the protein kinase, and with the fluorescently-labeled substrate, under conditions suitable for phosphorylation of the fluorescently-labeled substrate by the protein kinase, and measuring fluorescence intensity, a smaller change in fluorescence intensity in the presence of both the chemical compound and the fluorescently-labeled substrate than in the presence of the fluorescently-labeled substrate indicating that the chemical compound inhibits the protein kinase; wherein the fluorescently-labeled substrate comprises a peptide and at least one fluorophore, wherein a fluorophore is attached to a serine, a threonine, or a tyrosine on at least one terminal end of the peptide, and wherein phosphorylation of the substrate by the protein kinase occurs at the terminal serine, the terminal threonine, or the terminal tyrosine to which the fluorophore is attached and produces at least a 20% change in fluorescence intensity.

The present invention also provides a method for screening a plurality of chemical compounds not known to inhibit a protein kinase to identify a compound that inhibits the protein kinase, which comprises:

(a) separately contacting the protein kinase with both the plurality of chemical compounds and a fluorescently-labeled substrate for the protein kinase, and with the fluorescently-labeled substrate, under conditions suitable for phosphorylation of the fluorescently-labeled substrate by the protein kinase;

(b) determining whether a change in fluorescence intensity is smaller in the presence of both the plurality of chemical compounds and the fluorescently-labeled substrate than in the presence of the fluorescently-labeled substrate; and if so (c) separately determining for each compound included in the plurality of chemical compounds if the change in fluorescence intensity is smaller in the presence of both the compound and the fluorescently-labeled substrate than in the presence of the fluorescently-labeled substrate, a smaller change in fluorescence intensity indicating that the compound inhibits the protein kinase, so as to thereby identify any compound included in the plurality of chemical compounds that inhibits the protein kinase; wherein the fluorescently-labeled substrate comprises a peptide and at least one fluorophore, wherein a fluorophore is attached to a serine, a threonine, or a tyrosine on at least one terminal end of the peptide, and wherein phosphorylation of the substrate by the protein kinase occurs at the terminal serine, the terminal threonine, or the terminal tyrosine to which the fluorophore is attached and produces at least a 20% change in fluorescence intensity.

The present invention further provides a method for identifying a chemical compound that inhibits a protein kinase in a living cell, which comprises comparing the fluorescence intensity when a fluorescently-labeled substrate for the protein kinase is introduced into a cell which has not been contacted with the chemical compound, with the fluorescence intensity when the fluorescently-labeled substrate is introduced into a cell which has been contacted with the chemical compound, a smaller change in fluorescence intensity when the cell has been contacted with the chemical compound indicating that the compound inhibits the protein kinase in the living cell; wherein the fluorescently-labeled substrate comprises a peptide and at least one fluorophore, wherein a fluorophore is attached to a serine, a threonine, or a tyrosine on at least one terminal end of the peptide, and wherein phosphorylation of the substrate by the protein kinase occurs at the terminal serine, the terminal threonine, or the terminal tyrosine to which the fluorophore is attached and produces at least a 20% change in fluorescence intensity.

The invention provides a method of making a composition which comprises identifying a chemical compound as a protein kinase inhibitor by any of the methods described herein and admixing the compound with a carrier.

The invention also provides a method for determining if a protein kinase is active in a living cell, which comprises either introducing a fluorescently-labeled substrate for the protein kinase into the cell or contacting a lysate from the cell with the fluorescently-labeled substrate, and measuring fluorescence intensity, a change in fluorescence intensity indicating that the substrate has been phosphorylated by the protein kinase and that the protein kinase is active in the living cell; wherein the fluorescently-labeled substrate comprises a peptide and at least one fluorophore, wherein a fluorophore is attached to a serine, a threonine, or a tyrosine on at least one terminal end of the peptide, and wherein phosphorylation of the substrate by the protein kinase occurs at the terminal serine, the terminal threonine, or the terminal tyrosine to which the fluorophore is attached and produces at least a 20% change in fluorescence intensity.

In addition, the invention provides a method for diagnosing a disease state that is correlated with a known change in activity of a protein kinase compared to the activity of the protein kinase in a normal state, which comprises comparing the activity of the protein kinase in the normal state with the activity of the protein kinase in a state that is being diagnosed, a change in activity corresponding to the known change indicating that the state that is being diagnosed is a disease state;

wherein the activity of the protein kinase is measured using a fluorescently-labeled substrate that is phosphorylated by the protein kinase, wherein the fluorescently-labeled substrate comprises a peptide and at least one fluorophore, wherein a fluorophore is attached to a serine, a threonine, or a tyrosine on at least one terminal end of the peptide, and wherein phosphorylation of the substrate by the protein kinase occurs at the terminal serine, the terminal threonine, or the terminal tyrosine to which the fluorophore is attached and produces at least a 20% change in fluorescence intensity.

The invention also provides a substrate for a protein kinase, wherein the substrate comprises a peptide and at least one fluorophore, wherein a fluorophore is attached to a serine, a threonine, or a tyrosine on at least one terminal end of the peptide, and wherein phosphorylation by the protein kinase of the terminal serine, the terminal threonine, or the terminal tyrosine to which the fluorophore is attached produces at least a 20% change in fluorescence intensity.

The invention further provides a substrate for a protein kinase, wherein the substrate comprises (1) a peptide comprising a serine, a threonine, or a tyrosine on a terminal end of the peptide; (2) at least one fluorophore, wherein a fluorophore is attached to the serine, the threonine, or the tyrosine on the terminal end of the peptide; and (3) a photolabile side chain attached to the serine, the threonine, or the tyrosine on the terminal end of the peptide, wherein the photolabile side chain blocks transfer of a phosphoryl group from adenosine triphosphate to a hydroxyl moiety of the serine, the threonine, or the tyrosine so that the substrate cannot be phosphorylated by a protein kinase until the photolabile side chain is removed from the substrate.

The invention provides a chemical compound comprising a peptide and a fluorophore, wherein the compound is selected from the group consisting of the compounds set forth in Table 3.

The invention also provides a chemical compound comprising a peptide and a fluorophore, wherein the compound has the structure:

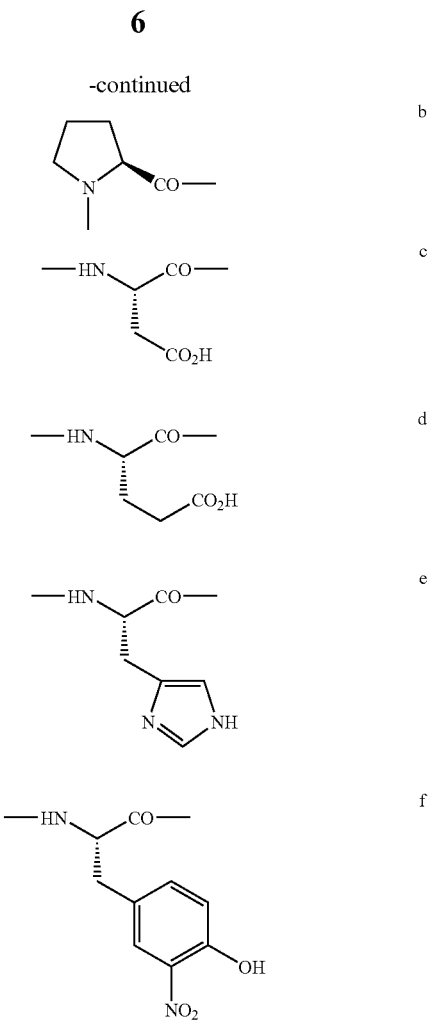

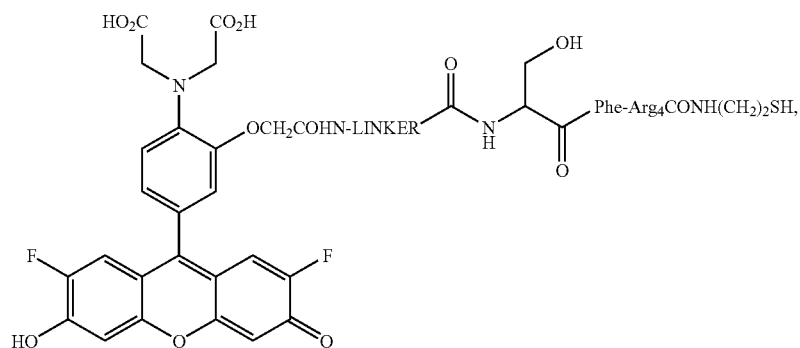

wherein the LINKER is selected from the group consisting of the following:

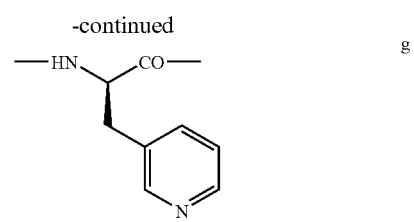

-continued

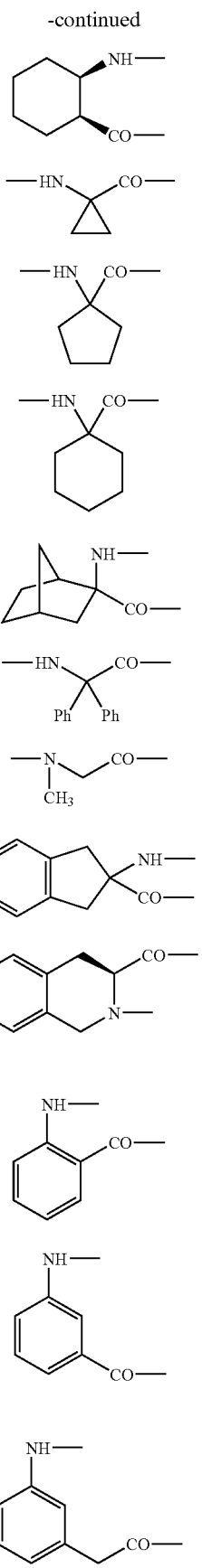

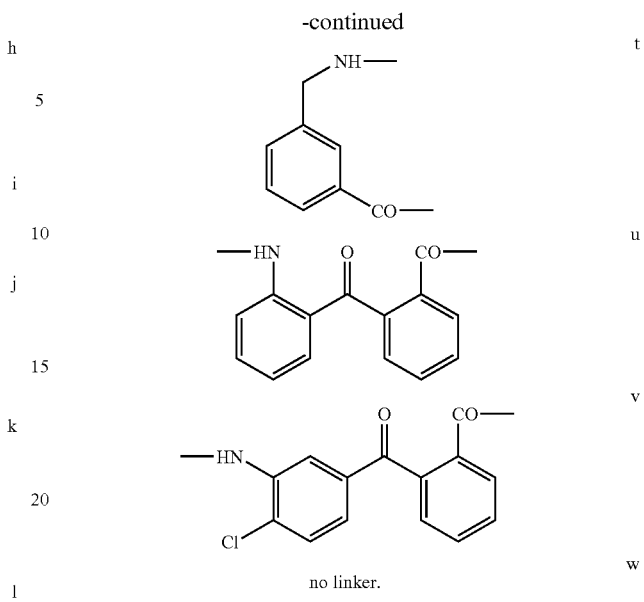

no linker.

The invention also provides a chemical compound comprising a peptide and at least one fluorophore, wherein a fluorophore is attached to a serine, a threonine, or a tyrosine on at least one terminal end of the peptide.

The invention further provides a chemical compound having the structure: fluorophore-LINKER-X-FRRRRK-amide (SEQ ID NO:3); wherein F is phenylalanine; K is lysine; R is arginine; and X is serine, threonine, or tyrosine.

The invention provides a chemical compound having the structure

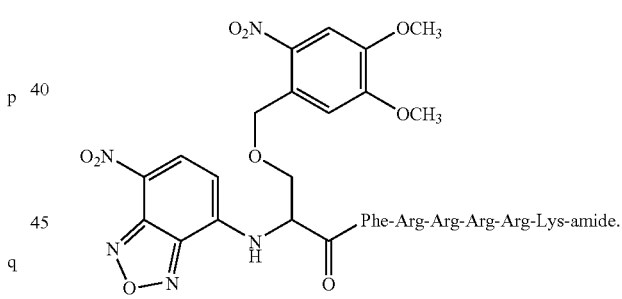

DETAILED DESCRIPTION OF THE INVENTION

Figure 1A:
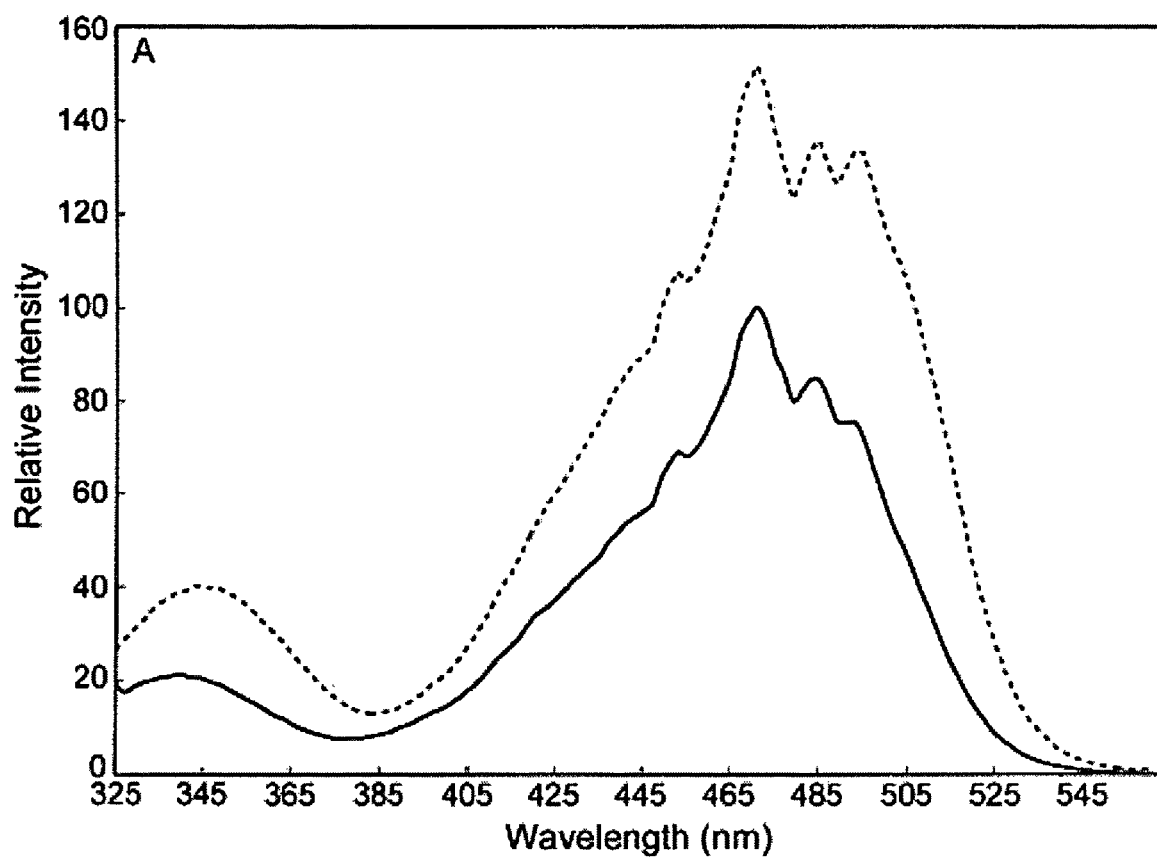
FIG. 1A-1B. Excitation (A) and emission (B) spectra of the substrate peptide 2 (solid line) and the phosphorylated species 3 (dashed line). The emission spectra in B were produced by exciting the 7-nitrobenz-2-oxa-1,3-diazole (NBD) fluorophore at its $\lambda_{max}$ (460 nm).

The present invention provides a method for identifying a chemical compound that inhibits a protein kinase, which comprises separately contacting the protein kinase with both the chemical compound and a fluorescently-labeled substrate for the protein kinase, and with the fluorescently-labeled substrate, under conditions suitable for phosphorylation of the fluorescently-labeled substrate by the protein kinase, and measuring fluorescence intensity, a smaller change in fluorescence intensity in the presence of both the chemical compound and the fluorescently-labeled substrate than in the presence of the fluorescently-labeled substrate indicating that the chemical compound inhibits the protein kinase; wherein the fluorescently-labeled substrate comprises a peptide and at least one fluorophore, wherein a fluorophore is attached to a serine, a threonine, or a tyrosine on at least one terminal end of the peptide, and wherein phosphorylation of the substrate by the protein kinase occurs at the terminal serine, the terminal threonine, or the terminal tyrosine to which the fluorophore is attached and produces at least a 20% change in fluorescence intensity.

The invention also provides a method for screening a plurality of chemical compounds not known to inhibit a protein kinase to identify a compound that inhibits the protein kinase, which comprises:
  (a) separately contacting the protein kinase with both the plurality of chemical compounds and a fluorescently-labeled substrate for the protein kinase, and with the fluorescently-labeled substrate, under conditions suitable for phosphorylation of the fluorescently-labeled substrate by the protein kinase;
  (b) determining whether a change in fluorescence intensity is smaller in the presence of both the plurality of chemical compounds and the fluorescently-labeled substrate than in the presence of the fluorescently-labeled substrate; and if so
  (c) separately determining for each compound included in the plurality of chemical compounds if the change in fluorescence intensity is smaller in the presence of both the compound and the fluorescently-labeled substrate than in the presence of the fluorescently-labeled substrate, a smaller change in fluorescence intensity indicating that the compound inhibits the protein kinase, so as to thereby identify any compound included in the plurality of chemical compounds that inhibits the protein kinase; wherein the fluorescently-labeled substrate comprises a peptide and at least one fluorophore, wherein a fluorophore is attached to a serine, a threonine, or a tyrosine on at least one terminal end of the peptide, and wherein phosphorylation of the substrate by the protein kinase occurs at the terminal serine, the terminal threonine, or the terminal tyrosine to which the fluorophore is attached and produces at least a 20% change in fluorescence intensity.

The invention further provides a method for identifying a chemical compound that inhibits a protein kinase in a living cell, which comprises comparing the fluorescence intensity when a fluorescently-labeled substrate for the protein kinase is introduced into a cell which has not been contacted with the chemical compound, with the fluorescence intensity when the fluorescently-labeled substrate is introduced into a cell which has been contacted with the chemical compound, a smaller change in fluorescence intensity when the cell has been contacted with the chemical compound indicating that the compound inhibits the protein kinase in the living cell; wherein the fluorescently-labeled substrate comprises a peptide and at least one fluorophore, wherein a fluorophore is attached to a serine, a threonine, or a tyrosine on at least one terminal end of the peptide, and wherein phosphorylation of the substrate by the protein kinase occurs at the terminal serine, the terminal threonine, or the terminal tyrosine to which the fluorophore is attached and produces at least a 20% change in fluorescence intensity.

The present application provides high throughput assays to identify protein kinase inhibitors. The efficacy of these inhibitors can be evaluated in cell based systems. Assays can be carried out using, for example, 96-well plates or chips which allow massive parallel measurements. As an analogous example, DNA microarrays have been used to sample time-dependent changes in gene expression patterns in response to environmental stimuli.[60] Analogous methods are also being used to assess changes in protein levels and/or activities.[61,77]

The invention also provides a method for determining if a protein kinase is active in a living cell, which comprises either introducing a fluorescently-labeled substrate for the protein kinase into the cell or contacting a lysate from the cell with the fluorescently-labeled substrate, and measuring fluorescence intensity, a change in fluorescence intensity indicating that the substrate has been phosphorylated by the protein kinase and that the protein kinase is active in the living cell; wherein the fluorescently-labeled substrate comprises a peptide and at least one fluorophore, wherein a fluorophore is attached to a serine, a threonine, or a tyrosine on at least one terminal end of the peptide, and wherein phosphorylation of the substrate by the protein kinase occurs at the terminal serine, the terminal threonine, or the terminal tyrosine to which the fluorophore is attached and produces at least a 20% change in fluorescence intensity.

The assays and substrates described herein can be used as powerful diagnostic tools, where there is a change in protein kinase activity that is correlated with a disease state. For example, cAMP-dependent protein kinase has been implicated in the activation of the androgen receptor,[49] the upregulation of which is strongly correlated with cancer of the prostrate. Activation of the androgen receptor through signaling pathways that modulate phosphorylation may result in androgen-independent growth of prostate cancer cells.[49] In addition, overexpression of the epidermal growth factor receptor, as well as erbB-2, via gene activation is directly correlated with a poor clinical outcome in breast and ovarian cancer.[50]

The invention provides a method for diagnosing a disease state that is correlated with a known change in activity of a protein kinase compared to the activity of the protein kinase in a normal state, which comprises comparing the activity of the protein kinase in the normal state with the activity of the protein kinase in a state that is being diagnosed, a change in activity corresponding to the known change indicating that the state that is being diagnosed is a disease state; wherein the activity of the protein kinase is measured using a fluorescently-labeled substrate that is phosphorylated by the protein kinase, wherein the fluorescently-labeled substrate comprises a peptide and at least one fluorophore, wherein a fluorophore is attached to a serine, a threonine, or a tyrosine on at least one terminal end of the peptide, and wherein phosphorylation of the substrate by the protein kinase occurs at the terminal serine, the terminal threonine, or the terminal tyrosine to which the fluorophore is attached and produces at least a 20% change in fluorescence intensity.

In any of the methods described herein, the change in fluorescence intensity when the substrate is phosphorylated by the protein kinase can be an increase in fluorescence intensity or a decrease in fluorescence intensity. In different embodiments, phosphorylation of the substrate by the protein kinase produces at least a 70% change in fluorescence intensity, or at least a 100% change in fluorescence intensity, or at least a 150% change in fluorescence intensity, or at least a 250% change in fluorescence intensity. In one embodiment, a metal ion chelator induces the change in fluorescence intensity. In different embodiments, the metal ion is a magnesium ion or a calcium ion.

The methods described herein can be used with a protein kinase that is a purified protein kinase, a protein kinase that is obtained from a cell lysate, or a protein kinase in a living cell. Fluorescently-labeled substrates can be introduced into cells, for example, by microinjection of the substrates into the cells or by attaching the substrates to a substance that renders the substrate cell permeable. The cell can be a cancer cell. The cell can be a cell that is in a known phase of the cell cycle. The cell lysate can also be from a cancer cell. The cell lysate can be from a cell that is in a known phase of the cell cycle.

The issue of when protein kinases are activated in response to a stimulus has previously proven difficult to address. Lysis of synchronized cell populations followed by capture of the kinase in question and measurement of its activity furnishes some information concerning catalytic status. Intracellular fluorometric probes of protein kinase activity offer the potential of real time assessment of signaling activity under physiologically relevant conditions. The direct visualization of protein kinase activity in living cells provides a genuine assessment of the efficacy and selectivity of protein kinase inhibitors in a physiological setting. In addition, the ability to visualize the activity of a protein kinase in real time furnishes a direct measurement of the activation of specific signaling pathways in response to extracellular stimuli.

The assays described herein can be used with inert or "caged" substrates[11-14,58,59,64] that are quiescent until activated by light or other means. In such cases, the substrate cannot be phosphorylated by the protein kinase until the substrate is activated. Such substrates are especially useful for use with whole cell assays, where the substrate can be activated when the cell is in a desired state, for example in a desired phase of the cell cycle. In addition, for example, for assays of PKA, photolytic release of cAMP from a membrane permeant ester, DMNB-cAMP, can be used.[67,68]

The caged substrate can comprise a caged serine, a caged threonine, or a caged tyrosine. The caged substrate can comprise a serine, a threonine, or a tyrosine with a photolabile side chain that blocks transfer of a phosphoryl group from adenosine triphosphate to a hydroxyl moiety of the serine, the threonine, or the tyrosine. The photolabile side chain can comprise the structure

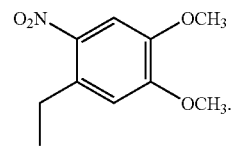

A preferred caged substrate is

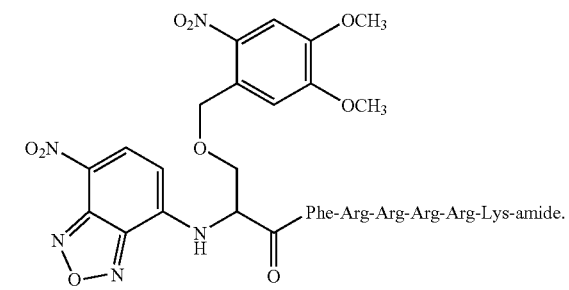

In any of the methods described herein, the substrate can be specific for a protein kinase subtype, for example protein kinase C, or isoforms α, β, and γ of protein kinase C. In other examples, the substrate is specific for protein kinase A, protein kinase B, protein kinase D, protein kinase G, Ca$^+$/calmodulin-dependent protein kinase, mitogen-activated protein kinase, protein kinase mos, protein kinase raf, protein tyrosine kinase, tyrosine kinase abl, tyrosine kinase src, tyrosine kinase yes, tyrosine kinase fps, tyrosine kinase met, cyclin-dependent protein kinase, or cdc2 kinase.

In one embodiment of the peptide substrate, one fluorophore is attached to one terminal end of the peptide. The terminal end can be the C-terminal end of the peptide or the N-terminal end of the peptide. In another embodiment, a fluorophore is attached to each terminal end of the peptide. In further embodiments, fluorophores with distinct photophysical properties are attached to different terminal ends of the peptide, or attached to one or both terminal ends and any nonterminal site on the peptide. For example, one fluorophore can be attached to a terminal end of the peptide and a second fluorophore, with photophysical properties distinct from the first fluorophore, can be attached to any nonterminal site on the peptide.

In cases where multiple fluorophores are attached to the substrate, the phosphorylation of the substrate by the protein kinase can also be detected using fluorescence resonance energy transfer (FRET) (e.g.[67,68,69]).

The fluorophore can be a 7-nitrobenz-2-oxa-1,3-diazole derivative or a fluorescein derivative. In other examples, the fluorophore can comprise a dansyl derivative, an acridine derivative, an Alexa Fluor derivative, a BODIPY derivative, an Oregon Green derivative, a Rhodamine Green derivative, a Rhodamine Red-X derivative, a Texas Red derivative, a Cascade Blue derivative, a Cascade Yellow derivative, a Marina Blue derivative, a Pacific Blue derivative, an AMCA-X derivative, or a coumarin derivative.

The fluorophore can be attached to the peptide by a linker. The linker can be a metal chelating linker. Preferably, the linker comprises a turn to position the fluorophore in a location closer to the terminal serine, the terminal threonine or the terminal tyrosine than the location the fluorophore would occupy in the absence of a turn in the linker. The linker can comprise one or more amino acids. In one embodiment, the linker does not comprise more than one amino acid. In one embodiment, the linker comprises non-amino acid residues and/or non-natural residues. In different embodiments, the linker can comprise, for example, a carboxamide linker, an aminobenzoic acid linker, a sulfonamide linker, a urea linker, a thiourea linker, an ester linker, a thioester linker, an alkylamine linker, an arylamine linker, an ether linker, or a thioether linker. The linker can be N-methyl glycine, L-proline, D-proline,

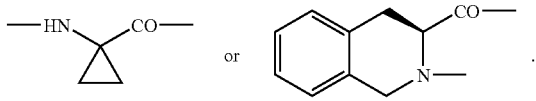

In different embodiments, the substrate is selected from the group consisting of:

wherein F is phenylalanine, K is lysine, and R is arginine; and wherein the LINKER is selected from the group consisting of N-methyl glycine, L-proline, D-proline,

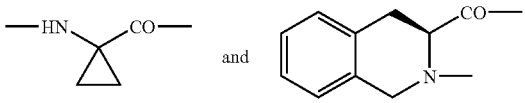

The peptide substrate can further comprise any one or more of a lipid, a carbohydrate or a nucleic acid.

The protein kinase inhibitor, for example, can be a non-peptidyl compound or can comprise a peptide that is not phosphorylated by the protein kinase. The inhibitor can be a competitive inhibitor which binds to the active site of the protein kinase or a non-competitive inhibitor which binds to a part of the protein kinase or the enzyme-substrate complex other than the active site.

The invention provides a method of making a composition which comprises identifying a chemical compound as a protein kinase inhibitor by any of the methods described herein and admixing the compound with a carrier. The composition can be a pharmaceutical composition and the carrier a pharmaceutically acceptable carrier.

The invention provides a protein kinase inhibitor identified by any of the methods described herein, wherein the compound was not previously known to inhibit the protein kinase.

The invention provides a substrate for a protein kinase, wherein the substrate comprises a peptide and at least one fluorophore, wherein a fluorophore is attached to a serine, a threonine, or a tyrosine on at least one terminal end of the peptide, and wherein phosphorylation by the protein kinase of the terminal serine, the terminal threonine, or the terminal tyrosine to which the fluorophore is attached produces at least a 20% change in fluorescence intensity.

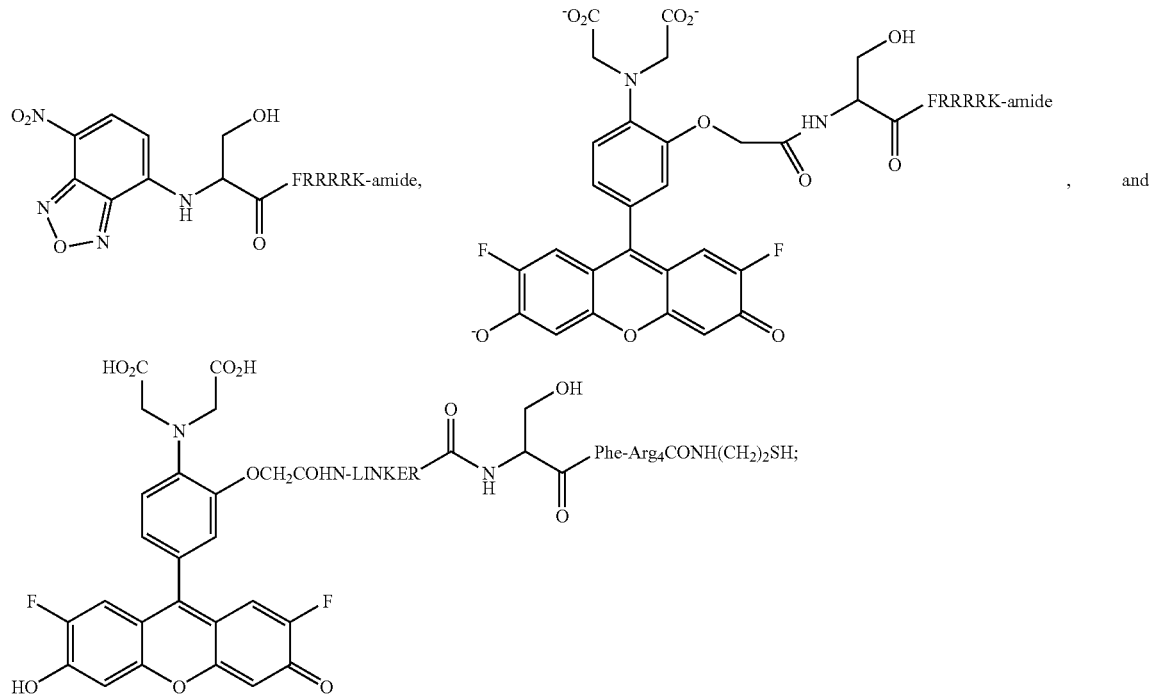

In one embodiment, a metal ion chelator induces the change in fluorescence intensity. In different embodiments, the metal ion is a magnesium ion or a calcium ion.

In one embodiment, the substrate cannot be phosphorylated by a protein kinase until the substrate is activated, for example until the substrate is activated by light. The substrate can comprise a serine, a threonine, or a tyrosine with a photolabile side chain that blocks transfer of a phosphoryl group from adenosine triphosphate to a hydroxyl moiety of the serine, the threonine, or the tyrosine. The photolabile side chain can comprise the structure

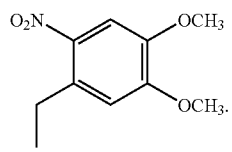

The invention also provides a substrate for a protein kinase, wherein the substrate comprises (1) a peptide comprising a serine, a threonine, or a tyrosine on a terminal end of the peptide; (2) at least one fluorophore, wherein a fluorophore is attached to the serine, the threonine, or the tyrosine on the terminal end of the peptide; and (3) a photolabile side chain attached to the serine, the threonine, or the tyrosine on the terminal end of the peptide, wherein the photolabile side chain blocks transfer of a phosphoryl group from adenosine triphosphate to a hydroxyl moiety of the serine, the threonine, or the tyrosine so that the substrate cannot be phosphorylated by a protein kinase until the photolabile side chain is removed from the substrate. The photolabile side chain can comprise the structure

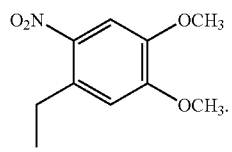

A preferred substrate with a photolabile side chain is

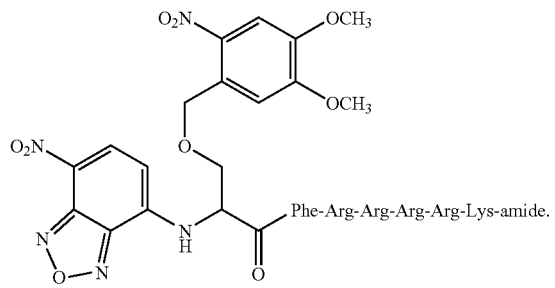

In one embodiment, after removal of the photolabile side chain from the substrate, phosphorylation by a protein kinase of the terminal serine, the terminal threonine, or the terminal tyrosine to which the fluorophore is attached produces at least a 20% change in fluorescence intensity. In one embodiment, a metal ion chelator induces the change in fluorescence intensity. In different embodiments, the metal ion is a magnesium ion or a calcium ion.

The change in fluorescence intensity when the substrate is phosphorylated by the protein kinase can be an increase in fluorescence intensity or a decrease in fluorescence intensity. In different embodiments, phosphorylation of the substrate by the protein kinase produces at least a 70% change in fluorescence intensity, or at least a 100% change in fluorescence intensity, or at least a 150% change in fluorescence intensity, or at least a 250% change in fluorescence intensity.

The substrate can be specific for a protein kinase subtype, for example protein kinase C, or isoforms α, β, and γ of protein kinase C. In other examples, the substrate is specific for protein kinase A, protein kinase B, protein kinase D, protein kinase G, $Ca^+$/calmodulin-dependent protein kinase, mitogen-activated protein kinase, protein kinase mos, protein kinase raf, protein tyrosine kinase, tyrosine kinase abl, tyrosine kinase src, tyrosine kinase yes, tyrosine kinase fps, tyrosine kinase met, cyclin-dependent protein kinase, or cdc2 kinase.

The substrate can further comprise any one or more of a carbohydrate, a lipid or a nucleic acid.

In one embodiment, one fluorophore is attached to one terminal end of the peptide. The terminal end can be the C-terminal end of the peptide or the N-terminal end of the peptide. In another embodiment, a fluorophore is attached to each terminal end of the peptide. In further embodiments, fluorophores with distinct photophysical properties are attached to different terminal ends of the peptide or to any nonterminal site on the peptide. For example, one fluorophore can be attached to a terminal end of the peptide and a second fluorophore, with photophysical properties distinct from the first fluorophore, can be attached to any nonterminal site on the peptide.

In different embodiments, the fluorophore is a 7-nitrobenz-2-oxa-1,3-diazole derivative or a fluorescein derivative. The fluorophore can also be selected from the group consisting of, for example, but not limited to, a dansyl derivative, an acridine derivative, an Alexa Fluor derivative, a BODIPY derivative, an Oregon Green derivative, a Rhodamine Green derivative, a Rhodamine Red-X derivative, a Texas Red derivative, a Cascade Blue derivative, a Cascade Yellow derivative, a Marina Blue derivative, a Pacific Blue derivative, an AMCA-X derivative, and a coumarin derivative.

In different embodiments, the fluorophore is attached to the peptide by a linker. The linker can be a metal chelating linker. Preferably, the linker comprises a turn to position the fluorophore in a location closer to the terminal serine, the terminal threonine or the terminal tyrosine than the location the fluorophore would occupy in the absence of a turn in the linker. The linker can comprise one or more amino acids. In one embodiment, the linker does not comprise more than one amino acid. In one embodiment, the linker comprises non-amino acid residues and/or non-natural residues. The linker, for example, can be selected from the group consisting of a carboxamide linker, an aminobenzoic acid linker, a sulfonamide linker, a urea linker, a thiourea linker, an ester linker, a thioester linker, an alkylamine linker, an arylamine linker, an ether linker, and a thioether linker. In different embodiments, the linker is selected from the group consisting of N-methyl glycine, L-proline, D-proline,

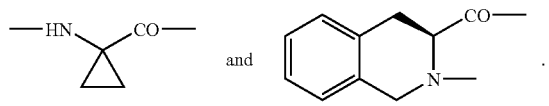

In different embodiments, the substrate is selected from the group consisting of:

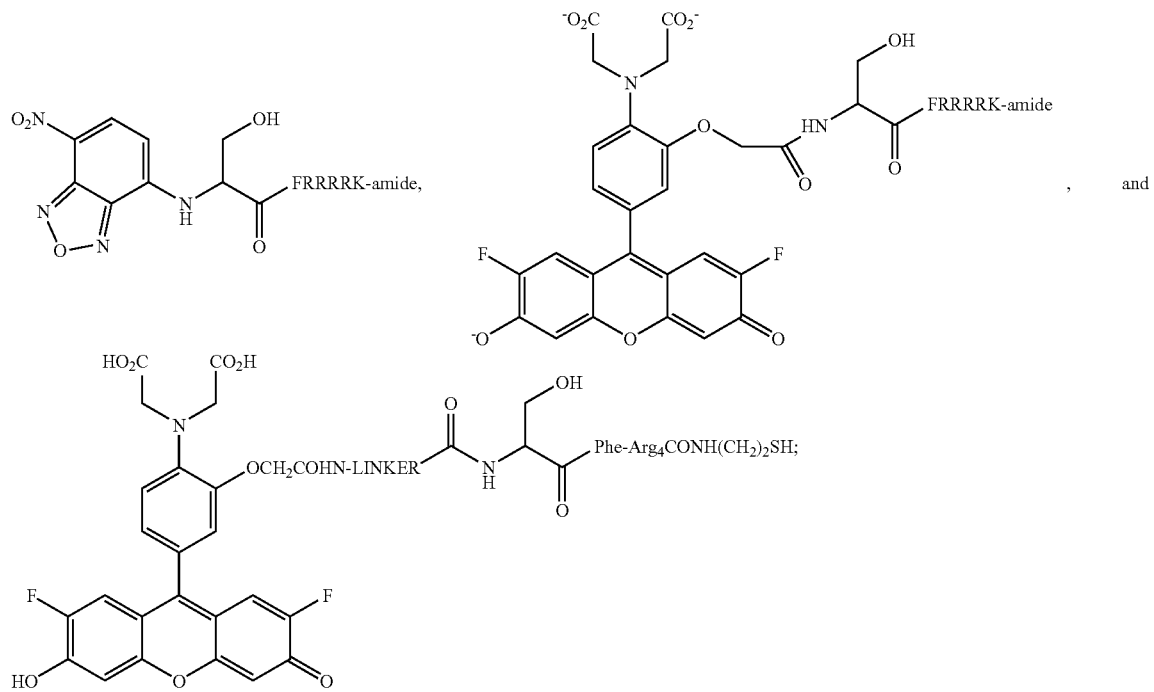

wherein F is phenylalanine, K is lysine, and R is arginine; and wherein the LINKER is selected from the group consisting of N-methyl glycine, L-proline, D-proline,

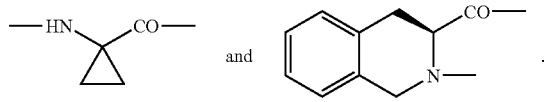

The invention provides a composition comprising any of the protein kinase substrates described herein and a carrier. In one embodiment, the composition is a pharmaceutical composition and the carrier is a pharmaceutically acceptable carrier.

The invention provides a chemical compound comprising a peptide and a fluorophore, wherein the compound is selected from the group consisting of the compounds set forth in Table 3. The invention provides a chemical compound selected from the group of compounds set forth in Table 3. The invention also provides a composition comprising any of the chemical compounds set forth in Table 3 and a carrier. In one embodiment, the composition is a pharmaceutical composition and the carrier is a pharmaceutically acceptable carrier.

The invention provides a chemical compound having the structure:

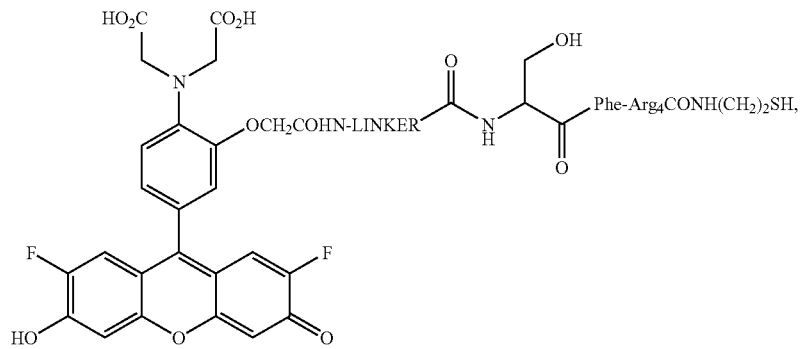

wherein the LINKER is selected from the group consisting of the following:
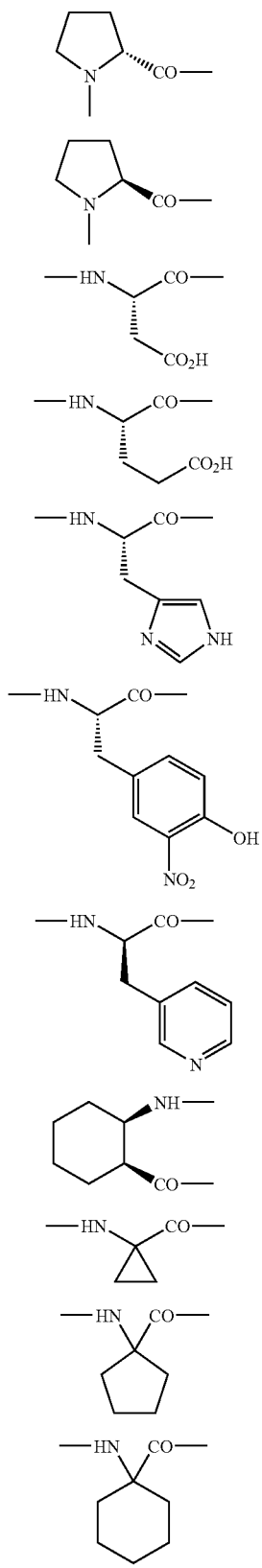
a
b
c
d
e
f
g
h
i
j
k
-continued
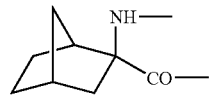
l
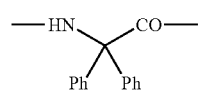
m
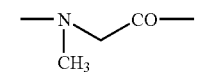
n
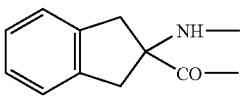
o
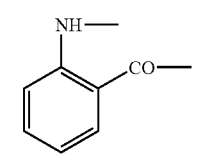
p
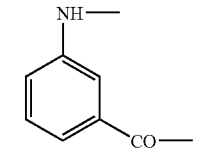
q
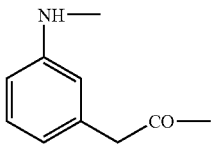
r
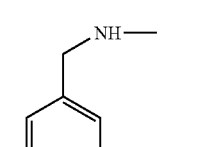
s
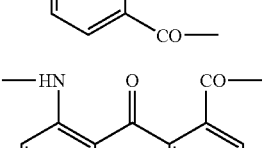
t
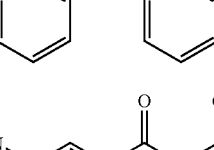
u
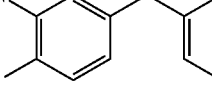
v
no linker.
w
The invention provides a chemical compound having the structure: fluorophore-LINKER-X-FRRRRK-amide (SEQ ID NO:3); wherein F is phenylalanine; K is lysine; R is arginine; and X is serine, threonine, or tyrosine.

The fluorophore can be a 7-nitrobenz-2-oxa-1,3-diazole derivative or a fluorescein derivative. The fluorophore can be selected from the group consisting of, for example, but not limited to, a dansyl derivative, an acridine derivative, an Alexa Fluor derivative, a BODIPY derivative, an Oregon Green derivative, a Rhodamine Green derivative, a Rhodamine Red-X derivative, a Texas Red derivative, a Cascade Blue derivative, a Cascade Yellow derivative, a Marina Blue derivative, a Pacific Blue derivative, an AMCA-X derivative, and a coumarin derivative.

The linker can be a metal chelating linker. Preferably, the linker comprises a turn to position the fluorophore in a location closer to the terminal serine, the terminal threonine or the terminal tyrosine than the location the fluorophore would occupy in the absence of a turn in the linker. The linker can comprise one or more amino acids. In one embodiment, the linker does not comprise more than one amino acid. In one embodiment, the linker comprises non-amino acid residues and/or non-natural residues. The linker can be selected from the group consisting of, for example, but not limited to, a carboxamide linker, an aminobenzoic acid linker, a sulfonamide linker, a urea linker, a thiourea linker, an ester linker, a thioester linker, an alkylamine linker, an arylamine linker, an ether linker, and a thioether linker. The linker can be selected from the group consisting of N-methyl glycine, L-proline, D-proline,

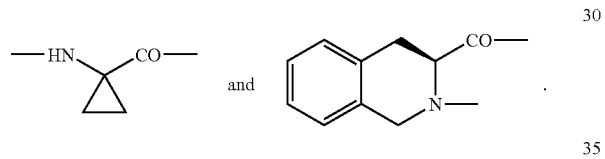

and

The LINKER can be selected from the group consisting of the following:

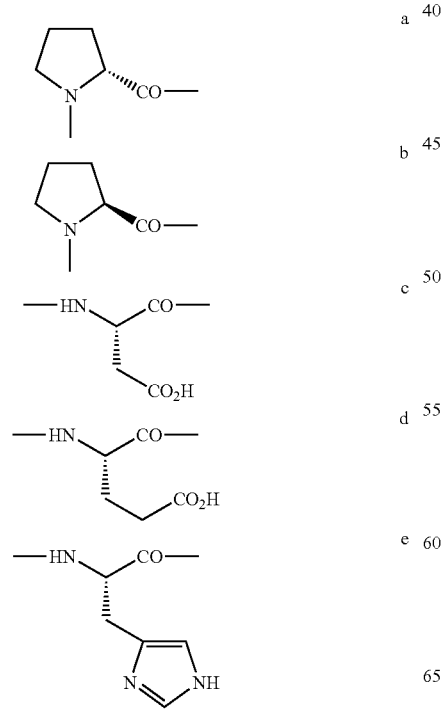

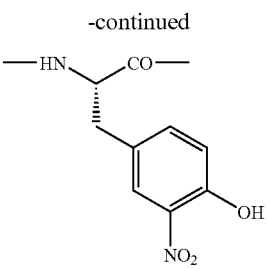 f

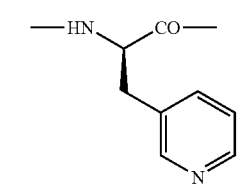 g

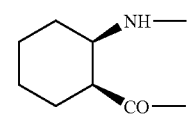 h

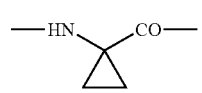 i

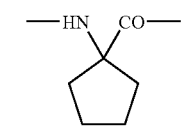 j

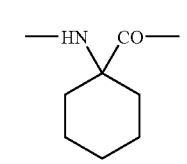 k

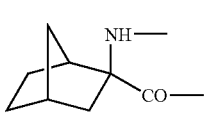 l

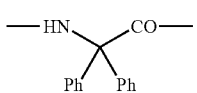 m

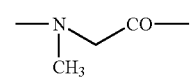 n

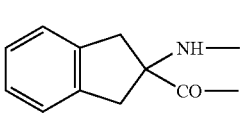 o

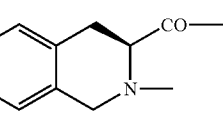 p

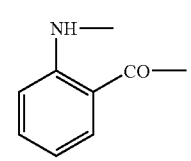 q

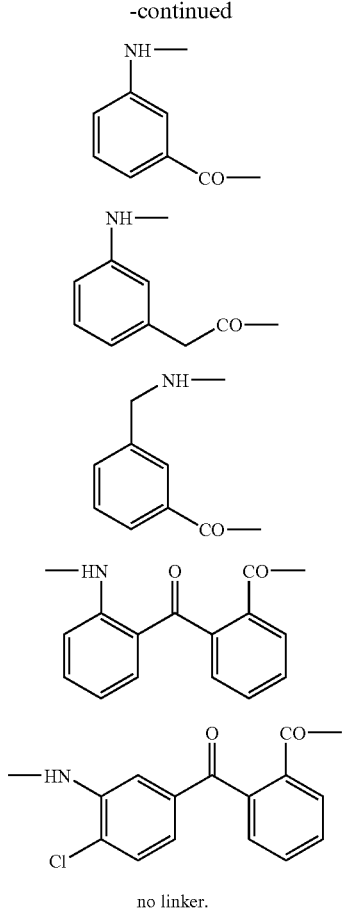

no linker.

The chemical compound can act as a substrate for a protein kinase. The chemical compound can be specific for a protein kinase subtype, for example protein kinase C or isoforms α, β, and γ of protein kinase C. The chemical compound can be specific for, for example, but not limited to, protein kinase A, protein kinase B, protein kinase D, protein kinase G, Ca$^+$/calmodulin-dependent protein kinase, mitogen-activated protein kinase, protein kinase mos, protein kinase raf, protein tyrosine kinase, tyrosine kinase abl, tyrosine kinase src, tyrosine kinase yes, tyrosine kinase fps, tyrosine kinase met, cyclin-dependent protein kinase, or cdc2 kinase.

The chemical compound can further comprise one or more of a carbohydrate, a lipid or a nucleic acid.

The invention also provides a chemical compound comprising a peptide and at least one fluorophore, wherein a fluorophore is attached to a serine, a threonine, or a tyrosine on at least one terminal end of the peptide.

The fluorophore can be attached to the C-terminal end of the peptide or to the N-terminal end of the peptide. A fluorophore can be attached to each terminal end of the peptide. Fluorophores with distinct photophysical properties can attached to different terminal ends of the peptide or to any nonterminal site on the peptide. For example, a first fluorophore can be attached to a terminal end of the peptide and a second fluorophore, with photophysical properties distinct from the first fluorophore, can be attached to any nonterminal site on the peptide. In different embodiments, the fluorophore is attached to serine, or to threonine, or to tyrosine on a terminal end of the peptide. If more than one fluorophore is used, the second fluorophore can be attached to serine, or to threonine, or to tyrosine on the second terminal end of the peptide. In further embodiments, the second fluorophore can be attached to any amino acid on a terminal end or on any nonterminal site on the peptide.

The fluorophore can be a 7-nitrobenz-2-oxa-1,3-diazole derivative or a fluorescein derivative. The fluorophore can be selected from the group consisting of, for example, but not limited to, a dansyl derivative, an acridine derivative, an Alexa Fluor derivative, a BODIPY derivative, an Oregon Green derivative, a Rhodamine Green derivative, a Rhodamine Red-X derivative, a Texas Red derivative, a Cascade Blue derivative, a Cascade Yellow derivative, a Marina Blue derivative, a Pacific Blue derivative, an AMCA-X derivative, and a coumarin derivative.

The fluorophore can be attached to the peptide by a linker. The linker can be a metal chelating linker. Preferably, the linker comprises a turn to position the fluorophore in a location closer to the terminal serine, the terminal threonine or the terminal tyrosine than the location the fluorophore would occupy in the absence of a turn in the linker. The linker can comprise one or more amino acids. In one embodiment, the linker does not comprise more than one amino acid. In one embodiment, the linker comprises non-amino acid residues and/or non-natural residues. The linker can be selected from the group consisting of, for example, but not limited to, a carboxamide linker, an aminobenzoic acid linker, a sulfonamide linker, a urea linker, a thiourea linker, an ester linker, a thioester linker, an alkylamine linker, an arylamine linker, an ether linker, and a thioether linker. The linker can be selected from the group consisting of N-methyl glycine, L-proline, D-proline,

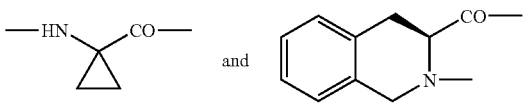

The linker can be selected from the group consisting of the following:

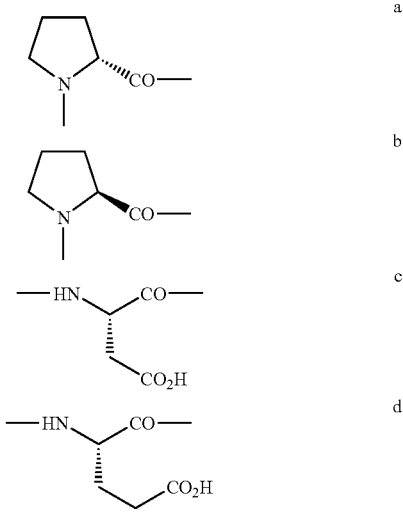

-continued

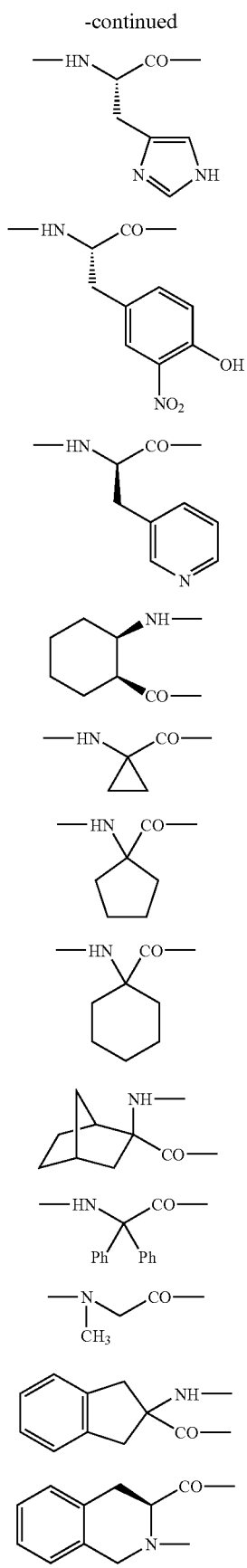
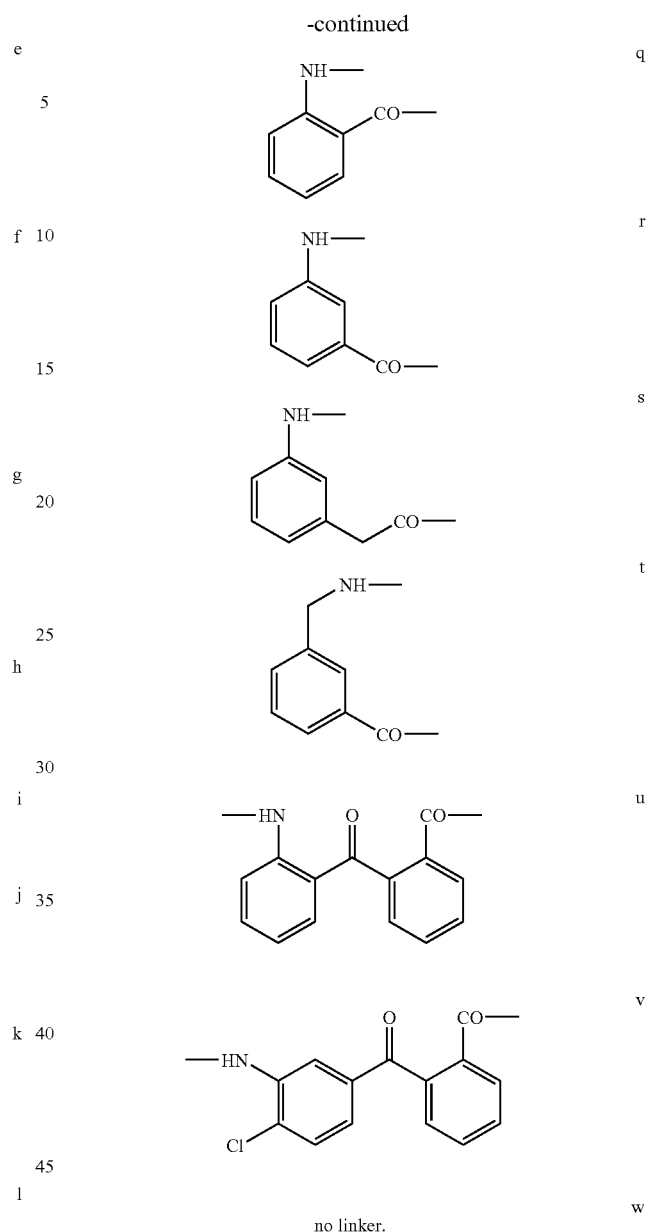

no linker.

The chemical compound can act as a substrate for a protein kinase. The chemical compound can be specific for a protein kinase subtype, for example protein kinase C or isoforms α, β, and γ of protein kinase C. The chemical compound can be specific for, for example, but not limited to, protein kinase A, protein kinase B, protein kinase D, protein kinase G, $Ca^+$/calmodulin-dependent protein kinase, mitogen-activated protein kinase, protein kinase mos, protein kinase raf, protein tyrosine kinase, tyrosine kinase abl, tyrosine kinase src, tyrosine kinase yes, tyrosine kinase fps, tyrosine kinase met, cyclin-dependent protein kinase, or cdc2 kinase.

The chemical compound can further comprise any one or more of a carbohydrate, a lipid or a nucleic acid.

The invention provides a chemical compound having the structure

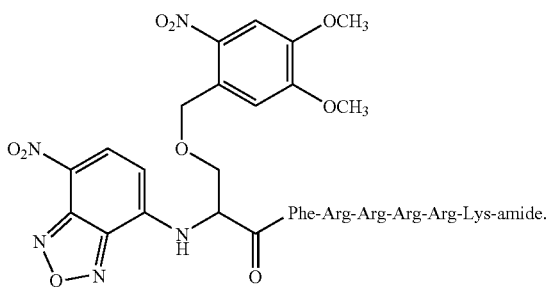

In one embodiment of chemical compounds described herein, a metal ion chelator induces a change in fluorescence intensity. In different embodiments, the metal ion is a magnesium ion or a calcium ion. In one embodiment, the change in fluorescence intensity is at least a 20% change in fluorescence intensity.

The invention also provides a composition comprising any of the chemical compounds described herein and a carrier. In one embodiment, the composition is a pharmaceutical composition and the carrier is a pharmaceutically acceptable carrier. As used herein, the term "carrier" encompasses any of the standard pharmaceutical carriers, such as a sterile isotonic saline, phosphate buffered saline solution, water, and emulsions, such as an oil/water or water/oil emulsions.

The protein kinase substrates described herein can be used in assays to identify inhibitors of protein kinase.

The invention provides a method of treating an affliction in a subject, wherein the affliction is treated by inhibition of a protein kinase, where the method comprises administering to the subject a compound identified by any of the methods described herein for identifying a compound that inhibits a protein kinase, where the compound is administered to the subject in an amount effective to treat the affliction. The invention also provides for the use of a compound, identified by any of the methods described herein for identifying a compound that inhibits a protein kinase, for the preparation of a composition for treating an affliction in a subject, wherein the affliction is treated by inhibition of a protein kinase. The affliction can be a cancer, e.g.[89-92]

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Example I

1. Materials and Methods

General—All chemicals were obtained from Aldrich, except for [$\gamma$-$^{32}$P] adenosine triphosphate (ATP) (obtained from New England Nuclear); bovine serum albumin, protease and phosphatase inhibitors (Sigma); protected amino acid derivatives and Rink resin (Advanced ChemTech); antibodies (Santa Cruz Biotech), and Liquiscint (National Diagnostics). The $\alpha$-, $\beta$II-, and $\gamma$-isoforms of protein kinase C were purchased from Panvera.

Peptide and library synthesis-Peptides and peptide libraries were synthesized using protocols analogous to those previously described.[24] Specific protocols are furnished for compounds 2 and 3.

Preparation of 7-nitrobenz-2-oxa-1,3-diazole (NBD)-NH-Ser-Phe-Arg$_4$-Lys-amide 2. A standard 9-fluorenylmethoxycarbonyl(Fmoc)/benzotriazol-1-yloxy-tris(dimethylamino) phosphonium hexafluorophosphate (Bop) peptide synthesis protocol was employed to synthesize this peptide on the Rink resin via an automated peptide synthesizer. Each amino acid was attached according to the following program (for 2 g resin scale): (a) 3×30 ml $CH_2Cl_2$; (b) 1×20 ml of 30% piperidine in $CH_2Cl_2$ (1 min.); (c) 1×30 ml 30% piperidine in $CH_2Cl_2$ (20 min.); (d) 2×30 ml $CH_2Cl_2$; (e) 1×30 ml isopropanol; (f) 3×30 ml $CH_2Cl_2$; (g) 1×30 ml 4 equivalents of N-methyl morpholine in $CH_2Cl_2$; (h) 3 equivalents of Fmoc-protected amino acid, Bop, hydroxybenzotriazole and 6 equivalents of N-methyl morpholine in 30 ml $CH_2Cl_2$/DMF (1:1) (60-90 min.) (the coupling time was 90 min for all the Arg residues, and 60 min for the other residues); (i) 3×30 ml $CH_2Cl_2$; 0) 3×30 ml of 33% ethanol in $CH_2Cl_2$; (k) 2×30 ml $CH_2Cl_2$. After completion of the desired amino acid sequence, the Fmoc group was removed with 30 ml of 30% piperidine (30 min.) and the resulting side chain-protected species, $H_2$N-Ser(tBu)-Phe-[Arg(Mtr)]$_4$-Lys(Boc)-[Rink Resin], was treated with 10 equivalents of NBD-Cl and N-methyl morpholine in 1:1 $CH_2Cl_2$/DMF (2 ml) for 24 hr, to furnish the resin-linked NBD-modified peptide: NBD-HN-Ser(tBu)-Phe-[Arg(Mtr)]$_4$-Lys(Boc)-[Rink Resin].

Preparation of $H_2$N-Ser-Phe-Arg$_4$-Lys(NBD)-amide 3. The protocol employed for peptide 2 was likewise used to synthesize 3 with the following exceptions: N-$\alpha$-Fmoc-N-$\epsilon$-1-(4,4-dimethyl-2,6-dioxocyclohex-1-ylidene)ethyl-Lys"Fmoc-Lys(Dde)" was used in place of Fmoc-Lys(tBoc). Upon synthesis of the Ac-HN-Ser(tBu)-Phe-[Arg(Mtr)]$_4$-Lys(Dde)-[Rink Resin], the Dde protecting group was removed with hydrazine and the $\epsilon$-amino moiety of Lys modified with NBD-Cl as described above. The NBD-peptide-Rink resins (i.e. 2 and 3) were deprotected and cleaved as follows: each peptide-resin (100 mg) was individually transferred to a small reaction vessel containing 1 ml of a 9:1 trifluoroacetic acid/thioanisole mixture. The reaction vessel was then shaken at room temperature for 10 h. The resin was filtered, under reduced pressure, and then washed twice with trifluoroacetic acid. The filtrates were then combined (~5 ml) and an 8-10 fold volume of cold anhydrous ether (~50 ml) was added in a drop-wise fashion. The mixture was kept at 4° C. for at least 1 h. The precipitated peptide was then collected via filtration through a fine sintered glass filter funnel under a light vacuum. The precipitate was washed with cold anhydrous ether (2×5 ml), dissolved in 10 ml of water, and finally lyophilized to provide the crude peptide. The peptides were then purified on a preparative high performance liquid chromatography (HPLC) using three Waters radial compression modules (25×10 cm) connected in series (gradient A: 0.1% trifluoroacetic acid in water; solvent B: 0.1% trifluoroacetic acid in acetonitrile: 0-3 min. (100% A); a linear gradient from 3-20 min. (75% A and 25% B); a steep final linear gradient to 90% B for cleaning purposes). Peptides 2 and 3 were characterized by mass spectrometry.

In the case of the library of 415 compounds described herein (Table 3), peptide 1 was cleaved from the Rink resin with 90% trifluoroacetic acid/10% thioanisole, purified by HPLC, and then separately acylated with fluorescent carboxylic and sulfonic acids (I), condensed with aryl aldehydes (II), or directly arylated (III) via nucleophilic aromatic substitution. Carboxylic, sulfonic and related acid derivatives are as follows: fluorescamine, acridine-9-carboxylic acid, 5-dimethylamino-naphthalene-1-sulfonic acid, N,N'-diBoc-3-guanidino-naphthalene-2-carboxylic acid, 3-amino-naphthalene-2-carboxylic acid, 1-hydroxy-naphthalene-2-carboxylic acid, 3-di-tert-butoxycarbonylmethylamino-naphthalene-2-carboxylic acid, isoquinoline-3-carboxylic acid, quinoline-2-carboxylic acid, quinoline-8-carboxylic acid, 6-carboxytetramethylrhodamine succinimidyl ester, and 1-(3-(succinimidyloxycarbonyl)benzyl)-4-(5-(4-methoxyphenyl) oxazol-2-yl) pyridinium bromide. Aldehydes and related derivatives are as follows: naphthalene-2,3-dicarbaldehyde/ cyanide, naphthalene-2,3-dicarbaldehyde/thiourea, naphthalene-2,3-dicarbaldehyde/dimethoxymethyl-amine, naphthalene-2,3-dicarbaldehyde/aminoguanidine, naphthalene-2,3-dicarbaldehyde/2-amino-pyridine, 2,4-dinitro-benzaldehyde, 5-(4-dimethylamino-phenyl)-penta-2,4-dienal, bis-(2-hydroxy-phenyl)-methanone, bis-(4-hydroxy-phenyl)-methanone, 2-hydroxy-3,5-dinitro-benzaldehyde, anthracene-9-carbaldehyde, phenanthrene-9-carbaldehyde, pyrene-1-carbaldehyde, 4-dimethylamino-benzaldehyde, 2-hydroxy-4-diethylamine-benzaldehyde, 3-(4-dimethylamino-phenyl)-propenal, 4-methoxy-benzaldehyde, 2-hydroxyl-5-methoxy-benzaldehyde, 4-hydroxyl-benzaldehyde, 2,4-dimethoxybenzaldehyde, 2-hydroxy-naphthalene-1-carbaldehyde, 4-nitro-benzaldehyde, 2-nitrobenzaldehyde, 4-hydroxy-5-nitrobenzaldehyde, 2,6-dichloro-benzaldehyde, 4-styryl-benzaldehyde, and 3-phenyl-propenal. Aryl halides and related derivatives are as follows: NBD-Cl, 1-fluoro-2,4-dinitro-benzene, 6-chloro-5-nitro-quinoline, 2-chloro-5-trichloromethyl-nicotinonitrile, 2-bromo-pyrimidine, 2-bromo-4,6-bis-(4-chloro-phenyl)-pyrimidine, 4-chloro-3,5-dinitro-benzonitrile, 2-fluoro-5-nitro-benzoic acid, 5-fluoro-2,4-dinitro-phenylamine, 1-fluoro-4-nitro-2-trifluoromethyl-benzene, 4-chloro-2,8-bis-trifluoromethyl-quinoline, 4-chloro-2-phenyl-quinazoline, and 2-chloro-3,5-dinitro-pyridine.

Radioactive PKC Assay—Radioactive assays were performed in duplicate at 30° C. The final assay volume totaled 40 µl and contained 62.5 mM HEPES (pH 7.4), 0.75 mM $CaCl_2$, 12.5 mM $MgCl_2$, 1 mM dithiothreitol, 0.5 mM EGTA, 7.5 µg/mL phosphatidylserine, 1.6 µg/mL diacylglycerol, and 10 ng of PKC. For the determination of the kinetic constants, the following concentrations were employed: 50 µM [$\gamma$-$^{32}$P] ATP (500-5000 cpm/pmol) and a substrate concentration that varied over a 10-fold range around the apparent $K_m$. Phosphorylation reactions were initiated by the addition of 10 µL of PKC from a stock solution (20 mM Tris-HCl at pH 7.5, 1 mM dithiothreitol, 1 mM EDTA, and 0.75 mg/mL bovine serum albumin) into 30 µL of assay buffer containing peptide substrate. Reactions were terminated after 5 min by spotting 25 µL aliquots onto phosphocellulose paper disks (2.1 cm in diameter). After 10 s, the disks were immersed in 10% glacial acetic acid and soaked with occasional stirring for at least 1 h. The acetic acid was decanted and the disks were collectively washed with four volumes of 0.5% $H_3PO_4$, 1 volume of water, followed by a final acetone rinse. The disks were air dried and then counted in a Beckman LS scintillation counter.

Fluorescent PKC assay-Fluorescence assays were performed in triplicate at 30° C. and initiated by addition of ATP to a 100 µL cuvette containing a 50 µL solution of PKC and peptide substrate 2. Final conditions: 62.5 mM HEPES pH 7.4, 3 mM $MgCl_2$, 0.3 mM $CaCl_2$, 0.1 mM EGTA, 1 mM DTT, 0.5 µg/mL phosphatidylserine, 0.1 µg/mL diacylglycerol, 1 mM ATP, and 13 nM PKC. After the addition of ATP, the solution was gently mixed and the time-dependent change in fluorescent intensity (excitation: 520 nm, emission: 560 mm) continuously monitored with a Photon Technology QM-1 spectrofluorimeter.

Preparation of Mitotic Cell Extracts-HeLa cells were synchronized for 16 h in the presence of 250 ng/ml nocodazole and mitotic cells collected by selective detachment. Nocodazole was removed prior to lysis by washing the cells 2 times with 10 ml of ice-cold phosphate-buffered saline (1.5 mM $KH_2PO_4$, 8 mM $Na_2HPO_4.7H_2O$, 2.6 mM KCl, 137 mM NaCl). The cells were then resuspended in a lysis buffer containing 50 mM Pipes pH 7.3, 5 mM $MgCl_2$, 0.2 mM EGTA, 1 M glycerol, 1 mM dithiothreitol, 0.5% Triton X-100, 1 mM PMSF, 10 µg/ml each of chymostatin, leupeptin and pepstatin and a 1:100 dilution of phosphatase inhibitor cocktail 1 (microcystin LR, cantharidin, and (−)-p-bromotetramisole) and phosphatase inhibitor cocktail 2 (sodium vanadate, sodium molybdate, sodium tartrate, and imidazole) (Sigma Chemical Co). The lysates were clarified by centrifugation at 4° C. for 5 minutes at 16,000 g and the concentration of the supernatant determined using the Bio-Rad protein assay (Bio-Rad Laboratories). The supernatant was diluted with Dilution Buffer (50 mM Tris pH 7.5, 10 mM $MgCl_2$, 0.2 mM EGTA, 2 mM dithithreitol, 10 µg/ml each of chymostatin, leupeptin and pepstatin and phosphatase inhibitor cocktails 1 and 2 as described above) to a final concentration of 4 mg/ml.

PKC activity in HeLa cell lysates—The PKC assay was initiated via the addition of 10 µL of HeLa mitotic lysate to a cuvette containing a pre-incubated (30° C.) 110 µL assay solution containing (final concentration) 10 µM peptide 2, 10 mM ATP, 750 µM $CaCl_2$, 12.5 mM $MgCl_2$, 500 µM EGTA, 1 mM dithiothreitol, 7.5 µg/mL phosphatidylserine, 1.6 µg/mL diacylglycerol in 20 mM Tris at pH 7.5. The time-dependent change in fluorescent intensity (excitation: 520 nm, emission: 560 nm) was continuously monitored with a Photon Technology QM-1 spectrofluorimeter. The conventional PKCs $\alpha$, $\beta$, and $\gamma$ were immunodepleted from the HeLa cell lysate via (i) preclearance with protein A Sepharose, (ii) incubation with the monoclonal cPKC antibody PKC (MC5) (Santa Cruz Biotech), (iii) addition of protein A Sepharose and subsequent centrifugation, and (iv) repetition of steps iii and iv. Protein A Sepharose was used for mock immunodepleted lysates. The absence of PKCs $\alpha$, $\beta$, and $\gamma$ was confirmed by Western blot analysis using antibodies targeted against the individual isoforms (Santa Cruz Biotech).

Microinjection Studies-Subconfluent, serum-starved (24 hr), HeLa cells were cultured on 22 mm coverslips in DMEM in a humidified atmosphere containing 5% $CO_2$. The NBD-containing peptide 2 (200 µM) in 50 mM Tris-HCl pH 7.2 was prefiltered through a 0.22 µm filter. Microinjections were performed with an Eppendorf (Brinkman Instruments, Westbury, N.Y.) 5246 microinjection apparatus mounted on the microscope inside the environmental chamber. The peptide was estimated to be diluted 10-fold upon microinjection, using the equation for volume (V) flow through a capillary tube:

$$\frac{V}{t} = \frac{\pi p r^4}{8 l \eta},$$

where p is the difference in pressure at the ends of the tube (290 hPa), r the radius (0.05 µm) and l the length (10 µm) of the tube, $\eta$ the viscosity of the injected solution ($0.69 \times 10^{-2}$ g/cm-sec), and t the total injection time (0.3 sec). The average volume of a fibroblast was taken as 2 pL.[18] 12-O-tetradecanoyl phorbol-13-acetate (TPA) (1 µM) was added to the media following microinjection to stimulate PKC activity. Time lapse images were collected with 2×2 binning using a Photometrics (Tuscon, Ariz.) Sensys cooled CCD camera mounted on an Olympus IX 70 inverted microscope (Melville, N.Y.) with a PlanApo 40X N. A. 0.75 objective, Ludl shutters (Hawthorne, N.Y.), and a filter set with an excitation wavelength of 460-500 nm and an emission wavelength of 510-560 nm. Images were collected at 30 second intervals (300 msec exposure time). Fluorescence intensity measurements were corrected using values from a standard photobleaching curve generated from control experiments with microinjected HeLa cells that had not been treated with TPA. Analysis of cell intensities over time was conducted using I.P. Lab and Microsoft Excel (Redmond, Oreg.). For experiments with the PKC inhibitor, the bisindolylmaleimide derivative GF 109203X (20 µM estimated intracellular concentration) was microinjected along with the NBD-peptide 2.

2. Results and Discussion

The design of a fluorescent sensor of protein kinase activity requires a substrate that contains a fluorophore positioned either near the site of phosphorylation or at a more remote site that responds to phosphorylation via a conformational change. In addition to Ser, Thr, and Tyr residues, protein kinases will catalyze the phosphorylation of a wide variety of unnatural amino acid analogs in active site-directed peptides.[19-23] The synthesis of these substrates is abetted by the fact that protein kinases phosphorylate alcohol-containing residues attached to the C- and/or N-terminus of appropriately designed peptides. Consequently, a wide variety of Ser analogs can be easily prepared and incorporated into the peptide substrate. For example, the peptide Ser-Phe-Arg-Arg-Arg-Arg-amide (SEQ ID NO:1) contains an N-terminal serine moiety that can be readily substituted with a virtually unlimited array of functional groups. Indeed, numerous N-substituted analogs of this peptide serve as are highly efficient substrates for the α, β, and γ isoforms of PKC. It was thus reasoned that a peptide of the general structure fluorophore-Ser-Phe-Arg-Arg-Arg-Arg-amide (SEQ ID NO:1) would also function as an effective PKC substrate. The single compact fluorophore-serine residue contains a fluorescent reporter that is confined to within a few angstroms of the hydroxyl moiety, the site of imminent phosphorylation. Consequently, phosphorylation of the serine alcohol could exert a dramatic affect on the photophysical properties of the adjacent fluorophore.

The peptide $H_2N$-Ser-Phe-Arg-Arg-Arg-Arg-Lys-amide (1) (SEQ ID NO:2) was prepared using an Fmoc-based protocol, spatially segregated, and the free N-terminal amine subsequently modified with an array of fluorophore-containing carboxylic acids (I), aromatic aldehydes (II), and electron deficient aryl halides (III). The imines generated in II were also reduced to the corresponding secondary amines IV ($NaCNBH_3$) and transformed, via aromatic nucleophilic substitution, to a variety of tertiary amines V (Scheme 1). This spatially segregated fluorophore-substituted peptide-based library contains a total of 415 distinct chemical entities (Table 3) and was screened for changes in fluorescence intensity in the presence of PKC and ATP under activating conditions. Interestingly, the overwhelming majority (414) of these peptide-linked fluorophores displayed little (<10%) or no fluorescence change upon exposure to PKC. The obvious explanation is that phosphorylation of the peptide fails to induce the desired change in photophysical properties of the appended fluorophore. However, it is also possible that introduction of fluorophores, at various sites along the peptide framework, interferes with PKC-catalyzed phosphorylation. The latter possibility is unlikely, particularly for simple N-monosubstituted peptides, since PKC will phosphorylate peptides containing a wide variety of structurally diverse functionality attached at and/or near the phosphorylatable serine moiety.[24] Nevertheless, a few representative members of the library were evaluated in depth (Table 1). The 7-nitrobenz-2-oxa-1,3-diazole (NBD) derivative 2 displays the greatest change in fluorescence intensity. By contrast, the dansyl and acridine derivatives exhibit phosphorylation-induced changes in fluorescence that are an order of magnitude less than that of NBD. The corresponding fluorescamine-treated peptide displays no fluorescence change as does the naphthalene-2,3-dicarbaldehyde/cyanide-treated species. One explanation for the poor fluorescence response of these particular peptides to PKC/ATP could be that these peptides serve as poor PKC substrates. This possibility was addressed by obtaining the PKCα-catalyzed $K_m$ and $V_{max}$ values using the [γ-$^{32}$P]ATP radioactive method.[25] As is clear from Table 1, all five peptides are reasonably effective substrates for PKCα.

The NBD-substituted peptide was subsequently examined in greater detail. The C-terminal-positioned Lys moiety allowed the comparison of fluorescence changes in response to phosphorylation as a function of NBD position (peptides 2 and 3, Scheme 2) relative to the serine moiety. The efficacy of peptides 2 and 3 as PKC substrates were initially assessed using the radioactive ATP assay.[25] Both peptides serve as efficient substrates for pure recombinant PKC α, β, and γ with $K_m$ and $k_{cat}$ values similar to other PKC peptide substrates (Table 2).

Figure 1B:
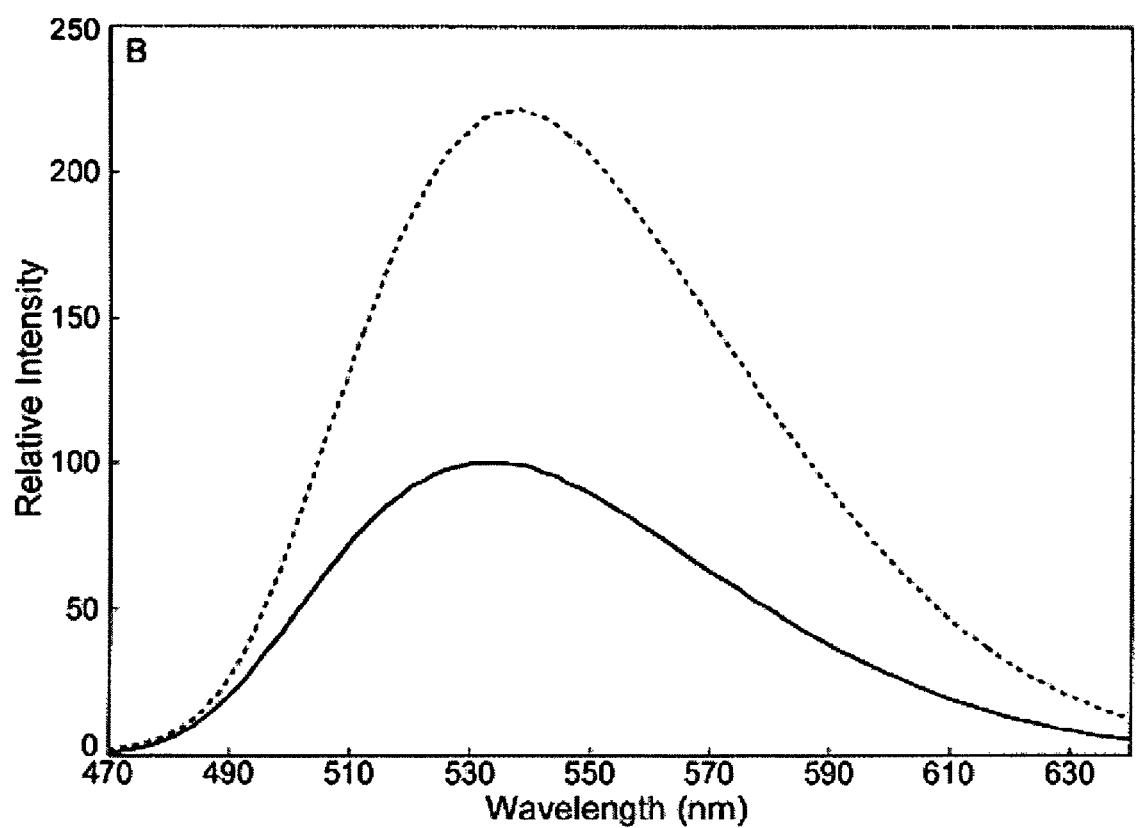

The excitation and emission spectra of peptide 2 and its phosphorylated counterpart are furnished in FIG. 1A-1B. The most dramatic difference in the excitation spectra of substrate and phosphorylated product is observed in the long wavelength region. Excitation of both NBD-peptide 2 and the corresponding phosphorylated derivative at 460 nm ($\lambda_{max}$) furnished a greater than 2-fold emission enhancement (>100%) in favor the phosphorylated peptide (FIG. 1B). In addition, excitation at a longer wavelength (520 nm) produced an even larger (2.5-fold) relative enhancement in the emission intensity of the NBD fluorophore bound to the phosphorylated peptide. In contrast, no change in fluorescence intensity was detected following phosphorylation of peptide 3. The $k_{cat}$ and $K_m$ values determined via spectrofluorimetry are modestly different from those acquired by the corresponding radioactive method (Table 2). These differences may reflect the slightly different conditions used in these assays, which were optimized to enhance fluorescence intensity changes (spectrofluorometric assay) or $k_{cat}/K_m$ (radioactive assay). The variance between the kinetic constants generated by these two different assays is small and, using either assay, peptide 2 exhibits favorable properties as a PKC substrate for the α, β, and γ isoforms.

Figure 2:
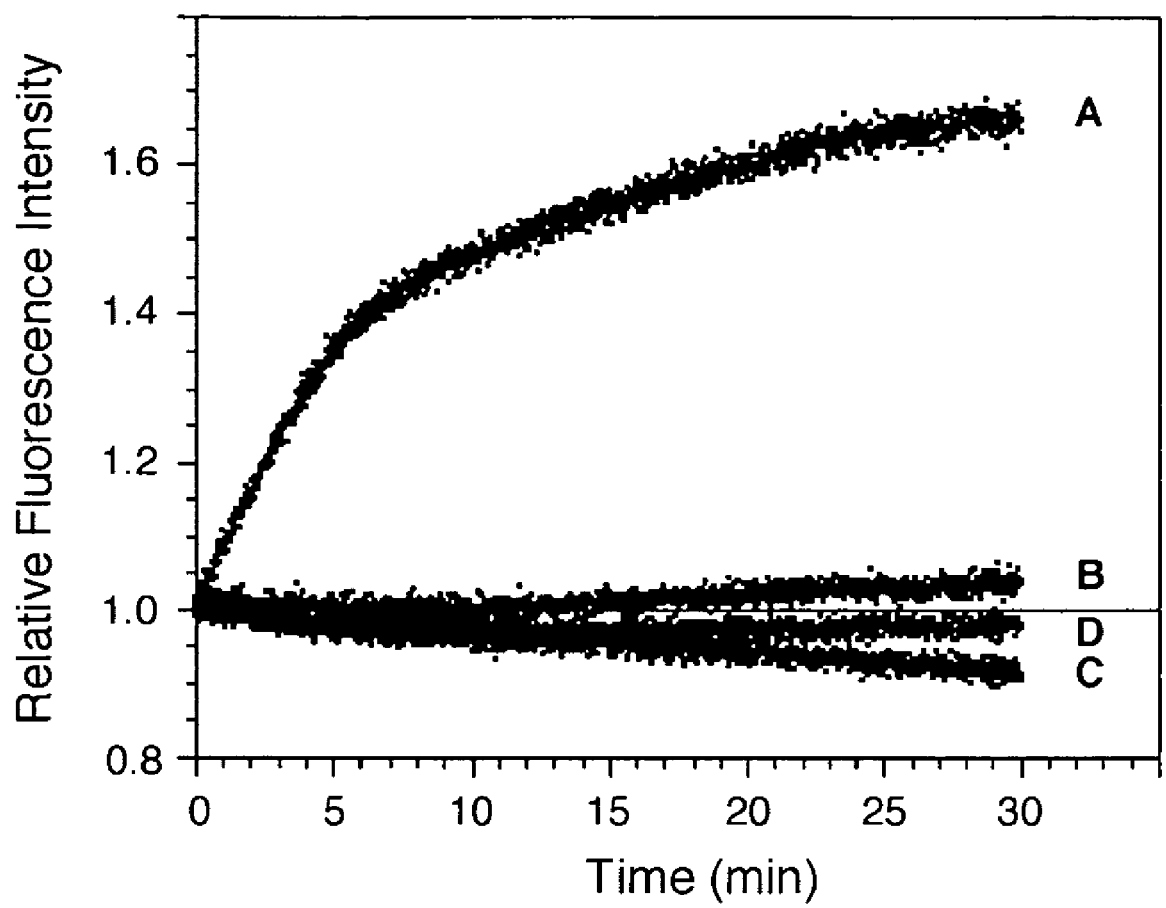
FIG. 2. PKC activity in mitotic HeLa cell lysates. The PKC assay was initiated by addition of the lysate to the assay buffer. Fluorescence change as a function of incubation time in the presence of cell lysate (plot A), in the absence of cell lysate (plot B), in the presence of cell lysate and 4.5 μM staurosporine (plot C), and in the presence of cPKC immunodepleted cell lysate (plot D).

Several laboratories have reported the upregulation of PKC activity during mitosis.[26-29] PKC mediates the phosphorylation of the regulatory light chain of myosin-II during mitosis.[30] Consequently, the ability of peptide 2 to report PKC activity in mitotic lysates from HeLa cells was examined. Crude mitotic cell extracts were prepared as previously described,[30] and the PKC assay initiated via addition of the cell lysate to an assay buffer containing peptide 2. As shown in FIG. 2, a linear increase in fluorescence intensity is observed in the first 10 minutes following addition of the cell lysate, which plateaus at approximately 1.7-fold above background. The protein kinase inhibitor staurosporine blocks the increase in fluorescence intensity observed upon mitotic cell lysate addition. Staurosporine,[31] like many protein kinase inhibitors,[32-33] targets a variety of protein kinases. Consequently, from these experiments, it is not clear whether the staurosporine-induced block of fluorescence is due to inhibition of PKC activity or the inhibition of other protein kinases that also catalyze the phosphorylation of peptide 2.

Figure 3:
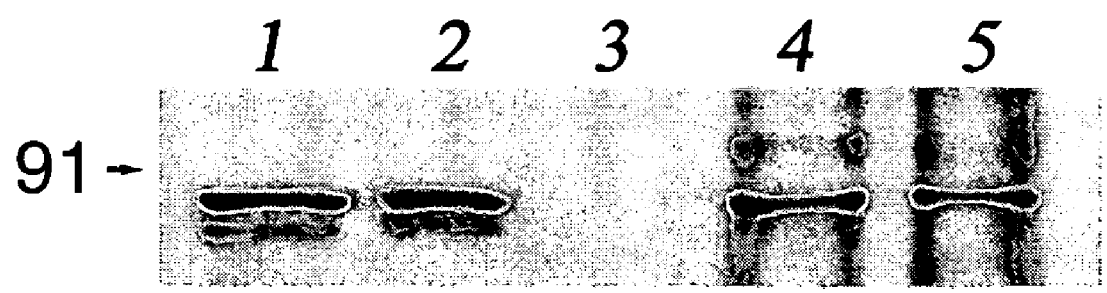
FIG. 3. Immunodepletion of PKC from mitotic cell lysates. Western blot analysis performed with anti-PKCα antibody. Lane 1, crude cell lysate. Lane 2, cell lysate precleared with Protein-A Sepharose. Lane 3, cell lysate following immunodepletion of PKC. Lane 4, PKC immunoprecipitate following initial treatment of the mitotic cell lysate. Lane 5, PKC immunoprecipitate following a second treatment of the mitotic cell lysate.

The question whether the peptide substrate 2 is selective for the conventional PKCs was addressed by immunodepleting the mitotic cell lysates of PKCs α, β, and γ using a commercially available antibody that recognizes all three PKC isoforms. Depletion of the individual α, β, and γ isoforms from the cell lysate was confirmed by immunoblot analysis using isoform-specific antibodies (shown for PKC α in FIG. 3). Analogous Western blots were performed for the β and γ PKC isoforms as well (data not shown). The immunodepleted lysate (FIG. 3, lane 3) was examined for PKC activity in the fluorescence assay. No change in fluorescence intensity was observed over the course of 1 hr (FIG. 2, plot D). The latter observation is consistent with the notion that the fluorescence enhancement observed with crude mitotic lysates is due to PKC. It is unlikely that a protein kinase downstream from PKC is responsible for the observed enhancement in fluorescence, since this putative downstream kinase would have already been activated in the cell lysate prior to immunodepletion of the conventional PKCs.

Figure 4:
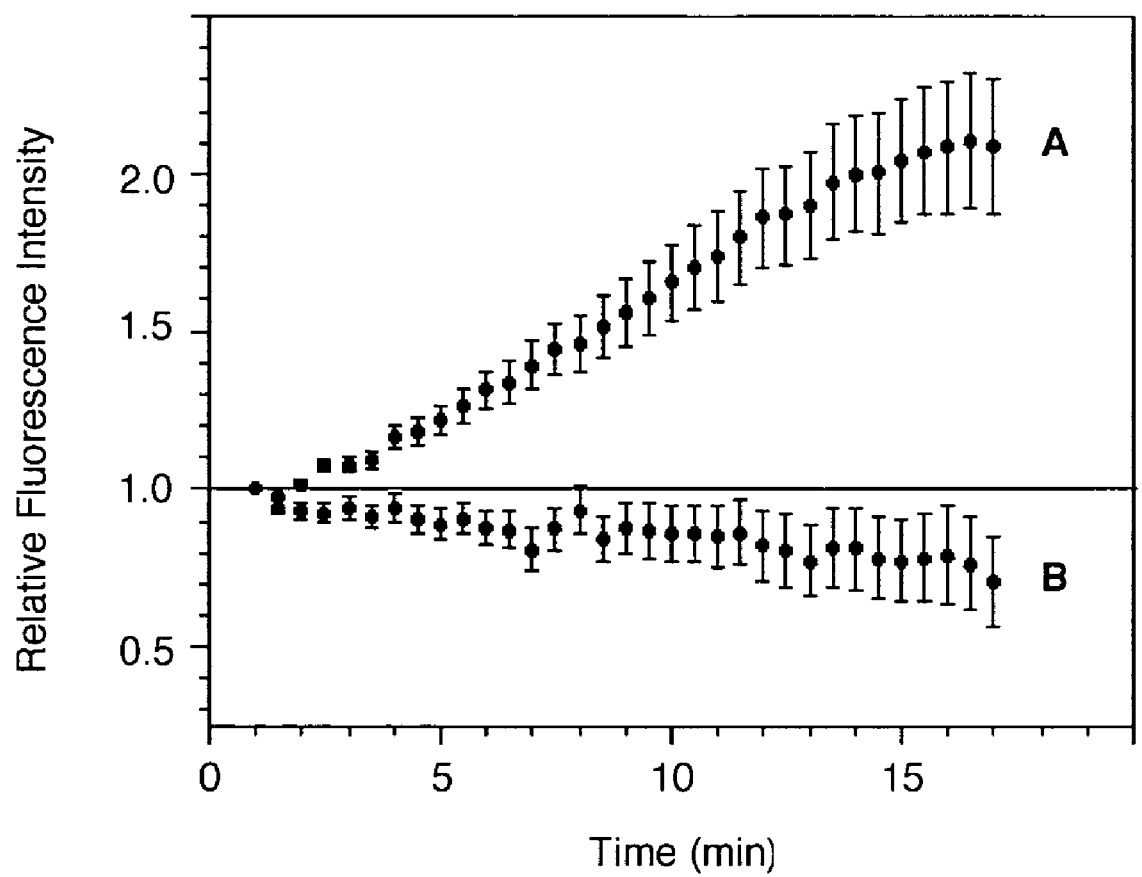
FIG. 4. TPA-induced time-dependent change in fluorescence intensity in HeLa cells containing the microinjected peptide 2 (plot A) and the microinjected peptide 2 in the presence of 20 µM GF 109203X (plot B). Time lapse fluorescence intensity measurements of TPA-stimulated HeLa cells microinjected with peptide 2. Combined data from 16 cells is furnished in plot A and from 14 cells is provided in plot B.

Given the enzymological and photophysical behavior displayed by peptide 2, the in vivo visualization of PKC activity was examined in live cells. Serum-starved HeLa cells were microinjected with the NBD-modified peptide and the cells subsequently exposed to TPA, a tumor promoting phorbol ester that potently and specifically activates PKC.[34] A change in fluorescence intensity is evident within 4 minutes of TPA exposure and significantly so by 8 minutes. A comparison of the curves generated in the lysate (FIG. 2) and live cell (FIG. 4) assays demonstrate that both curves display an essentially linear increase in fluorescence intensity within the first 10 min of exposure to activated PKC, followed by a plateau phase shortly thereafter. The overall enhancement in fluorescence intensity displayed by peptide 2 in living cells is 2-fold, whereas the cell lysate-based experiments furnish an overall 1.7-fold increase in fluorescence. In an additional series of experiments, the NBD-peptide PKC substrate was co-injected with the known PKC inhibitor, GF 109203X.[35] This inhibitor effectively blocks the TPA-induced enhancement in cellular fluorescence. Although the $K_i$ value for GF 109203X is in the low nanomolar range, micromolar concentrations of GF 109203X were used to block in vivo PKC activity due to the presence of high intracellular levels of ATP.

In summary, a fluorescent substrate for PKC has been constructed using a strategy that positions the reporter-group directly on the residue undergoing phosphorylation. A library of fluorescently-labeled PKC peptide substrates was prepared. The lead derivative displays a phosphorylation-induced fluorescence change that allows the visualization of real time PKC activity in both cell lysates and living cells. Furthermore, immunodepletion experiments suggest that the fluorescently-tagged peptide is selectively, if not exclusively, phosphorylated by the conventional PKCs. The PKC biosensor strategy outlined herein takes advantage of the ease with which peptides can be modified to create libraries of structurally altered analogs. However, the inherent synthetic mutability of peptides is not just limited to library construction. For example, it may be possible to simultaneously monitor more than one protein kinase by affixing fluorophores with distinct photophysical properties to the N- or C-termini of appropriately designed active site-directed peptides. Furthermore, there exists the potential for temporal and spatial control over when and where the substrate is phosphorylated via the preparation of "caged" analogs[11-14] (see Example III). In addition to protein kinase C,[45] many other protein kinases are known to phosphorylate peptides that contain N- or C-terminally appended serine, threonine, or tyrosine residues. These protein kinases include cdc2 kinase,[47] cAMP-dependent protein kinase,[45] cyclic guanosine monophosphate (cGMP)-dependent protein kinase, tyrosine kinase src,[19] and tyrosine kinase abl.[46] Consequently, the approaches demonstrated herein with respect to protein kinase C are expected to have broad applicability to protein kinases.

TABLE 1

PKCα-catalyzed phosphorylation of selected library members. Fluorescence enhancement upon phosphorylation (% Change) was obtained by spectrofluorimetry and $K_m$ and $k_{cat}$ values were acquired using the standard $[\gamma-^{32}P]$ATP radioactive assay.[25]

| Fluorophore-peptide | Fluorophore Reagent | % Change | $K_m$ (μM) | $k_{cat}$ (min$^{-1}$) |
|---|---|---|---|---|
| 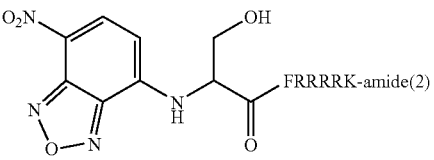 | NBD-Cl | 150% | 9.0 ± 1.0 | 380 ± 20 |
| 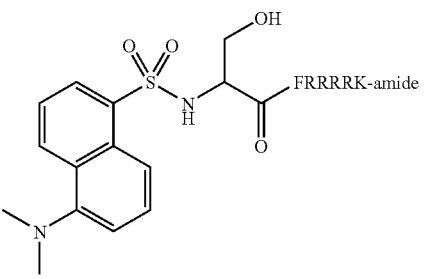 | Dansyl chloride | 20% | 28 ± 3 | 170 ± 10 |

TABLE 1-continued

PKCα-catalyzed phosphorylation of selected library members. Fluorescence enhancement upon phosphorylation (% Change) was obtained by spectrofluorimetry and $K_m$ and $k_{cat}$ values were acquired using the standard $[\gamma\text{-}^{32}P]ATP$ radioactive assay.[25]

| Fluorophore-peptide | Fluorophore Reagent | % Change | $K_m$ (μM) | $k_{cat}$ (min$^{-1}$) |
|---|---|---|---|---|
| (9-acridinecarboxamide-Ser-FRRRRK-amide structure) | 9-Acridinecarboxylic acid | 20% | 13 ± 2 | 20 ± 2 |
| (cyano-naphthoisoindole-Ser-FRRRRK-amide structure) | Cyanide/Naphthalene-2,3-dicarbaldehyde | — | 70 ± 1 | 220 ± 10 |
| (fluorescamine-Ser-FRRRRK-amide structure) | Fluorescamine | — | 280 ± 60 | 25 ± 4 |

Abbreviations of amino acids: F = Phe = phenylalanine; K = Lys = lysine; R = Arg = arginine.

TABLE 2

Kinetic constants associated with the phosphorylation of peptides 2 and 3 by recombinant human PKCs α, β, and γ.

| Substrate | Assay | Kinetic constants | PKCα | PKCβ | PKCγ |
|---|---|---|---|---|---|
| NBD-SFR$_4$K (peptide 2) | Radioactive | $K_m$ (μM) | 9.0 ± 1.0 | 9.2 ± 0.4 | 5.0 ± 1.0 |
| | | $k_{cat}$ (min$^{-1}$) | 380 ± 20 | 180 ± 10 | 210 ± 20 |
| | | $k_{cat}/K_m$ (min$^{-1}$ μM$^{-1}$) | 42 ± 5 | 23 ± 2 | 42 ± 9 |
| | Fluorescence | $K_m$ (μM) | 29 ± 3 | 27 ± 4 | 30 ± 5 |
| | | $k_{cat}$ (min$^{-1}$) | 170 ± 30 | 94 ± 9 | 190 ± 40 |
| | | $k_{cat}/K_m$ (min$^{-1}$ μM$^{-1}$) | 5.9 ± 1 | 3.5 ± 0.6 | 6.3 ± 1.7 |
| SFR$_4$K (ε-NBD) (peptide 3) | Radioactive | $K_m$ (μM) | 19 ± 1 | Not determined | Not determined |
| | | $k_{cat}$ (min$^{-1}$) | 210 ± 10 | | |
| | | $k_{cat}/K_m$ (min$^{-1}$ μM$^{-1}$) | 11 ± 1 | | |
| | Fluorescence | $K_m$ (μM) | No Fluorescence Intensity Change | | |
| | | $k_{cat}$ (min$^{-1}$) | | | |
| | | $k_{cat}/K_m$ (min$^{-1}$ μM$^{-1}$) | | | |

Abbreviations of amino acids: F = Phe = phenylalanine; K = Lys = lysine; R = Arg = arginine; R$_4$ = R-R-R-R; S = Ser = serine.

Scheme 1

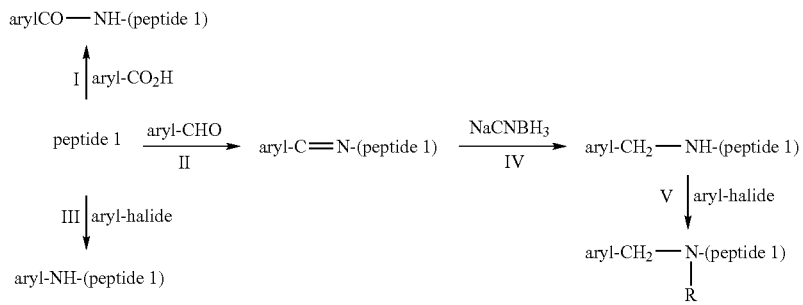

peptide 1: H$_2$N-Ser-Phe-Arg-Arg-Arg-Arg-Lys-amide

Scheme 2

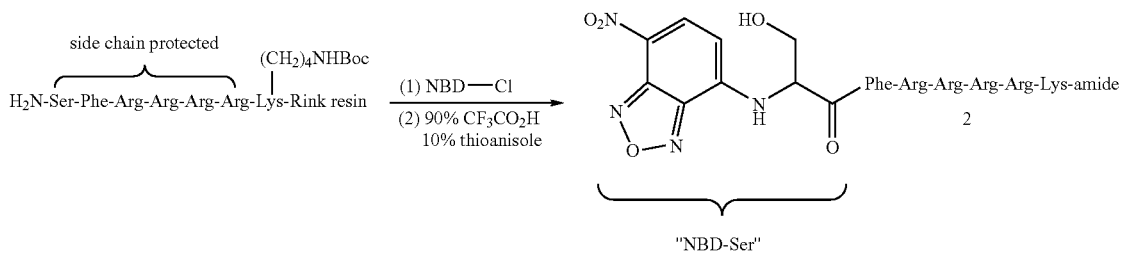

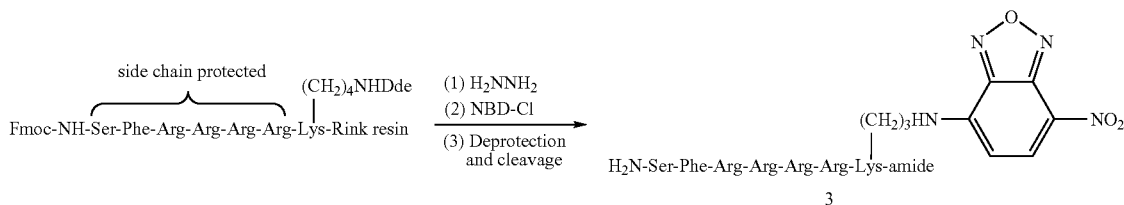

Table 3. Structures of 415 compounds tested. The % change observed in fluorescence intensity upon phosphorylation of the compound by protein kinase C is shown in the right column. Numbering of compounds for the purpose of this Table is arbitrary and does not correspond to compound numbers elsewhere in the specification. The compound labeled as compound 21 in Table 3 is the same as compound 2 in Example I, which is also shown in Scheme 2. Note that Table 3 does not include peptide 1 shown in Scheme 1 and compound 3 shown in Scheme 2.

| STRUCTURE | formula | mol weight | % |
|---|---|---|---|
| Aldehydes to Amines | | | |
| Compound 1 | C49H83N21O9 | 1110.33 | <10% |
| Compound 2 | C50H85N21O9 | 1124.3568 | <10% |
| Compound 3 | C50H85N21O10 | 1140.3562 | <10% |

-continued

| STRUCTURE | formula | mol weight | % |
|---|---|---|---|
| Compound 4 | C51H87N21O10 | 1154.383 | <10% |
| Compound 5 | C51H88N22O8 | 1137.3988 | <10% |
| Compound 6 | C51H88N22O9 | 1153.3982 | <10% |

-continued

| STRUCTURE | formula | mol weight | % |
|---|---|---|---|
| Compound 7 | C49H82N22O10 | 1139.3282 | <10% |
| Compound 8 | C49H82N22O10 | 1139.3282 | <10% |
| Compound 9 | C49H81N23O12 | 1184.3258 | <10% |

-continued

| STRUCTURE | formula | mol weight | % |
|---|---|---|---|
| Compound 10 | C49H82N22O11 | 1155.3276 | <10% |
| Compound 11 | C49H81N23O13 | 1200.3252 | <10% |
| Compound 12 | C49H81Cl2N21O8 | 1163.2208 | <10% |

-continued

| STRUCTURE | formula | mol weight | % |
|---|---|---|---|
| Compound 13 | C51H85N21O8 | 1120.3684 | <10% |
| Compound 14 | C53H90N22O8 | 1163.4366 | <10% |
| Compound 15 | C51H84N22O10 | 1165.366 | <10% |

-continued

| STRUCTURE | formula | mol weight | % |
|---|---|---|---|
| Compound 16 | C57H89N21O8 | 1196.466 | <10% |
| Compound 17 | C53H85N21O9 | 1160.3898 | <10% |
| Compound 18 | C57H87N21O8 | 1194.4502 | <10% |

| STRUCTURE | formula | mol weight | % |
|---|---|---|---|
| Compound 19 | C57H87N21O8 | 1194.4502 | <10% |
| Compound 20 | C59H89N21O8 | 1220.488 | <10% |

Aryl halides

| | formula | mol weight | % |
|---|---|---|---|
| Compound 21 | C48H78N24O11 | 1167.2984 | 150% |

-continued

| STRUCTURE | formula | mol weight | % |
|---|---|---|---|
| Compound 22 | C56H85N23O8 | 1208.4368 | <10% |
| Compound 23 | C51H83N23O8 | 1146.366 | <10% |

| STRUCTURE | formula | mol weight | % |
|---|---|---|---|
| Compound 24 | C49H78Cl3N23O8 | 1223.6635 | <10% |
| Compound 25 | C58H85Cl2N23O8 | 1303.3648 | <10% |

-continued

| STRUCTURE | formula | mol weight | % |
|---|---|---|---|
| Compound 26 | C49H78N24O12 | 1195.3088 | <10% |
| Compound 27 | C49H79N23O14 | 1214.3088 | <10% |
| Compound 28 | C49H80N22O12 | 1169.3112 | <10% |

-continued
| STRUCTURE | formula | mol weight | % |
|---|---|---|---|
| 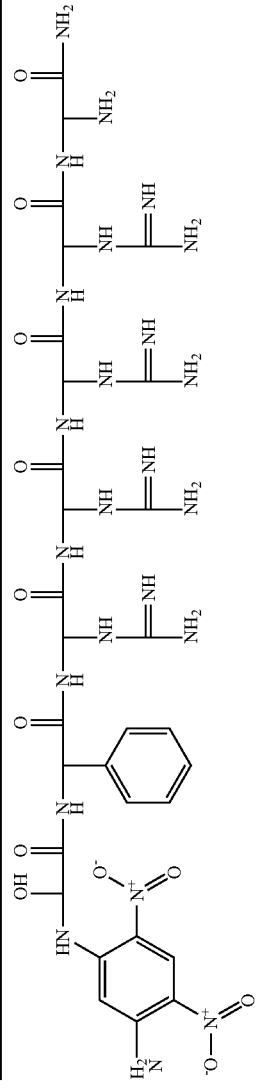 Compound 29 | C48H80N24O12 | 1185.3136 | <10% |
| 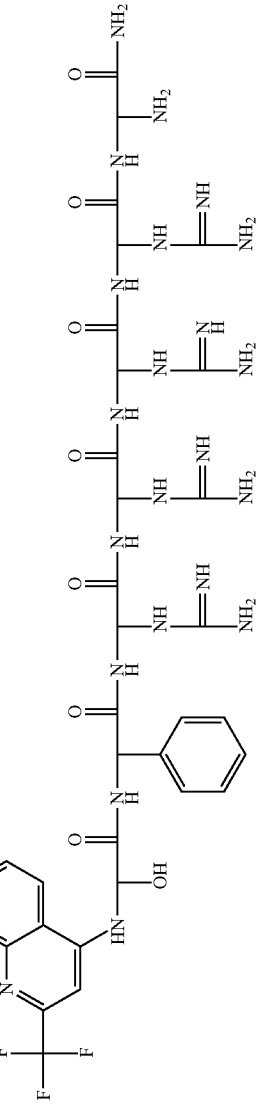 Compound 30 | C53H80F6N22O8 | 1267.348 | <10% |
| 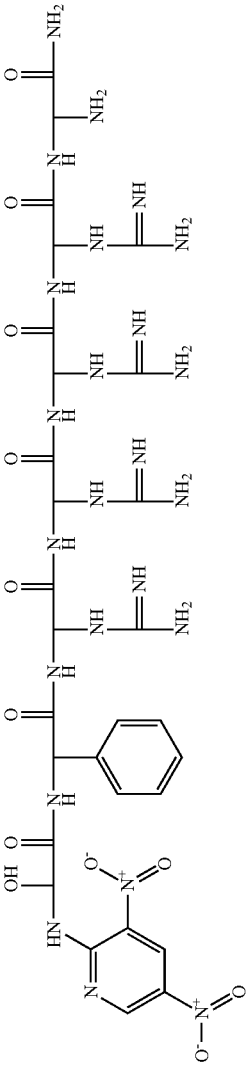 Compound 31 | C47H78N24O12 | 1171.2868 | <10% |

| STRUCTURE | formula | mol weight | % |
|---|---|---|---|
| Compound 32 | C49H79F3N22O10 | 1193.2997 | <10% |
| Compound 33 | C48H79N23O12 | 1170.299 | <10% |

| STRUCTURE | formula | mol weight | % |
|---|---|---|---|
| Compound 34 | C46H79N23O8 | 1082.2794 | <10% |
| Compound 35 | C65H95N23O11 | 1374.613 | <10% |

Carboxylic Acids

-continued

| STRUCTURE | formula | mol weight | % |
|---|---|---|---|
| Compound 38 | C56H84N22O9 | 1209.4216 | 20% |
| Compound 39 | C53H83N21O10 | 1174.3734 | <10% |
| Compound 40 | C54H87N24O9+ | 1216.4367 | <10% |

-continued

| STRUCTURE | formula | mol weight | % |
|---|---|---|---|
| Compound 41 | C57H88N22O13 | 1289.4618 | <10% |
| Compound 42 | C59H87N21O9 | 1234.4716 | <10% |
| Compound 43 | C53H84N22O9 | 1173.3886 | <10% |

-continued
| STRUCTURE | formula | mol weight | % |
|---|---|---|---|
| 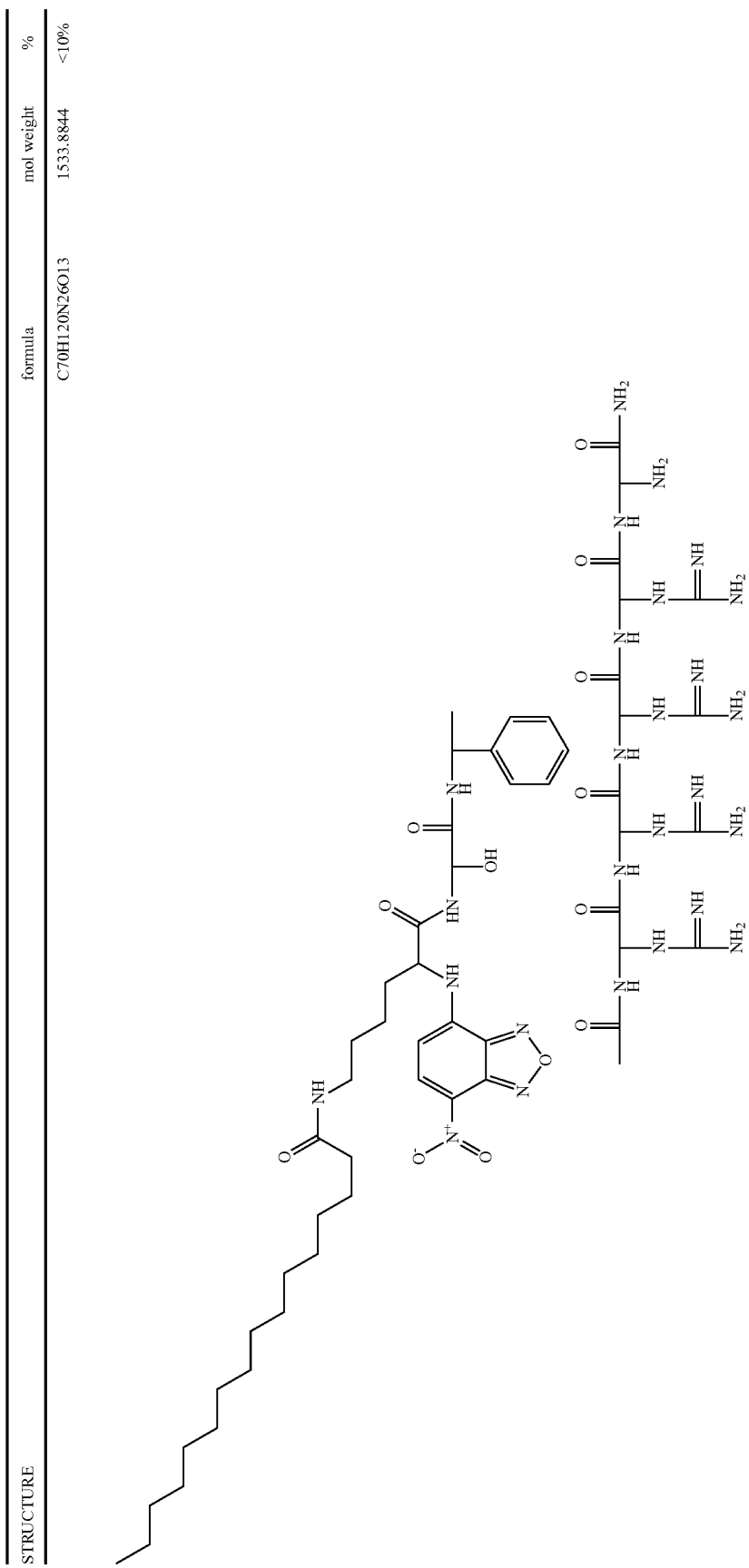 Compound 44 | C70H120N26O13 | 1533.8844 | <10% |

-continued
| STRUCTURE | formula | mol weight | % |
|---|---|---|---|
| 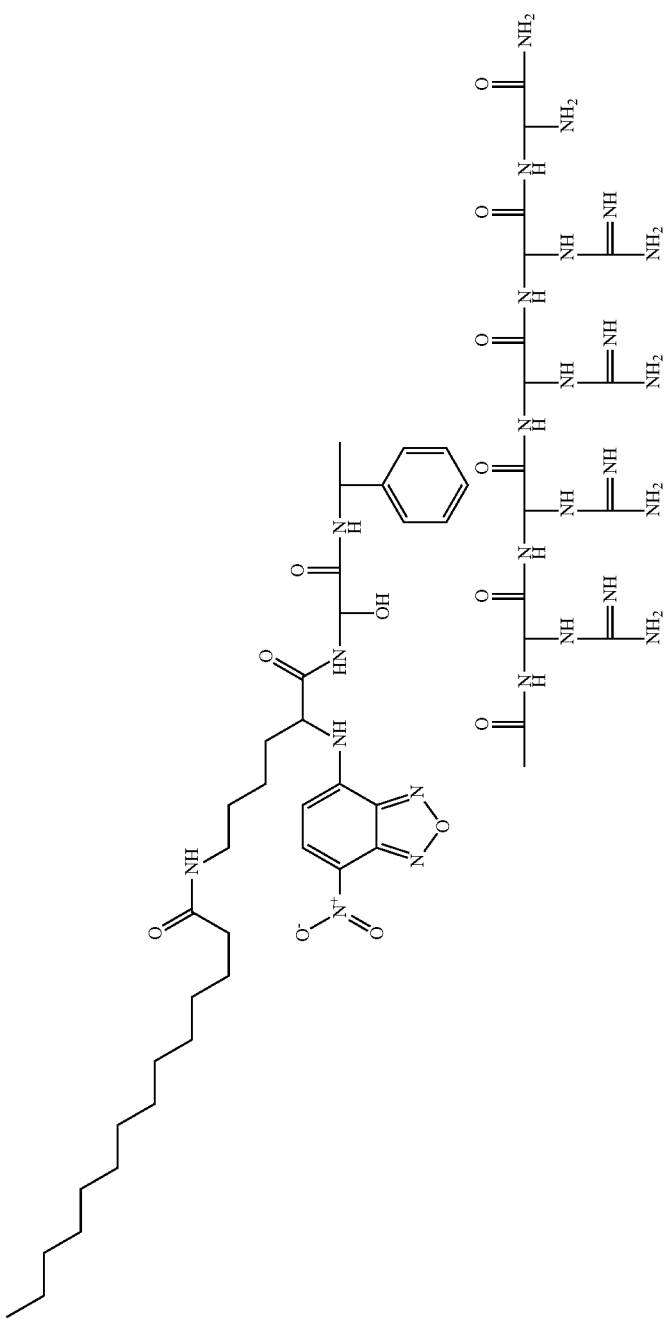 Compound 45 | C68H116N26O13 | 1505.8308 | <10% |

| STRUCTURE | formula | mol weight | % |
|---|---|---|---|
| Compound 46 | C64H99N23O17 | 1462.63 | <10% |
| Compound 47 | C52H82N22O9 | 1159.3618 | <10% |

-continued

| STRUCTURE | formula | mol weight | % |
|---|---|---|---|
| Compound 48 | C52H82N22O9 | 1159.3618 | <10% |
| Compound 49 | C52H82N22O9 | 1159.3618 | <10% |
| Compound 50 | C66H98N23O10+ | 1373.6483 | <10% |

| STRUCTURE | formula | mol weight | % |
|---|---|---|---|
| Compound 51 | C54H88N22O10S | 1237.4906 | 20% |
| Compound 52 (Imine) | C53H83N21O9 | 1158.374 | <10% |
| Compound 53 | C57H87N21O8 | 1194.4502 | <10% |

-continued

| STRUCTURE | formula | mol weight | % |
|---|---|---|---|
| Compound 54 | C57H85N21O8 | 1192.4344 | <10% |
| Compound 55 | C49H79N23O13 | 1198.3094 | <10% |
| Compound 56 | C51H86N22O9 | 1151.3824 | <10% |

| STRUCTURE | formula | mol weight | % |
|---|---|---|---|
| Compound 57 | C55H90N22O8 | 1187.4586 | <10% |
| Compound 58 | C53H88N22O8 | 1161.4208 | <10% |
| Compound 59 | C51H83N21O8 | 1118.3526 | <10% |

-continued

| STRUCTURE | formula | mol weight | % |
|---|---|---|---|
| Compound 60 | C59H87N21O8 | 1218.4722 | <10% |
| Compound 61 | C50H83N21O9 | 1122.341 | <10% |
| Compound 62 | C50H83N21O10 | 1138.3404 | <10% |

-continued

| STRUCTURE | formula | mol weight | % |
|---|---|---|---|
| Compound 63 | C57H85N21O8 | 1192.4344 | <10% |
| Compound 64 | C49H81N21O9 | 1108.3142 | <10% |
| Compound 65 | C49H80N22O10 | 1137.3124 | <10% |

-continued

| STRUCTURE | formula | mol weight | % |
|---|---|---|---|
| Compound 66 | C51H85N21O10 | 1152.3672 | <10% |
| Compound 67 | C49H80N22O10 | 1137.3124 | <10% |
| Compound 68 | C49H79Cl2N21O8 | 1161.205 | <10% |

-continued

| STRUCTURE | formula | mol weight | % |
|---|---|---|---|
| Compound 69 | C49H80N22O11 | 1153.3118 | <10% |
| Compound 70 | C55H85N21O10 | 1200.4112 | <10% |
| Compound 71 | C55H85N21O10 | 1200.4112 | <10% |

| STRUCTURE | formula | mol weight | % |
|---|---|---|---|
| dbl NBD label | | | <10% |
| Compound 72 | | | |
| Compound 73 | | | <10% |

-continued

| STRUCTURE | formula | mol weight | % |
|---|---|---|---|
| Compound 74 | | | <10% |
| Compound 75 | | | <10% |

| STRUCTURE | formula | mol weight | % |
|---|---|---|---|
| Arylation (Compound 76) | | | <10% |
| ketimine_fluorescamine (Compound 77) | | | <10% |

| STRUCTURE | formula | mol weight | % |
|---|---|---|---|
| -continued  Compound 78 | | | <10% |
| ethylenediamine 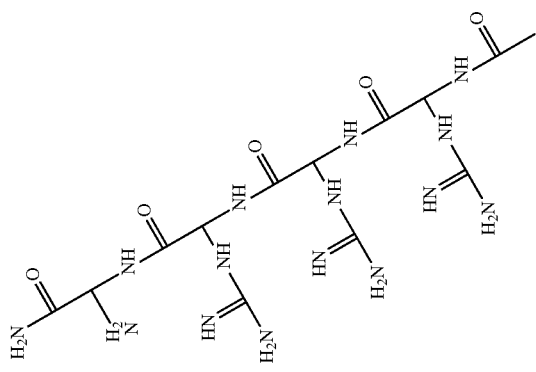 | | | <10% |

| STRUCTURE | formula | mol weight | % |
|---|---|---|---|
| Compound 79 | | | <10% |

-continued

| STRUCTURE | formula | mol weight | % |
|---|---|---|---|
| Compound 80 | aminoAla analogs | | <10% |
| Compound 81 | | | |

| STRUCTURE | formula | mol weight | % |
|---|---|---|---|
| 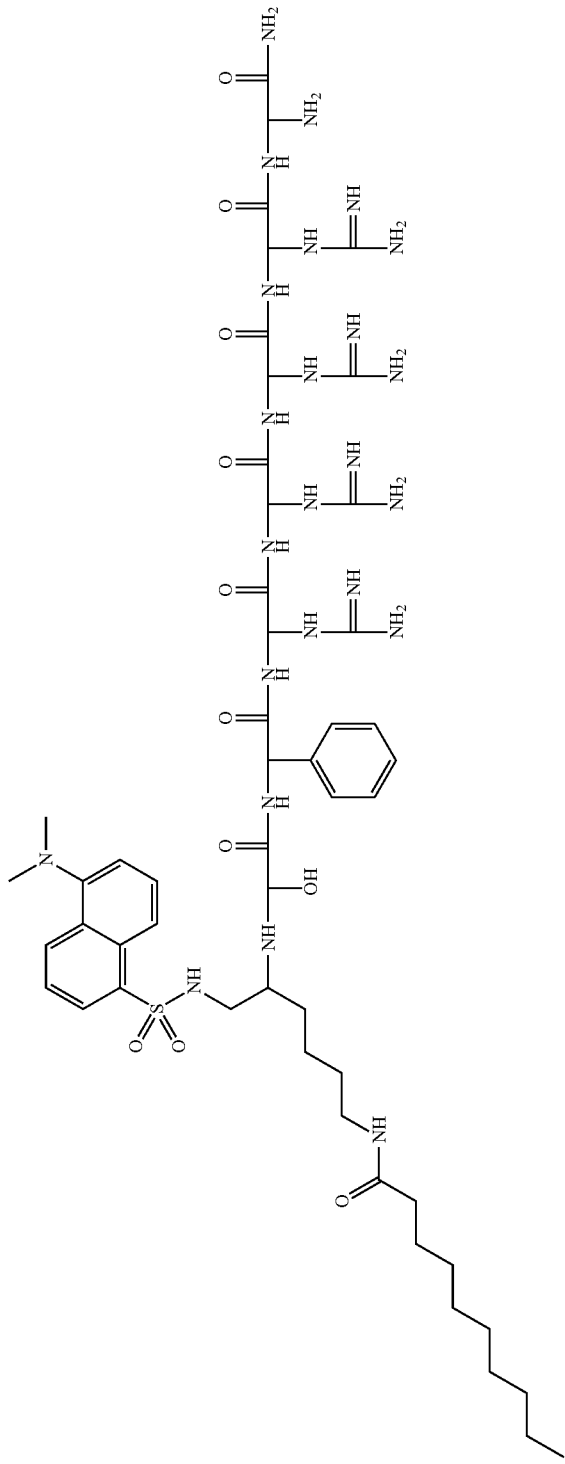  Compound 82 | | | <10% |

| STRUCTURE | formula | mol weight | % |
|---|---|---|---|
| 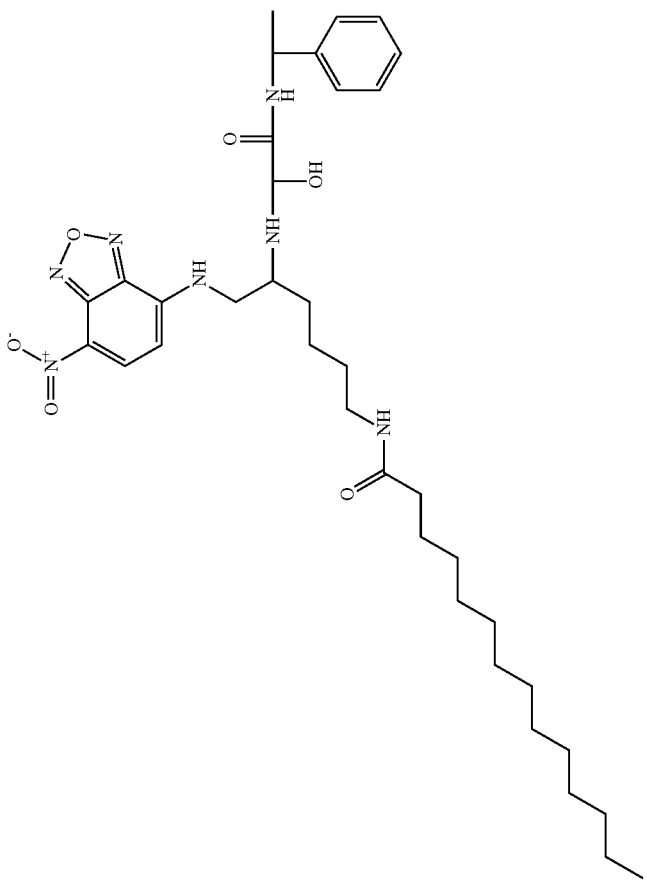 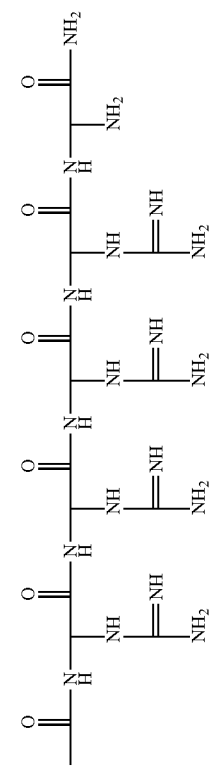 Compound 83 | | | <10% |

| STRUCTURE | formula | mol weight | % |
|---|---|---|---|
| -continued | | | |
| Compound 84 | | | <10% |

| STRUCTURE | formula | mol weight | % |
|---|---|---|---|
| Compound 85 | | | <10% |
| Compound 86 | | | <10% |
| Compound 87 | | | <10% |

| STRUCTURE | formula | mol weight | % |
|---|---|---|---|
| Compound 88 (dialdehyde + nucleophile) | | | <10% |
| Compound 89 | | | <10% |

| STRUCTURE | formula | mol weight | % |
|---|---|---|---|
| Compound 90 | | | <10% |
| Compound 91 | | | <10% |

| STRUCTURE | formula | mol weight | % |
|---|---|---|---|
| Compound 92 | | | <10% |
| Compound 93 | | | <10% |

-continued

| STRUCTURE | formula | mol weight | % |
|---|---|---|---|
| Compound 94 | C45H72N22O10 | 1081.2052 | <10% |
| Compound 95 | C47H67N22O10 | 1109.2588 | <10% |
| (third compound) | C48H78N22O10 | 1123.2856 | <10% |

Combi aldehydes + Aryl halides

-continued

| STRUCTURE | formula | mol weight | % |
|---|---|---|---|
| Compound 96 | | | |
| Compound 97 | C49H72N22O11 | 1145.2486 | <10% |
| Compound 98 | C51H76N22O12 | 1189.3016 | <10% |

-continued
| STRUCTURE | formula | mol weight | % |
|---|---|---|---|
| 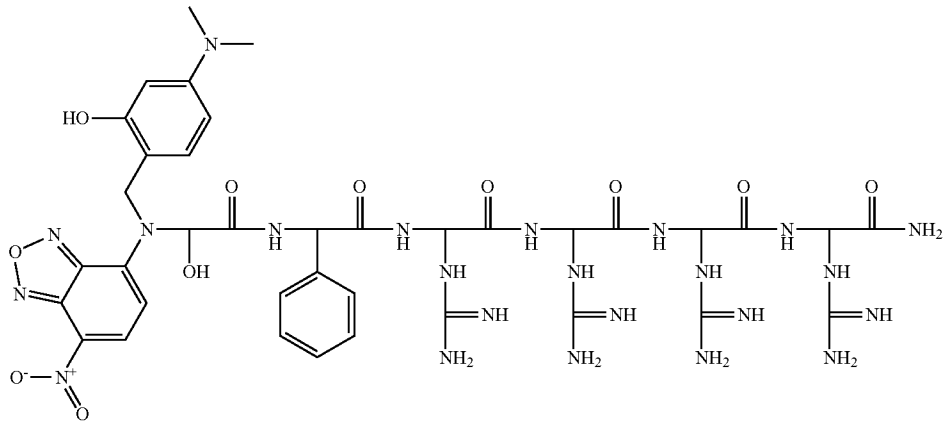 Compound 99 | C51H77N23O11 | 1188.3168 | <10% |
| 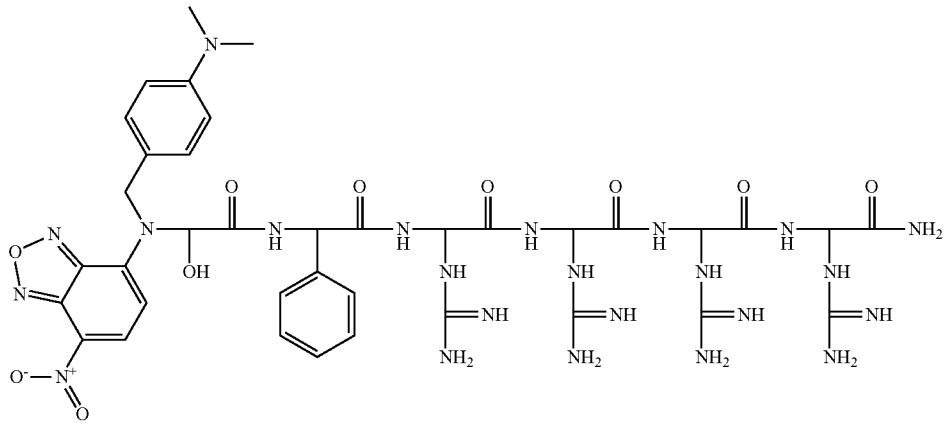 Compound 100 | C51H77N23O10 | 1172.3174 | <10% |

-continued

| STRUCTURE | formula | mol weight | % |
|---|---|---|---|
| Compound 101 | C49H73N23O12 | 1176.2626 | <10% |
| Compound 102 | C49H71N23O12 | 1174.2468 | <10% |

| STRUCTURE | formula | mol weight | % |
|---|---|---|---|
| Compound 103 | C49H71N23O13 | 1190.2462 | <10% |
| Compound 104 | C49H70Cl2N22O10 | 1198.1394 | <10% |

-continued
| STRUCTURE | formula | mol weight | % |
|---|---|---|---|
| Compound 105 | C49H72N23O14 | 1221.2602 | <10% |
| Compound 106 | C49H72N24O15 | 1237.2596 | <10% |
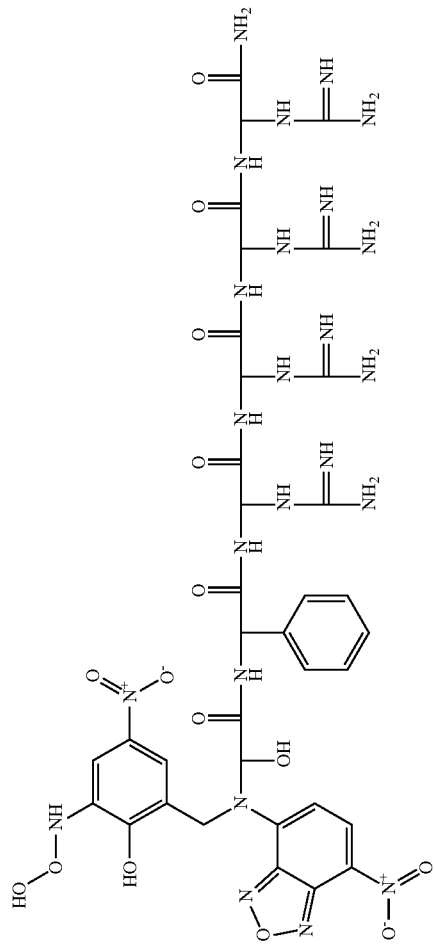

-continued
| STRUCTURE | formula | mol weight | % |
|---|---|---|---|
| 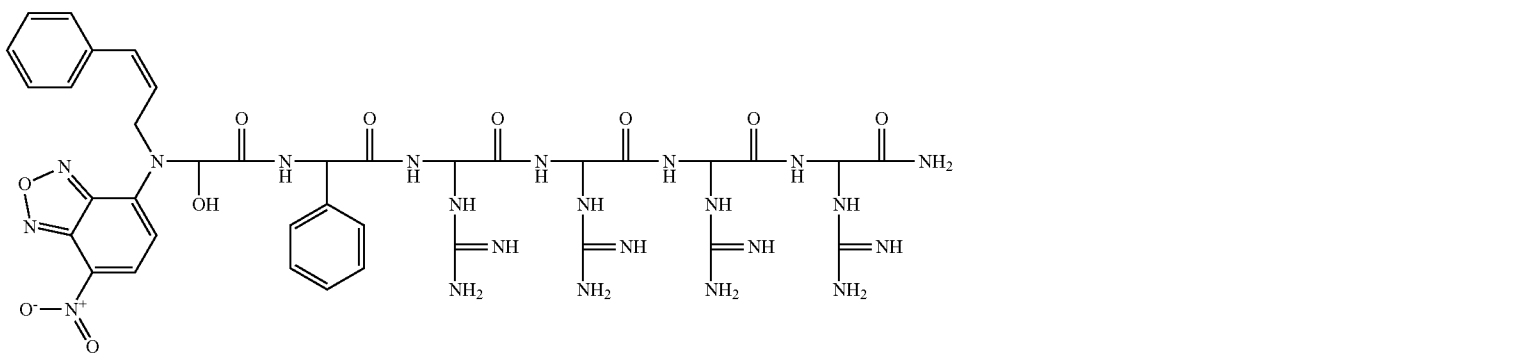 Compound 107 | C51H74N22O10 | 1155.287 | <10% |
| 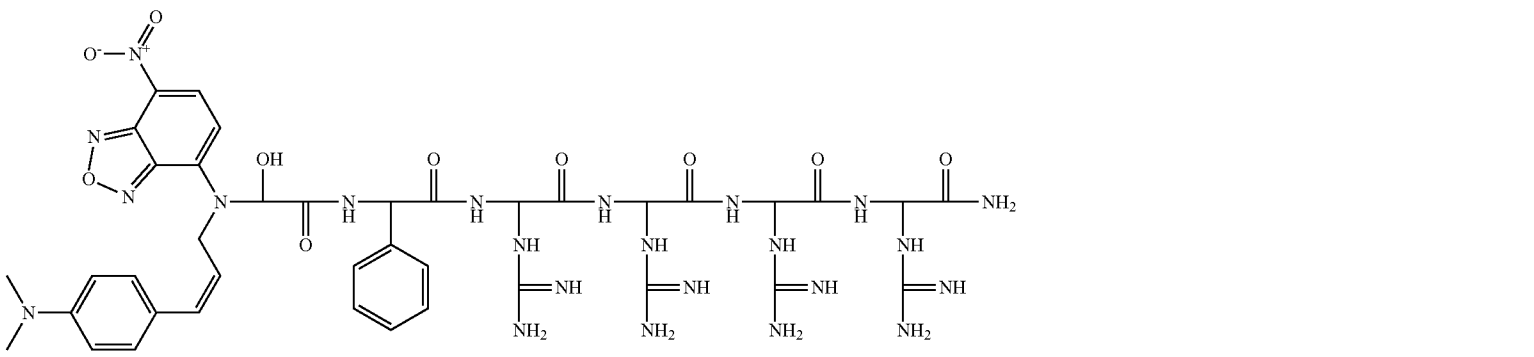 Compound 108 | C53H79N23O10 | 1198.3552 | <10% |

-continued

| STRUCTURE | formula | mol weight | % |
|---|---|---|---|
| Compound 109 | C51H75N23O12 | 1202.3004 | <10% |
| Compound 110 | C57H78N22O10 | 1231.3846 | <10% |

-continued

| STRUCTURE | formula | mol weight | % |
|---|---|---|---|
| Compound 111 | C53H74N22O11 | 1195.3084 | <10% |
| Compound 112 | C59H78N22O10 | 1255.4066 | <10% |

-continued
| STRUCTURE | formula | mol weight | % |
|---|---|---|---|
| 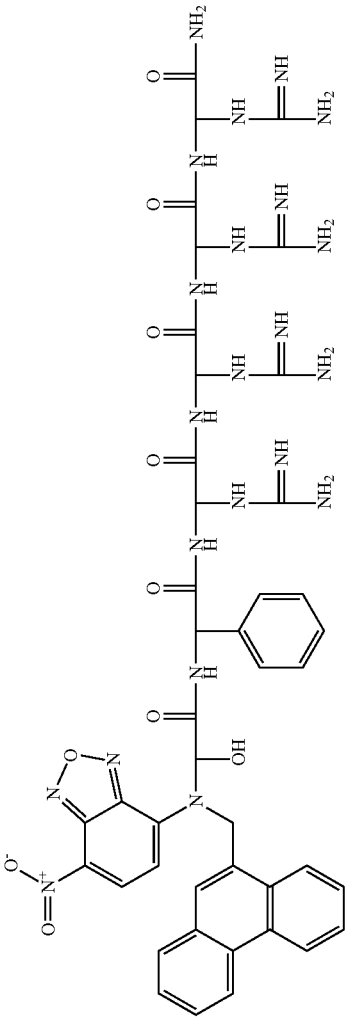
Compound 113 | C57H76N22O10 | 1229.3688 | <10% |
| 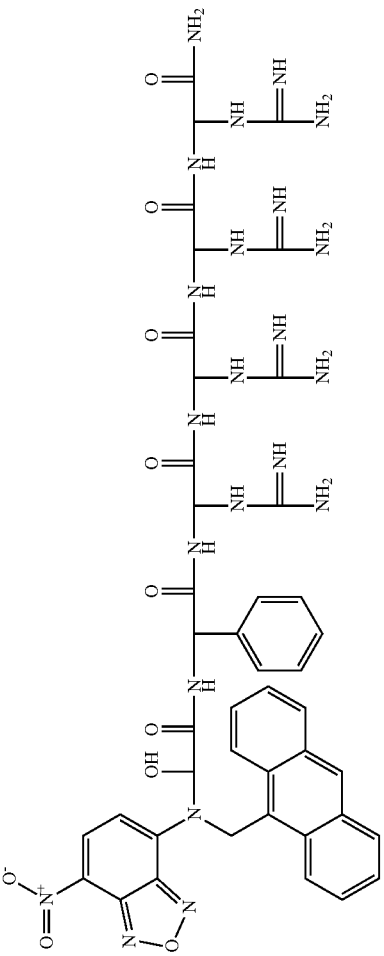
Compound 114 | C57H76N22O10 | 1229.3688 | <10% |

-continued

| STRUCTURE | formula | mol weight | % |
|---|---|---|---|
| Compound 115 | C50H74N22O11 | 1159.2754 | <10% |
| Compound 116 | C50H74N22O12 | 1175.2748 | <10% |

-continued
| STRUCTURE | formula | mol weight | % |
|---|---|---|---|
| 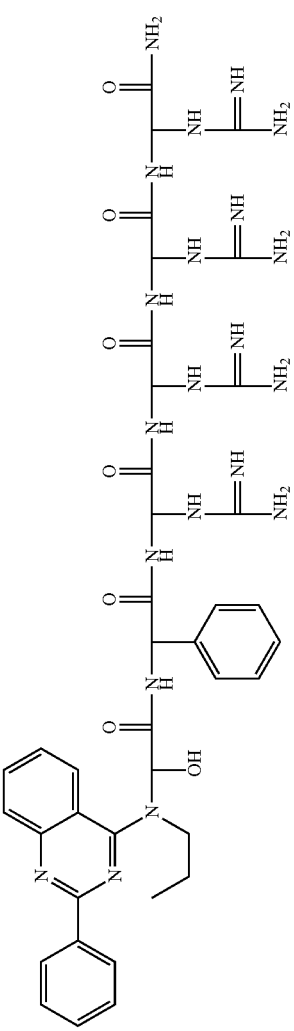 Compound 117 | C53H79N21O7 | 1122.3436 | <10% |
| 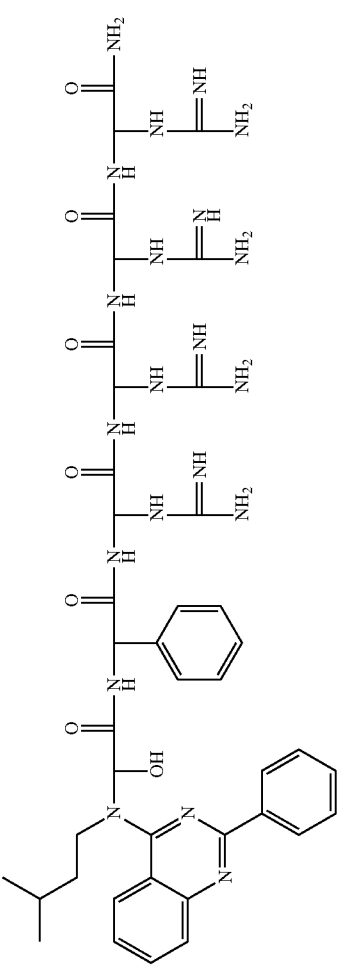 Compound 118 | C55H83N21O7 | 1150.3972 | <10% |

-continued

| STRUCTURE | formula | mol weight | % |
|---|---|---|---|
| Compound 119 | C56H85N21O7 | 1164.424 | <10% |
| Compound 120 | C57H79N21O8 | 1186.387 | <10% |

-continued

| STRUCTURE | formula | mol weight | % |
|---|---|---|---|
| Compound 121 | C59H83N21O9 | 1230.44 | <10% |
| Compound 122 | C59H84N22O8 | 1229.4552 | <10% |

| STRUCTURE | formula | mol weight | % |
|---|---|---|---|
| Compound 123 | C59H84N22O7 | 1213.4558 | <10% |
| Compound 124 | C57H80N22O9 | 1217.401 | <10% |

| STRUCTURE | formula | mol weight | % |
|---|---|---|---|
| Compound 125 | C57H78N22O9 | 1215.3852 | <10% |
| Compound 126 | C57H78N22O10 | 1231.3846 | <10% |

-continued

| STRUCTURE | formula | mol weight | % |
|---|---|---|---|
| Compound 127 | C57H77Cl2N21O7 | 1239.2778 | <10% |
| Compound 128 | C57H79N23O11 | 1262.3986 | <10% |

-continued

| STRUCTURE | formula | mol weight | % |
|---|---|---|---|
| Compound 129 | C57H79N23O12 | 1278.398 | <10% |
| Compound 130 | C59H81N21O7 | 1195.4254 | <10% |

| STRUCTURE | formula | mol weight | % |
|---|---|---|---|
| 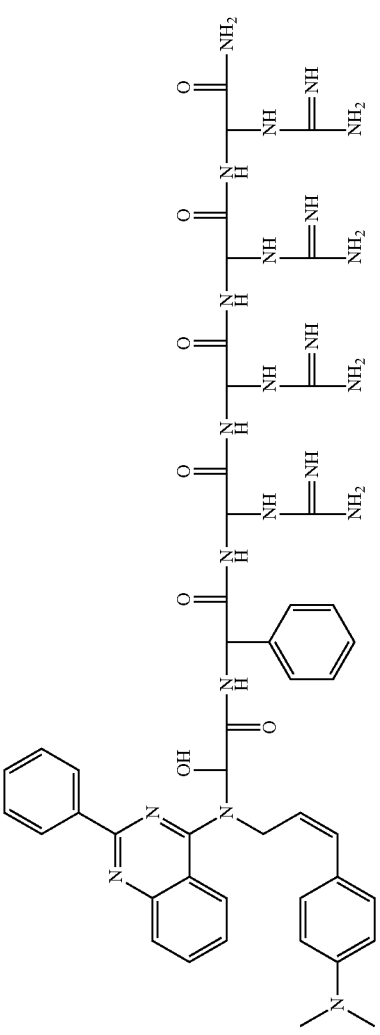 Compound 131 | C61H86N22O7 | 1239.4936 | <10% |
| 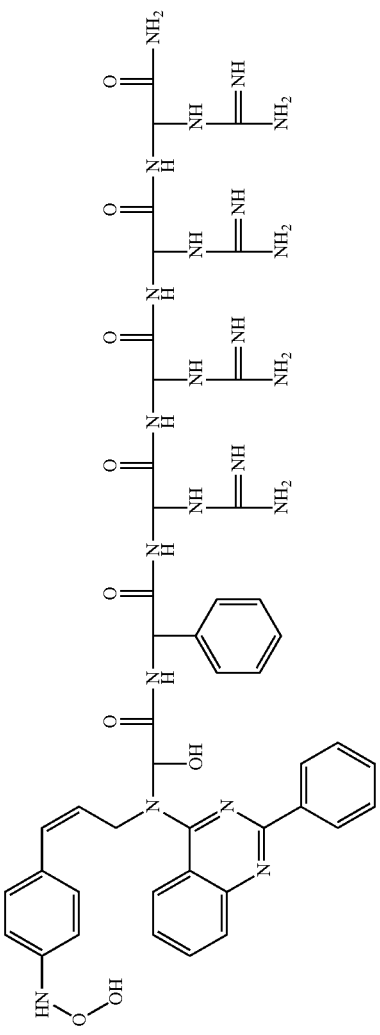 Compound 132 | C59H82N22O9 | 1243.4388 | <10% |

-continued
| STRUCTURE | formula | mol weight | % |
|---|---|---|---|
| 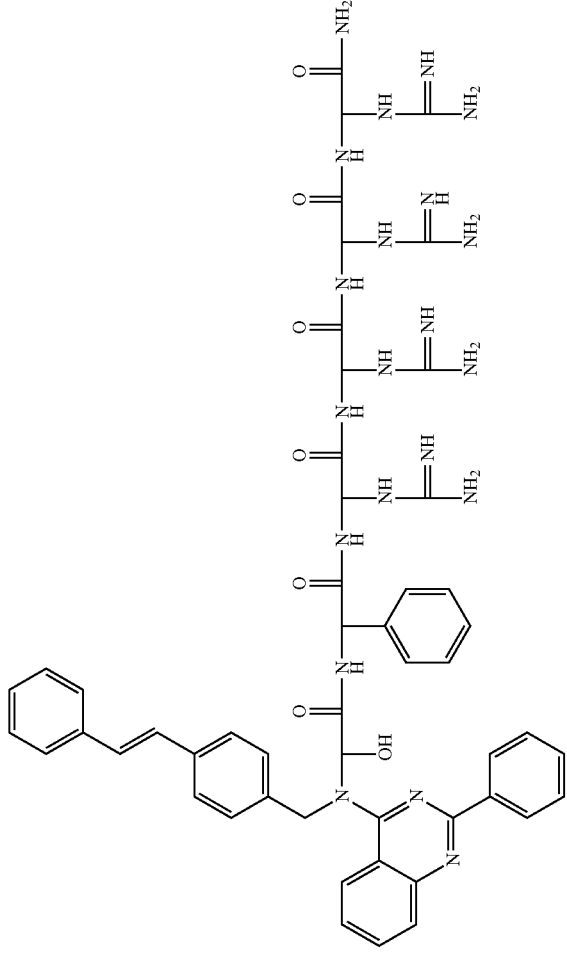 Compound 133 | C65H85N21O7 | 1272.523 | <10% |
| 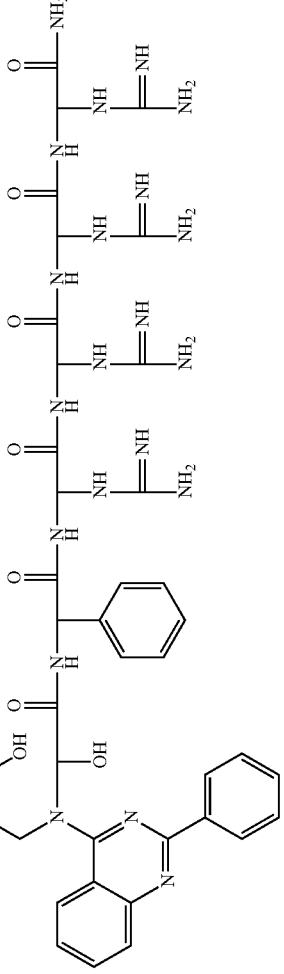 Compound 134 | C61H81N21O8 | 1236.4468 | <10% |

-continued

| STRUCTURE | formula | mol weight | % |
|---|---|---|---|
| Compound 135 | C67H85N21O7 | 1296.545 | <10% |
| Compound 136 | C65H83N21O7 | 1270.5072 | <10% |

| STRUCTURE | formula | mol weight | % |
|---|---|---|---|
| Compound 137 | C65H82N21O7 | 1270.5072 | <10% |
| Compound 138 | C58H81N21O8 | 1200.4138 | <10% |

| STRUCTURE | formula | mol weight | % |
|---|---|---|---|
| 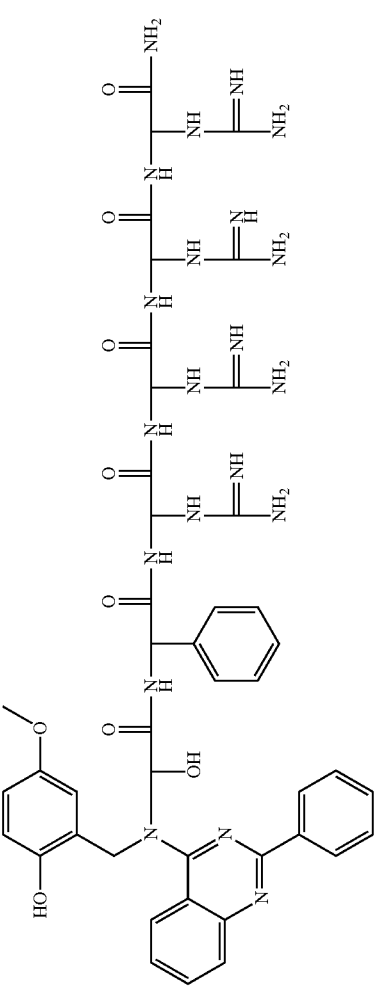  Compound 139 | C58H81N21O9 | 1216.4132 | <10% |
| 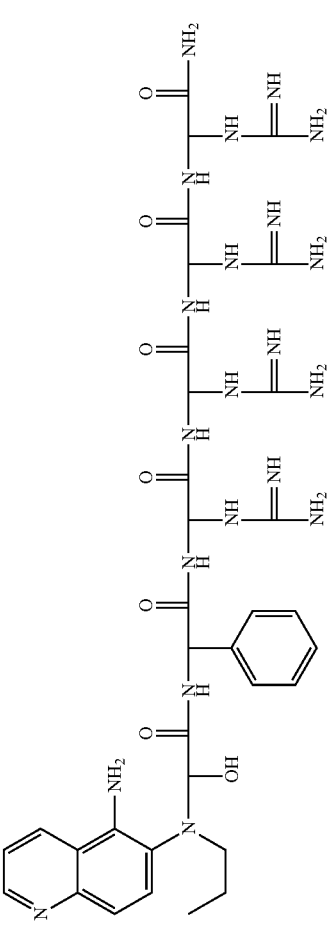  Compound 140 | C48H77N21O7 | 1060.2728 | <10% |

-continued

| STRUCTURE | formula | mol weight | % |
|---|---|---|---|
| Compound 141 | C50H81N21O7 | 1088.3264 | <10% |
| Compound 142 | C51H83N21O7 | 1102.3532 | <10% |

| STRUCTURE | formula | mol weight | % |
|---|---|---|---|
| Compound 143 | C52H77N21O8 | 1124.3162 | <10% |
| Compound 144 | C54H81N21O9 | 1168.3692 | <10% |

| STRUCTURE | formula | mol weight | % |
|---|---|---|---|
| Compound 145 | C54H82N22O8 | 1167.3844 | <10% |
| Compound 146 | C54H82N22O7 | 1151.385 | <10% |

| STRUCTURE | formula | mol weight | % |
|---|---|---|---|
| Compound 147 | C52H78N22O9 | 1155.3302 | <10% |
| Compound 148 | C52H76N22O9 | 1153.3144 | <10% |

-continued

| STRUCTURE | formula | mol weight | % |
|---|---|---|---|
| Compound 149 | C52H76N22O10 | 1169.3138 | <10% |
| Compound 150 | C52H75Cl2N21O7 | 1177.207 | <10% |

| STRUCTURE | formula | mol weight | % |
|---|---|---|---|
| Compound 151 | C52H77N23O11 | 1200.3278 | <10% |
| Compound 152 | C52H77N23O12 | 1218.3272 | <10% |

| STRUCTURE | formula | mol weight | % |
|---|---|---|---|
| Compound 153 | C54H79N21O7 | 1134.3546 | <10% |
| Compound 154 | C56H84N22O7 | 1177.4228 | <10% |
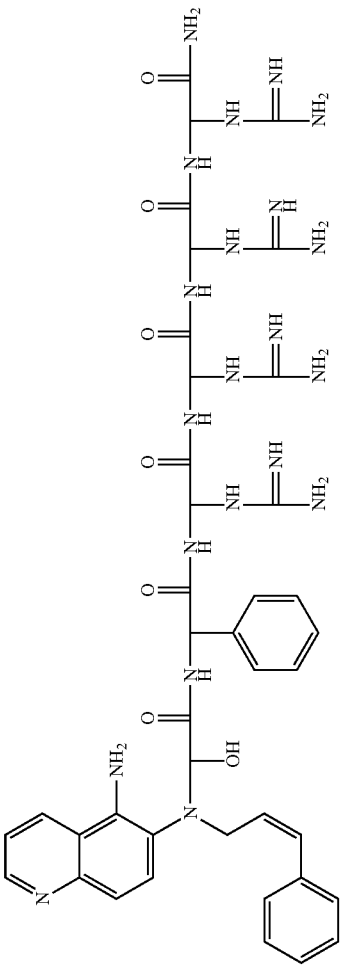
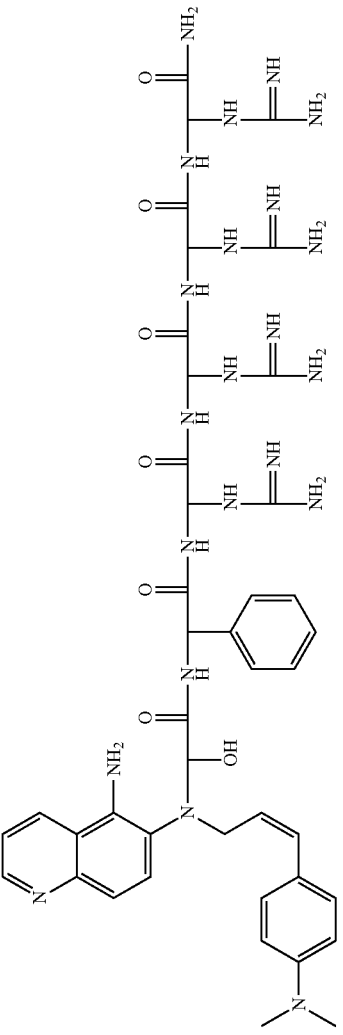

-continued
| STRUCTURE | formula | mol weight | % |
|---|---|---|---|
| Compound 155 | C54H80N22O9 | 1181.368 | <10% |
| Compound 156 | C60H83N21O7 | 1210.4522 | <10% |
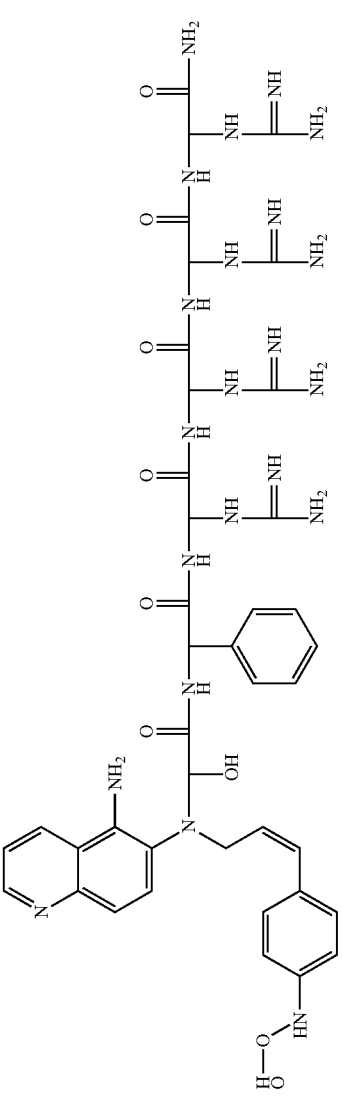
Compound 155
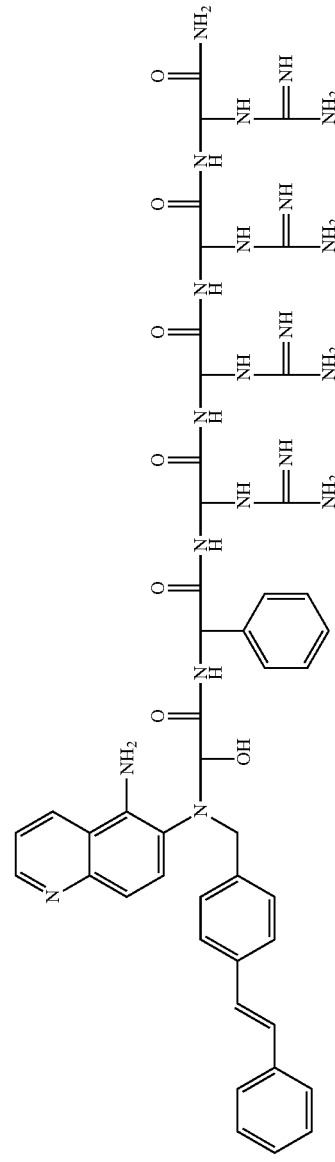
Compound 156

-continued

| STRUCTURE | formula | mol weight | % |
|---|---|---|---|
| Compound 157 | C56H79N21O8 | 1174.376 | <10% |
| Compound 158 | C62H83N21O7 | 1234.4742 | <10% |

| STRUCTURE | formula | mol weight | % |
|---|---|---|---|
| Compound 159 | C60H81N21O7 | 1208.4364 | <10% |
| Compound 160 | C60H81N21O7 | 1208.4364 | <10% |

| STRUCTURE | formula | mol weight | % |
|---|---|---|---|
| Compound 161 | C53H79N21O8 | 1138.343 | <10% |
| Compound 162 | C53H79N21O9 | 1154.3424 | <10% |

| STRUCTURE | formula | mol weight | % |
|---|---|---|---|
| Compound 163 | C46H72Cl3N21O7 | 1137.5703 | <10% |
| Compound 164 | C48H76Cl3N21O7 | 1165.6239 | <10% |
| Compound 165 | C49H78Cl3N21O7 | 1179.6507 | <10% |

-continued
| STRUCTURE | formula | mol weight | % |
|---|---|---|---|
| 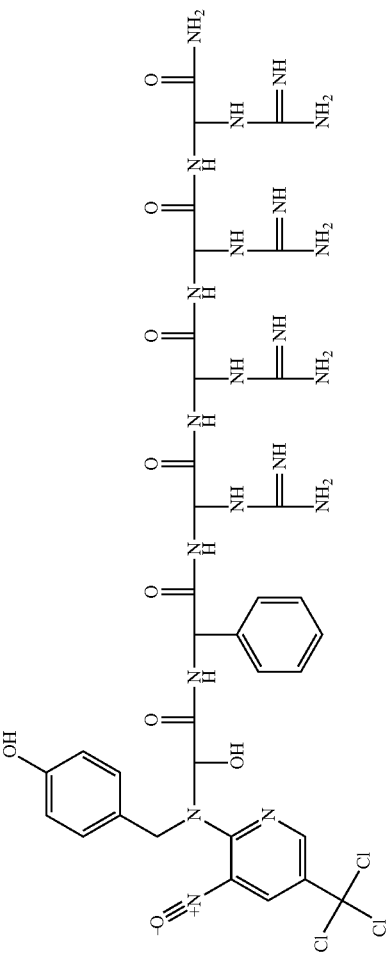Compound 166 | C50H72Cl3N21O8 | 1201.6137 | <10% |
| 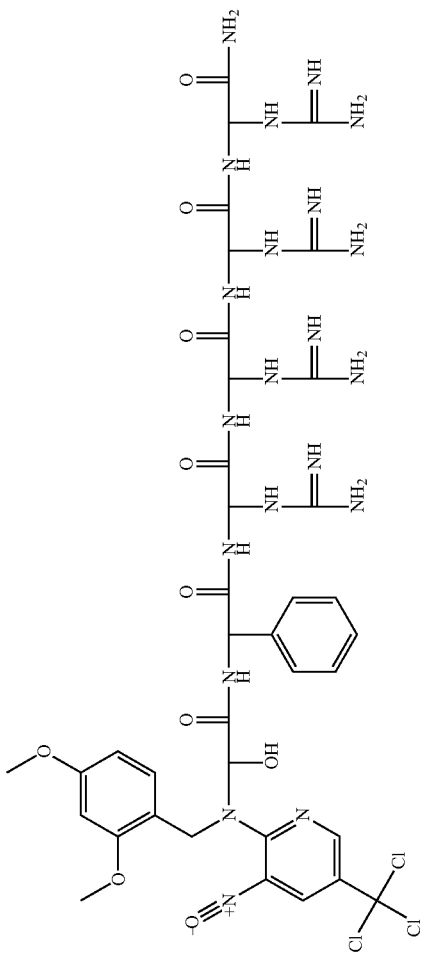Compound 167 | C52H76Cl3N21O9 | 1245.6667 | <10% |

-continued

| STRUCTURE | formula | mol weight | % |
|---|---|---|---|
| Compound 168 | C52H77Cl3N22O8 | 1244.6819 | <10% |
| Compound 169 | C52H77Cl3N22O7 | 1228.6825 | <10% |

| STRUCTURE | formula | mol weight | % |
|---|---|---|---|
| Compound 170 | C50H73Cl3N22O9 | 1232.6277 | <10% |
| Compound 171 | C50H71Cl3N22O9 | 1230.6119 | <10% |

-continued
| STRUCTURE | formula | mol weight | % |
|---|---|---|---|
| Compound 172 | C50H71Cl3N22O10 | 1246.6113 | <10% |
| Compound 173 | C50H70Cl5N21O7 | 1254.5045 | <10% |
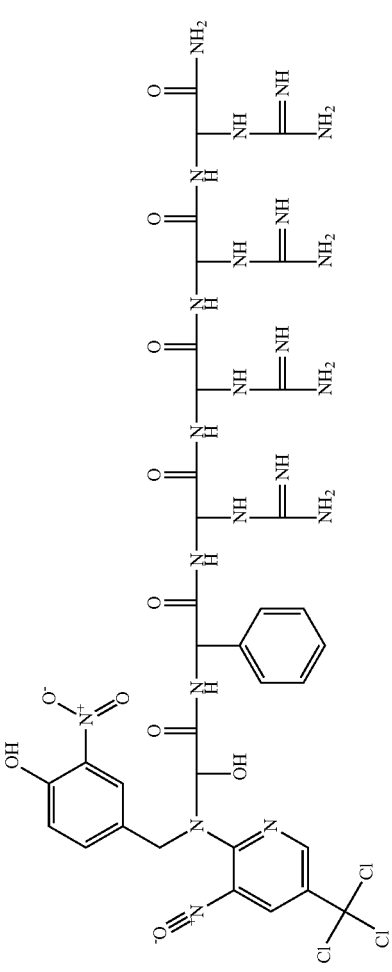
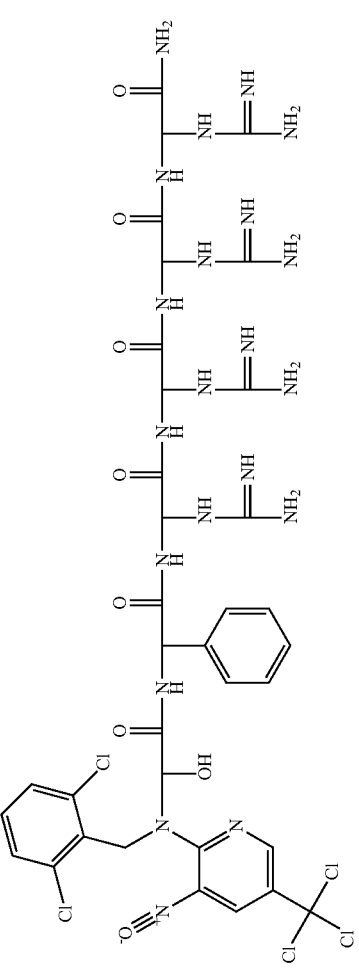

-continued
| STRUCTURE | formula | mol weight | % |
|---|---|---|---|
| Compound 174 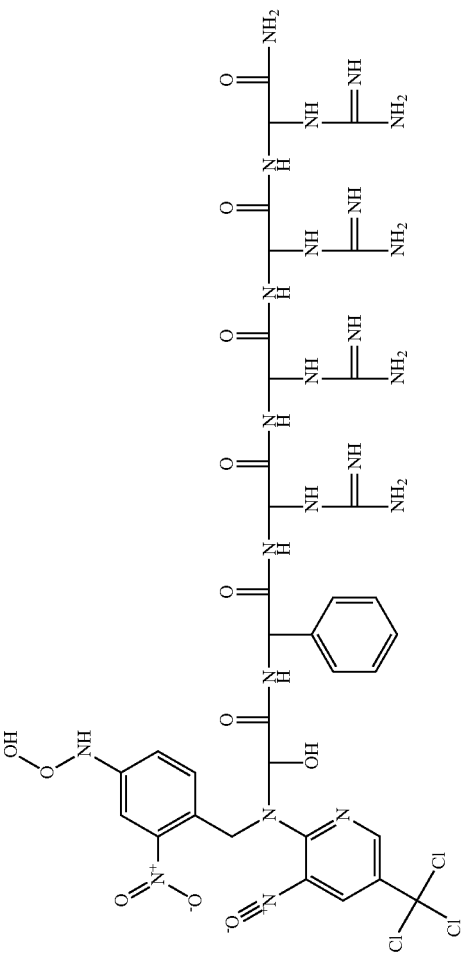 | C50H72Cl3N23O11 | 1277.6253 | <10% |
| Compound 175 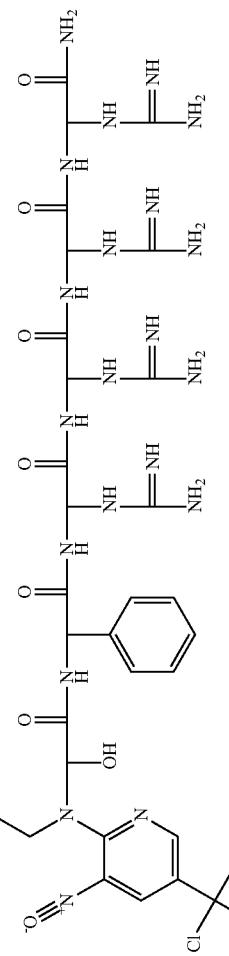 | C50H72Cl3N23O12 | 1293.6247 | <10% |

-continued

| STRUCTURE | formula | mol weight | % |
|---|---|---|---|
| Compound 176 | C52H74Cl3N21O7 | 1211.6521 | <10% |
| Compound 177 | C54H79Cl3N22O7 | 1254.7203 | <10% |

-continued

| STRUCTURE | formula | mol weight | % |
|---|---|---|---|
| Compound 178 | C52H75Cl3N22O9 | 1258.6655 | <10% |
| Compound 179 | C58H78Cl3N21O7 | 1287.7497 | <10% |

-continued

| STRUCTURE | formula | mol weight | % |
|---|---|---|---|
| Compound 180 | C54H74Cl3N21O8 | 1251.6735 | <10% |
| Compound 181 | C60H78Cl3N21O7 | 1311.7717 | <10% |

-continued
| STRUCTURE | formula | mol weight | % |
|---|---|---|---|
| 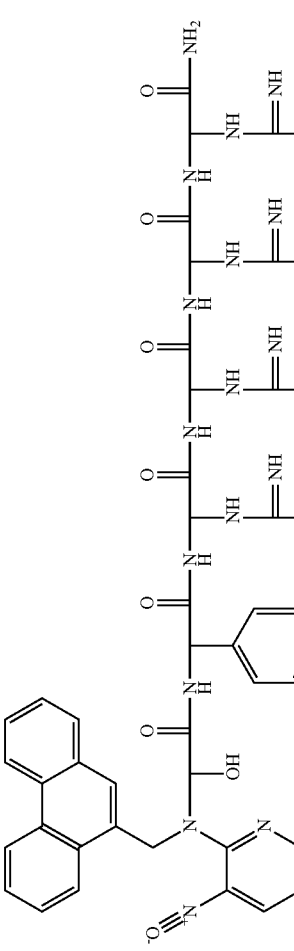  Compound 182 | C58H76Cl3N21O7 | 1285.7339 | <10% |
| 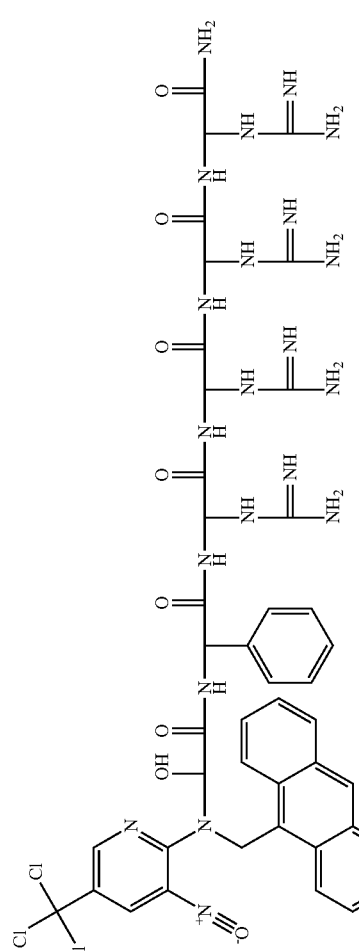  Compound 183 | C58H76Cl3N21O7 | 1285.7339 | <10% |

| STRUCTURE | | formula | mol weight | % |
|---|---|---|---|---|
| 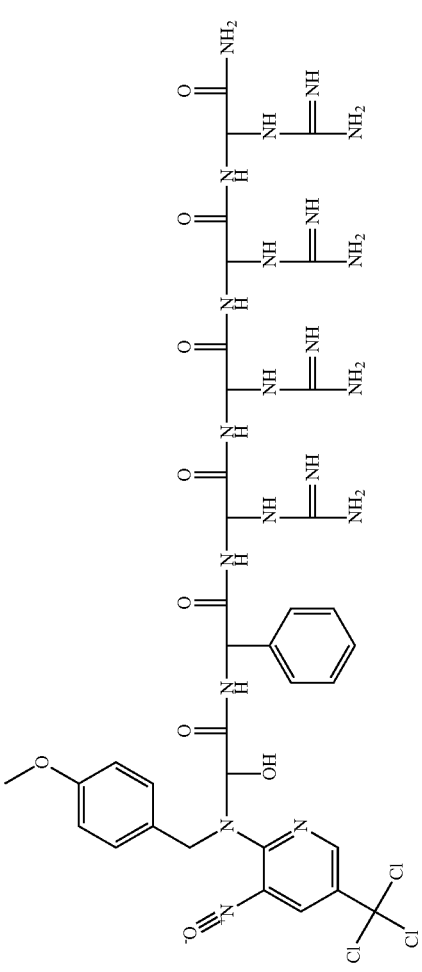
Compound 184 | | C51H74Cl3N21O8 | 1215.6405 | <10% |
| 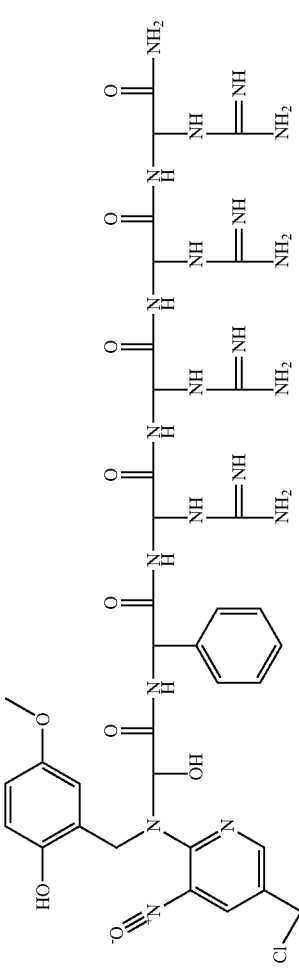
Compound 185 | | C51H74Cl3N21O9 | 1231.6399 | <10% |

| STRUCTURE | formula | mol weight | % |
|---|---|---|---|
| Compound 186 | C55H79Cl2N21O7 | 1217.2716 | <10% |
| Compound 187 | C57H83Cl2N21O7 | 1245.3252 | <10% |

| STRUCTURE | formula | mol weight | % |
|---|---|---|---|
| Compound 188 | C58H85Cl2N21O7 | 1259.352 | <10% |
| Compound 189 | C59H79Cl2N21O8 | 1281.315 | <10% |

-continued

| STRUCTURE | formula | mol weight | % |
|---|---|---|---|
| Compound 190 | C61H83Cl2N21O9 | 1325.368 | <10% |
| Compound 191 | C61H84Cl2N22O8 | 1324.3832 | <10% |

| STRUCTURE | formula | mol weight | % |
|---|---|---|---|
| Compound 192 | C61H84Cl2N22O7 | 1308.3838 | <10% |
| Compound 193 | C59H80Cl2N22O9 | 1312.329 | <10% |

-continued
| STRUCTURE | formula | mol weight | % |
|---|---|---|---|
| 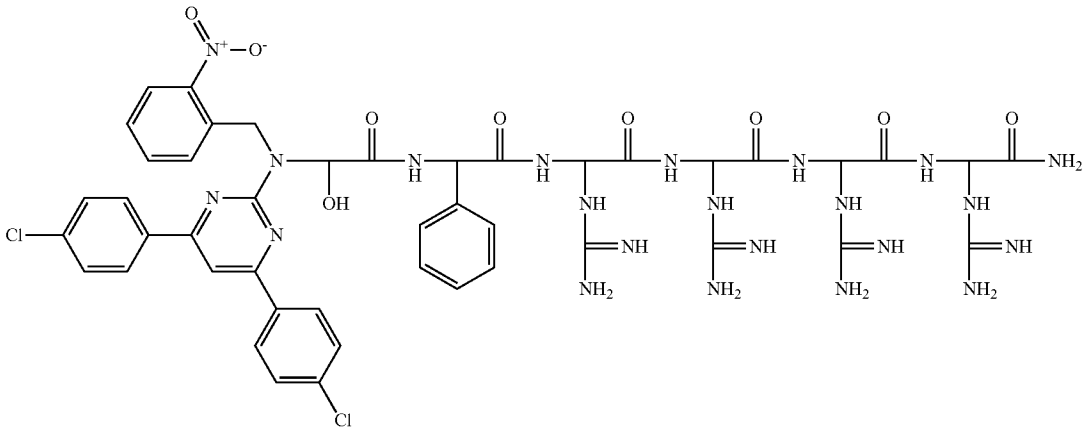 Compound 194 | C59H78Cl2N22O9 | 1310.3132 | <10% |
| 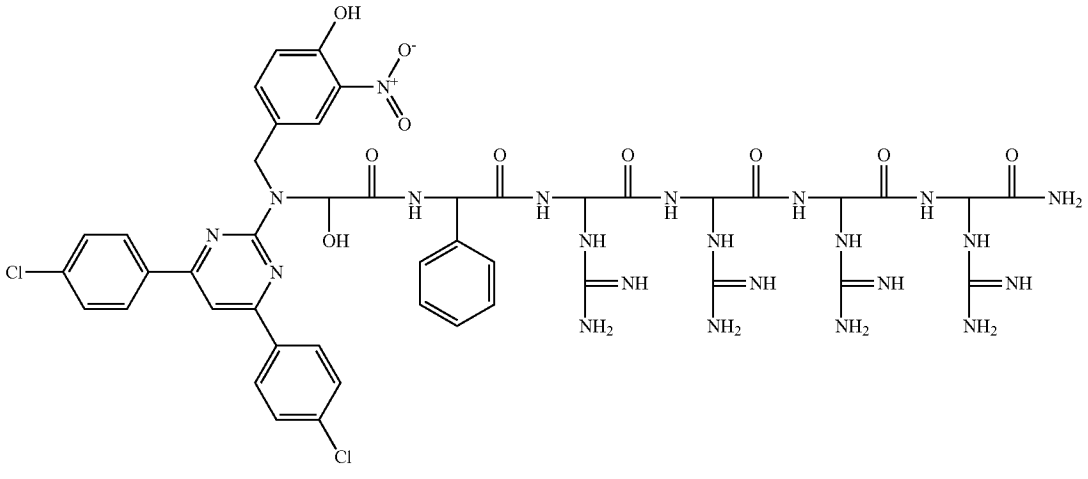 Compound 195 | C59H78Cl2N22O10 | 1326.3126 | <10% |

| STRUCTURE | formula | mol weight | % |
|---|---|---|---|
| Compound 196 | C59H77Cl4N21O7 | 1334.2058 | <10% |
| Compound 197 | C59H79Cl2N23O11 | 1357.3266 | <10% |

| STRUCTURE | formula | mol weight | % |
|---|---|---|---|
| Compound 198 | C59H79Cl2N23O12 | 1373.326 | <10% |
| Compound 199 | C61H81Cl2N21O7 | 1291.3534 | <10% |

| STRUCTURE | formula | mol weight | % |
|---|---|---|---|
| Compound 200 | C63H86Cl2N22O7 | 1334.4216 | <10% |
| Compound 201 | C61H82Cl2N22O9 | 1338.3668 | <10% |

-continued
| STRUCTURE | formula | mol weight | % |
|---|---|---|---|
| Compound 202 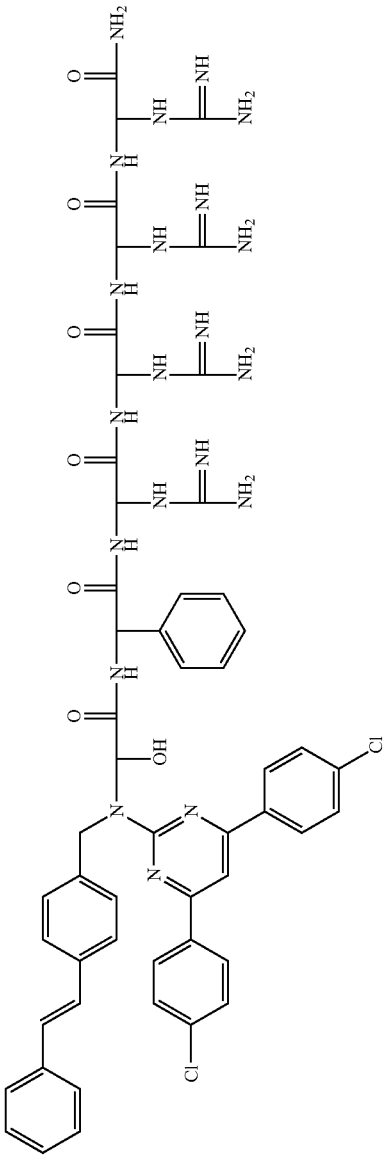 | C67H85Cl2N21O7 | 1367.451 | <10% |
| Compound 203 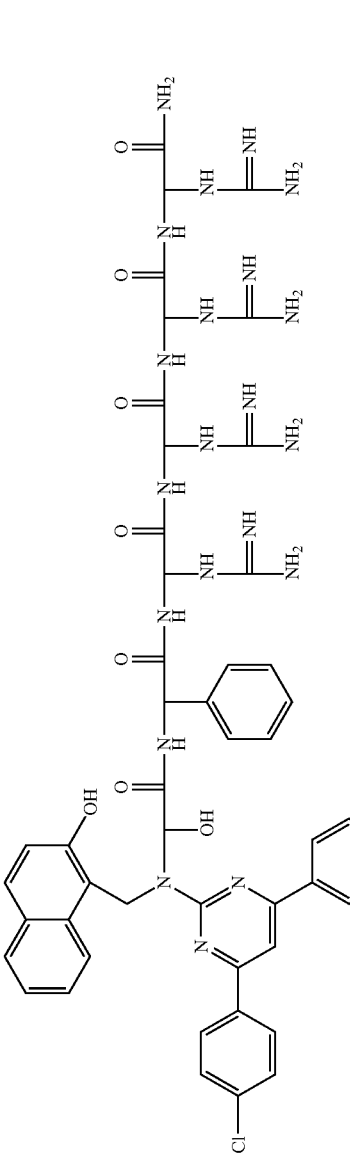 | C63H81Cl2N21O8 | 1331.3748 | <10% |

-continued
| STRUCTURE | formula | mol weight | % |
|---|---|---|---|
| 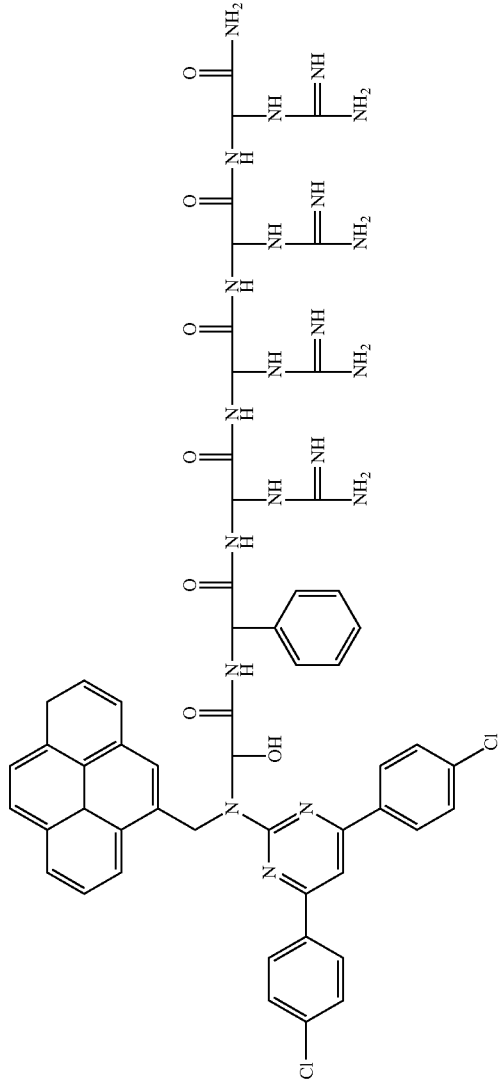 Compound 204 | C69H85Cl2N21O7 | 1391.473 | <10% |
| 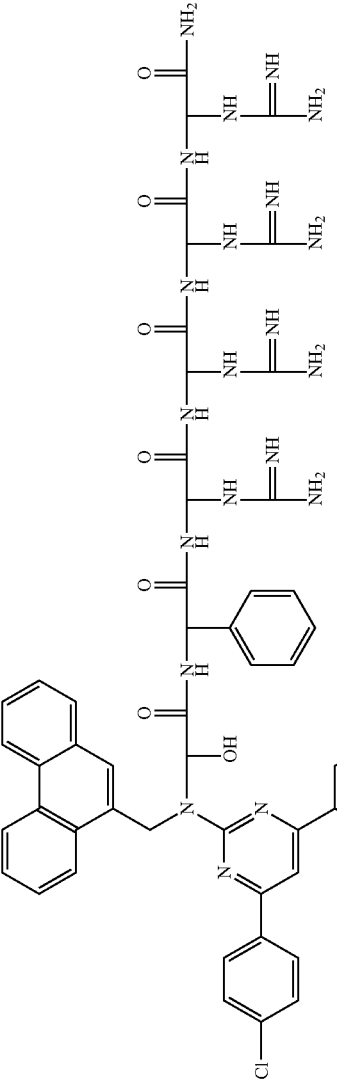 Compound 205 | C67H83Cl2N21O7 | 1365.4352 | <10% |

-continued
| STRUCTURE | formula | mol weight | % |
|---|---|---|---|
| 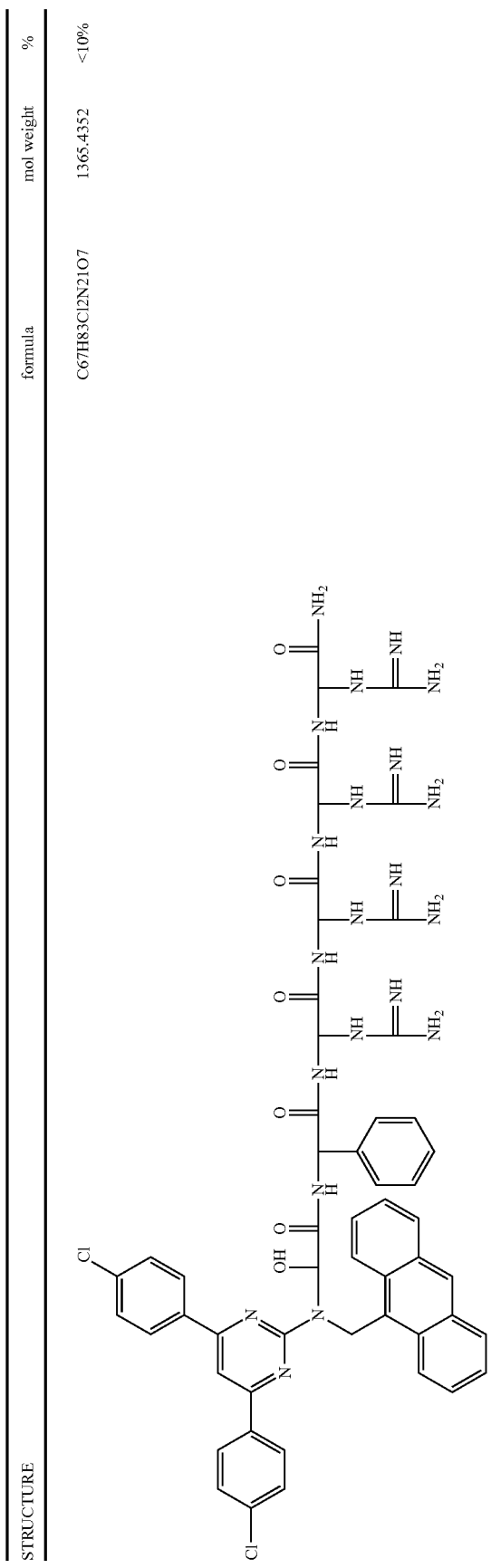
Compound 206 | C67H83Cl2N21O7 | 1365.4352 | <10% |
| 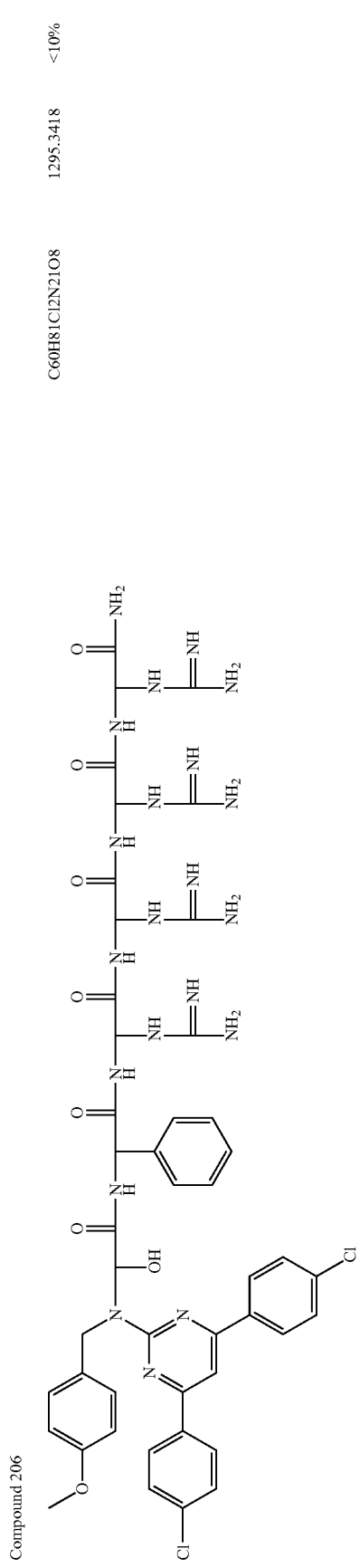
Compound 207 | C60H81Cl2N21O8 | 1295.3418 | <10% |

| STRUCTURE | formula | mol weight | % |
|---|---|---|---|
| Compound 208 | C60H81Cl2N21O9 | 1311.3412 | <10% |
| Compound 209 | C46H72N22O11 | 1109.2156 | <10% |

| STRUCTURE | formula | mol weight | % |
|---|---|---|---|
| 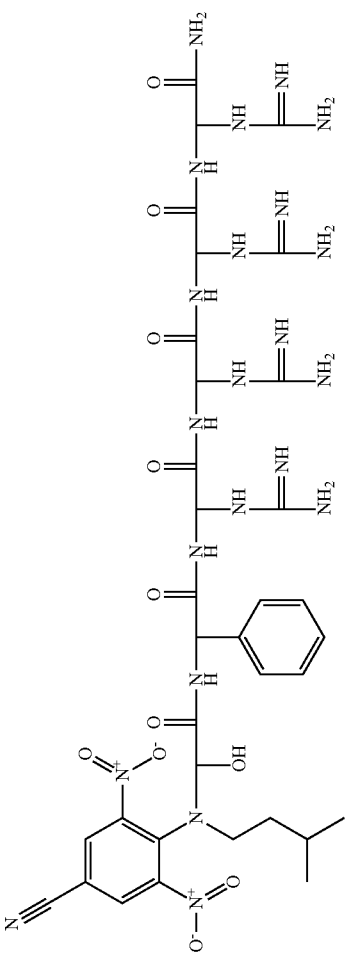 Compound 210 | C48H76N22O11 | 1137.2692 | <10% |
| 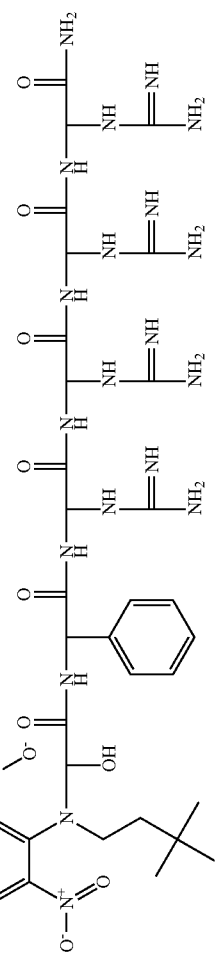 Compound 211 | C49H78N22O11 | 1151.296 | <10% |

| STRUCTURE | formula | mol weight | % |
|---|---|---|---|
| Compound 212 | C50H72N22O12 | 1173.259 | <10% |
| Compound 213 | C52H76N22O13 | 1217.312 | <10% |

| STRUCTURE | formula | mol weight | % |
|---|---|---|---|
| Compound 214 | C52H77N23O12 | 1216.3272 | <10% |
| Compound 215 | C52H77N23O11 | 1200.3278 | <10% |

| STRUCTURE | formula | mol weight | % |
|---|---|---|---|
| Compound 216 | C50H73N23O13 | 1204.273 | <10% |
| Compound 217 | C50H71N23O13 | 1202.2572 | <10% |

-continued
| STRUCTURE | formula | mol weight | % |
|---|---|---|---|
| 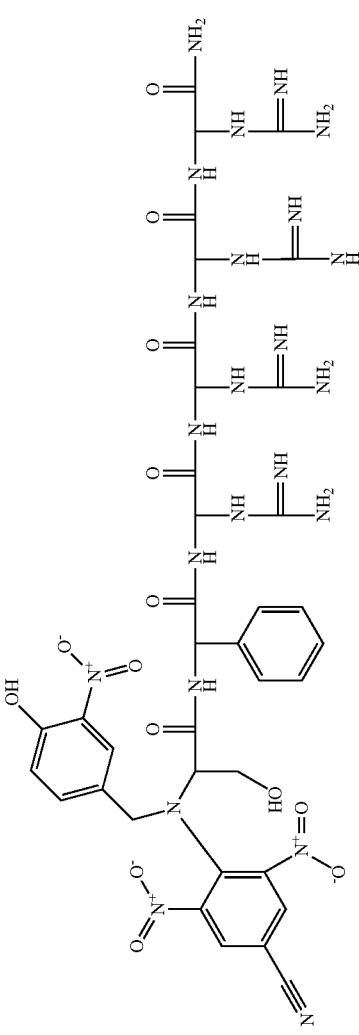 Compound 218 | C50H71N23O14 | 1218.2566 | <10% |
| 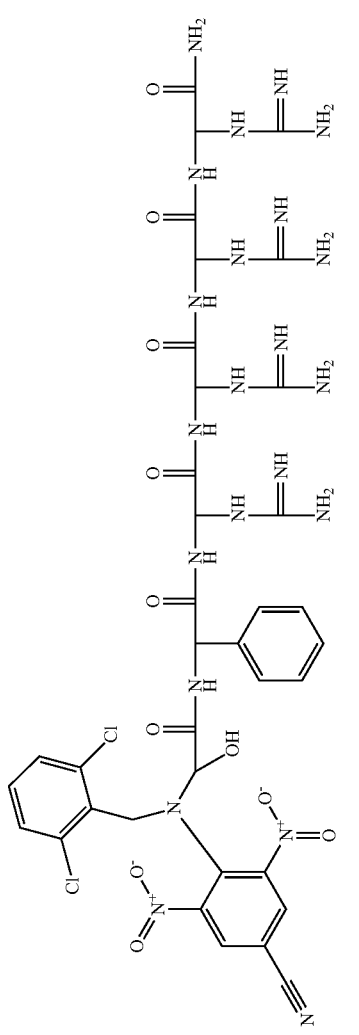 Compound 219 | C50H70Cl2N22O11 | 1226.1498 | <10% |

-continued
| STRUCTURE | formula | mol weight | % |
|---|---|---|---|
| Compound 220 | C50H72N23O15 | 1249.2706 | <10% |
| Compound 221 | C50H72N24O16 | 1265.27 | <10% |
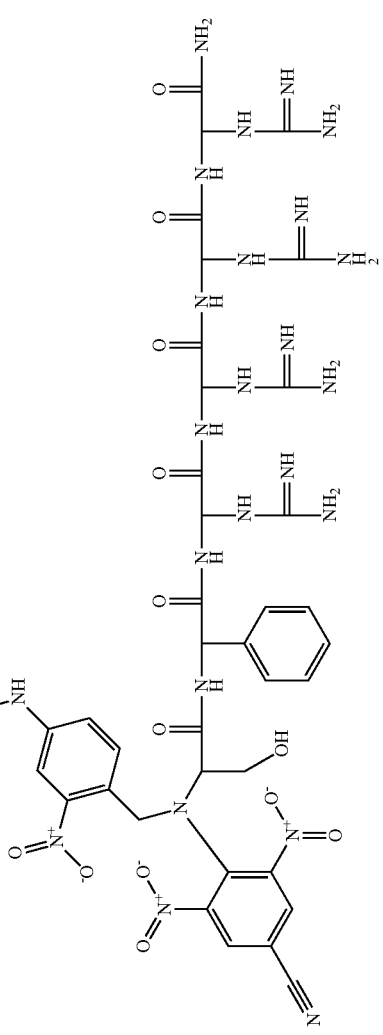
Compound 220
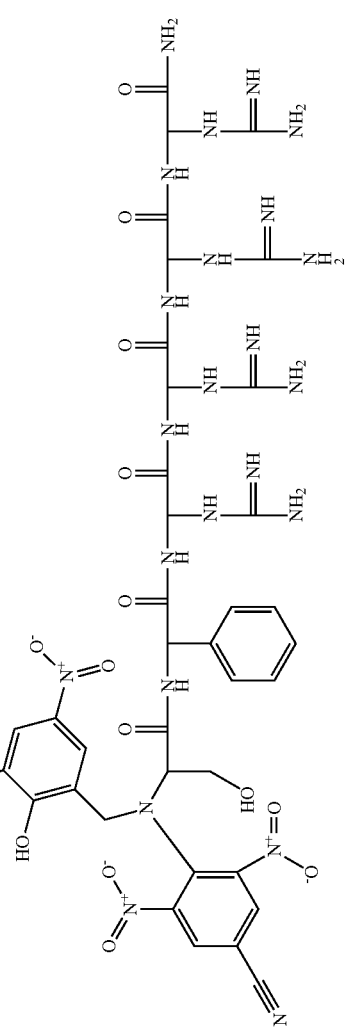
Compound 221

| STRUCTURE | formula | mol weight | % |
|---|---|---|---|
| Compound 222 | C52H74N22O11 | 1183.2974 | <10% |
| Compound 223 | C54H79N23O11 | 1226.3656 | <10% |

-continued

| STRUCTURE | formula | mol weight | % |
|---|---|---|---|
| Compound 224 | C52H75N23O13 | 1230.3108 | <10% |
| Compound 225 | C58H78N22O11 | 1259.395 | <10% |

| STRUCTURE | formula | mol weight | % |
|---|---|---|---|
| Compound 226 | C54H74N22O12 | 1223.3188 | <10% |
| Compound 227 | C60H78N22O11 | 1283.417 | <10% |

| STRUCTURE | formula | mol weight | % |
|---|---|---|---|
| Compound 228 | C58H76N22O11 | 1257.3792 | <10% |
| Compound 229 | C58H76N22O11 | 1257.3792 | <10% |
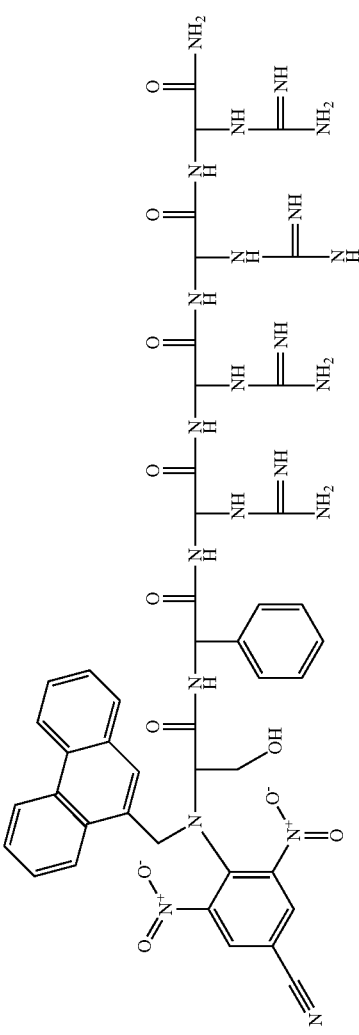
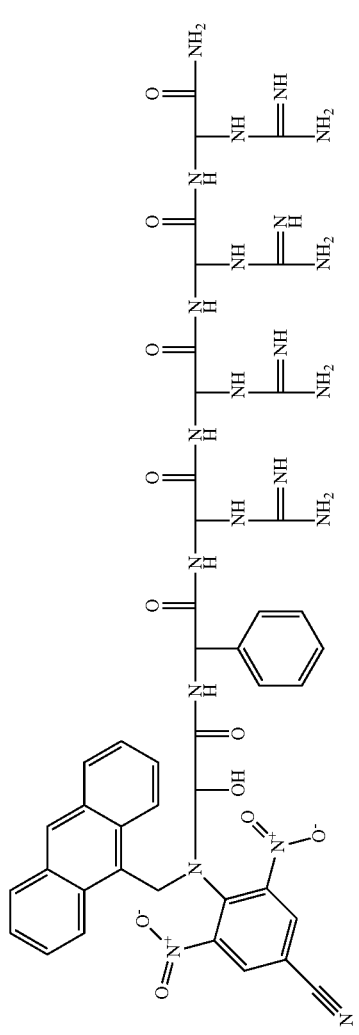

| STRUCTURE | formula | mol weight | % |
|---|---|---|---|
| 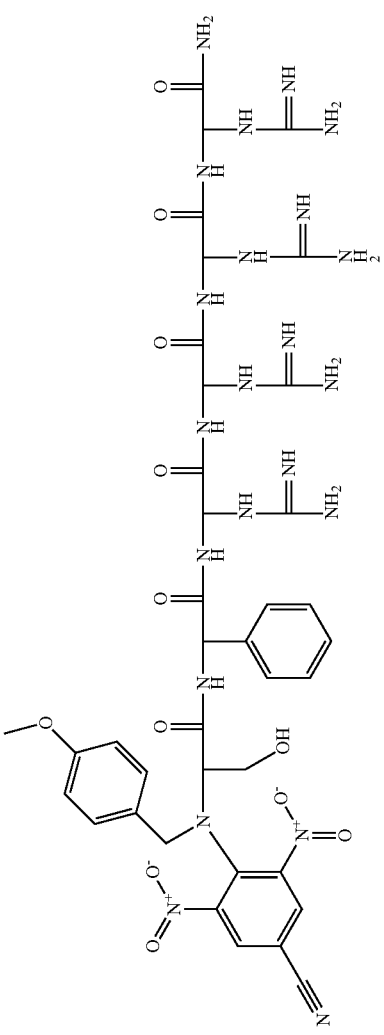 Compound 230 | C51H74N22O12 | 1187.2858 | <10% |
| 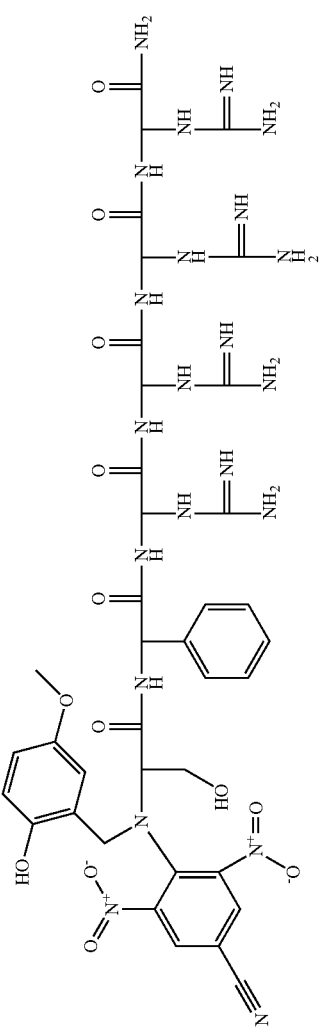 Compound 231 | C51H47N22O13 | 1203.2852 | <10% |

-continued

| STRUCTURE | formula | mol weight | % |
|---|---|---|---|
| Compound 232 | C46H73N21O13 | 1128.2156 | <10% |
| Compound 233 | C48H77N21O13 | 1156.2692 | <10% |

-continued
| STRUCTURE | formula | mol weight | % |
|---|---|---|---|
| 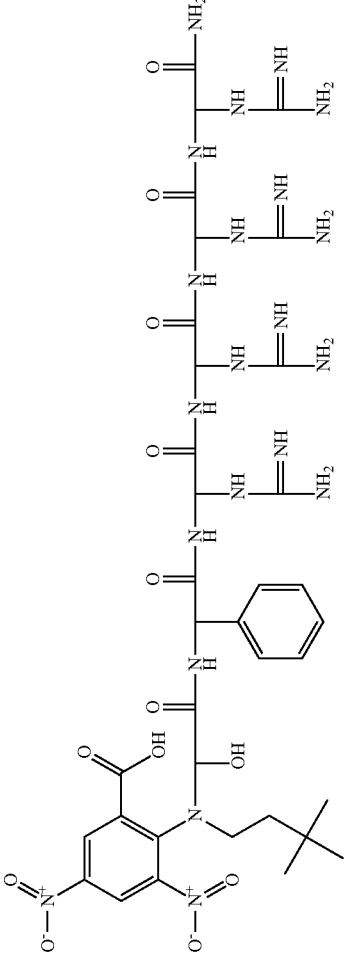
Compound 234 | C49H79N21O13 | 1170.296 | <10% |
| 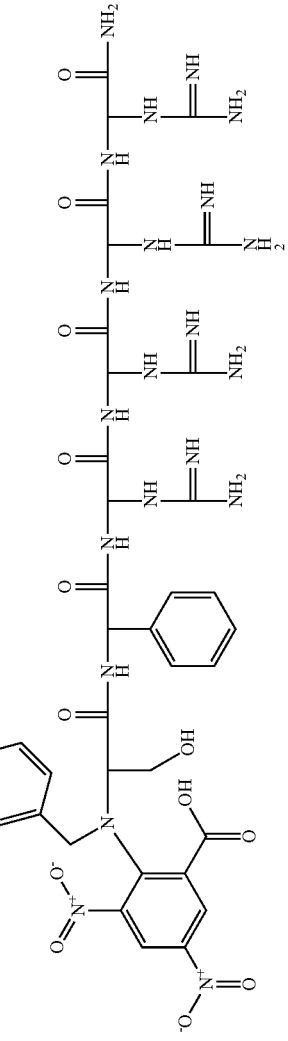
Compound 235 | C50H73N21O14 | 1192.259 | <10% |

-continued

| STRUCTURE | formula | mol weight | % |
|---|---|---|---|
| Compound 236 | C52H77N21O15 | 1236.312 | <10% |
| Compound 237 | C52H78N22O14 | 1235.3272 | <10% |

| STRUCTURE | formula | mol weight | % |
|---|---|---|---|
| Compound 238 | C52H78N22O13 | 1219.3278 | <10% |
| Compound 239 | C50H74N22O15 | 1223.273 | <10% |

| STRUCTURE | formula | mol weight | % |
|---|---|---|---|
| Compound 240 | C50H72N22O15 | 1221.2572 | <10% |
| Compound 241 | C50H72N22O16 | 1237.2566 | <10% |

-continued

| STRUCTURE | formula | mol weight | % |
|---|---|---|---|
| Compound 242 | C50H71Cl2N21O13 | 1245.1498 | <10% |
| Compound 243 | C50H73N23O17 | 1268.2706 | <10% |

| STRUCTURE | formula | mol weight | % |
|---|---|---|---|
| 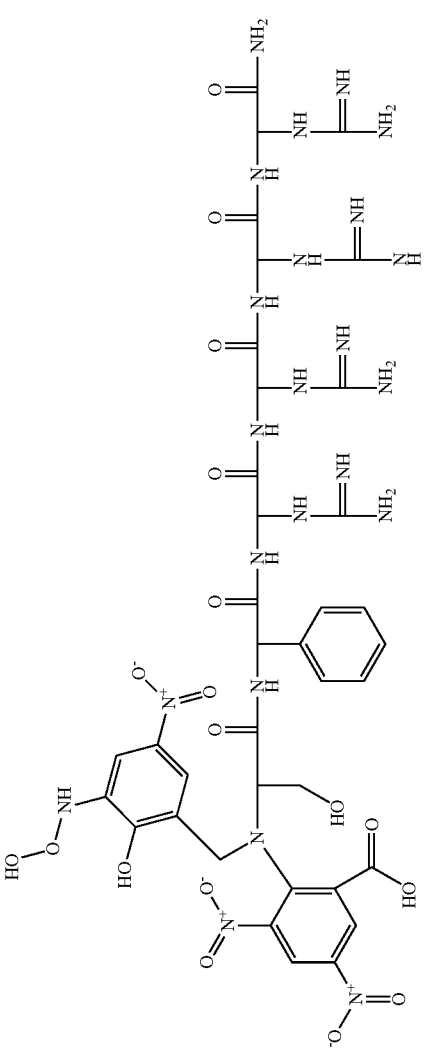 Compound 244 | C50H73N23O18 | 1284.27 | <10% |
| 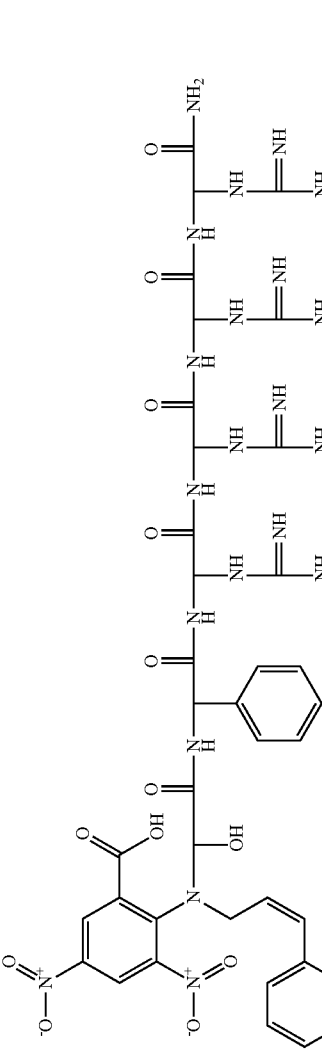 Compound 245 | C52H75N21O13 | 1202.2974 | <10% |

| STRUCTURE | formula | mol weight | % |
|---|---|---|---|
| Compound 246 | C54H80N22O13 | 1245.3656 | <10% |
| Compound 247 | C52H76N22O15 | 1249.3108 | <10% |

| STRUCTURE | formula | mol weight | % |
|---|---|---|---|
| 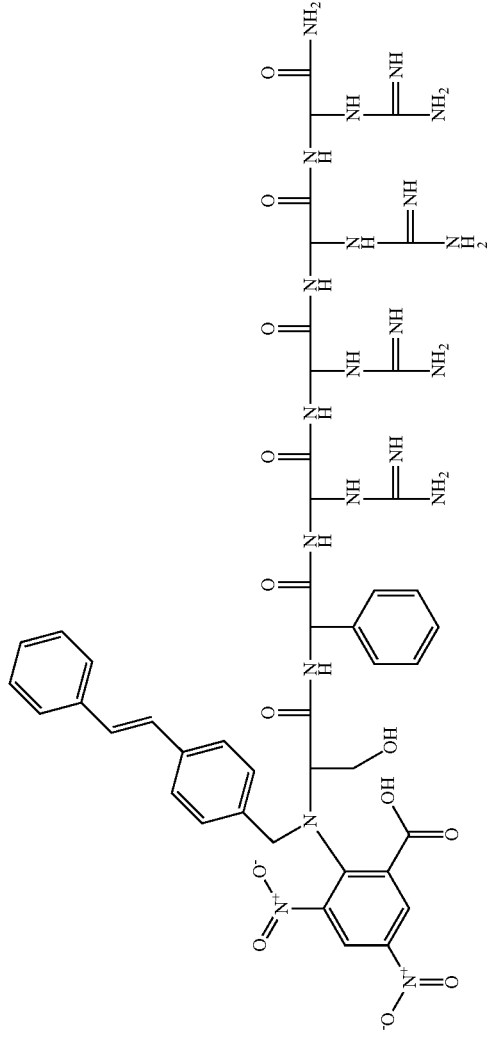 Compound 248 | C58H79N21O13 | 1278.395 | <10% |
| 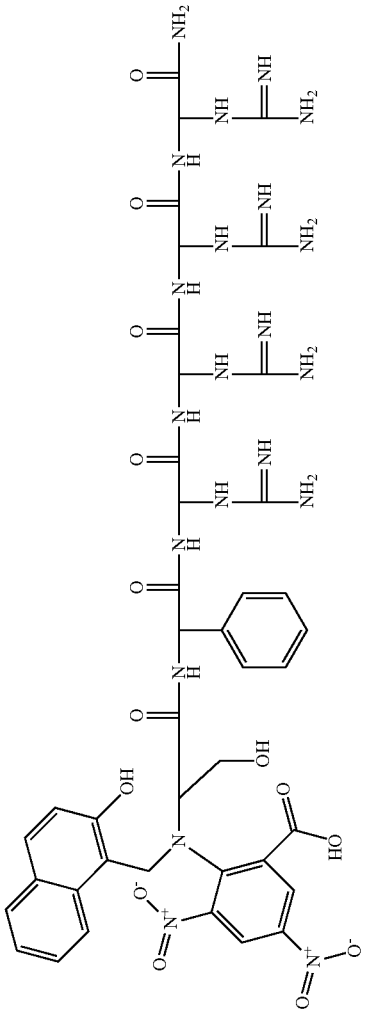 Compound 249 | C54H75N21O14 | 1242.3188 | <10% |

-continued

| STRUCTURE | formula | mol weight | % |
|---|---|---|---|
| Compound 250 | C60H79N21O13 | 1302.417 | <10% |
| Compound 251 | C58H77N21O13 | 1276.3792 | <10% |

| STRUCTURE | formula | mol weight | % |
|---|---|---|---|
| 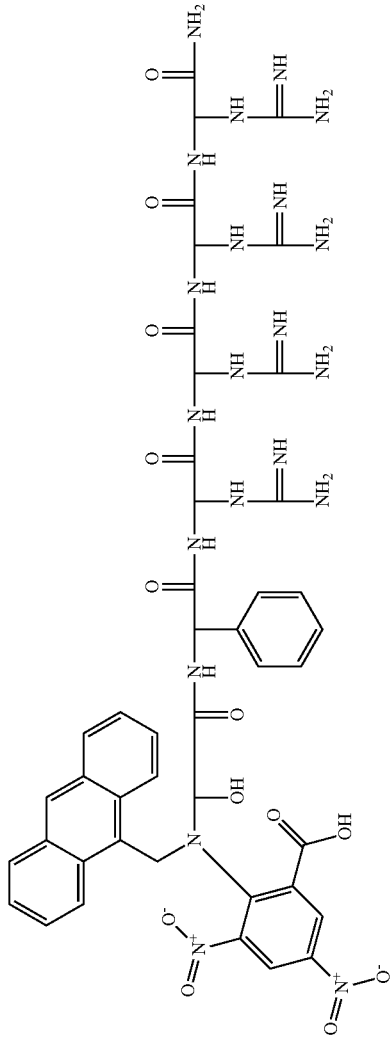 Compound 252 | C58H77N21O13 | 1276.3792 | <10% |
| 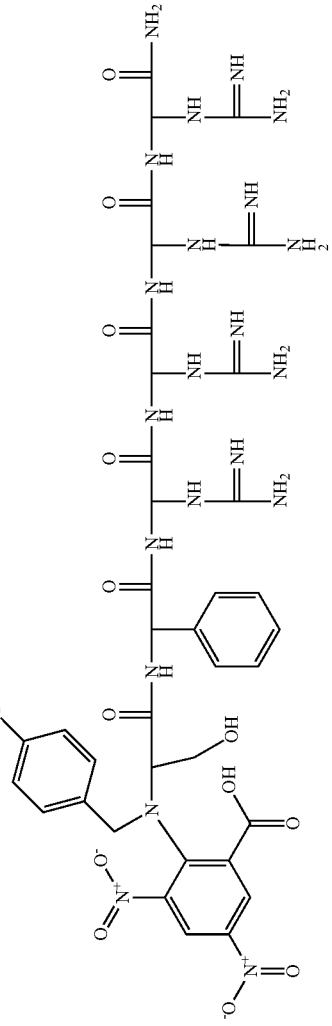 Compound 253 | C51H75N21O14 | 1206.2858 | <10% |

-continued

| STRUCTURE | formula | mol weight | % |
|---|---|---|---|
| Compound 254 | C51H75N21O15 | 1222.2852 | <10% |
| Compound 255 | C46H74N20O11 | 1083.218 | <10% |

-continued

| STRUCTURE | formula | mol weight | % |
|---|---|---|---|
| Compound 256 | C48H78N20O11 | 1111.2716 | <10% |
| Compound 257 | C49H80N20O11 | 1125.2984 | <10% |

| STRUCTURE | formula | mol weight | % |
|---|---|---|---|
| Compound 258 | C50H74N20O12 | 1147.2614 | <10% |
| Compound 259 | C52H78N20O13 | 1191.3144 | <10% |

-continued

| STRUCTURE | formula | mol weight | % |
|---|---|---|---|
| Compound 260 | C52H79N21O12 | 1190.3296 | <10% |
| Compound 261 | C52H79N21O11 | 1174.3302 | <10% |

| STRUCTURE | formula | mol weight | % |
|---|---|---|---|
| 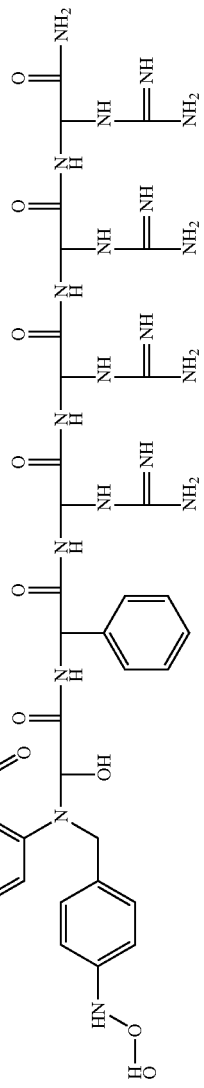 Compound 262 | C50H75N21O13 | 1178.2754 | <10% |
| 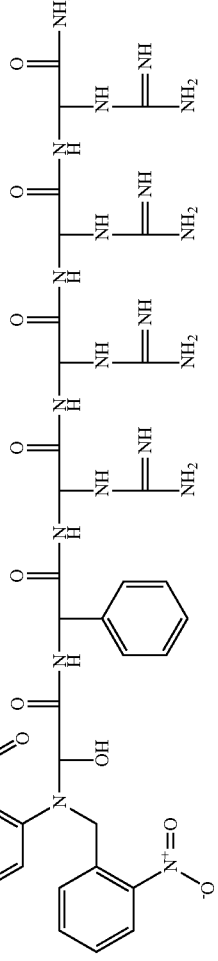 Compound 263 | C50H73N21O13 | 1176.2596 | <10% |

-continued

| STRUCTURE | formula | mol weight | % |
|---|---|---|---|
| Compound 264 | C50H73N21O14 | 1192.259 | <10% |
| Compound 265 | C50H72Cl2N20O11 | 1200.1522 | <10% |

| STRUCTURE | formula | mol weight | % |
|---|---|---|---|
| Compound 266 | C50H74N22O15 | 1223.273 | <10% |
| Compound 267 | C50H74N22O16 | 1239.2724 | <10% |

| STRUCTURE | formula | mol weight | % |
|---|---|---|---|
| Compound 268 | C52H76N20O11 | 1157.2998 | <10% |
| Compound 269 | C54H81N21O11 | 1200.368 | <10% |

| STRUCTURE | formula | mol weight | % |
|---|---|---|---|
| Compound 270 | C52H77N21O13 | 1204.3132 | <10% |
| Compound 271 | C58H80N20O11 | 1233.3974 | <10% |

| STRUCTURE | formula | mol weight | % |
|---|---|---|---|
| Compound 272 | C54H76N20O12 | 1197.3212 | <10% |
| Compound 273 | C60H80N20O11 | 1257.4194 | <10% |

| STRUCTURE | formula | mol weight | % |
|---|---|---|---|
| Compound 274 | C58H78N20O11 | 1231.3816 | <10% |
| Compound 275 | C58H78N20O11 | 1231.3816 | <10% |

| STRUCTURE | formula | mol weight | % |
|---|---|---|---|
| 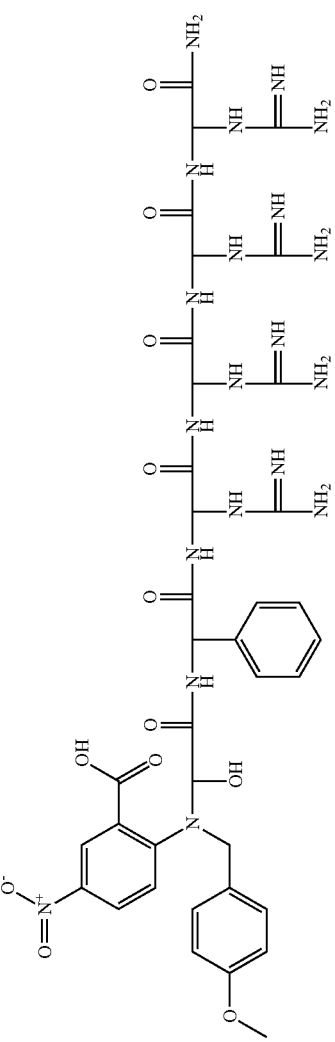<br>Compound 276 | C51H76N20O12 | 1161.2882 | <10% |
| 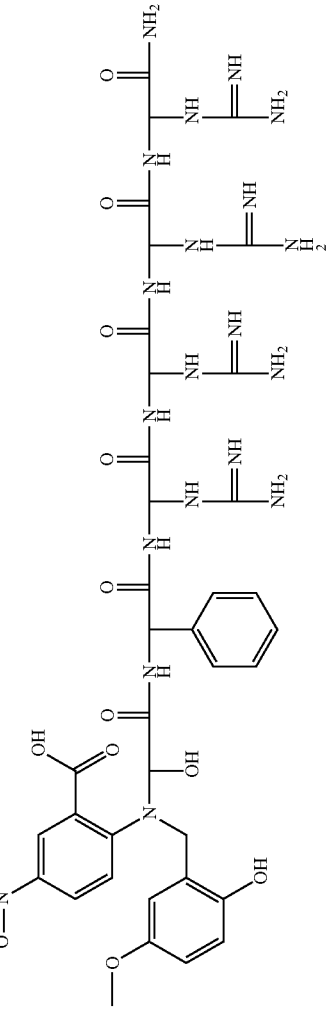<br>Compound 277 | C51H76N20O13 | 1177.2876 | <10% |

| STRUCTURE | formula | mol weight | % |
|---|---|---|---|
| Compound 278 | C45H74N22O11 | 1099.2204 | <10% |
| Compound 279 | C47H78N22O11 | 1127.274 | <10% |

-continued

| STRUCTURE | formula | mol weight | % |
|---|---|---|---|
| Compound 280 | C48H80N22O11 | 1141.3008 | <10% |
| Compound 281 | C49H74N22O12 | 1163.2638 | <10% |

-continued
| STRUCTURE | formula | mol weight | % |
|---|---|---|---|
| 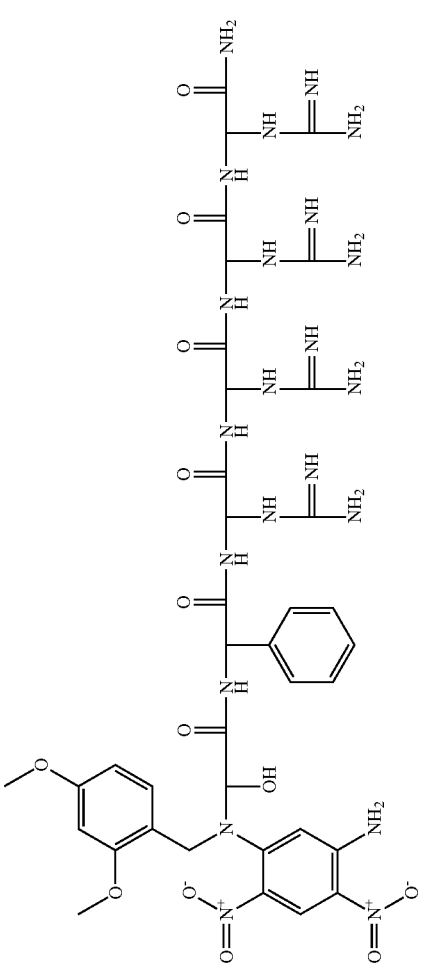 Compound 282 | C51H78N22O13 | 1207.3168 | <10% |
| 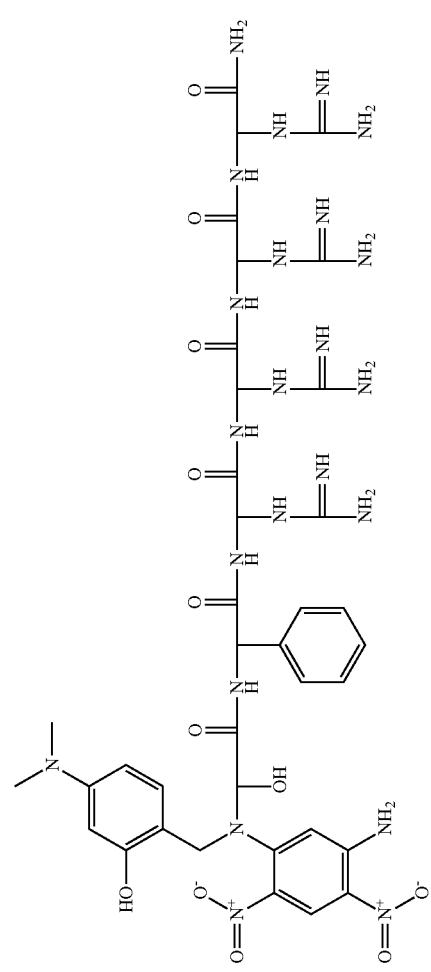 Compound 283 | C51H79N23O12 | 1206.332 | <10% |

-continued

| STRUCTURE | formula | mol weight | % |
|---|---|---|---|
| Compound 284 | C51H79N23O11 | 1190.3326 | <10% |
| Compound 285 | C49H75N23O13 | 1194.2778 | <10% |

| STRUCTURE | formula | mol weight | % |
|---|---|---|---|
| Compound 286 | C49H73N23O13 | 1192.262 | <10% |
| Compound 287 | C49H73N23O14 | 1208.2614 | <10% |

| STRUCTURE | formula | mol weight | % |
|---|---|---|---|
| 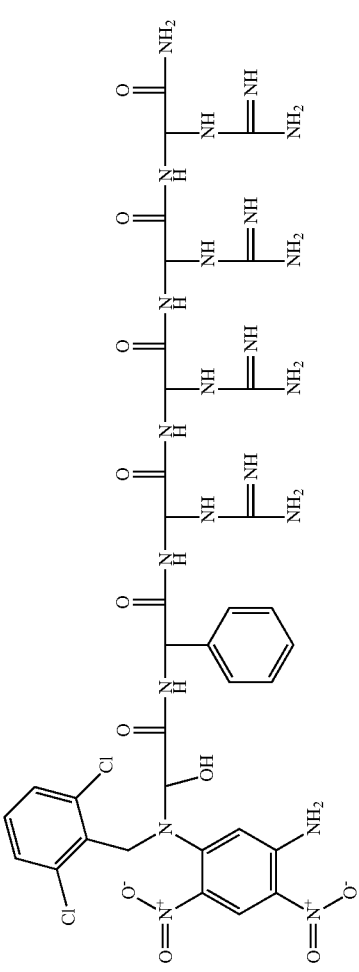 Compound 288 | C49H72Cl2N22O11 | 1216.1546 | <10% |
| 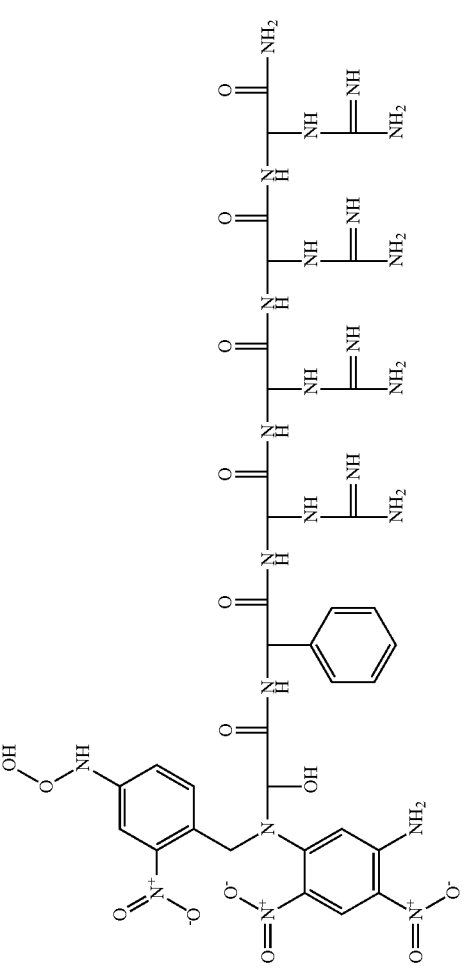 Compound 289 | C49H74N24O15 | 1239.2754 | <10% |

-continued

| STRUCTURE | formula | mol weight | % |
|---|---|---|---|
| Compound 290 | C49H74N24O16 | 1255.2748 | <10% |
| Compound 291 | C51H76N22O11 | 1173.3022 | <10% |

-continued

| STRUCTURE | formula | mol weight | % |
|---|---|---|---|
| Compound 292 | C53H81N23O11 | 1216.3704 | <10% |
| Compound 293 | C51H77N23O13 | 1220.3156 | <10% |

-continued
| STRUCTURE | formula | mol weight | % |
|---|---|---|---|
| 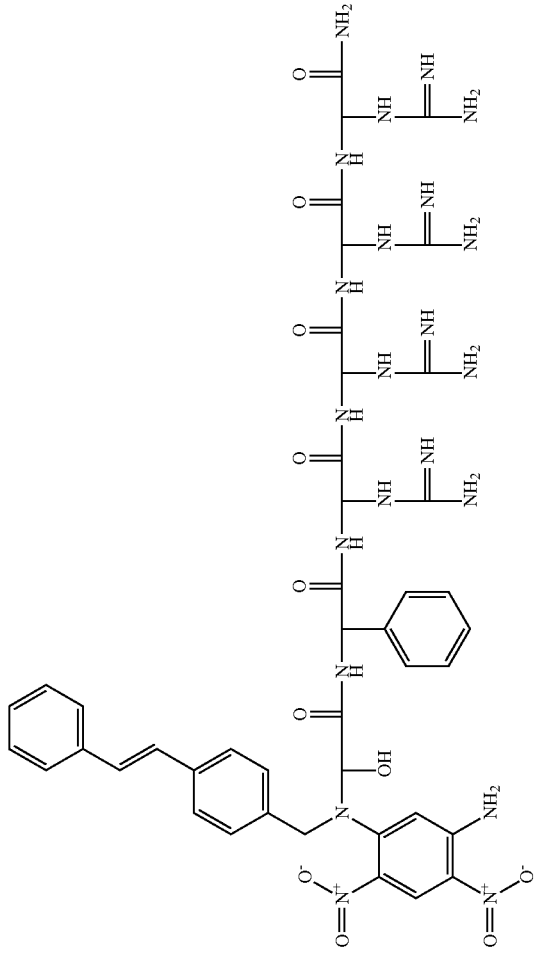 Compound 294 | C57H80N22O11 | 1249.3998 | <10% |
| 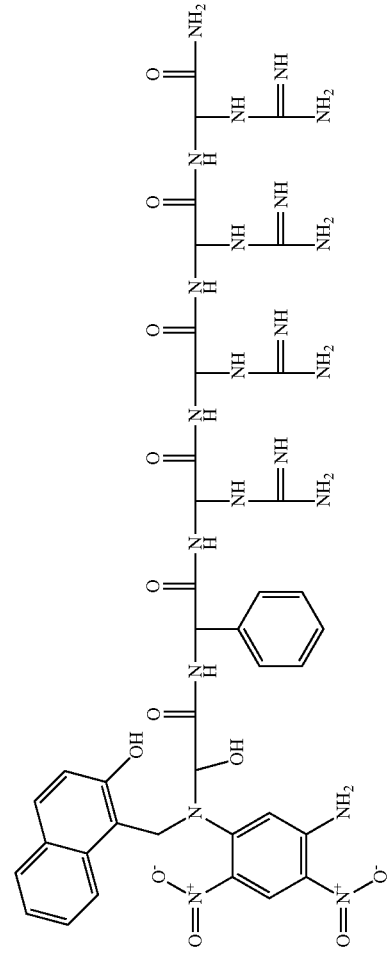 Compound 295 | C53H76N22O12 | 1213.3236 | <10% |

| STRUCTURE | formula | mol weight | % |
|---|---|---|---|
| Compound 296 | C59H80N22O11 | 1273.4218 | <10% |
| Compound 297 | C57H78N22O11 | 1247.384 | <10% |

-continued
| STRUCTURE | formula | mol weight | % |
|---|---|---|---|
| 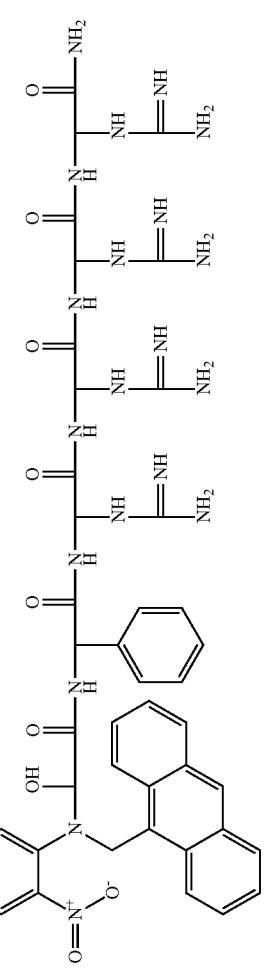 Compound 298 | C57H78N22O11 | 1247.384 | <10% |
| 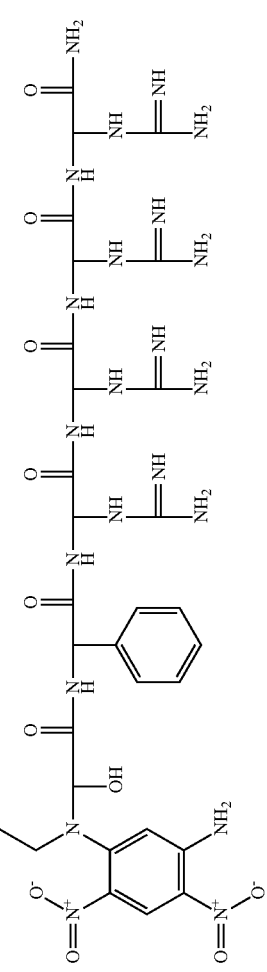 Compound 299 | C50H76N22O12 | 1177.2906 | <10% |

| STRUCTURE | formula | mol weight | % |
|---|---|---|---|
| Compound 300 | C50H76N22O13 | 1193.29 | <10% |
| Compound 301 | C50H74F6N20O7 | 1181.2548 | <10% |
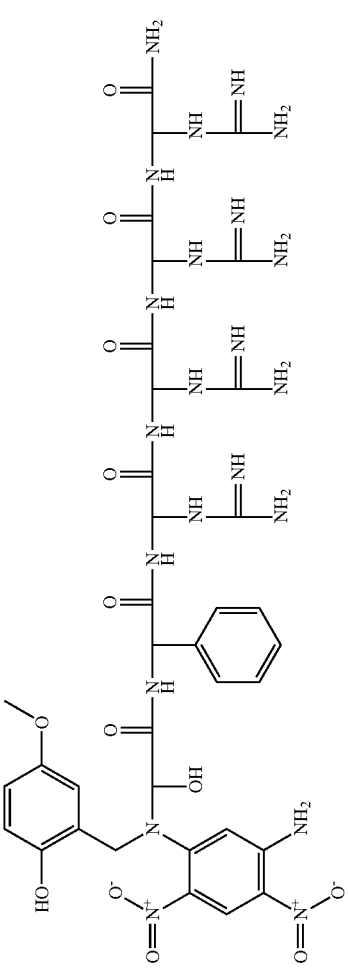
Compound 300
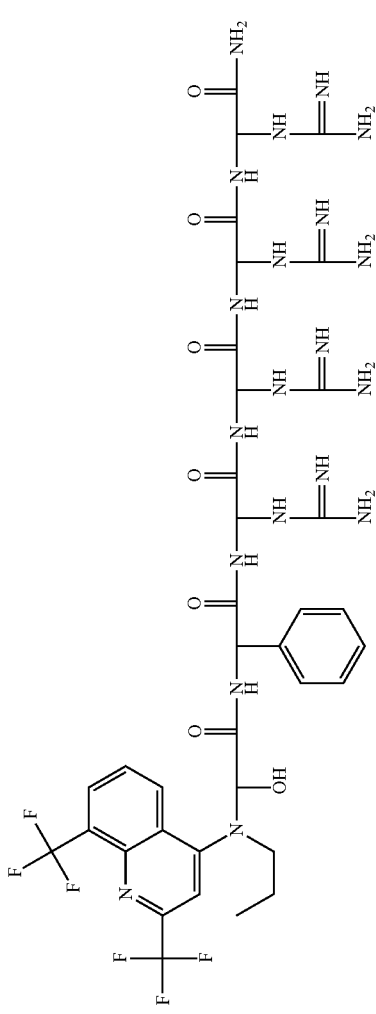
Compound 301

| STRUCTURE | formula | mol weight | % |
|---|---|---|---|
| Compound 302 | C52H78F6N20O7 | 1209.3084 | <10% |
| Compound 303 | C53H80F6N20O7 | 1223.3352 | <10% |

-continued

| STRUCTURE | formula | mol weight | % |
|---|---|---|---|
| Compound 304 | C54H74F6N20O8 | 1245.2982 | <10% |
| Compound 305 | C56H78F6N20O9 | 1289.3512 | <10% |

| STRUCTURE | formula | mol weight | % |
|---|---|---|---|
| Compound 306 | C56H79F6N21O8 | 1288.3664 | <10% |
| Compound 307 | C56H79F6N21O7 | 1272.367 | <10% |

| STRUCTURE | formula | mol weight | % |
|---|---|---|---|
| Compound 308 | C54H75F6N21O10 | 1276.3122 | <10% |
| Compound 309 | C54H73F6N21O9 | 1274.2964 | <10% |
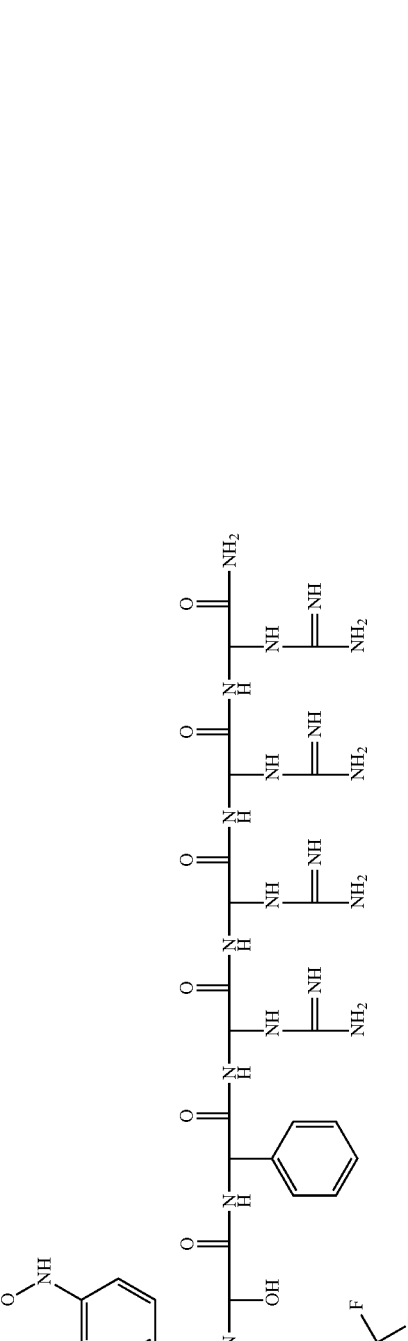
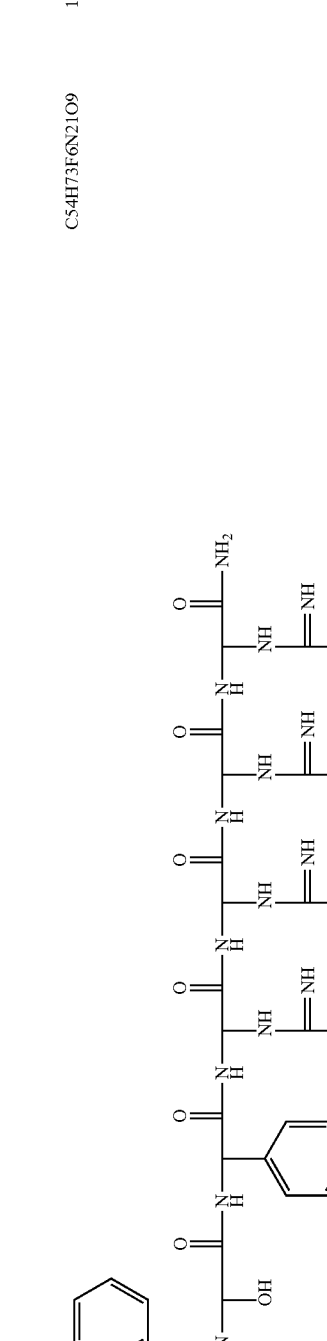

-continued
| STRUCTURE | formula | mol weight | % |
|---|---|---|---|
| 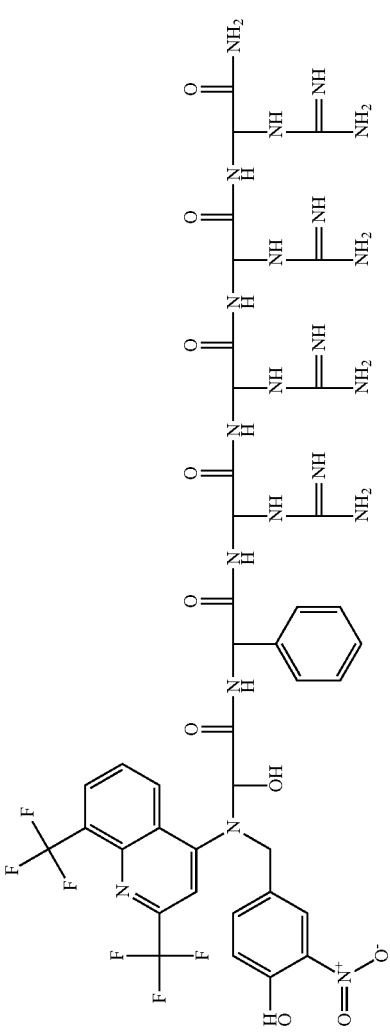 Compound 310 | C54H73F6N21O10 | 1290.2958 | <10% |
| 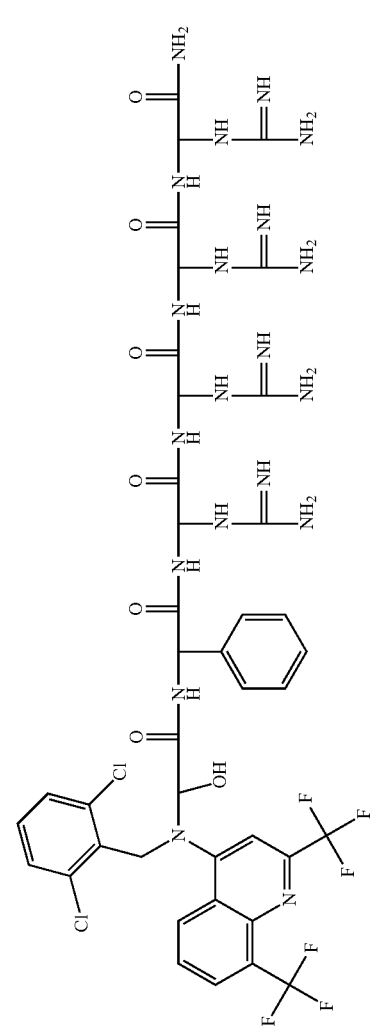 Compound 311 | C54H72Cl2F6N20O7 | 1298.189 | <10% |

| STRUCTURE | formula | mol weight | % |
|---|---|---|---|
| Compound 312 | C54H74F6N22O11 | 1321.3098 | <10% |
| Compound 313 | C54H74F6N22O12 | 1337.3092 | <10% |

| STRUCTURE | formula | mol weight | % |
|---|---|---|---|
| 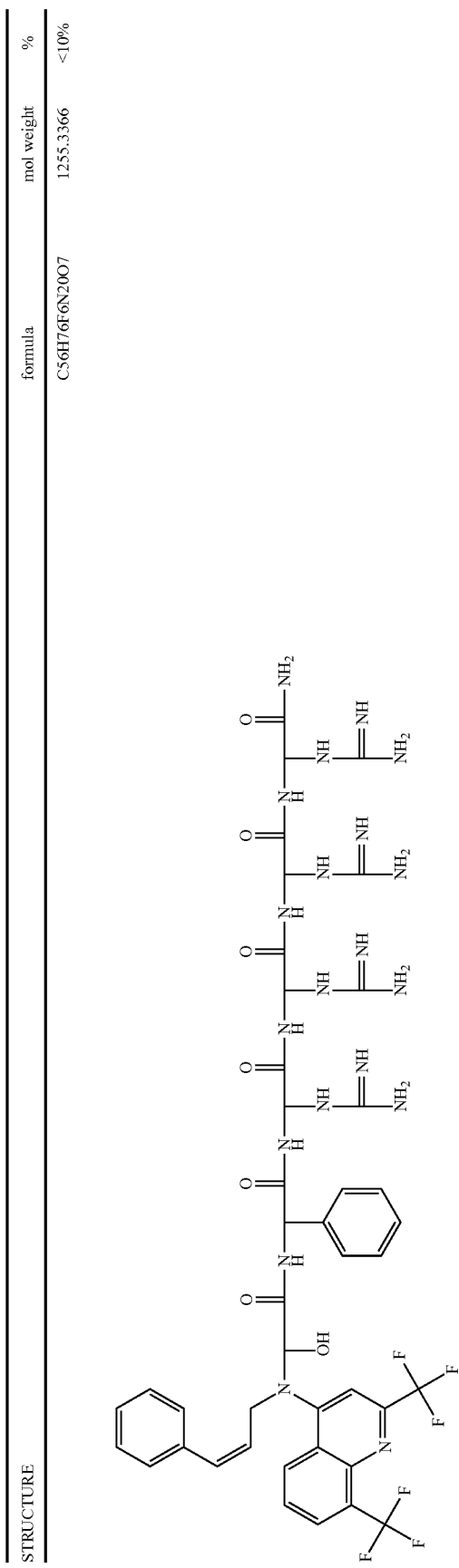 Compound 314 | C56H76F6N20O7 | 1255.3366 | <10% |
| 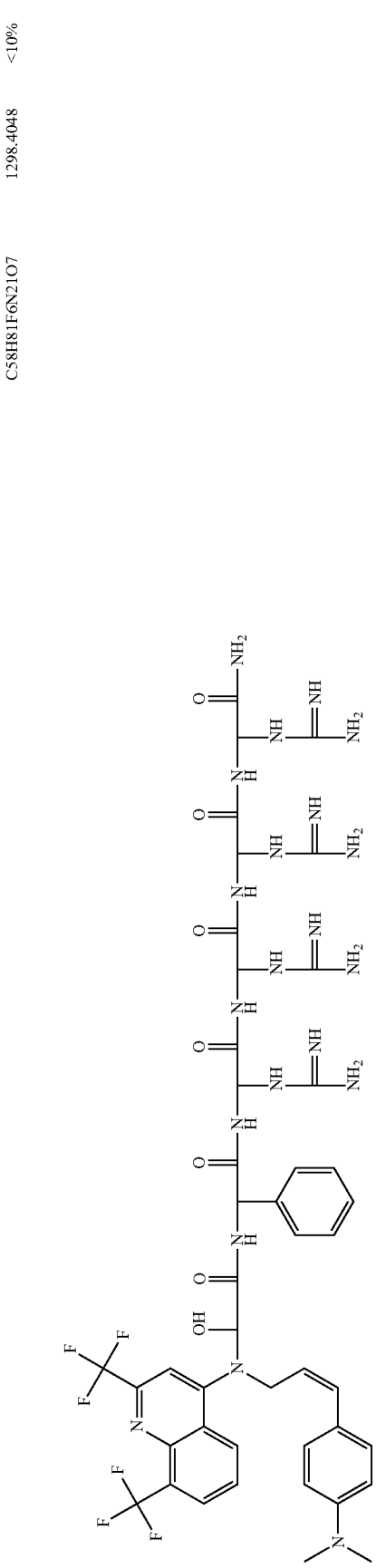 Compound 315 | C58H81F6N21O7 | 1298.4048 | <10% |

| STRUCTURE | formula | mol weight | % |
|---|---|---|---|
| 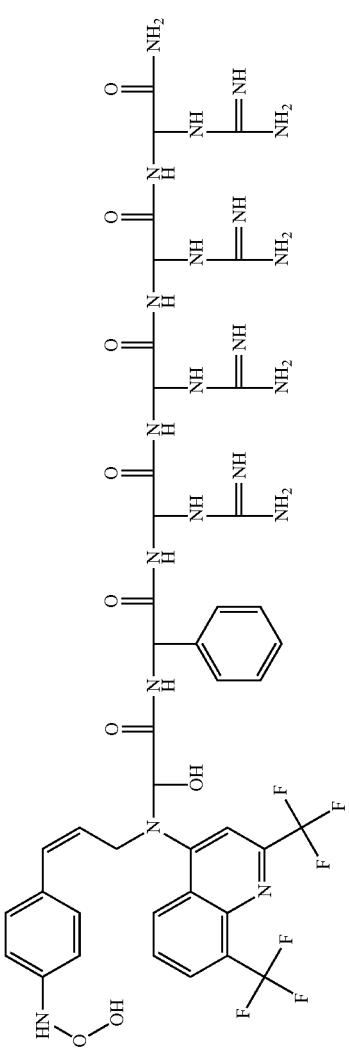 Compound 316 | C56H77F6N21O9 | 1302.35 | <10% |
| 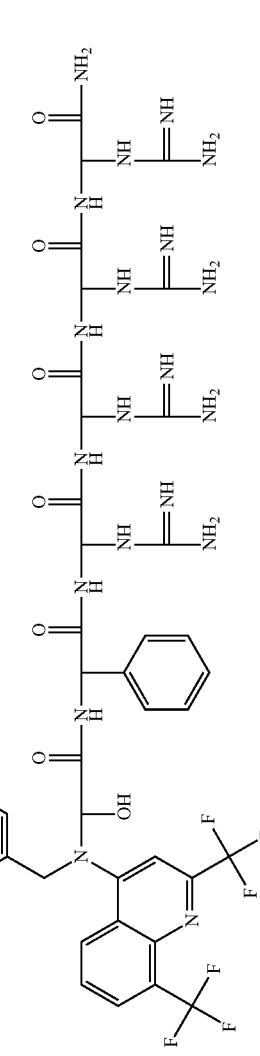 Compound 317 | C62H80F6N20O7 | 1331.4342 | <10% |

-continued

| STRUCTURE | formula | mol weight | % |
|---|---|---|---|
| Compound 318 | C58H76F6N20O8 | 1295.358 | <10% |
| Compound 319 | C64H80F6N20O7 | 1355.4562 | <10% |

| STRUCTURE | formula | mol weight | % |
|---|---|---|---|
| Compound 320 | C62H78F6N20O7 | 1329.4184 | <10% |
| Compound 321 | C62H78F6N20O7 | 1329.4184 | <10% |

| STRUCTURE | formula | mol weight | % |
|---|---|---|---|
| Compound 322 | C55H76F6N20O8 | 1259.325 | <10% |
| Compound 323 | C55H76F6N20O9 | 1275.3244 | <10% |

| STRUCTURE | formula | mol weight | % |
|---|---|---|---|
| 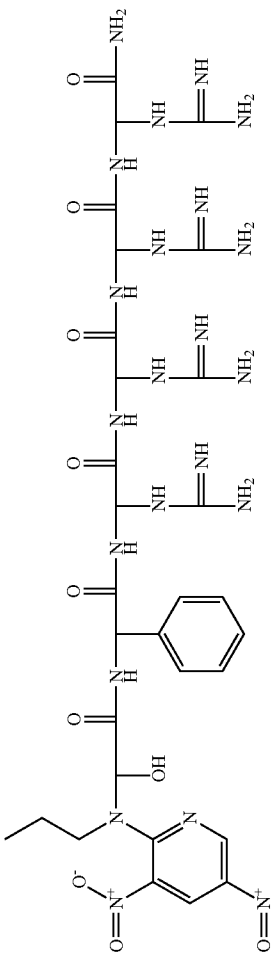 Compound 324 | C44H72N22O11 | 1085.1936 | <10% |
| 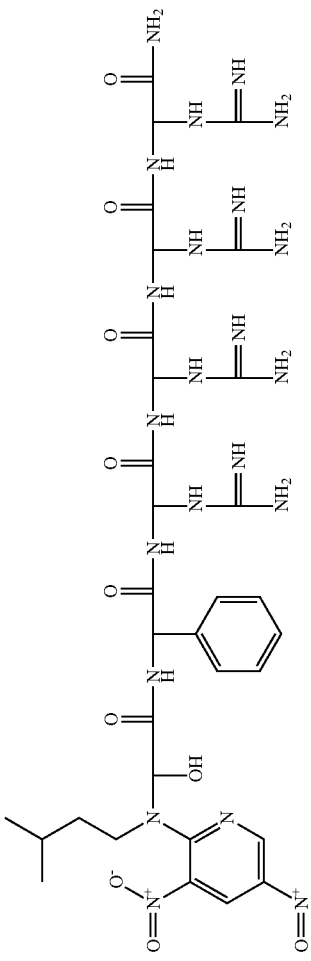 Compound 325 | C46H76N22O11 | 1113.2472 | <10% |

-continued

| STRUCTURE | formula | mol weight | % |
|---|---|---|---|
| Compound 326 | C47H78N22O11 | 1127.274 | <10% |
| Compound 327 | C48H72N22O12 | 1149.237 | <10% |

| STRUCTURE | formula | mol weight | % |
|---|---|---|---|
| Compound 328 | C50H76N22O13 | 1193.29 | <10% |
| Compound 329 | C50H77N23O12 | 1192.3052 | <10% |

| STRUCTURE | formula | mol weight | % |
|---|---|---|---|
| Compound 330 | C50H77N23O11 | 1176.3058 | <10% |
| Compound 331 | C48H73N23O13 | 1180.251 | <10% |

-continued

| STRUCTURE | formula | mol weight | % |
|---|---|---|---|
| Compound 332 | C48H71N23O13 | 1178.2352 | <10% |
| Compound 333 | C48H71H23O14 | 1194.2346 | <10% |

| STRUCTURE | formula | mol weight | % |
|---|---|---|---|
| Compound 334 | C48H70Cl2N22O11 | 1202.1278 | <10% |
| Compound 335 | C48H72N24O15 | 1225.2486 | <10% |

| STRUCTURE | formula | mol weight | % |
|---|---|---|---|
| Compound 336 | C48H72N24O16 | 1241.248 | <10% |
| Compound 337 | C50H74N22O11 | 1159.2754 | <10% |
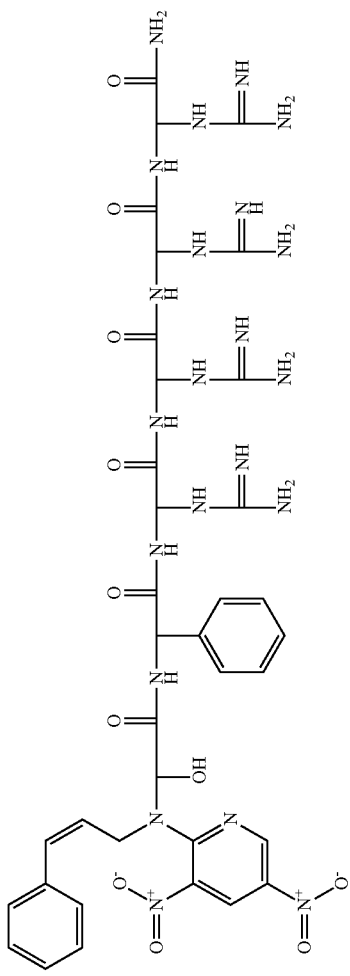

| STRUCTURE | formula | mol weight | % |
|---|---|---|---|
| 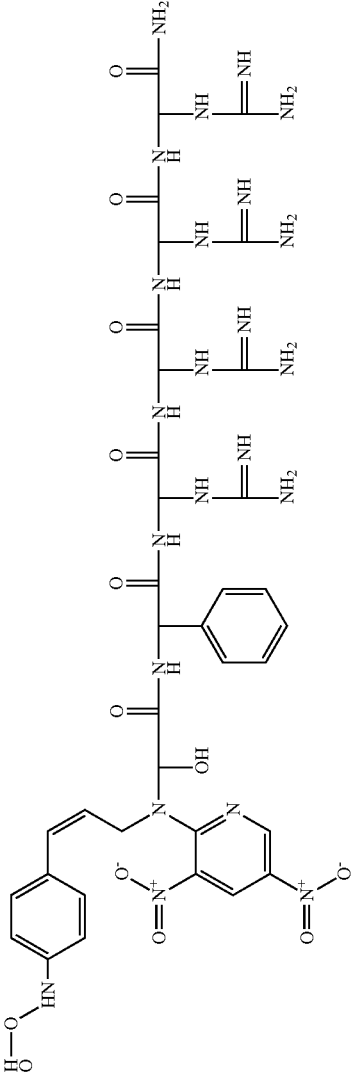 Compound 338 | C52H79N23O11 | 1202.3436 | <10% |
| 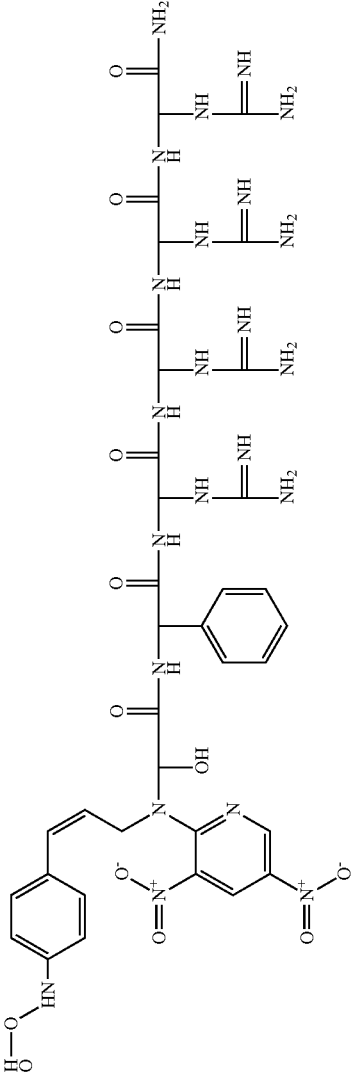 Compound 339 | C50H75N23O13 | 1206.2888 | <10% |

-continued
| STRUCTURE | formula | mol weight | % |
|---|---|---|---|
| 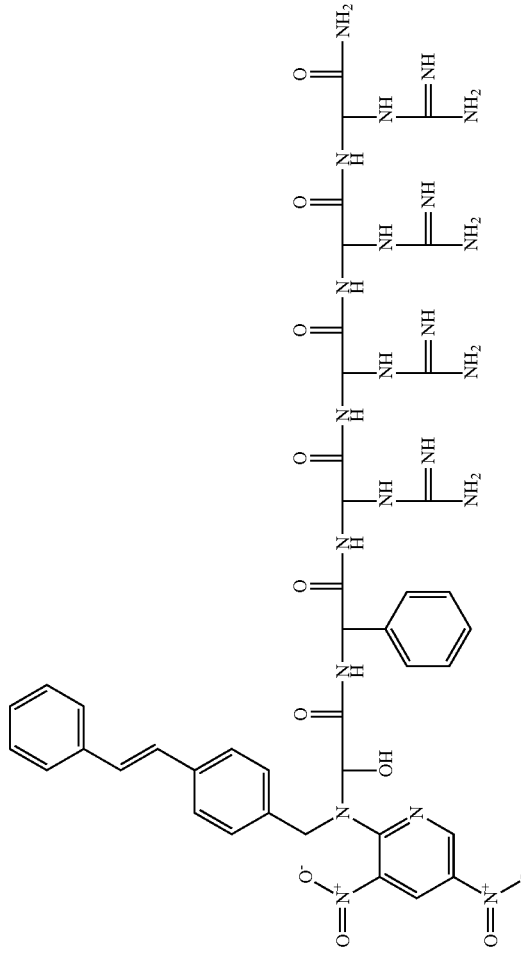 Compound 340 | C56H78N22O11 | 1235.373 | <10% |
| 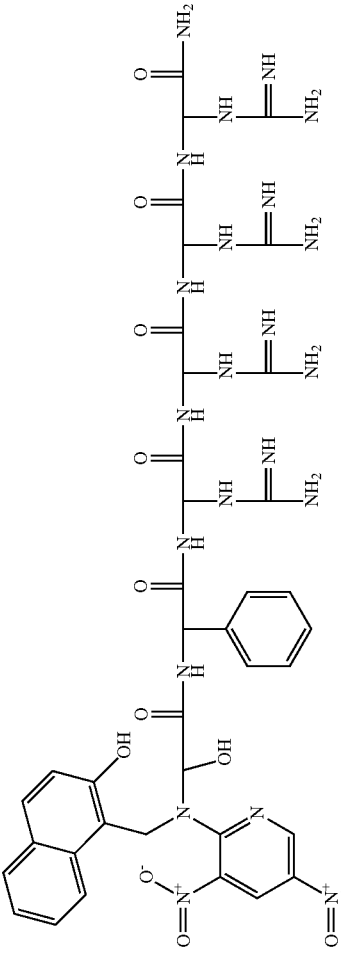 Compound 341 | C52H74N22O12 | 1199.2968 | <10% |

| STRUCTURE | formula | mol weight | % |
|---|---|---|---|
| -continued | | | |
| Compound 342 | C58H78N22O11 | 1259.395 | <10% |
| Compound 343 | C56H76N22O11 | 1233.3572 | <10% |
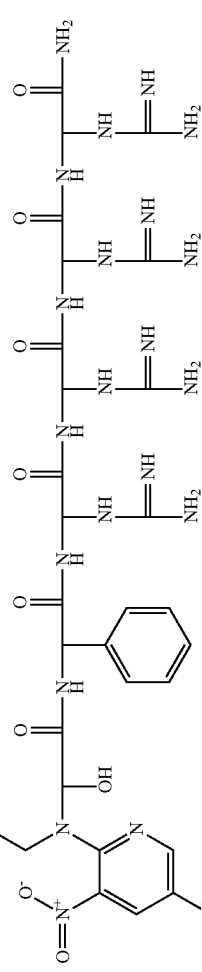
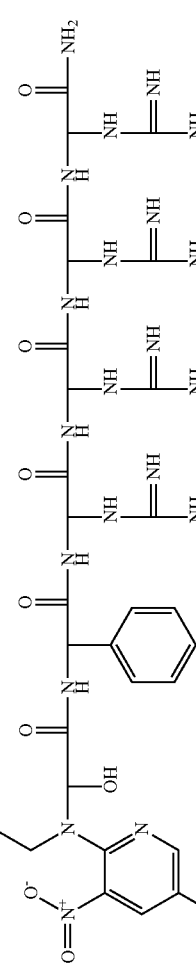

-continued

| STRUCTURE | formula | mol weight | % |
|---|---|---|---|
| Compound 344 | C56H76N22O11 | 1233.3572 | <10% |
| Compound 345 | C49H74N22O12 | 1163.2638 | <10% |

| STRUCTURE | formula | mol weight | % |
|---|---|---|---|
| Compound 346 | C49H74N22O13 | 1179.2632 | <10% |
| Compound 347 | C46H73F3N20O9 | 1107.2065 | <10% |

| STRUCTURE | formula | mol weight | % |
|---|---|---|---|
| 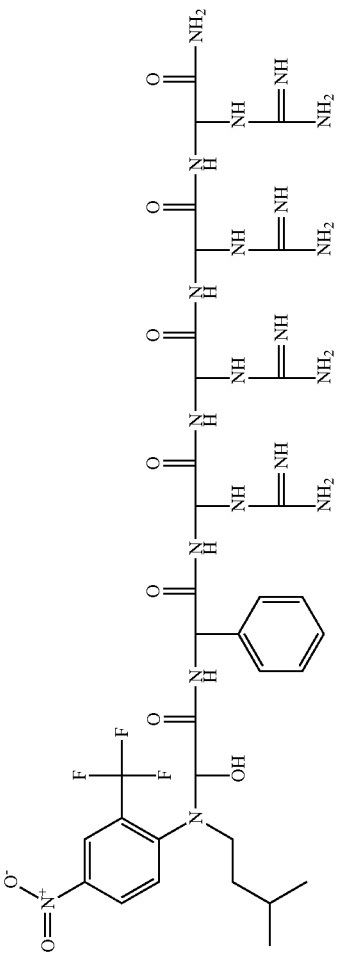 Compound 348 | C48H77F3N20O9 | 1135.2601 | <10% |
| 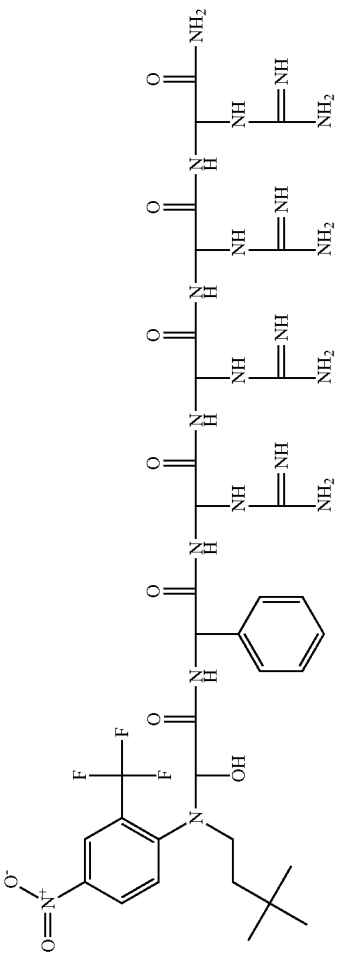 Compound 349 | C49H79F3N20O9 | 1149.2869 | <10% |

| STRUCTURE | formula | mol weight | % |
|---|---|---|---|
| 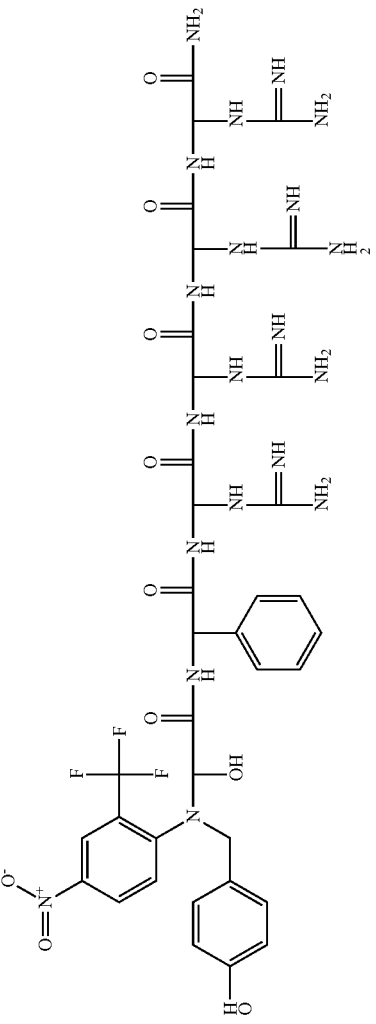
Compound 350 | C50H73F3N20O10 | 1171.2499 | <10% |
| 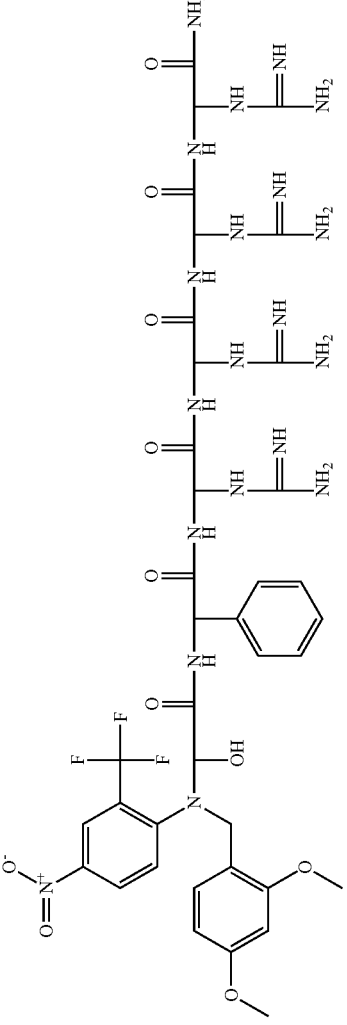
Compound 351 | C52H77F3N20O11 | 1215.3029 | <10% |

| STRUCTURE | formula | mol weight | % |
|---|---|---|---|
| Compound 352 | C52H78F3N21O10 | 1214.3181 | <10% |
| Compound 353 | C52H78F3N21O9 | 1198.3187 | <10% |

| STRUCTURE | formula | mol weight | % |
|---|---|---|---|
| Compound 354 | C50H74F3N21O11 | 1202.2639 | <10% |
| Compound 355 | C50H72F2N21O11 | 1200.2481 | <10% |

| STRUCTURE | formula | mol weight | % |
|---|---|---|---|
| Compound 356 | C50H72F3N21O12 | 1216.2475 | <10% |
| Compound 357 | C50H71Cl2F3N20O9 | 1224.1407 | <10% |

| STRUCTURE | formula | mol weight | % |
|---|---|---|---|
| Compound 358 | C50H73F3N22O13 | 1247.2615 | <10% |
| Compound 359 | C50H73F3N22O14 | 1263.2609 | <10% |

-continued

| STRUCTURE | formula | mol weight | % |
|---|---|---|---|
| Compound 360 | C52H75F3N20O9 | 1181.2883 | <10% |
| Compound 361 | C54H80F3N21O9 | 1224.3565 | <10% |

| STRUCTURE | formula | mol weight | % |
|---|---|---|---|
| Compound 362 | C52H76F3N21O11 | 1228.3017 | <10% |
| Compound 363 | C58H79F3N20O9 | 1257.3859 | <10% |

| STRUCTURE | formula | mol weight | % |
|---|---|---|---|
| 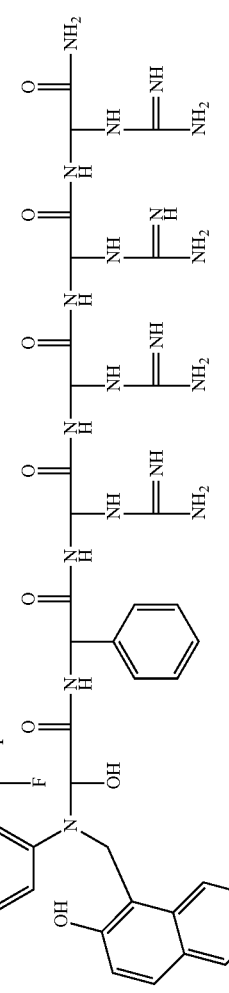
Compound 364 | C54H75F3N20O10 | 1221.3097 | <10% |
| 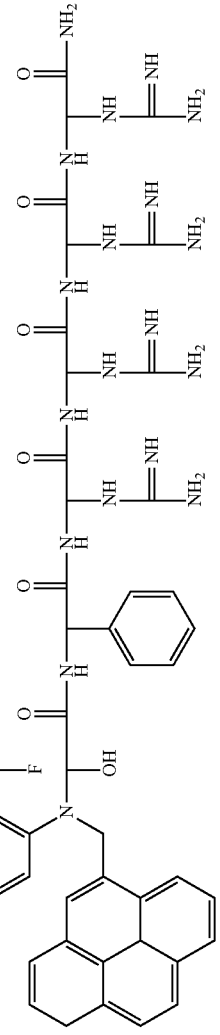
Compound 365 | C60H79F3N20O9 | 1281.4079 | <10% |

| STRUCTURE | formula | mol weight | % |
|---|---|---|---|
| 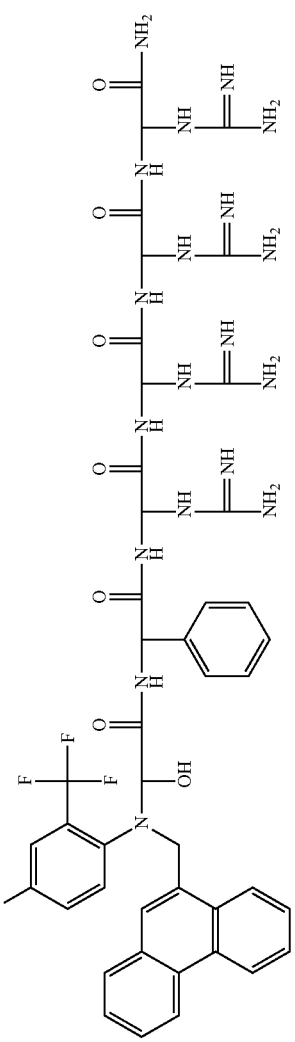 Compound 366 | C58H77F3N20O9 | 1255.3701 | <10% |
| 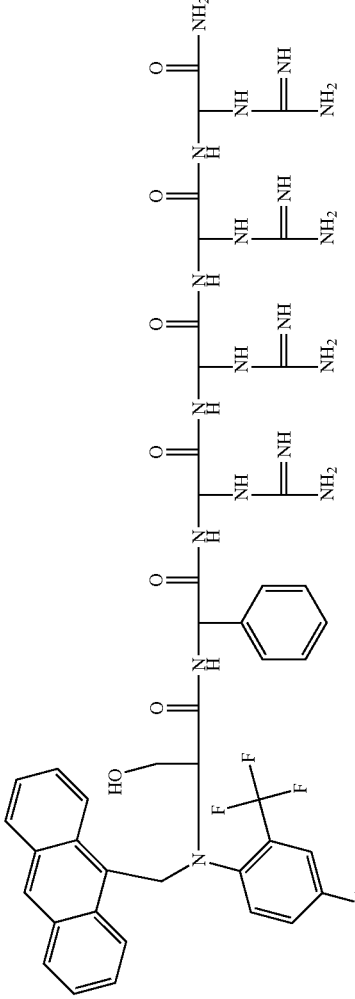 Compound 367 | C58H77F3N20O9 | 1255.3701 | <10% |

| STRUCTURE | formula | mol weight | % |
|---|---|---|---|
| Compound 368 | C51H75F3N20O10 | 1185.2767 | <10% |
| Compound 369 | C51H75F3N20O11 | 1201.2761 | <10% |

-continued

| STRUCTURE | formula | mol weight | % |
|---|---|---|---|
| Compound 370 | C45H73N21O11 | 1084.2058 | <10% |
| Compound 371 | C47H77N21O11 | 1112.2594 | <10% |

| STRUCTURE | formula | mol weight | % |
|---|---|---|---|
| Compound 372 | C48H79N21O11 | 1126.2862 | <10% |
| Compound 373 | C49H73N21O12 | 1148.2492 | <10% |

| STRUCTURE | formula | mol weight | % |
|---|---|---|---|
| Compound 374 | C51H77N21O13 | 1192.3022 | <10% |
| Compound 375 | C51H78N22O12 | 1191.3174 | <10% |

| STRUCTURE | formula | mol weight | % |
|---|---|---|---|
| Compound 376 | C51H78N22O11 | 1175.318 | <10% |
| Compound 377 | C49H74N22O13 | 1179.2632 | <10% |

-continued

| STRUCTURE | formula | mol weight | % |
|---|---|---|---|
| Compound 378 | C49H72N22O13 | 1177.2474 | <10% |
| Compound 379 | C49H72N22O14 | 1193.2468 | <10% |

-continued

| STRUCTURE | formula | mol weight | % |
|---|---|---|---|
| Compound 380 | C49H71Cl2N21O11 | 1201.14 | <10% |
| Compound 381 | C49H73N23O15 | 1224.2608 | <10% |

| STRUCTURE | formula | mol weight | % |
|---|---|---|---|
| Compound 382 | C49H73N23O16 | 1240.2602 | <10% |
| Compound 383 | C51H75N21O11 | 1158.2876 | <10% |

| STRUCTURE | formula | mol weight | % |
|---|---|---|---|
| Compound 384 | C53H80N22O11 | 1201.3558 | <10% |
| Compound 385 | C51H76N22O13 | 1205.301 | <10% |

| STRUCTURE | formula | mol weight | % |
|---|---|---|---|
| Compound 386 | C57H79N21O11 | 1234.3852 | <10% |
| Compound 387 | C53H75N21O12 | 1198.309 | <10% |

| STRUCTURE | formula | mol weight | % |
|---|---|---|---|
| 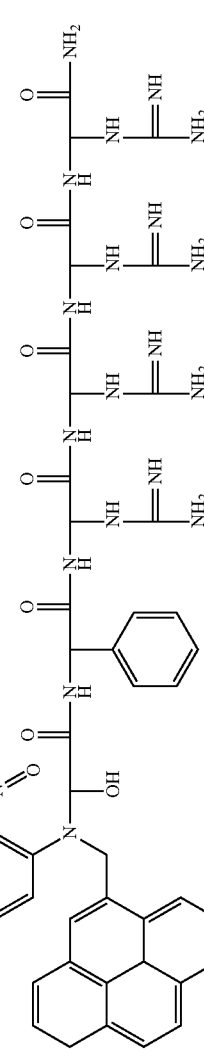
Compound 388 | C59H79N21O11 | 1258.4072 | <10% |
| 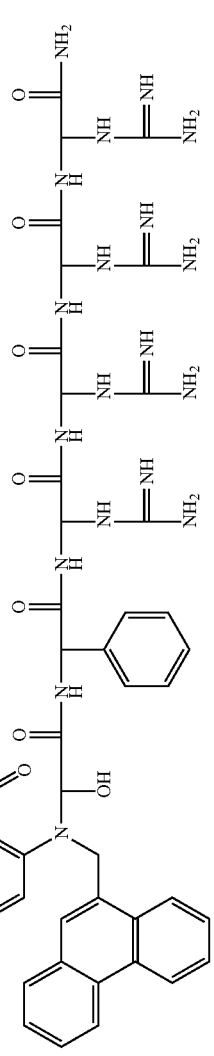
Compound 389 | C57H77N21O11 | 1232.3694 | <10% |

-continued

| STRUCTURE | formula | mol weight | % |
|---|---|---|---|
| Compound 390 | C57H77N21O11 | 1232.3694 | <10% |
| Compound 391 | C50H75N21O12 | 1162.276 | <10% |

| STRUCTURE | formula | mol weight | % |
|---|---|---|---|
| 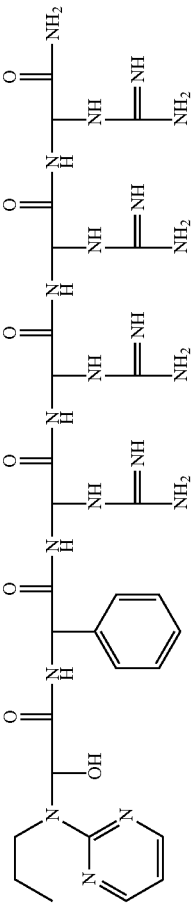 Compound 392 | C50H75N21O13 | 1178.2754 | <10% |
| 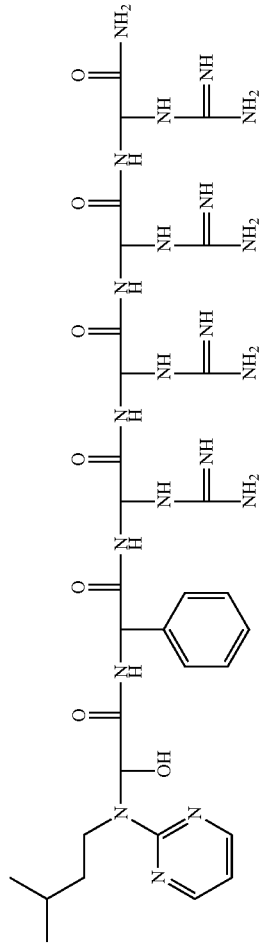 Compound 393 | C43H73N21O7 | 996.1862 | <10% |
| Compound 394 | C45H77N21O7 | 1024.2398 | <10% |

| STRUCTURE | formula | mol weight | % |
|---|---|---|---|
| Compound 395 | C46H79N21O7 | 1038.2666 | <10% |
| Compound 396 | C47H73N21O8 | 1060.2296 | <10% |
| Compound 397 | C49H77N21O9 | 1104.2826 | <10% |

| STRUCTURE | formula | mol weight | % |
|---|---|---|---|
| Compound 398 | C49H78N22O8 | 1103.2978 | <10% |
| Compound 399 | C49H78N22O7 | 1087.2984 | <10% |
| Compound 400 | C47H74N22O9 | 1091.2436 | <10% |

-continued

| STRUCTURE | formula | mol weight | % |
|---|---|---|---|
| Compound 401 | C47H72N22O9 | 1089.2278 | <10% |
| Compound 402 | C47H72N22O10 | 1105.2272 | <10% |
| Compound 403 | C47H71Cl2N21O7 | 1113.1204 | <10% |

-continued
| STRUCTURE | formula | mol weight | % |
|---|---|---|---|
| 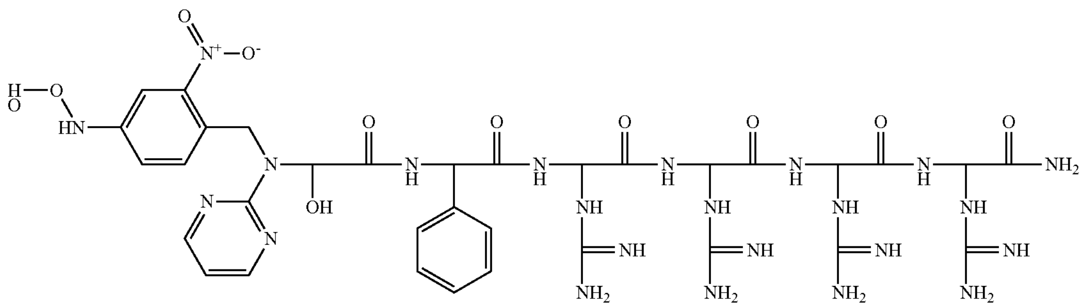 | C47H73N23O11 | 1136.2412 | <10% |
| Compound 404 | C47H73N23O12 | 1152.2406 | <10% |
| Compound 405 | C49H75N21O7 | 1070.268 | <10% |
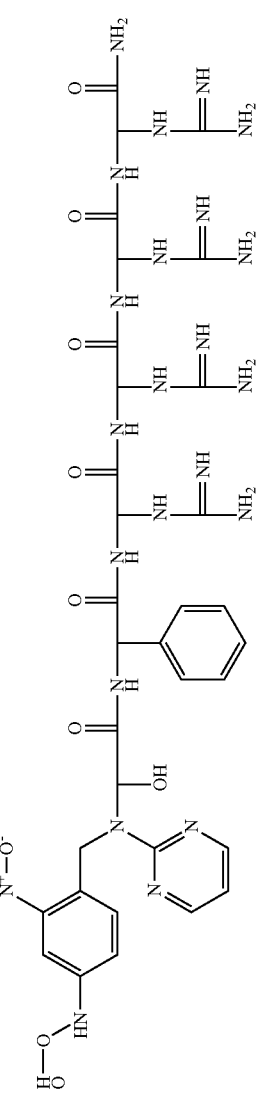

-continued

| STRUCTURE | formula | mol weight | % |
|---|---|---|---|
| Compound 406 | C51H80N22O7 | 1113.3362 | <10% |
| Compound 407 | C49H76N22O9 | 1117.2814 | <10% |
| Compound 408 | | | |

-continued

| STRUCTURE | formula | mol weight | % |
|---|---|---|---|
| Compound 409 | C55H79N21O7 | 1146.3656 | <10% |
| Compound 410 | C51H75N21O8 | 1110.2894 | <10% |
| Compound 411 | C57H79N21O7 | 1170.3876 | <10% |

-continued

| STRUCTURE | formula | mol weight | % |
|---|---|---|---|
| Compound 412 | C55H77N21O7 | 1144.3498 | <10% |
| Compound 413 | C55H77N21O7 | 1144.3498 | <10% |

| STRUCTURE | formula | mol weight | % |
|---|---|---|---|
| Compound 414 | C48H75N21O8 | 1074.2564 | <10% |
| Compound 415 | C48H75N21O9 | 1090.2558 | <10% |

Example II

1. Materials, Methods, and Detailed Synthesis of Compounds

General Procedures. For all compounds, $^1$H NMR, $^{13}$C NMR and $^{19}$F NMR spectra were recorded on a Bruker AC-300 (300 MHz) NMR spectrometer. Proton and carbon chemical shifts are reported relative to TMS using either TMS or the residue solvent signal as internal standard. Carbon NMRs are proton-decoupled, and coupling constants to fluorine are not reported. Fluorine chemical shifts are reported relative to $CF_3COOH$ (−78.5 ppm) as an external standard. Electrospray mass spectra (ESI) data were obtained from the Laboratory for Macromolecular Analysis and Proteomics of the Albert Einstein College of Medicine. All moisture and air sensitive experiments were performed under a positive pressure of $N_2$ or Ar in oven dried glassware. Reagent and anhydrous solvents were bought from Aldrich Chemical Company and used without further purification.

The numbering of compounds in Example II is independent of the numbering used in Examples I and III.

Synthesis of 1,3-Dimethoxy-4-fluorobenzene (3). Synthesis was carried out using the procedures describe in Wei-Chuan Sun et al.[52]

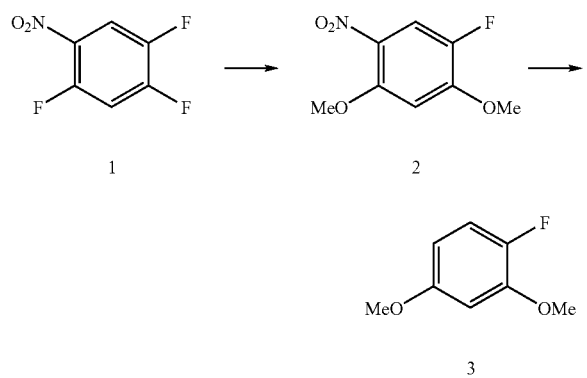

Synthesis of 5-Fluoro-2,4-dimethoxy-benzonitrile (5). Sodium methoxide (25% wt in MeOH, 32 mL) was added dropwise to a solution of 2,4,5-trifluorobenzonitrile (10 g, 63.7 mmol) in MeOH (160 mL) under nitrogen at 0° C. The resulting reaction mixture was stirred at reflux for 48 h. The reaction was then quenched with 1 M citric acid and the MeOH was removed in vacuo. The residue was taken up in EtOAc, washed with brine, dried over $Na_2SO_4$, concentrated in vacuo and recrystallized from EtOAc/hexane to furnish the desired product in 95% yield (11 g). $^1$H NMR (300 MHz, $CDCl_3$) δ 7.25 (d, 1H, J=10.2 Hz), 6.52 (d, 1H, J=6.8 Hz), 3.97 (s, 3H), 3.93 (s, 3H); $^{13}$C NMR (75 MHz, $CDCl_3$) δ 159.3, 159.2, 152.8, 152.6, 147.6, 144.4, 119.8, 119.5, 115.8, 115.7, 97.4, 97.3, 92.1, 92.0, 56.6, 56.5; $^{19}$F NMR (282 MHz, $CDCl_3$) δ −143.4 (dd, 1 F); mass spectrum, calculated for $C_9H_8FNO_2$ (MH$^+$) 182.1, Found 182.1.

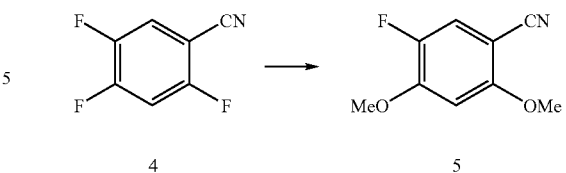

5-Fluoro-2,4-dimethoxy-benzoic acid (6). A solution of 3.1 g (17.2 mmol) of 2,4-dimethoxy-5-fluorobenzonitrile and 100 mL of 6N aqueous sodium hydroxide in 200 mL of methanol was stirred at reflux overnight, cooled to 0° C., acidified to pH 1-2 with 6N aqueous hydrochloric acid, and partitioned between ethyl acetate and brine. The organic extract was dried over $Na_2SO_4$, and the solvents were removed in vacuo to give crude 2,4-dimethoxy-5-fluorobenzoic acid as a light-yellow solid. Recrystallization from ethyl acetate and hexane afforded 3.2 g (93%) of 6 as a white solid. $^1$H NMR (300 MHz, DMSO-$d_6$) δ 12.4 (s, 1H), 7.49 (d, 1H, J=12 Hz), 6.83 (d, 1H, J=7.2 Hz), 3.92 (s, 3H), 3.84 (s, 3H); $^{13}$C NMR (75 MHz, DMSO-$d_6$) δ 165.5, 165.5, 156.7, 151.1, 151.0, 146.3, 143.2, 117.9, 117.6, 111.2, 111.1, 99.3, 56.6, 56.4; $^{19}$F NMR (282 MHz, DMSO-$d_6$) δ −146.2 (dd, 1F); mass spectrum, calculated for $C_9H_9FO_4$ (MH$^+$) 201.1, Found 200.9.

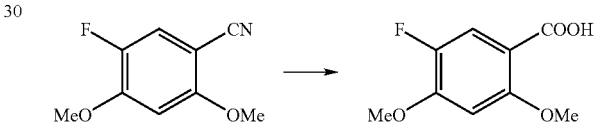

5,5'-difluoro-2, 2',4,4'-tetrahydroxybenzophenone (7). 2,4-dimethoxy-5-fluorobenzoic acid 6 (5.4 g, 27 mmol) in dry $CH_2Cl_2$ (100 mL) was treated with 10.6 mL of oxalyl chloride under an Ar atmosphere and stirred at room temperature overnight. The excess reagent and solvent were removed under reduced pressure. The residue, 2,4-dimethoxy-5-fluorobenzoyl chloride, was redissolved in anhydrous $CH_2Cl_2$ (125 mL). 1,3-dimethoxy-4-fluorobenzene 3 (3.29 mL, 26 mmol) and $AlCl_3$ (10.8 g, 81 mmol) were added at 0° C. After stirring at 0° C. for 1 h, the reaction mixture was allowed to warm to room temperature for 67 h, the mixture was then hydrolyzed with 1M HCl (300 mL) at 0° C. and extracted with EtOAc. The combined organic layers were washed with brine, dried over $Na_2SO_4$ and concentrated in vacuo. The crude product was purified by flash column chromatography, eluting with 30%-40% EtOAc in hexane to yield 7 (3.3 g, 44%) as a yellow solid. $^1$H NMR (300 MHz, MeOH-$d_4$) 7.14 (d, 2H, J=11.5 Hz), 6.46 (d, 2H, J=7.4 Hz); $^{13}$C NMR (75 MHz, MeOH-$d_4$) δ 199.1, 159.0, 152.9, 152.7, 147.7, 144.5, 119.2, 118.9, 114.2, 114.1, 106.1, 106.0; $^{19}$F NMR (282 MHz, MeOH-$d_4$). δ −149.8 (dd, 2F).

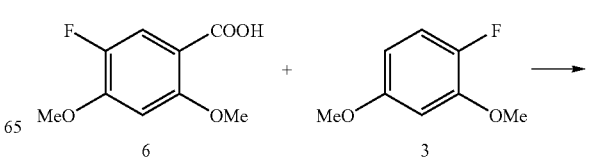

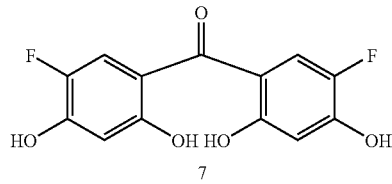

7

2,7-Difluoro-3,6-dihydroxy-xanthen-9-one (8).

Compound 7 (0.75 g, 2.66 mmol) was heated in a sealed tube with $H_2O$ (30 mL) at 200-220 0° C. for 2-3 h. On cooling, 2,7-difluoro-3,6-dihydroxyxanthone 8 precipitated out. The product was collected by filtration and washed with $H_2O$ to give 8 (0.58 g, 83%) as a light yellow solid. $^1$H NMR (300 MHz, DMSO-$d_6$) δ 11.4 (s, 2H), 7.67 (d, 2H, J=10.9 Hz), 6.96 (d, 2H, J=7.1 Hz); $^{13}$C NMR (75 MHz, DMSO-$d_6$) δ 173.1, 153.1, 152.0, 151.8, 150.4, 147.2, 112.6, 112.5, 111.1, 110.8, 104.7, 104.6; $^{19}$F NMR (282 MHz, DMSO-$d_6$) δ −139.0 (dd, 2F); mass spectrum, calculated for $C_{13}H_6F_2O_4$ (MH$^+$) 265.0, Found 264.9.

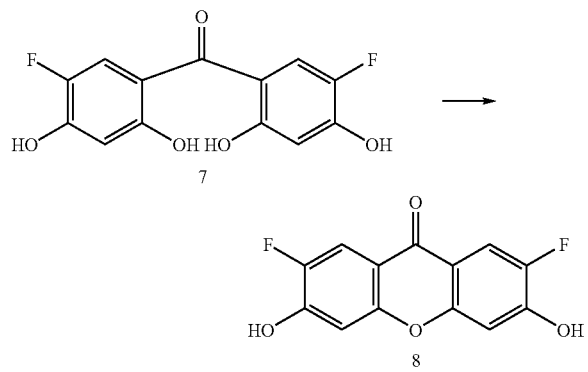

2,7-Difluoro-3,6-bis-(2-methoxyethoxymethoxy)-xanthen-9-one (9).

A cloudy solution of 8 (2.4 g, 9.1 mmol) in dry THF (50 mL) was treated with sodium hydride (1.1 g, 45.8 mmol) at 0° C. under an Ar atmosphere. The mixture was stirred at 0° C. for 30 min and then 2-methoxyethoxymethyl chloride (5.2 mL, 45.8 mmol) was added. The mixture was stirred at 0° C. for an additional 30 min and then warmed to room temperature overnight. The reaction mixture was cooled to 0° C., quenched with 1M citric acid (50 mL), and then extracted with EtOAc. The combined organic layers were washed with brine, dried over $Na_2SO_4$ and concentrated in vacuo. The crude product was purified by flash column chromatography, eluting with $CH_2Cl_2$/hexane/EtOAc=1:1:0.4 to yield 2.6 g (65%) of 9 as a white solid. $R_f$=0.47 (in $CH_2Cl_2$/hexane/EtOAc=1:1:0.4); $^1$H NMR (300 MHz, CDCl$_3$) δ 7.91 (d, 2H, J=10.6 Hz), 7.28 (d, 2H, J=6.5 Hz), 5.46 (s, 4H), 3.91 (m, 4H), 3.60 (m, 4H), 3.39 (s, 6H); $^{13}$C NMR (75 MHz, CDCl$_3$) δ 174.4, 153.3, 153.2, 151.4, 151.0, 150.9, 148.2, 115.2, 115.1, 111.8, 111.6, 104.8, 94.2, 71.3, 68.6, 59.0; $^{19}$F NMR (282 MHz, CDCl$_3$) δ −137.0 (dd, 2 F); mass spectrum, calculated for $C_{21}H_{22}F_2O_8$ (MH$^+$) 441.1, Found 441.0.

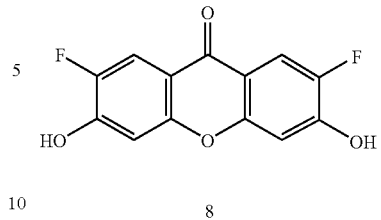

8

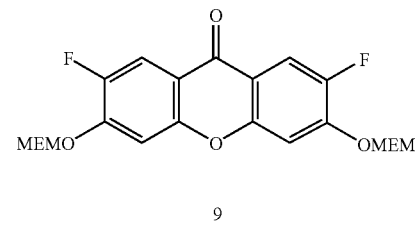

9

[tert-Butoxycarbonylmethyl-(2-hydroxy-phenyl)-amino]-acetic acid tert-butyl ester (11).

A solution of 2-aminophenol (10) (5.0 g, 45.8 mmol) and NaI (3.44 g, 23 mmol) in dry $CH_3CN$ (150 mL) was treated with 1,8-bis(dimethylamino) naphthalene (21.6 g, 100.8 mmol) followed by t-butyl bromoacetate (14.2 mL, 96.2 mmol) under an Ar atmosphere and stirred at reflux overnight. After the mixture was cooled to room temperature, the precipitated salts were filtered off and washed with additional EtOAc. The combined organic layers were washed with brine, dried over $Na_2SO_4$ and concentrated in vacuo. The crude product was purified by flash column chromatography, eluting with $CH_2Cl_2$/hexane/EtOAc=1:4:0.2 to yield 12.3 g (80%) of the desired product (11) as a light yellow oil. $R_f$=0.3 (in $CH_2Cl_2$/hexane/EtOAc=1:4:0.2); $^1$H NMR (300 MHz, CDCl$_3$) δ 7.29 (dd, 7.9 and 1.5 Hz, 1H), 7.07 (m, 1H), 6.94 (dd, 8.1 and 1.5 Hz, 1H), 6.79 (m, 1H), 5.30 (s, 1H), 3.74 (s, 4H), 1.46 (s, 18H); $^{13}$C NMR (75 MHz, CDCl$_3$) δ 171.2, 153.6, 137.4, 127.3, 126.0, 119.9, 115.6, 81.9, 57.0, 28.0; mass spectrum, calculated for $C_{18}H_{27}NO_5$ (MH$^+$) 338.2, Found 337.9.

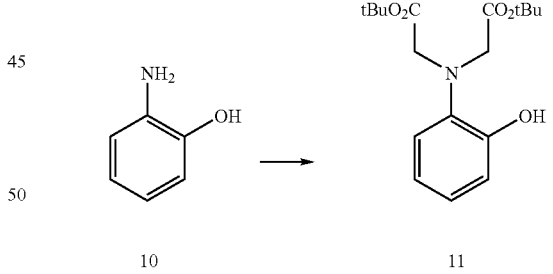

10                                  11

[(2-Benzyloxy-phenyl)-tert-butoxycarbonylmethyl-amino]-acetic acid tert-butyl ester (12).

A solution of [tert-Butoxycarbonylmethyl-(2-hydroxy-phenyl)-amino]-acetic acid tert-butyl ester (11) (7.4 g, 21.9 mmol) in dry THF (50 mL) was treated with sodium hydride (0.81 g, 33.8 mmol) at 0° C. under an Ar atmosphere. After stirring at 0° C. for 30 min, benzyl bromide (3.9 mL, 32.7 mmol) was added. The mixture was stirred at 0° C. for another 30 min and then warmed to room temperature overnight. The reaction mixture was quenched with $H_2O$ and extracted with EtOAc. The combined organic layers were washed with brine, dried over $Na_2SO_4$ and concentrated in vacuo. The crude product was purified by flash column chromatography, eluting with CH$_2$Cl$_2$/hexane/EtOAc=1:4:0.2 to yield 6.3 g (67%) of the desired product 12 as a colorless oil. R$_f$=0.33 (in CH$_2$Cl$_2$/hexane/EtOAc=1:4:0.2); $^1$H NMR (300 MHz, CDCl$_3$) δ 7.45-7.28 (m, 5H), 6.84 (m, 4H), 5.12 (s, 2H), 4.08 (s, 4H), 1.40 (s, 18H); $^{13}$C NMR (75 MHz, CDCl$_3$) δ 170.5, 150.5, 139.6, 137.5, 128.4, 127.6, 127.2, 121.9, 121.4, 119.4, 114.7, 81.0, 70.9, 54.6, 28.0; mass spectrum, calculated for C$_{25}$H$_{33}$NO$_5$ (MH$^+$) 428.2, Found 427.9.

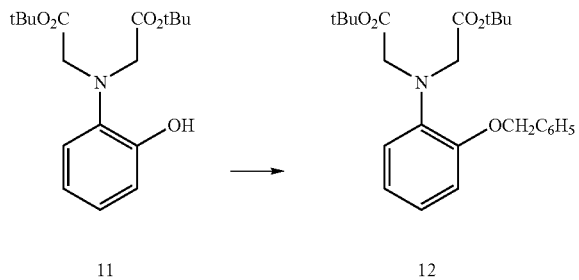

11      12

[(2-Benzyloxy-4-bromo-phenyl)-tert-butoxycarbonylmethyl-amino]-acetic acid tert-butyl ester (13). To a −78° C. solution of [(2-Benzyloxy-phenyl)-tert-butoxycarbonylmethyl-amino]-acetic acid tert-butyl ester (6.3 g, 14.7 mmol) in CH$_2$Cl$_2$ (100 mL) was added pyridine (1.8 mL, 22.1 mmol) followed by bromine (0.91 mL, 17.6 mmol) under an Ar atmosphere. After 30 min, the mixture was allowed to warm to room temperature and then washed with water, 5% sodium bicarbonate, and brine. The organic layer was dried over Na$_2$SO$_4$ and concentrated in vacuo. The crude product was purified by flash column chromatography, eluting with CH$_2$Cl$_2$/hexane/EtOAc=1:4:0.2 to yield 5.9 g (79%) of 13 as a white solid. R$_f$=0.43 (in CH$_2$Cl$_2$/hexane/EtOAc=1:4:0.2); $^1$H NMR (300 MHz, CDCl$_3$) δ 7.45-7.26 (m, 5H), 6.99 (m, 2H), 6.73 (m, 1H), 5.09 (s, 2H), 4.04 (s, 4H), 1.41 (s, 18H); $^{13}$C NMR (75 MHz, CDCl$_3$) δ 170.1, 151.1, 138.7, 136.6, 128.6, 127.9, 127.4, 124.1, 120.5, 117.6, 113.7, 81.2, 71.2, 54.5, 28.0; mass spectrum, calculated for C$_{25}$H$_{32}$BrNO$_5$ (MH$^+$) 506.2, Found 505.8.

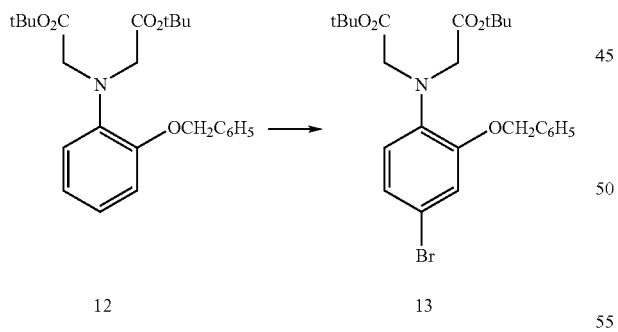

12      13

({2-Benzyloxy-4-[2,7-difluoro-9-hydroxy-3,6-bis-(2-methoxyethoxymethoxy)-9H xanthen-9-yl]-phenyl}-tert-butoxycarbonylmethyl-amino)-acetic acid tert-butyl ester (14). The bromide 13 (807 mg, 1.59 mmol) was dissolved in 20 mL THF/2-methyltetrahydrofuran (1:1) and cooled to −105° C. in a liquid N$_2$/diethyl ether bath. After stirring at −105° C. for 10 min, 4.5 mL of tert-butyllithium (1.1 M in pentanes) was added dropwise. Stirring was continued for another 15 min. 2,7-difluoro-3,6-bis-(2-methoxyethoxymethoxy)-xanthen-9-one 9 (912 mg, 2.07 mmol) dissolved in THF (10 mL) was added dropwise to the reaction mixture. The mixture was stirred at −105° C. for 30 min, the cooling bath removed, and the reaction solution was then stirred for an additional 15 min. The resulting mixture was added to 150 mL NH$_4$Cl(sat) and extracted twice with EtOAc. The combined organic layers were washed with brine, dried over Na$_2$SO$_4$ and concentrated in vacuo. The crude product was purified by flash column chromatography, eluting with 50% EtOAc in hexane (with 0.1% Et$_3$N) to yield 956 mg (69%) of 14 as a orange-red oil. R$_f$=0.33 (in 50% EtOAc/hexane); $^1$H NMR (300 MHz, CDCl$_3$) δ 7.32-7.27 (m, 5H), 6.97 (d, 2H, J=6.98 Hz), 6.86 (m, 3H), 6.72 (m, 2H), 5.30 (s, 4H), 5.05 (s, 2H), 4.02 (s, 4H), 3.85 (m, 4H), 3.56 (m, 4H), 3.36 (s, 6H), 1.38 (s, 18H); $^{13}$C NMR (75 MHz, CDCl$_3$) δ 170.5, 150.8, 149.3, 147.6, 145.6, 145.5, 145.4, 145.2, 140.5, 138.4, 136.9, 128.3, 127.7, 127.5, 119.9, 119.8, 119.3, 118.4, 115.2, 114.9, 113.0, 104.9, 94.5, 81.0, 71.4, 70.6, 69.7, 68.1, 58.9, 54.6, 28.0; 19F NMR (282 MHz, CDCl$_3$) δ −139.0 (dd, 2 F); mass spectrum, calculated for C$_{46}$H$_{55}$F$_2$NO$_{13}$ (MH$^+$) 868.4, Found 867.8.

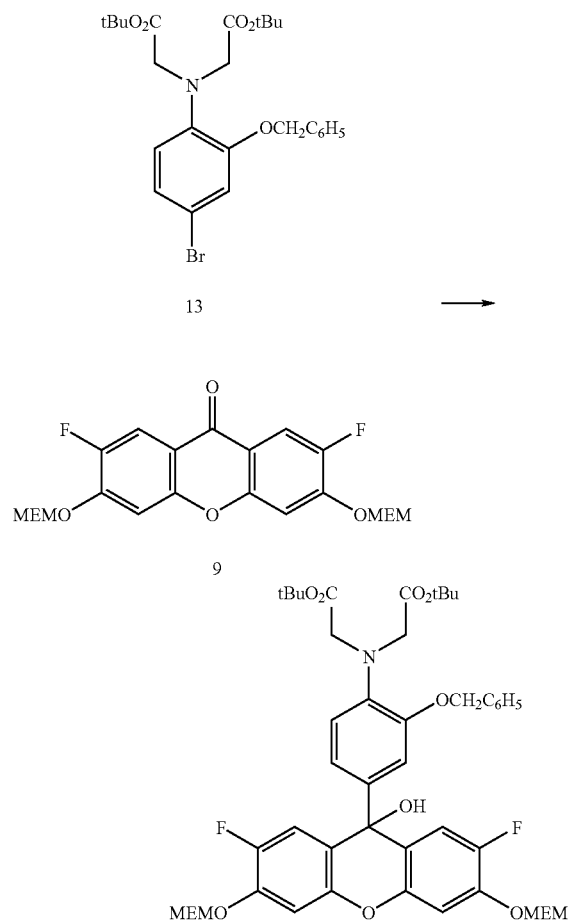

(tert-Butoxycarbonylmethyl-{4-[2,7-difluoro-9-hydroxy-3,6-bis-(2-methoxyethoxymethoxy)-9H-xanthen-9-yl]-2-hydroxy-phenyl}-amino)-acetic acid tert-butyl ester (15). To a solution of 14 (956 mg, 1.1 mmol) in 95% ethanol (25 mL) and EtOAc (25 mL) was added 10% Pd/C (130 mg). The resulting mixture was stirred at room temperature overnight under H$_2$ (1 atm). The catalyst was then removed by filtration and, after evaporation to dryness, the crude product was purified by flash column chromatography, eluting with 40% EtOAc in hexane (with 0.1% Et$_3$N) to yield 671 mg (78%) of 15 as a light yellow oil. R$_f$=0.3 (in 40% EtOAc/hexane); $^1$H NMR (300 MHz, CDCl$_3$) δ 8.1 (s, 1H), 7.18 (d, 1H, J=8.0 Hz), 6.95 (d, 2H, J=7.2 Hz), 6.69 (m, 3H), 6.57 (m, 1H), 5.28 (s, 4H), 4.94 (s, 1H), 3.85 (m, 4H), 3.69 (s, 4H), 3.57 (m, 4H), 3.38 (s, 6H), 1.41 (s, 18H); $^{13}$C NMR (75 MHz, CDCl$_3$) δ 171.2, 153.8, 150.6, 147.4, 146.5, 144.8, 144.4, 144.2, 136.3, 126.3, 119.6, 116.7, 116.6, 116.1, 115.8, 115.5, 105.9, 94.6, 81.9, 71.4, 68.0, 59.0, 56.9, 43.1, 27.9; $^{19}$F NMR (282 MHz, CDCl$_3$) δ −140.4 (dd, 2 F); mass spectrum, calculated for C$_{46}$H$_{55}$F$_2$NO$_{13}$ (M−17) 761.3, Found 761.7.

dried over Na$_2$SO$_4$ and concentrated in vacuo. The crude product was purified by flash column chromatography, eluting with 40% EtOAc in Hexane (with 0.1% Et$_3$N) to yield 453 mg (76%) of 16 as a light yellow oil. R$_f$=0.28 (in 40% EtOAc/hexane); $^1$H NMR (300 MHz, CDCl$_3$) δ 7.32 (m, 5H), 6.96 (d, 2H, J=7.2 Hz), 6.86 (d, 1H, J=8.4 Hz), 6.72 (dd, 1H, J=7.8 and 1.5 Hz), 6.59 (m, 3H), 5.28 (s, 4H), 5.15 (s, 2H), 4.89 (s, 1H), 4.64 (s, 2H), 4.01 (s, 4H), 3.86 (m, 4H), 3.58 (m, 4H), 3.39 (s, 6H), 1.39 (s, 18H); $^{13}$C NMR (75 MHz, CDCl$_3$) 6170.3, 168.8, 150.7, 149.9, 147.5, 146.6, 146.5, 144.4, 144.3, 139.1, 138.9, 135.3, 128.6, 128.4, 128.3, 122.9, 120.0, 117.0, 116.9, 116.2, 116.1, 115.8, 105.9, 94.7, 81.2, 71.5, 68.1, 66.7, 66.6, 59.0, 54.5, 42.6, 28.0; $^{19}$F NMR (282 MHz, CDCl$_3$) δ −140.2 (dd, 2 F); mass spectrum, calculated for C$_{46}$H$_{55}$F$_2$NO$_{13}$ (M−17) 909.4, Found 910.1.

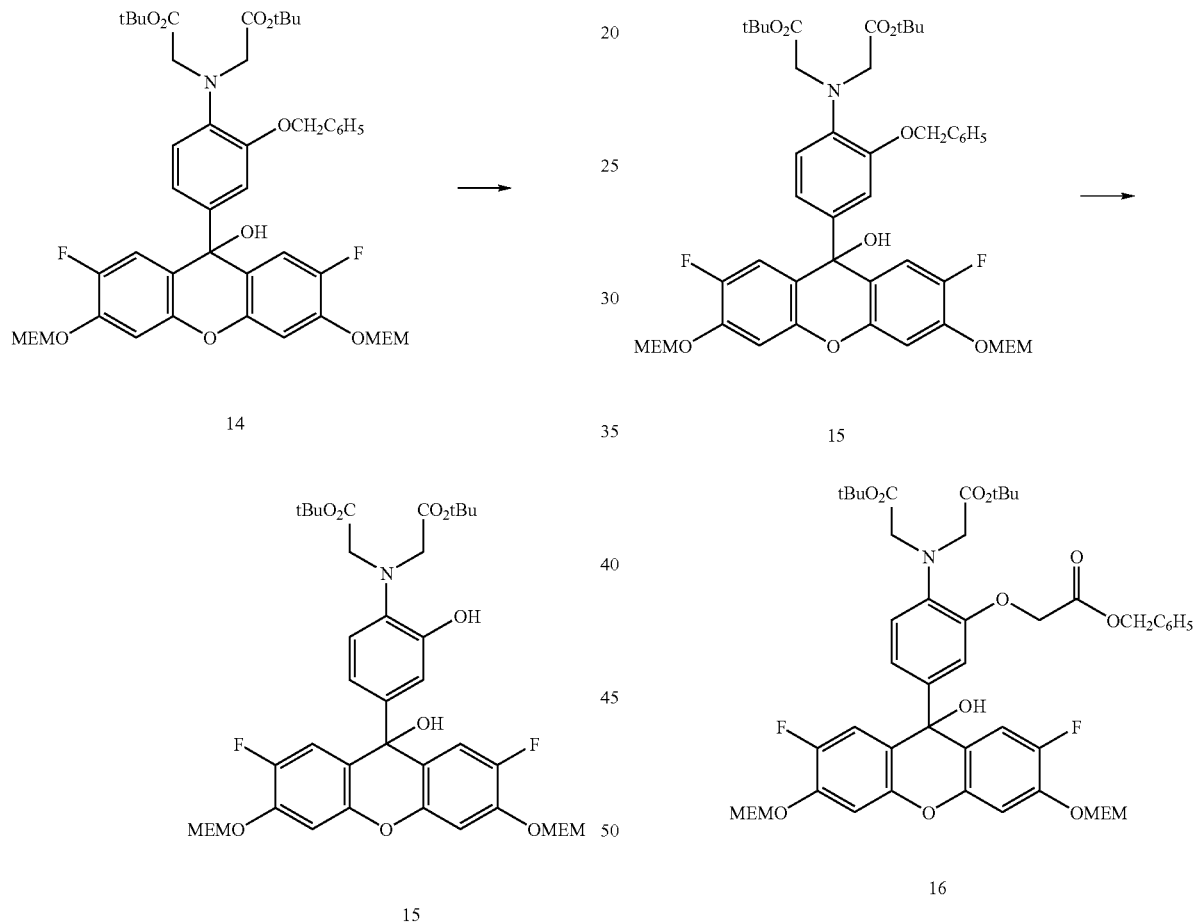

14

15

15

16

({2-Benzyloxycarbonylmethoxy-4-[2,7-difluoro-9-hydroxy-3,6-bis-(2-methoxyethoxymethoxy)-9H-xanthen-9-yl]-phenyl}-tert-butoxycarbonylmethyl-amino)-acetic acid tert-butyl ester (16). A solution of 15 (497 mg, 0.64 mmol) in DMF (10 mL) was treated with sodium hydride (18.5 mg, 0.77 mmol) at 0° C. under an Ar atmosphere. After stirring at 0° C. for 30 min, benzyl 2-bromoacetate (0.15 mL, 0.96 mmol) was added. The mixture was stirred at 0° C. for another 30 min and then warmed to room temperature overnight. The solvent was evaporated to dryness and extracted with EtOAc/H$_2$O. The combined organic layers were washed with brine, {2-(Bis-tert-butoxycarbonylmethyl-amino)-5-[2,7-difluoro-9-hydroxy 3,6-bis-(2-methoxy-ethoxymethoxy)-9H-xanthen-9-yl]-phenoxy}-acetic acid (18). To a solution of 17 (743 mg, 0.80 mmol) in 95% ethanol (25 mL) and EtOAc (25 mL) was added 10% Pd/C (135 mg). The resulting mixture was stirred at room temperature overnight under H$_2$ (1 atm). The catalyst was then removed by filtration and, after evaporation to dryness, the crude product was purified by flash column chromatography, eluting with 10% MeOH in CH$_2$Cl$_2$ to yield 595 mg (89%) of 18 as a red foaming solid. R$_f$=0.43 (in 10% MeOH/CH$_2$Cl$_2$); $^1$H NMR (300 MHz, CDCl$_3$) δ 10.0 (br, 1H), 6.93 (d, 2H, J=7.2 Hz), 6.86 (d, 1H, J=8.2 Hz), 6.71

(dd, 1H, J=8.2 and 1.3 Hz), 6.62 (m, 3H), 5.24 (s, 4H), 4.93 (s, 1H), 4.53 (s, 2H), 3.91 (s, 4H), 3.83 (m, 4H), 3.56 (m, 4H), 3.35 (s, 6H), 1.34 (s, 18H); $^{13}$C NMR (75 MHz, CDCl$_3$) δ 171.0, 170.5, 150.6, 150.5, 147.4, 146.4, 146.3, 144.4, 144.2, 140.8, 138.7, 122.3, 120.7, 116.6, 116.5, 115.9, 115.6, 115.4, 105.9, 94.6, 81.7, 71.3, 67.9, 67.3, 58.8, 55.0, 42.7, 27.8; $^{19}$F NMR (282 MHz, CDCl$_3$) δ −140.0 (dd, 2 F); mass spectrum, calculated for C$_{46}$H$_{55}$F$_2$NO$_{13}$ (M−17) 819.3, Found 819.8.

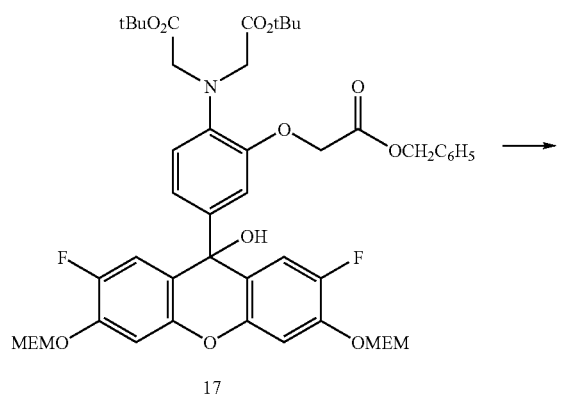

17

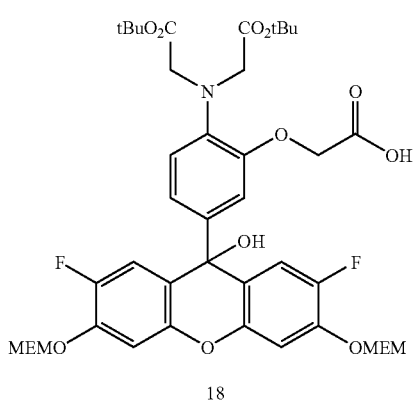

18

H$_2$N-Ser(tBu)-Phe-[Arg(Mtr)]$_4$-cystamine-Tentagel Resin (19). Cystamine dihydrochloride (10 eq, 2.25 g) was added to a mixture of TentaGel S COOH resin (90 μm, 5 g, 0.2 mmol/g), BOP (1.2 eq, 0.53 g), HOBt (1.2 eq, 0.184 g), N-methylmorpholine (NMM) (30 eq, 3.3 mL) in 20 mL DMF and subsequently shaken overnight at ambient temperature. The free amine substitution level was determined as 0.01 mmol/g. This low substitution level is ideal for our purposes since this not only ensures a higher coupling yield but, in addition, larger quantities of resin (with greater weight accuracy) can be subsequently introduced into the 96-well plates. The peptide NH$_2$-Ser(tBu)-Phe-[Arg(Mtr)]$_4$ was synthesized on the cystamine-substituted TentaGel resin using an Fmoc solid phase peptide synthesis protocol.

General protocol for the preparation of the fluorophore-peptide conjugates (21 (Scheme 3) and 23). Both compound 23 and the corresponding linker-based library 21 (23 compounds) were prepared using the same protocol, with the exception that the library members were synthesized in a solvent resistant 96-well filter plate. 10 mg of the peptide-TentaGel resin 19 was introduced into 23 individual wells of a 96-well filter plate. In addition, each well contained a Fmoc-linker-COOH (10 eq), O-benzotriazol-1-yl-N,N,N',N'-tetramethyluronium hexafluorophosphate (10 eq), 1-hydroxybenztriazole (10 eq), and N-methylmorpholine (20 eq) in 100 μL DMF. A total of 22 different Fmoc-linker-COOH linkers were employed. One additional well was reserved for the species that does not contain a linker. The plate was shaken overnight and then each well was subjected to a series of wash steps (3×200 μL DMF, 3×200 μL water, 3×200 μL DMF, 3×200 μL CH$_2$Cl$_2$, 2×200 μL MeOH, 2×200 μL 50 mM Tris pH 7.5). The N-terminal Fmoc protecting group was removed via double exposure to 30% piperidine in DMF for 30 min and then each well was subjected to a series of wash steps (3×200 μL DMF, 3×200 μL water, 3×200 μL DMF, 3×200 μL CH$_2$Cl$_2$, 2×200 μL MeOH, 2×200 μL 50 mM Tris pH 7.5). The side chain protecting groups on the peptide were removed via treatment with 95% trifluoroacetic acid/2.5% thioanisole/2.5% H$_2$O at room temperature overnight to furnish 20. Each well was subsequently subjected to a series of wash steps (3×200 μL DMF, 3×200 μL water, 3×200 μL DMF, 3×200 μL CH$_2$Cl$_2$, 2×200 μL MeOH, 2×200 μL 50 mM Tris pH 7.5). {2-(Bis-tert-butoxycarbonylmethyl-amino)-5-[2,7-difluoro-9-hydroxy 3,6-bis-(2-methoxy-ethoxymethoxy)-9H-xanthen-9-yl]-phenoxy}-acetic acid (18) (5 eq) was coupled to the peptide-TentaGel resin 20 under standard conditions [O-benzotriazol-1-yl-N,N,N',N'-tetramethyluronium hexafluorophosphate (5 eq), 1-hydroxybenztriazole (5 eq), and N-methylmorpholine (10 eq) in 100 μL DMF]. The attached xanthene was then deprotected and fully aromatized via exposure to 95% trifluoroacteic acid/5% H$_2$O. The fluorophore-peptide conjugates were cleaved from the disulfide-containing resin with 10 mM dithiothreitol (DTT) in Tris buffer (1×200 μL for 1 Hr; 2×150 μL for 1 hr each) and filtered into a receiving set of 96-well plates using a vacuum manifold to furnish the library 21, shown below.

Mass spectrum, calculated for compound 21a 1544.7, Found 1624.0 (M+79.9); calculated for 21b 1544.7, Found 1544.0; calculated for 21c 1562.6, Found 1562.0; calculated for 21d 1576.7, Found 1576.0; calculated for 21e 1584.7.7, Found 1584.0; calculated for 21f 1655.7, Found 1657.0 (M+2); calculated for 21g 1595.7, Found 1596.0; calculated for 21h 1572.7, Found 1572.0; calculated for 21i 1530.6, Found 1530.0; calculated for 21j 1558.7, Found 1558.0; calculated for 21k 1572.7, Found 1574.0; calculated for 21l 1584.0, Found 1584.0 (M+2); calculated for 21m 1518.0, Found 1518.0; calculated for 21n 1517.7, Found 1518.0; calculated for 21o 1606.7, Found 1607.0; calculated for 21p 1606.7, Found 1607.0 (M+2); calculated for 21q 1566.7, Found no identifiable mass ion; calculated for 21r 1566.7, Found 1566.0; calculated for 21s 1580.7, Found 1581.0; calculated for 21t 1580.7, Found 1581.0; calculated for 21u 1670.7, Found no identifiable mass ion; calculated for 21v 1796.2, Found no identifiable mass ion; calculated for 21w 1447.5, Found 1447.0.

Scheme 3. Synthesis of library 21.
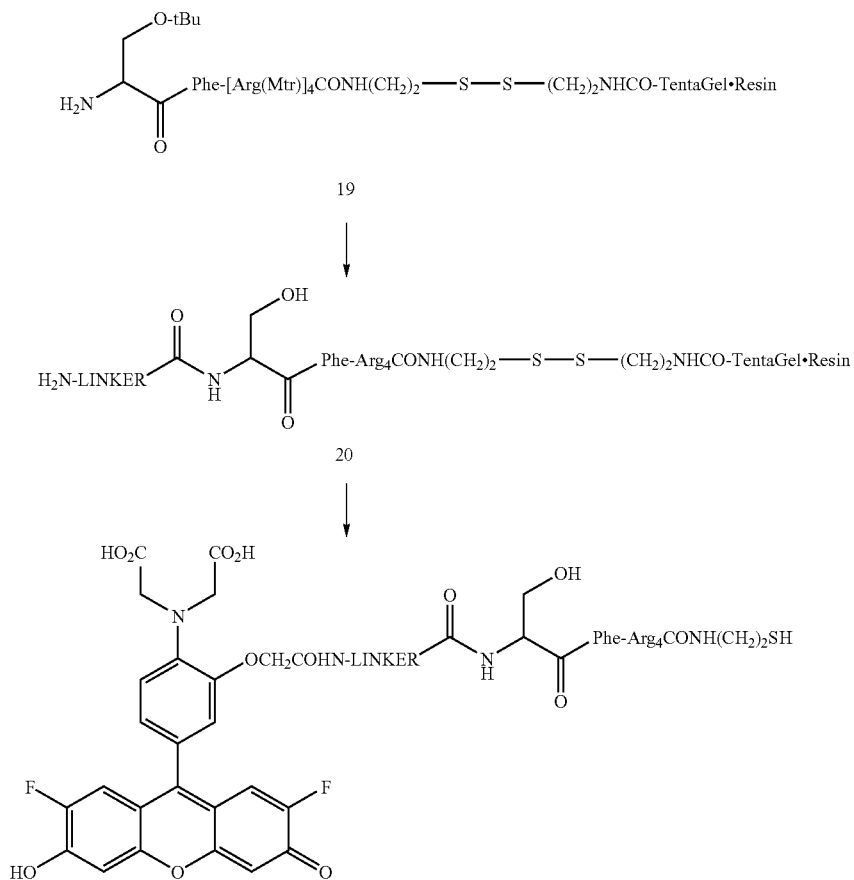
21 (library of 22 compounds)
Starting materials for the 22 linker monomers (plus compound w (no linker)) employed in the preparation of library 21 are shown below:
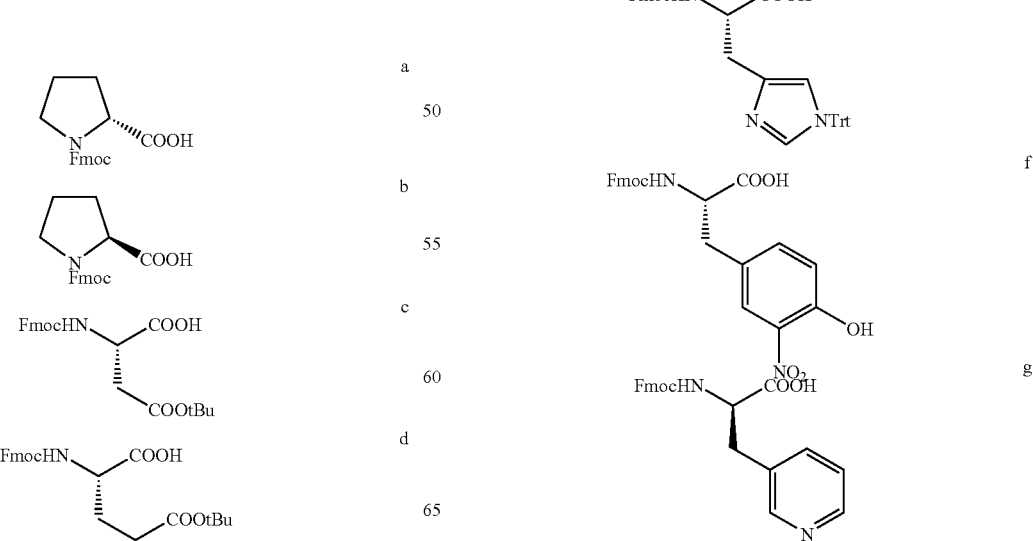

-continued h 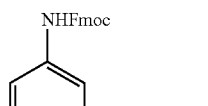

i 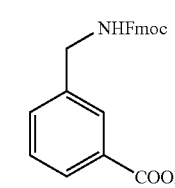

j k 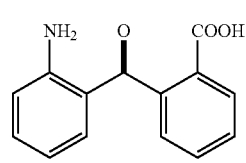

l

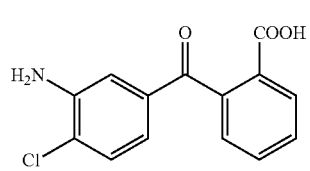

m n no linker.

-continued

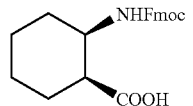
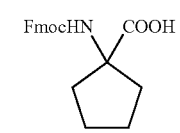
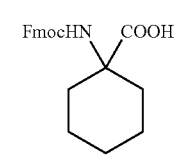
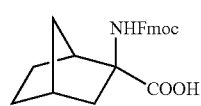
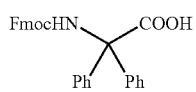
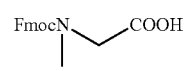
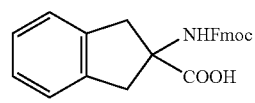
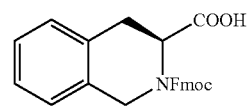
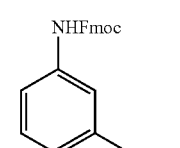

o p q r s t u v w

Protein kinase C assay. The kinase-catalyzed reaction was performed in triplicate at 30° C. and initiated by addition of ATP to a solution of PKCα and fluorophore-appended peptide substrate 23 (except in the case of the library, where the assays were performed in a 96 well plate using a fluorescence plate reader). Final conditions: 62.5 mM HEPES, 3 mM MgCl$_2$, 0.3 mM CaCl$_2$, 0.1 mM EGTA, 1 mM DTT, 0.5 μg/mL phosphatidylserine, 0.1 μg/mL diacylglycerol, 1 mM ATP, and 13 nM PKCα (pH 7.4). After the addition of ATP, the solution was gently mixed and the time-dependent change in fluorescent intensity ($\lambda_{excitation}$=494 mm; $\lambda_{emission}$=521 nm) continuously monitored with a Photon Technology QM-1 spectrofluorimeter.

Ca$^{2+}$ titration assay. The Ca$^{2+}$ Calibration Kit #2 (purchased from Molecular Probes) was employed for these studies. The fluorescent peptide was dissolved in two buffers, one without (SOLUTION A: 10 mM MOPs, 100 mM KCl, 10 mM EGTA, pH 7.2) and one with (SOLUTION B: 10 mM MOPs, 100 mM KCl, 10 mM CaEGTA, pH 7.2) Ca$^{2+}$. The final concentration of the peptide in both buffers was 1 μM. Solution A was (200 μL) added to the microcuvette and the fluorescence was recorded ($\lambda_{excitation}$=494 nm; $\lambda_{emission}$=521 nm). This was the fluorescence intensity with 0 Ca$^{+2}$. A series of solutions containing the following free Ca$^{2+}$ concentrations (based on the K$_d$ of CaEGTA at pH 7.2=150.3 nM) was prepared: 0.038 μM, 0.065 μM, 0.1 μM, 0.15 μM, 0.225 μM, 0.351 μM, 0.602 μM, 1.35 μM, and 39.8 μM.

2. Results and Discussion

An example of a fluorescent sensor that samples biologically relevant processes is the family of $Ca^{2+}$ indicators (e.g. compound 22 in Scheme 4, below) developed by Tsien and his colleagues.[39-41] Formation of the $Ca^{2+}$-fluorophore complex, via coordination to the 2 iminodiacetic acid moieties, is manifested by a dramatic fluorescence change. Tsien has proposed that $Ca^{2+}$ coordination induces a twist about the aryl amine bond, altering the coupling between the nitrogen lone pair and the aromatic ring system.[39-41]

A peptide-based species (compound 23 in Scheme 4) was designed that contains some of the structural features present in 22. Specifically, phosphorylation of 23 should generate a $M^{2+}$ receptor site comprised of two carboxylates and the newly introduced phosphate (24). Upon divalent metal ion coordination, a fluorescence change should transpire via a mechanism analogous to that described for the $Ca^{2+}$ indicators.

This strategy is made possible by the observation that protein kinases will phosphorylate alcohol-containing residues attached to the N- or C-terminus of appropriately designed peptides,[20,24] which allows the fluorophore to be directly attached to the phosphorylatable residue (e.g. 23). With these features in mind, the initial synthetic target was compound 18, which contains the requisite functionality in protected form, along with a free carboxylate that can be activated and condensed with the N-terminus of the peptide $H_2N$-Ser-Phe-Arg-Arg-Arg-Arg-resin (SEQ ID NO:1). The latter sequence serves as a substrate for protein kinase C (PKC).[24]

The synthesis of the fluorescein precursor compound 18 is shown in Scheme 5. The xanthene half of 18 was synthesized from the xanthone precursor 7. The latter was prepared via the Friedel-Crafts acylation of 3[42] with 6. The product was subsequently heated in a sealed tube to furnish the xanthone 8 and the phenol moieties then protected as 2-methoxyethoxymethyl (MEM)[43] ethers (9). The aromatic precursor (13) to the "northern" half of compound 18 was prepared in three steps from commercially available o-aminophenol (described above). Compound 13 contains a doubly protected iminodiacetic acid moiety and a benzylated phenol. The latter will ultimately be debenzylated so that it can serve as the attachment site for the peptide. Compound 13 was lithiated at −105° C. and coupled to 9, to furnish adduct 14 in 69% yield. The benzylated phenol in 14 was transformed in three steps to the desired carboxylic acid (18), and then coupled to $H_2N$-Ser(O-tBu)-Phe-[(Arg)Mtr]$_4$-resin (prepared via standard Fmoc solid phase peptide synthesis on the Rink resin). Finally, exposure of the resin-appended fluorophore-peptide to 95% $CF_3CO_2H$ resulted in the simultaneous cleavage of the peptide from the resin, MEM ether deprotection, and complete aromatization of the tricyclic nucleus via loss of the tertiary hydroxyl moiety to yield 23.

Peptide 23 serves as a substrate for the $Ca^{2+}$-dependent PKCα and displays a 140% increase in fluorescence intensity upon phosphorylation, nearly an order of magnitude greater than previously described protein kinase monitoring systems.[6-10,38] In addition, the difluorofluorescein moiety in 23 is an extremely bright fluorophore ($\epsilon$=78,000 cm$^{-1}$ M$^{-1}$ and $\Phi$=0.60) and thus, is easily an order of magnitude more sensitive than fluorophores that have been previously used to observe protein kinase activity.[42] Although the $K_m$ value (26.5 μM) for the PKCα-catalyzed phosphorylation of 23 is quite good, the corresponding $V_{max}$ (0.32 μmol/min-mg) is an order of magnitude less than ideal. The large, negatively charged fluorophore, which is positioned adjacent to the site of phosphorylation, might interfere with the ability of the PKC active site to accommodate the serine moiety.

The possibility of fluorophore-mediated disruption of the kinase-catalyzed reaction was addressed by preparing a small library of 22 derivatives of 23 using the synthetic strategy outlined in Scheme 3. A series of turn-promoting/metal chelating LINKERs was inserted between the peptide and the fluorophore (21), which might allow the serine moiety to be more optimally accommodated within the active site. Following phosphorylation, the turn-inducing/chelating ability of the LINKER should enable the iminodiacetic acid carboxylates to assume a position that promotes metal coordination. The library of 22 compounds was prepared on a cystamine-derivatized TentaGel resin,[44] which contains a disulfide bridge between the peptide and the resin (19). The side chain protected peptide 19 was split into 22 portions of 10 mg each and added to a solvent resistant multiwell filter plate. 22 Fmoc-amino acids ("LINKER"s, see above) were added to individual wells and condensed with 19. The Fmoc group was removed (20) and the product coupled to compound 18. 95% $CF_3CO_2H$ was subsequently employed to simultaneously deprotect the phenol and carboxylic acid moieties and transform the xanthene nucleus into the fluorescein derivative. Finally, all 22 compounds were cleaved from the Tentagel resin with PKC assay buffer, which contains dithiothreitol. The library members (21) (see above) were filtered into a receiving plate and then assayed under standard conditions with monitoring for both the magnitude and rate of fluorescence change. Several fluorophore-LINKER-peptide analogs were identified that display promising enzymological and photophysical properties (Table 4). N-methyl glycine serves as the LINKER in the lead protein kinase substrate. Phosphorylation of the latter generates a 264% enhancement in fluorescence intensity and proceeds with a $V_{max}$ of 8.5 μmol/min-mg and a $K_m$ of 20.5 μM. Indeed, the $V_{max}$ is more than an order of magnitude greater than that displayed by compound 23, which lacks a LINKER residue between the fluorophore and the peptide.

Saturating [$Ca^{2+}$] produces 1.2- and 2.0-fold fluorescence enhancements in 23 and 21 (N-Me Gly), respectively. By contrast, enhancements of 5- and 23-fold were observed with the chemically synthesized phosphorylated analogs of 23 and 21, respectively. However, the large metal-induced fluorescence change in the phosphorylated species appears to be partly offset by a reduction in the inherent (i.e. metal-free) fluorescence of the phosphopeptides.

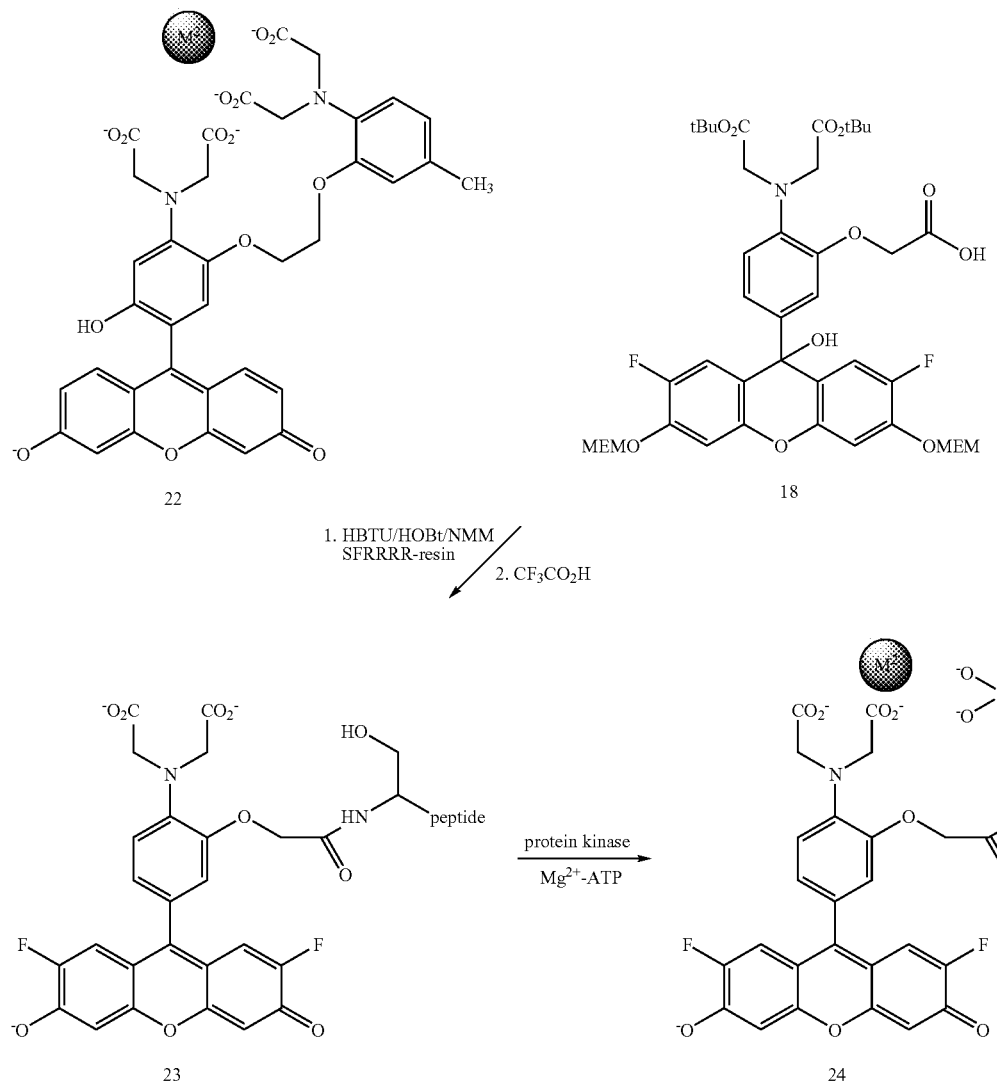
Scheme 4
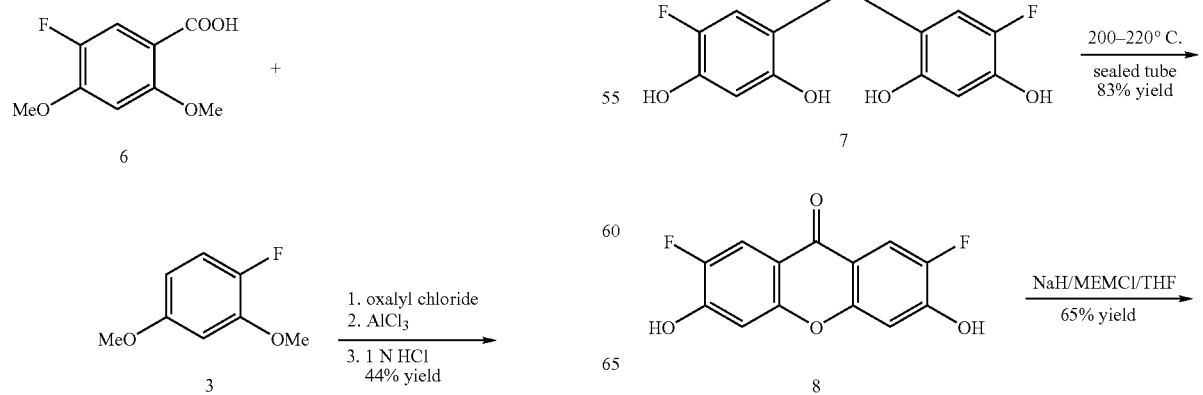
Scheme 5. Synthesis of fluorescein precursor 18.

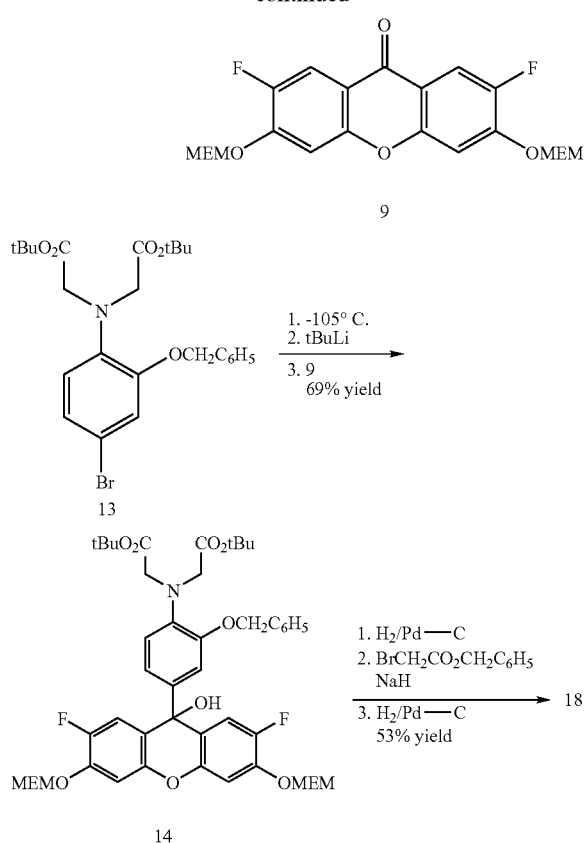

TABLE 4

$V_{max}$, $K_m$, and fluorescence change associated with the PKC-catalyzed phosphorylation of peptides 21 (5 different linkers), 23, and AcSFRRRRK (SEQ ID NO: 2).

| LINKER | $V_{max}$ (μmol/min-mg) | $K_m$ (μM) | % Change Fluorescence |
|---|---|---|---|
| L-proline | 1.9 | 63.0 | 150% |
| D-proline | 1.0 | 23.5 | 156% |
| N-Me glycine | 8.5 | 20.5 | 264% |
| a | 1.7 | 25.0 | 164% |
| b | 2.2 | 24.9 | 157% |
| Peptide 23 | 0.32 | 26.5 | 140% |
| AcSFRRRRK | 24 | 10 | — |

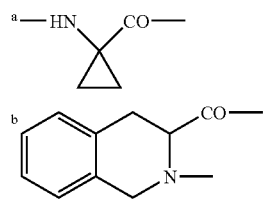

Example III

Light-Activated ("Caged") Probe of Protein Kinase Activity

1. Materials, Methods, and Detailed Synthesis of Compounds

Chemicals and solvents were purchased from Fisher, Sigma, and Aldrich, except for piperidine, protected amino acids, 1-hydroxybenzotriazole (HOBt), benzotriazole-1-yloxytris-pyrrolidinophosphonium hexafluorophosphate (PyBOP), and Rink resin which were obtained from Advanced Chemtech and Bachem. Deuterated chloroform ($CDCl_3$) for NMR spectroscopy was purchased from Cambridge Isotope Laboratories. PKCα was purchased from PanVera. Silica gel for flash chromatography (40 mm, 60 Å pore diameter) was purchased from VWR International, and silica gel plates (0.25 mm, $UV_{254}$) for thin layer chromatography (TLC) were purchased from Analtech.

The numbering of compounds in Example III is independent of the numbering used in Examples I and II.

Fluorescence assays were performed using a Photon Technology QM-1 spectrofluorimeter, and irradiation experiments utilized an Oriel Mercury Arc Lamp (Model 69907) equipped with a 360 nm colored glass filter (300-400 nm band pass) and an infrared (1R) filter. $^1H$ and $^{13}C$ nuclear magnetic resonance (NMR) spectra were recorded on a Brucker DRX300 ($^1H$: 300 MHz, $^{13}C$: 75 MHz) spectrometer. All NMR chemical shifts (δ) are reported as ppm (parts per million) values and coupling constants (J) in hertz (Hz). $^1H$ and $^{13}C$ NMR signals were referenced relative to the chloroform ($^1H$: 7.24 ppm, $^{13}C$: 77.0 ppm) solvent signal. Mass spectra by MALDI (Matrix Assisted Laser Desorption Ionization) were analyzed on an Applied Biosystems Voyager-DE STR mass spectrometer, and mass spectra by ESI (Electrospray Ionization) were analyzed on a Finnigan LCQ mass spectrometer equipped with a quadrupole ion trap. High pressure liquid chromatography (HPLC) analysis was performed using a Rainin Dynamax SD-200 solvent delivery system. Analyses were carried out either on analytical scale (Varian Microsorb-MV C-18, 300 Å particle size, 250×4.6 mm) or on preparative scale using three radial compression modules (Waters Delta-Pak C-18, 300 Å particle size, 25×10 cm) connected in series.

Synthesis of N-(9-Fluorenylmethyloxycarbonyl)-L-serine allyl ester (Compound 3). N-α-Fmoc-L-Serine (1.64 g, 5.01 mmol) and $NaHCO_3$ (0.43 g, 5.06 mmol) in 16 mL of water were combined with a solution of 2.00 g of tricaprylmethylammonium chloride (aliquot 336) and allyl bromide (3.20 g, 26.5 mmol) in 30 mL of methylene chloride, and the suspension was vigorously stirred at room temperature for 24 hours. Water (50 mL) was added to the reaction mixture, and the suspension was extracted with methylene chloride (3×50 mL). The combined organics were dried ($Na_2SO_4$) and concentrated under reduced pressure, and the crude residue was purified by silica gel chromatography (3:2 hexanes:ethyl acetate) to yield 3 as a white solid (1.70 g, 93%): $^1H$ NMR (300 MHz, $CDCl_3$) δ 2.12 (bs, 1H), 3.92 (d, J=9.0, 1H), 4.01 (d, J=9.0, 1H), 4.20 (t, J=6.8, 1H), 4.41 (m, 3H), 4.67 (d, J=5.3, 2H), 5.25 (dd, J=10.4 and 1.0, 1H), 5.32 (dd, J=17.2 and 1.0, 1H), 5.72 (d, J=6.1, 1H), 5.88 (ddt, J=17.2, 10.4 and 5.3, 11H), 7.29 (t, J=7.4, 2H), 7.39 (t, J=7.4, 2H), 7.58 (d, J=7.4, 2H), 7.75 (d, J=7.4, 2H); $^{13}C$ NMR (75 MHz, $CDCl_3$) δ 47.1, 56.1, 63.3, 66.4, 67.2, 119.0, 120.0, 125.1, 127.1, 127.7, 131.3, 141.3, 143.6, 143.8, 156.2, 170.1.

Synthesis of 4,5-dimethoxy-2-nitrobenzyl trichloroacetimidate (Compound 4). 4,5-dimethoxy-2-nitrobenzyl alcohol (1.23 g, 5.77 mmol) was dissolved in 40 mL of anhydrous methylene chloride and stirred at room temperature under nitrogen. Anhydrous K$_2$CO$_3$ (2.05 g, 14.8 mmol), trichloroacetonitrile (2.10 g, 10.0 mmol), and anhydrous triethylamine (720 mg, 7.12 mmol) were added to the solution and the reaction mixture stirred at room temperature for 24 hours. Methylene chloride (60 mL) was added to the reaction mixture, and the suspension sequentially washed with 0.5 N HCl and saturated NaCl. The organic layer was dried and concentrated under reduced pressure, and the resulting crude solid recrystallized to yield 4 as an orange powder (1.61 g, 85%): $^1$H NMR (300 MHz, CDCl$_3$) δ 3.94 (s, 3H), 3.94 (s, 3H), 5.76 (s, 2H), 7.21 (s, 1H), 7.73 (s, 1H), 8.48 (s, 1H); $^{13}$C NMR (75 MHz, CDCl$_3$) δ 56.4, 67.5, 91.2, 108.1, 109.2, 127.3, 139.4, 148.1, 153.8, 161.7.

Synthesis of N-(9-Fluorenylmethyloxycarbonyl)-O-(4,5-dimethoxy-2-nitrobenzyl)-L-serine allyl ester (Compound 5) (see Scheme 6 below). Triflic acid (4 µL) was added to an anhydrous methylene chloride (4 µL) solution of Fmoc-serine allyl ester 3 (140 mg, 0.38 mmol) and the acetimidate 4 (530 mg, 1.48 mmol) kept under nitrogen at room temperature. The resulting dark green solution was stirred for 20 min at room temperature. Further addition of triflic acid (4 µL) was performed twice at 20 min intervals. TLC analysis indicated that 4 had disappeared following the final addition of triflic acid. Chloroform (25 mL) and silica gel (~2 g) were added to the reaction mixture and then concentrated under reduced pressure. The crude residue, adsorbed on silica, was purified by silica gel chromatography (3:1 hexanes:ethyl acetate) to yield 5 as a light yellow solid (61 mg, 29%): $^1$H NMR (300 MHz, CDCl$_3$) δ 3.90 (m, 1H), 3.91 (s, 3H), 3.92 (s, 3H), 4.06 (dd, J=9.3 and 3.0, 1H), 4.21 (t, J=7.0, 1H), 4.37 (dd, J=10.5 and 7.0, 1H), 4.45 (dd, J=10.5 and 7.0, 1H), 4.63 (m, 1H), 4.67 (d, J=5.3, 2H), 4.91 (AB quartet, J$_{AB}$=15.4, 2H), 5.20 (d, J=10.5, 1H), 5.30 (d, J=17.2, 1H), 5.69 (d, J=8.4, 1H), 5.87 (ddt, J=17.2, 10.5 and 5.3, 1H), 7.14 (s, 1H), 7.28 (t, J=7.4, 2H), 7.37 (t, J=7.4, 2H), 7.58 (m, 2H), 7.68 (s, 1H), 7.73 (d, J=7.4, 2H); $^{13}$C NMR (75 MHz, CDCl$_3$) δ 47.1, 54.6, 56.3, 56.4, 66.2, 67.1, 70.2, 71.1, 107.9, 109.4, 118.8, 120.0, 125.0, 127.0, 127.7, 129.9, 131.3, 139.0, 141.3, 143.6, 143.8, 147.7, 153.8, 155.9, 169.9.

Synthesis of N-(9-Fluorenylmethyloxycarbonyl)-O-(4,5-dimethoxy-2-nitrobenzyl)-L-serine (Compound 6). The caged serine allyl ester 5 (73 mg, 0.13 mmol) was dissolved in chloroform (3.5 mL) and acetic acid (0.1 mL). N-methylmorpholine (0.4 mL), and Pd(Ph$_3$P)$_4$ (462 mg, 0.40 mmol) were added to the solution. The reaction mixture was stirred for 4 hours at room temperature, and the reaction was quenched by the addition of 0.1 N HCl (30 mL). The suspension was extracted with ethyl acetate, dried (Na$_2$SO$_4$), and concentrated under reduced pressure. The crude residue was purified by silica gel chromatography (39:1 chloroform:methanol) to yield 6 as a light yellow solid: $^1$H NMR (300 MHz, CDCl$_3$) δ 3.78 (m, 1H), 3.84 (s, 3H), 3.88 (s, 3H), 4.08 (d, J=7.9, 1H), 4.19 (t, J=6.7, 1H), 4.38 (dd, J=10.4 and 6.7, 1H), 4.45 (dd, J=10.4 and 6.7, 1H), 4.62 (m, 1H), 4.86 (AB quartet, J$_{AB}$=15.2, 2H), 5.70 (d, J=8.3, 1H), 7.04 (s, 1H), 7.27 (t, J=7.3, 2H), 7.36 (t, J=7.3, 2H), 7.56 (m, 2H), 7.60 (s, 1H), 7.71 (d, J=7.3, 2H), 8.25 (bs, 1H); $^{13}$C NMR (75 MHz, CDCl$_3$) δ 47.0, 54.3, 56.2, 67.3, 70.2, 70.8, 107.8, 109.2, 120.0, 125.0, 127.1, 127.8, 129.5, 139.0, 141.3, 143.5, 147.6, 153.7, 156.1, 174.9. HRMS (FAB) m/z 523.1721 (M+H$^+$); Calculated for C$_{27}$H$_{26}$N$_2$O$_9$ (M+H$^+$): 523.1717.

Synthesis of Peptides 1 and 2.

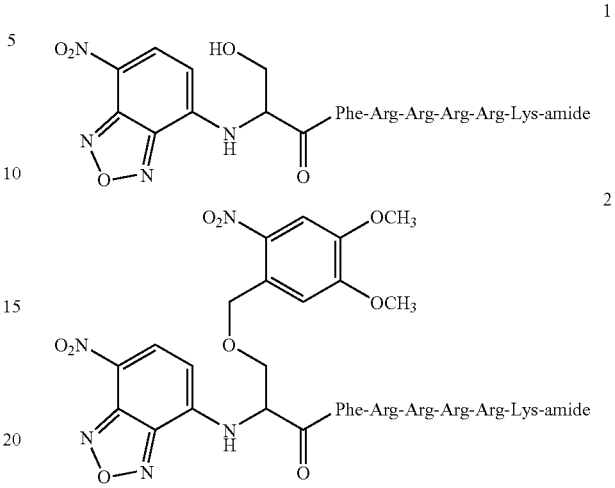

The peptides were synthesized using a standard Fmoc/benzotriazole-1-yl-oxy-tris-pyrrolidino-phosphonium hexafluorophosphate (PyBOP) peptide synthesis protocol. Each amino acid was attached to the rink amide resin (500 mg, 0.6 mmol/g) via manual solid phase synthesis according to the following protocol: (a) 1×15 mL of 30% piperidine in DMF (30 min); (b) 2×15 mL of methylene chloride; (c) 2×15 mL of isopropyl alcohol; (d) 2×15 mL of DMF; (e) Three equivalents of the Fmoc-protected amino acid, PyBOP, HOBt hydrate, and six equivalents of N-methyl morpholine in 15 mL of DMF (120 min) (f) 2×15 mL of methylene chloride; (g) 2×15 mL of isopropyl alcohol; (h) 2×15 mL of DMF. After the addition of Fmoc-phenylalanine, a 10% aliquot of the resin was removed and the appropriate Fmoc-serine derivative was attached to the resin as described above. After completion of the peptide synthesis, the Fmoc was removed with 3 mL of 30% piperidine in DMF (30 min), and the deprotected peptide treated with 10 equivalents of 4-chloro-7-nitrobenzofurazan (NBD-Cl) and 5 equivalents of diisopropylethylamine (DIEA) in 3 mL of DMF to furnish the resin-linked peptide. The resin was transferred to a 20 mL glass vial, and the peptide was cleaved from the resin using 5 mL of 95:2.5:2.5 trifluoroacetic acid (TFA):triisopropylsilane:H$_2$O (6 hr). The resin was filtered using a sintered glass filter funnel, and the filtrate was washed with 25% TFA in methylene chloride. The supernatant was concentrated to ~2 mL under a stream of nitrogen, and ethyl ether (25 mL) was added to the remaining supernatant. The resulting suspension was extracted with H$_2$O (2×25 mL), and the aqueous extracts were lyophilized, redissolved in H$_2$O (30 mL), and purified by preparative reverse-phase HPLC (gradient A: 0.1% TFA in H$_2$O; solvent B: 0.1% TFA in acetonitrile; 12 mL/min): 0-3 min (100% gradient A); a linear gradient from 3 to 40 min (50% gradient A and 50% solvent B); a steep final linear gradient to 100% solvent B for cleaning purposes. After isolation from the HPLC, samples were lyophilized to yield peptides 1 (13 mg, 32% yield) and 2 (12 mg, 34% yield) as a yellow powder. LRMS (ESI) for 1: m/z 1166.6 (M$^+$); Calculated for C$_{48}$H$_{78}$N$_{24}$O$_{11}$ (M$^+$) 1166.6. LRMS (ESI) for 2: m/z 1361.8 (M$^+$); Calculated for C$_{57}$H$_{87}$N$_{25}$O$_{15}$ (M$^+$) 1361.7.

Fluorescence PKC assay. In a 100 µL cuvette, a solution (97 µL) containing irradiated or non-irradiated peptide 2 (60 µM initial concentration), assay buffer, and ATP was allowed to equilibrate at 30° C. for 3 min and the reaction was then initiated via addition of a PKCα stock solution (3 μL). Final conditions were as follows: 61.5 mM HEPES, pH 7.4, 3.0 mM $MgCl_2$, 0.3 mM $CaCl_2$, 0.8 mM dithiothreitol, 0.5 μg/mL phosphatidylserine, 0.1 mg/mL diacylglycerol, 1 mM ATP, 0.1 mM EDTA, 0.1 mM EGTA, 7.5 mM NaCl, 0.002% Triton X-100, 1.5% glycerol, and 43 nM PKC. The assay solution was gently mixed and continuously monitored for time-dependent change in fluorescent intensity (exitation, 520 nm; emission, 560 nm).

Figure 5:
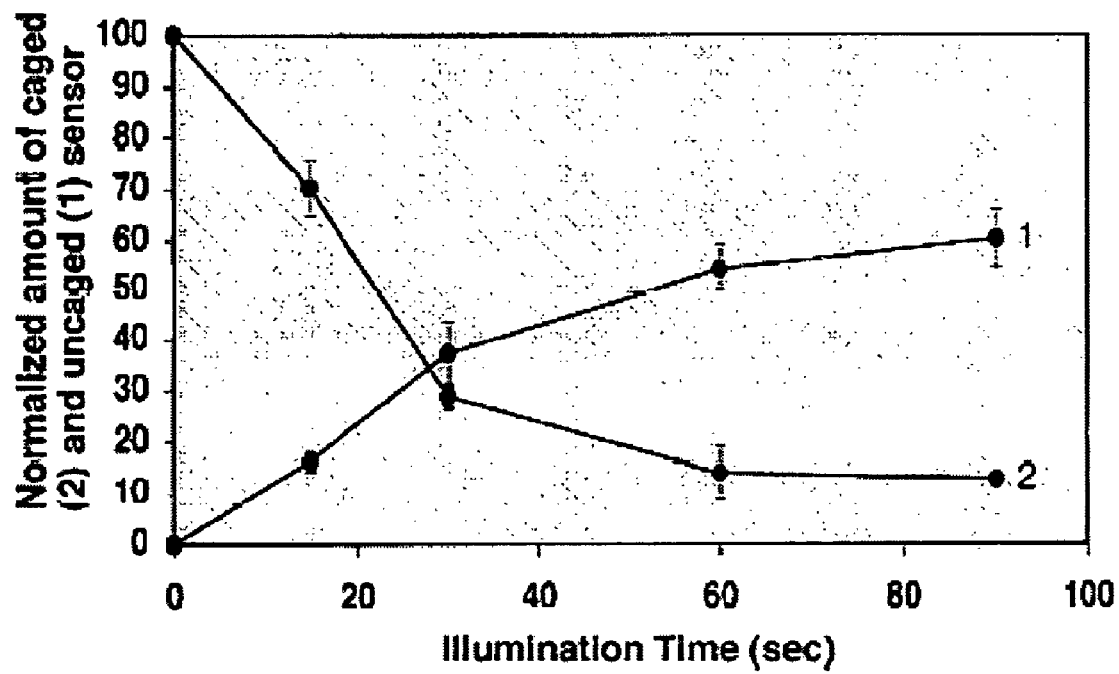
FIG. 5. Irradiation of caged peptide (2) for various times intervals and the extent of conversion to uncaged sensor (1). See Example III for details.

Irradiation of the caged peptide for various times intervals and the extent of conversion to uncaged sensor, and the effect on the PKC catalyzed time-dependent change influorescence (FIG. 5). The caged peptide 2 (24 μL, 500 μM) was placed in a 1000 μL cuvette and cooled to 0° C. The sample was irradiated at 150 W for 0, 15, 30, 60, or 90 sec. A 12 μL aliquot was removed and analyzed for change in fluorescence intensity. Another 10 μL aliquot was analyzed by analytical scale reverse-phase HPLC (gradient A: 0.1% TFA in $H_2O$; solvent B: 0.1% TFA in acetonitrile; 1 mL/min): 0-3 min (100% gradient A,); a linear gradient from 3 to 40 min (50% gradient A and 50% solvent B); a steep final linear gradient to 100% solvent B for cleaning purposes. Peptide 2 and its uncaged analogue 1 was quantified by their absorbance at 465 nm and normalized relative to the HPLC peak areas of their pure reference compounds. Average values of three determinations were obtained to calculate the peptide ratios and a standard deviation was calculated to determine the error.

Time-dependent change influorescence before and after the in situ irradiation of the caged peptide. The PKC assays were performed as described herein. The caged peptide 2 was incubated at 30° C. with PKCα and ATP, and the change in fluorescence measured for 10, 20, or 30 min. The cuvette was removed from the spectrofluorimeter and irradiated at 150 W for 90 sec. The sample was allowed to re-equilibrate to 30° C. for 1 min and then re-analyzed for change in fluorescence intensity as a function of time.

Time-dependent change in fluorescence following irradiation of 2 at two different time points. The PKC assays were performed as described herein. The caged peptide 2 was irradiated at 150 W for 60 sec in the assay buffer containing PKCα and ATP. The sample was then incubated at 30° C. and the change in fluorescence measured for 20 min. The cuvette was then removed from the spectrofluorimeter and again irradiated at 150 W for 60 sec. The sample was allowed to re-equilibrate at 30° C. for 1 min and then re-analyzed for change in fluorescence intensity.

Quantum yield determination for the photoconversion of 2 to 1. A 200 μL solution of 2-nitrobenzaldehyde (300 μM) or 2 (300 μM) in 5 mM HEPES (pH 7.4) was placed in a 1 mL cuvette and irradiated at 150 W for 15 sec or 60 sec, respectively. The product, 2-nitrosobenzoic acid, was quantified by its absorbance at 260 nm and normalized relative to the HPLC peak areas of its precursor (2-nitrobenzaldehyde). The product, 1, was quantified by its absorbance at 465 nm and normalized relative to the HPLC peak areas of a standard sample of 1. Average values of three determinations were utilized, and the quantum yield was determined by the following equation: 0.5(%⅟60 sec)/(%2-nitrosobenzoic acid/15 sec). The quantum yield for the photoconversion of 2 to 1 is 0.059±0.005 based on the reported quantum yield of 0.5 for the photoconversion of 2-nitrobenzaldehyde to 2-nitrosobenzoic acid.[79]

Cell-based studies. HeLa cells were cultured on Lab-Tek II Chamber Slide (single well glass slide) (Nalge Nunc International Corp., Naperville, Ill.) at 50,000 cells/mL with total volume of 2 mL of serum free Dulbeco's modified Eagle's medium in humidified atmosphere containing 5% $CO_2$. The caged NBD-containing peptide 2 was dissolved in doubly distilled $H_2O$ at the concentration of 200 μM and was prefiltered through a 0.22 μm filter. Cells were microinjected using a commercial microinjection system (Transjectors 5246, Eppendorf, Westbury, N.Y.) at an estimated final concentration of 20 μM for the caged peptide. Following microinjection, cells were exposed to 365 nm at 1 $J/cm^2$ to activate the PKC sensor. Immediately after UV treatment, TPA (1 μM) was added into the media to stimulate PKC activity. Time-lapse images were collected with 2×2 binning using a Photometrics (Tuscon, Ariz.) Sensys cooled CCD camera mounted on an Olympus 1×70 inverted microscope (Melville, N.Y.) with a PlanApo 40X N. A. 0.75 objective, Ludl shutters (Hawthorne, N.Y.), and a filter set with an excitation wavelength of 460-500 nm and an emission wavelength of 510-560 nm. Images were collected at 0.5 min, 2 min, 5 min, 10 min, 15 min, 20 min, and 30 min after addition of TPA or phosphate buffered saline (PBS) as negative control (1000 ms exposure time). Images and fluorescence intensity measurements were obtained from both TPA stimulated cells and control cells for photobleaching studies. Images and fluorescence intensity measurements were also collected from caged and uncaged PKC sensors in cells stimulated with TPA.

2. Synthesis of Caged Compound, Results, and Discussion

Two different strategies were envisioned for the construction of caged protein kinase sensors. PKC is known to recognize peptides containing appropriately positioned arginine residues.[80] Consequently, a substrate harboring multiply caged arginine moieties[11] should be resistant to PKC-catalyzed phosphorylation until activated by light. Alternatively, the presence of a single photolytically sensitive substituent on the phosphorylatable serine hydroxyl should likewise preclude PKC-catalyzed phosphoryl transfer. Caged thiophosphorylated and phosphorylated threonine and serine residues[81-83] and chain caged serine have been reported;[87-88] however, it is believed that a side chain caged protein kinase fluorescent substrate has not previously been described. The latter offers the advantage, relative to a peptide containing multiply caged residues, that only a single functional group need be photolytically liberated (peptide 2) to generate the active protein kinase fluorescent reporter. A caged serine was prepared as outlined in Scheme 6. The key step, benzylation of the serine side chain hydroxyl, was achieved using the trichloroacetimidate 4 in the presence of a catalytic amount of triflic acid.[84-85] The Fmoc derivative 6 was subsequently employed to create the active site-directed peptide 2 via solid phase peptide synthesis as described above.

Scheme 6

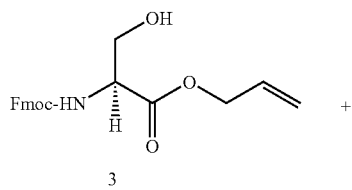

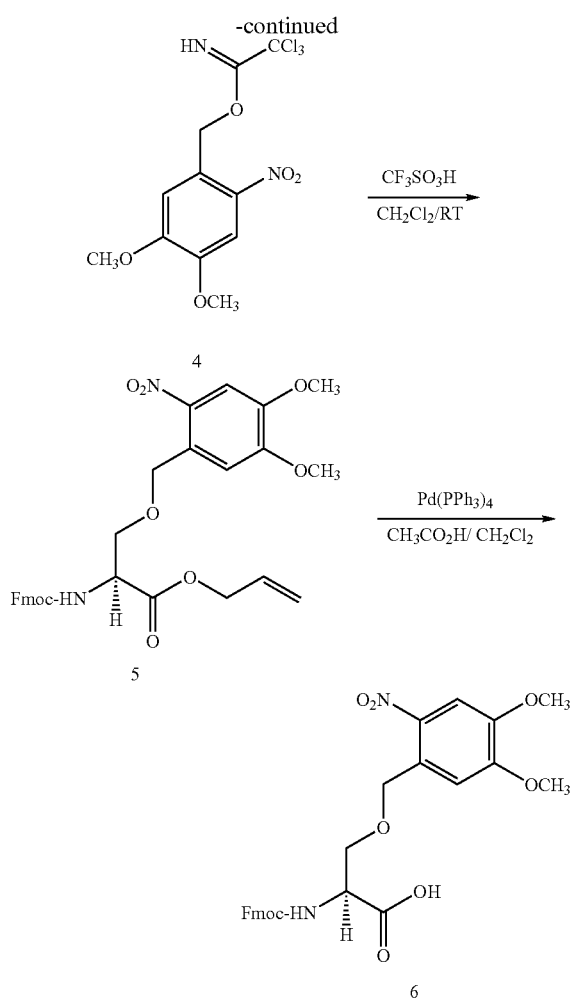

Figure 6:
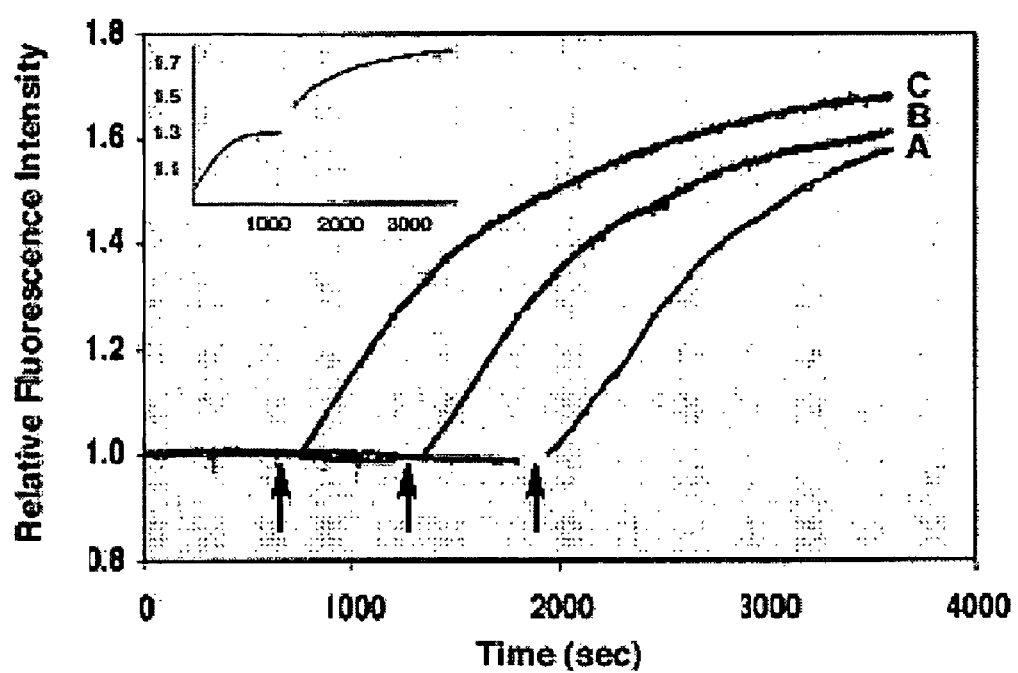
FIG. 6. Time-dependent change in fluorescence before and after in situ illumination of caged peptide. The caged peptide 2 (Example III) was incubated at 30° C. with PKCα and the change in fluorescence measured for 10 (A), 20 (B), or 30 (C) min. Samples were then irradiated at the indicated time points. Insert: partial photolysis of 2 followed by a second exposure to brief illumination.

As would be expected for a peptide lacking a free hydroxyl group, compound 2 fails to serve as a substrate for PKC (FIG. 6). Two potentially useful attributes of the caged substrate include (1) sampling of protein kinase activity at a time of choice and (2) control over the amount of active substrate available for phosphorylation. The former is illustrated in FIG. 6, where the caged substrate 2 is incubated with active PKC for various time intervals (10, 20, and 30 min) and then subsequently photoactivated (Hg arc lamp for 90 sec). A broad bandpass filter (300-400 nm with $\lambda_{max}$ @ 360 nm) was employed to protect the nitrobenzofurazan fluorophore from photobleaching and an infrared (1R) filter was used to shield PKC from heat inactivation. Peptide 2 is completely inert as a PKC substrate irrespective of PKC incubation time. Furthermore, identical robust fluorescence responses are immediately observed following photolysis, irrespective of the pre-photolysis PKC incubation time.

Figure 7:
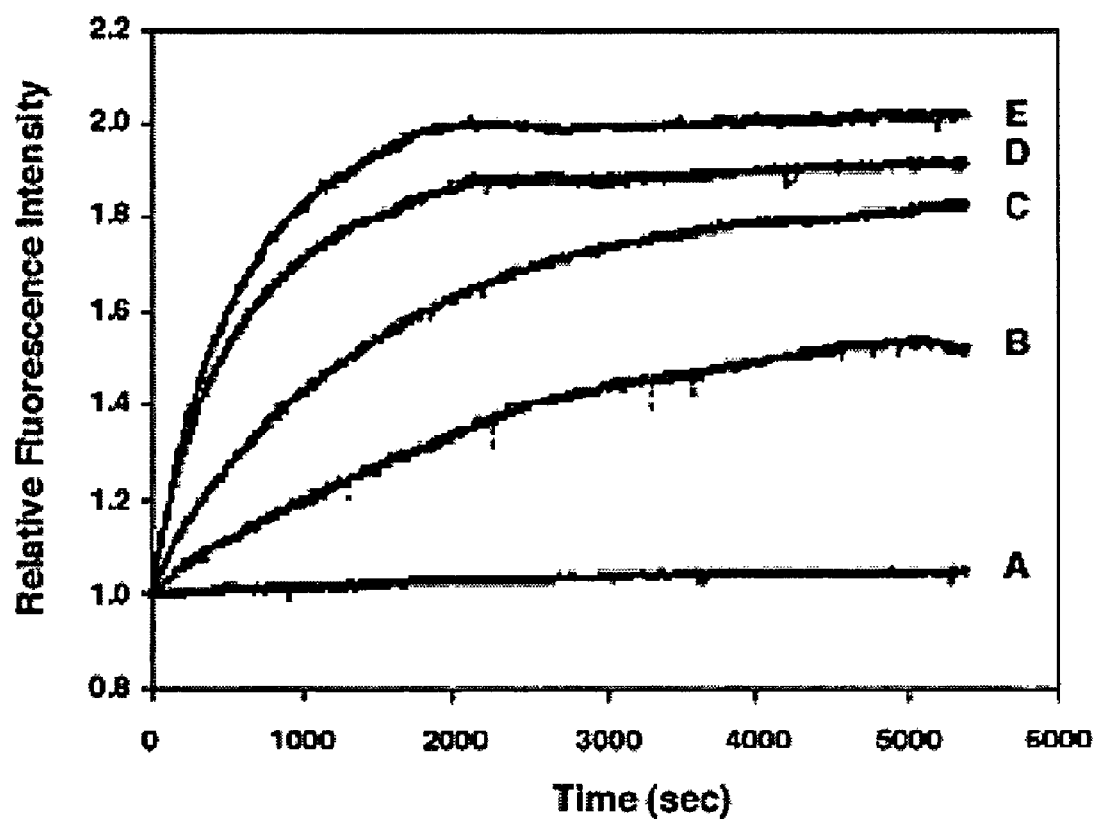
FIG. 7. Fluorescence change as a function of irradiation time. Peptide 2 (Example III) was illuminated for (A) 0, (B) 15, (C) 30, (D) 45, and (E) 90 sec and PKCα-catalyzed activity subsequently sampled via fluorescence change.

HPLC analysis revealed that the maximal conversion of caged to uncaged substrate is approximately 60%. The quantum yield for photolytic conversion is 0.06 as determined by actinometry.[79] Although a 90 sec irradiation time is required for maximal in vitro formation of the uncaged substrate, intracellular uncaging should proceed more rapidly due to an enhanced photon flux through a comparatively smaller cellular volume.[86] Furthermore, as illustrated in FIG. 7, total photon flux can be used to control the amount of free protein kinase probe liberated.

Both the timing and amount of sensor release can be controlled in a single experiment (FIG. 6, insert). Approximately half of compound 2 was photochemically converted to the active probe 1 in the presence of PKC, as indicated by the observed change in fluorescence. Subsequent illumination of the reaction mixture afforded additional free sensor, which likewise furnished a fluorescent response. These experiments demonstrate that it is not only possible to control the timing of protein kinase activity sampling, but that activity measurements can be performed at multiple stages as a function of cellular events. The latter is noteworthy since it establishes that inert sensor can be held in reserve so that kinase activity can be assessed at future time points.

Figure 8:
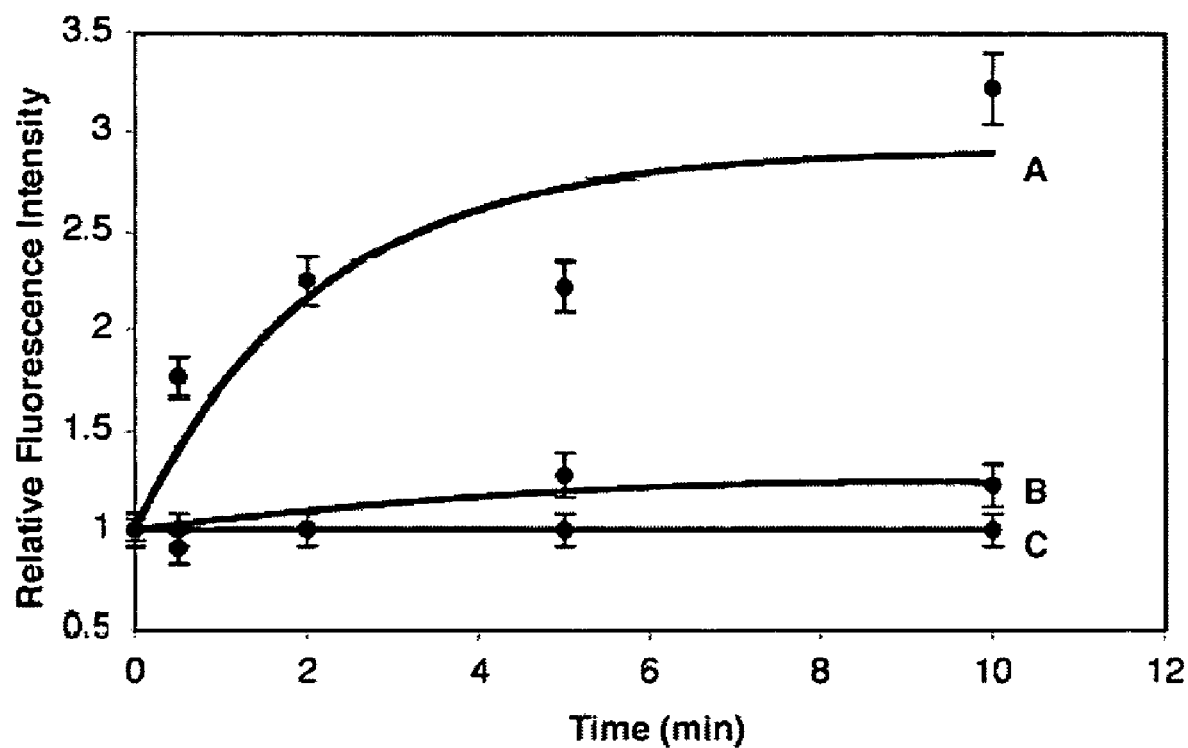
FIG. 8. Intracellular fluorescence change as a function of time following irradiation and/or TPA treatment. HeLa cells were microinjected with peptide 2 (Example III) and subsequently (A) irradiated and treated with TPA, (B) treated with TPA in the absence of light, and (C) irradiated in the absence of TPA.

The light-induced sampling of protein kinase activity was also examined in living cells. The caged protein kinase fluorescent substrate 2 was introduced into HeLa cells via microinjection. Exposure of cells to the phorbol ester TPA activates PKC. Compound 1 serves as a specific sensor for the conventional isoforms of PKC in living cells. However, HeLa cells containing the caged derivative 2 fail to display a fluorescent response upon exposure to TPA alone or upon exposure to light in the absence of TPA. By contrast, a robust response is observed when compound 2-containing HeLa cells are both illuminated and treated with TPA (FIG. 8).

Prior to the present disclosure, none of the fluorescent reporters described to date allow control over when protein kinase activity sampling is performed. The latter property is extremely valuable in a number of instances. For example, cells harboring constitutively active protein kinases can render the intracellular loading of a kinase sensor and the subsequent observation of activity at a well-defined time point problematic. Furthermore, protein kinases can exhibit intermittent activity as a function of some cellular event, such as with PKC, which appears to be activated at several distinct stages during mitosis.[26-30] In general, the ability to control when protein kinase activity is measured with respect to multiple cellular signposts provides the opportunity to collect a large series of parallel temporally-offset samplings of protein kinase action. Disclosed herein is a caged protein kinase sensor prepared by modifying the free hydroxyl group of a phosphorylatable serine moiety with a photolabile side chain appendage that blocks phosphoryl transfer. It is believed that compound 2 represents the first example of a caged fluorescent reporter of intracellular enzymatic activity. The caged sensor allows one to (1) sample PKC activity with exquisite temporal precision, (2) control the amount of active sensor available for phosphorylation, and (3) examine protein kinase activity at multiple time points.

REFERENCES

1. Sebolt-Leopold, J. S. (2000) Development of anticancer drugs targeting the MAP kinase pathway. *Oncogene* 19: 6594-6599.
2. Popoli, M., Mori, S., Brunello, N., Perez, J., Gennarelli, M., and Racagni, G. (2001) Serine/threonine kinases as molecular targets of antidepressants: implications for pharmacological treatment and pathophysiology of affective disorders. *Pharmacol. Ther.* 89: 149-170.
3. Agarwal, R. (2000) Cell signaling and regulators of cell cycle as molecular targets for prostate cancer prevention by dietary agents. *Biochem. Pharmacol.* 60: 1051-1059.
4. Senderowicz, A. M. (2001) Development of cyclin-dependent kinase modulators as novel therapeutic approaches for hematological malignancies. *Leukemia* 15: 1-9.
5. Lawrence, D. S., and Niu, J. (1998) Protein kinase inhibitors: the tyrosine-specific protein kinases. *Pharmacol. Ther.* 77: 81-114.
6. Ng, T., Squire, A., Hansra, G., Bornancin, F., Prevostel, C., Hanby, A., Harris, W., Barnes, D., Schmidt, S., Mellor, H., Bastiaens, P. I. H., and Parker, P. J. (1999) Imaging protein kinase Calpha activation in cells. *Science* 283: 2085-2089.
7. Nagai, Y., Miyazaki, M., Aoki, R., Zama, T., Inouye, K., Hirose, K., Iino, M., and Hagiwara, M. (2000) A fluorescent indicator for visualizing cAMP-induced phosphorylation in vivo. *Nat. Biotechnol.* 18: 313-316.
8. Post, P. L., Trybus, K. M., and Taylor, D. L. (1994) A genetically engineered, protein-based optical biosensor of myosin II regulatory light chain phosphorylation. *J. Biol. Chem.* 269, 12880-12887.
9. McIlroy, B. K., Walters, J. D., and Johnson, J. D. (1991) Phosphorylation-dependent binding of a synthetic MARCKS peptide to calmodulin. *Anal. Biochem.*, 195, 148-152.
10. Bowman, B. F., Peterson, J. A., and Stull, J. T. (1992) Pre-steady-state kinetics of the activation of rabbit skeletal muscle myosin light chain kinase by Ca2+/calmodulin. *J. Biol. Chem.* 267 5346-5354.
11. Wood, J., Koszelak, M., Liu, J., and Lawrence, D. S. (1998) *J. Amer. Chem. Soc.* 120, 7145-7146.
12. Marriot, G., and Walker, J. W. (1999) *Trends Plant Sci.* 4, 330-334.
13. Curley, K., and Lawrence, D. S. (1999) Caged regulators of signaling pathways. *Pharmacol. Therap.*, 82, 347-354.
14. Walker, J. W., Gilbbert, S. H., Drummond, R. M., Yamada, M., Sreekumar, R., Carraway, R. E., Ikebe, M., and Fay, F. S. (1998) Signaling pathways underlying eosinophil cell motility revealed by using caged peptides. *Proc. Natl. Acad. Soc. U.S.A.* 95, 1568-1573.
15. Pirrung, M. C., Drabik, S. J., Ahamed, J., and Ali, H. (2000) Caged chemotactic peptides. *Bioconjug. Chem.* 11, 679-681.
16. Tatsu, Y., Shigeri, Y., Ishida, A., Kameshita, I., Fujisawa, H., and Yumoto, N. (1999) Synthesis of caged peptides using caged lysine: application to the synthesis of caged AIP, a highly specific inhibitor of almodulin-dependent protein kinase II. *Bioorg. Med. Chem. Lett.* 9, 1093-1096.
17. Pan, P., and Bayley, H. (1997) Caged cysteine and thiophosphoryl peptides. *FEBS Lett.* 405, 81-85.
18. Kislauski, E. H., Zhu, X.-C., and Singer, R. (1997) beta-Actin messenger RNA localization and protein synthesis augment cell motility. *J. Cell Biol.* 136, 1263-1270.
19. Lee, T. R., Niu, J., and Lawrence, D. S. (1995) The extraordinary active site substrate specificity of pp60c-src. A multiple specificity protein kinase. *J. Biol. Chem.*, 270, 5375-5380.
20. Kwon, Y.-G., Mendelow, M., and Lawrence, D. S. (1994) *J. Biol. Chem.*, 269, 16725-16729.
21. Lee, T. R., Mendelow, M., Srinivasan, J., Kwon, J.-G., and Lawrence, D. S. (1993) *J. Amer. Chem. Soc.* 115, 9888-9891.
22. Yan, X., Lawrence, D. S., Corbin, J. D., and Francis, S. H. (1996) *J. Amer. Chem. Soc.* 118, 11684-11685.
23. Lee, T. R., Niu, J., and Lawrence, D. S. (1994) Phenol kinase activity of the serine/threonine-specific cAMP-dependent protein kinase: steric and electronic effects. *Biochemistry* 33, 4245-4250.
24. Yan, X., Curley, K., and Lawrence, D. S. (2000) The specificity of the protein kinase C alpha, betaII and gamma isoforms as assessed by an unnatural alcohol-appended peptide library. *Biochem. J.* 349, 709-715.
25. Glass, D. B., Masaracchia, R. A., Feramisco, J. R., and Kemp, B. E. (1978) Isolation of phosphorylated peptides and proteins on ion exchange papers. *Anal. Biochem.* 87, 566-575.
26. Goss, V. L., Hocevar, B. A., Thompson, L. J., Stratton, C. A., Burns, D. J., and Fields, A. P. (1994) Identification of nuclear beta II protein kinase C as a mitotic lamin kinase. *J. Biol. Chem.* 269, 19074-19080.
27. Collas, P. (1999) Sequential PKC- and Cdc2-mediated phosphorylation events elicit zebrafish nuclear envelope disassembly. *J. Cell Sci.* 112, 977-987.
28. Passalacqua, M., Patrone, M., Sparatore, B., Pedrazzi, M., Melloni, E., and Pontremoli, S. (1999) Protein kinase C-theta is specifically activated in murine erythroleukaemia cells during mitosis. FEBS Lett. 1999 Jun. 25; 453(3):249-53. *FEBS Lett.* 453, 249-253.
29. Takai, Y., Ogawara, M., Tomono, Y., Moritih, C., Imajoh-Ohmi, S., Tsutsumi, O., Taketani, Y., and Inagaki, M. (1996) Mitosis-specific phosphorylation of vimentin by protein kinase C coupled with reorganization of intracellular membranes. *J. Cell Biol.* 133, 141-149.
30. Varlamova, O., Spektor, A. and Bresnick, A. R. (2001) Protein kinase C mediates phosphorylation of the regulatory light chain of myosin-II during mitosis. *J Muscle Res. Cell Motil.* 22, 243-250.
31. Way, K. J., Chou, E., and King, G. L. (2000) Identification of PKC-isoform-specific biological actions using pharmacological approaches. Trends Pharmacol. Sci. 21, 181-187.
32. Lingameneni, R., Vysotskaya, N., Duch, D. S., and Hemmings Jr., H. C. (2000) Inhibition of voltage-dependent sodium channels by Ro 31-8220, a 'specific' protein kinase C inhibitor. *FEBS Lett.* 473, 265-268.
33. Davies, S. P., Reddy, H., Caivano, M., and Cohen, P. (1999) *Biochem. J.* 351, 95-105.
34. Gschwendt, M., Kittstein, W., and Marks F. (1991) Protein kinase C activation by phorbol esters: do cysteine-rich regions and pseudosubstrate motifs play a role? *Trends Biochem. Sci.* 16, 167-169.
35. Goekjian, P. G., and Jirousek, M. R. (1999) Protein kinase C in the treatment of disease: signal transduction pathways, inhibitors, and agents in development. *Curr. Med. Chem.* 6, 877-903.
36. Pines, J. Four-dimensional control of the cell cycle. *Nat. Cell Biol.* 1999, 1:E73-9.
37. Blatt, N. B.; Glick, G. D. Signaling pathways and effector mechanisms pre-programmed cell death. *Bioorg. Med. Chem.* 2001, 9, 1371-1384.
38. Lee, C. L.; Linton, J.; Soughayer, J. S.; Sims, C. E.; Allbritton, N. L. Localized measurement of kinase activation in oocytes of *Xenopus laevis. Nat. Biotechnol.* 1999, 17, 759-762.
39. Grynkiewicz, G.; Poenie, M.; Tsien, R. Y. A new generation of Ca2+ indicators with greatly improved fluorescence properties. *J. Biol. Chem.* 1985, 260, 3440-3450.
40. Minta, A.; Kao, J. P. Y.; Tsien, R. Y. Fluorescent indicators for cytosolic calcium based on rhodamine and fluorescein chromophores. *J. Biol. Chem.* 1989, 264, 8171-8178.
41. Tsien, R. Y. Fluorescent probes of cell signaling. *Ann. Rev. Neurosci.* 1989, 12, 227-253.
42. Sun, W.-C., Gee, K. R.; Klaubert, D. H.; Haugland, R. P. *J. Org. Chem.* 1997, 62, 6469-6475.
43. Corey, E. J.; Gras, J.-L.; Ulrich, P. *Tetrahedron Lett.* 1976, 809-813.
44. Lee, T. R.; Lawrence, D. S. Acquisition of high-affinity, SH2-targeted ligands via a spatially focused library. *J Med Chem.* 1999, 42, 784-787.
45. Kwon, Y G, Mendelow, M, Srinivasan J, Lee T R, Pluskey S, Salerno A, and Lawrence, D S. The active site substrate specificity of the cAMP-dependent protein kinase. *J. Biol. Chem.* 268: 10713-16, 1993.
46. Lee, T R, Till, J H, Lawrence, D S, Miller W T. Precision substrate targeting of protein kinases v-Abl and c-Src. *J. Biol. Chem.* 270: 27022-26, 1995.
47. Srinivasan, J, Koszelak, M, Kwon, Y-G, Lawrence, D S. The design of peptide-based substrates for the cdc2 protein kinase. *Biochemical J* 309: 927-31, 1995

48. Wood J S, Yan X, Mendelow M, Corbin J D, Francis, S H, Lawrence, D S. Precision substrate targeting of protein kinases. *J. Biol. Chem.* 271: 174-179, 1996.
49. Nazareth L V and Weigel N L. Activation of the human androgen receptor through a protein kinase A signaling pathway. *J. Biol. Chem.* 271: 19900-7, 1996.
50. Dhingra K, Hortobagyi, G N. Critical evaluation of prognostic factors. *Semin. Oncol.* 23:436-45, 1996.
51. Bramson H N, Thomas N, DeGrado W F, Kaiser E T. *J. Amer. Chem. Soc.* 102: 7156-7, 1980.
52. Wei-Chuan Sun, Kyle R. Gee, Dieter H. Klaubert and Richard P. Haugland; *J. Org. Chem.* 1997, 62, 6469-6475.
53. Zhou, S.; Cantley, L. C. Recognition and Specificity in Protein Tyrosine Kinase-Mediated Signalling. *Trends Biochem. Sci.* 1995, 20, 470-475.
54. Lev-Ram, V.; Jiang, T.; Wood, J.; Lawrence, D. S.; Tsien, R. Y. Synergies and Coincidence Requirements Between NO, cGMP, and $Ca^{2+}$ in the Induction of Cerebellar Long-Term Depression. *Neuron* 1997, 18, 1025-1038.
55. Dostmann, W. R.; Taylor, M. S.; Nickl, C. K.; Brayden, J. E.; Frank, R.; Tegge, W. J. Highly Specific, Membrane-Permeant Peptide Blockers of cGMP-Dependent Protein Kinase Ialpha Inhibit NO-Induced Cerebral Dilation. *Proc Natl Acad Sci USA* 2000, 97, 14772-7.
56. Yan, X.; Curley, K.; Lawrence, D. S. The Specificity of the Protein Kinase C Alpha, Beta and Gamma Isoforms as Assessed by an Unnatural Alcohol-Appended Peptide Library. *Biochem. J.* 2000, 349, 709-715.
57. Kwon, Y. G.; Mendelow, M.; Lawrence, D. S. The Active Site Substrate Specificity of Protein Kinase C. *J. Biol. Chem.* 1994, 269, 4839-4844.
58. Adams, S. R.; Tsien, R. Y. Controlling Cell Chemistry with Caged Compounds. *Annu. Rev. Physiol.* 1993, 55, 755-784.
59. McCray, J. A.; Trentham, D. R. Properties and Uses of Photoreactive Caged Compounds. *Annu. Rev. Biophys. Biophys. Chem.* 1989, 18, 239-270.
60. Blohm, D. H.; Guiseppe-Elie, A. New developments in microarray technology. *Curr Opin Biotech* 2001, 12, 41-7.
61. Fung, E. T.; Thulasiraman, V.; Weinberger, S. R.; Dalmasso, E. A. Protein biochips for differential profiling. *Curr Opin Biotech* 2001, 12, 65-9.
62. Hunter, T. Protein kinases and phosphatases: the yin and yang of protein phosphorylation and signaling. *Cell* 80: 225-236, 1995.
63. Hunter, T. A thousand and one protein kinases. *Cell* 50: 823-829, 1987.
64. Ghosh, M.; Ichetovkin, I.; Song, X.; Condeelis, J. S.; Lawrence, D. S. Light-Induced F-Actin Severing Via A Caged Cofilin. *J. Amer. Chem. Soc.* 2002, 124, 2440-2441.
65. Czemik A J, Girault J-A, Naim A C, Chen J, Snyder G, Kebabian J, Greengard P. Production of phosphorylation state-specific antibodies. *Methods Enzymol.* 201: 264-283, 1991.
66. Verveer P J, Wouters F S, Reynolds A R, Bastiaens P I, Quantitative imaging of lateral ErbB1 receptor signal propagation in the plasma membrane. *Science* 290: 1567-70, 2000.
67. Nerbonne J M, Richard S, Nargeot J, Lester H A. New photoactivatable cyclic nucleotides produce intracellular jumps in cyclic AMP and cyclic GMP concentrations. *Nature* 310: 74-76, 1984.
68. Zhang J, Ma Y, Taylor SS, and Tsien RY. Genetically encoded reporters of protein kinase A activity reveal impact of substrate tethering. *Proc. Nat. Acad. Sci.* 98: 14997-15002, 2001.
69. Ting A Y, Kain K H, Klemke R L and Tsien R Y. Genetically encoded fluorescent reporters of protein tyrosine kinase activities in living cells. *Proc. Nat. Acad. Sci.* 98: 15003-8, 2001.
70. Higashi H, Sato K, Omori A, Sekiguchi M, Ohtake A, Kudo Y. Imaging of Ca2+/calmodulin-dependent protein kinase II activity in hippocampal neurones. *NeurOReport* 7: 2695-700, 1996.
71. Higashi H, Sato K, Ohtake A, Omori A, Yoshida S, Kudo Y. Imaging of cAMP-dependent protein kinase activity in living neural cells using a novel fluorescent substrate. *FEBS Lett.* 414: 55-60, 1997.
72. Ventura C, Maioli M. Protein kinase C control of gene expression. *Crit. Rev. Eukaryot. Gene Expr.* 11: 243-67, 2001.
73. Formisano P, Beguinot F. The role of protein kinase C isoforms in insulin action. *J. Endocrinol. Invest.* 24: 460-7, 2001.
74. Carter C A. Protein kinase C as a drug target: implications for drug or diet prevention and treatment of cancer. *Curr. Drug Targets* 1: 163-83, 2000.
75. Barry O P and Kazanietz M G. Protein kinase C isozymes, novel phorbol ester receptors and cancer chemotherapy. *Curr. Pharm. Des.* 7: 1725-44, 2001.
76. Swannie H C, Kaye S B. Protein kinase C inhibitors. *Curr. Oncol. Rep.* 4: 37-46, 2002.
77. Lawrence D S. Functional proteomics: large scale analysis of protein kinase activity. *Genome Biol.* 2(2): REVIEWS1007, 2001.
78. Black JD. Protein kinase C-mediated regulation of the cell cycle. *Frontiers in Bioscience* 5: d406-423, 2000.
79. Allen, J. M.; Allen, S. K.; Baertschi, S. W. 2-Nitrobenzaldehyde: a convenient UV-A and UV-B chemical actinometer for drug photostability testing. *J. Pharm. Biomed. Anal.* 2000, 24, 167-178.
80. Nishikawa, K.; Toker, A.; Johannes, F. J.; Songyang, Z.; Cantley, L. C. *J. Biol. Chem.* 1997, 272, 952-960.
81. Bayley, H.; Pan, P. *FEBS Lett.* 1997, 405, 81-85.
82. Zou, K.; Cheley, S.; Givens, R. S.; Bayley, H. *J. Amer. Chem. Soc.* 2002, 124, 8220-8229.
83. Rothman D. M.; Vazquez, M. E.; Vogel, E. M.; Imperiali, B. *Org. Lett.* 2002, 4, 2856-2868.
84. Iversen, T.; Bundle, D. R. *J. Chem. Soc. Chem. Commun.* 1981, 1240-1241.
85. Wessel, H.-P.; Iversen, T.; Bundle, D. R. *J. Chem. Soc. Perkin Trans.* 1985, 1, 2247-2250.
86. Mitchison, T. J. *J. Cell Biol.* 1989, 109, 637-652.
87. Pirrung, M. C.; Nunn, D. S. *Bioorg. Med. Chem. Lett.* 1992, 2, 1489-92.
88. Cook, S. N.; Jack, W. E.; Xiong, X.; Danley, L. E.; Ellman, J. A.; Schultz, P. G.; Noren, C. *J. Angew. Chem. Int. Ed. Engl.* 1995, 34, 1629-30.
89. Dancey J, Sausville E A. Issues and progress with protein kinase inhibitors for cancer treatment. Nat Rev Drug Discov. 2003 April; 2(4):296-313.
90. McJilton M A, Van Sikes C, Wescott G G, Wu D, Foreman T L, Gregory C W, Weidner D A, Harris Ford O, Morgan Lasater A, Mohler J L, Terrian D M. Protein kinase C varepsilon interacts with Bax and promotes survival of human prostate cancer cells. Oncogene. 2003 Sep. 11; 22(39):6014-24.
91. Farrow B, Rychahou P, Murillo C, O'connor K L, Iwamura T, Evers B M. Inhibition of pancreatic cancer cell growth and induction of apoptosis with novel therapies directed against protein kinase A. Surgery. 2003 August; 134(2):197-205.
92. Stergiopoulos S G, Stratakis C A. Human tumors associated with Carney complex and germline PRKAR1A mutations: a protein kinase A disease! FEBS Lett. 2003 Jul. 3; 546(1):59-64.

What is claimed is:

1. A substrate for a protein kinase, wherein the substrate is selected from the group consisting of:

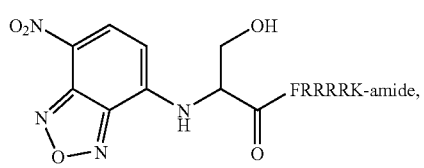

(SEQ ID NO: 3)

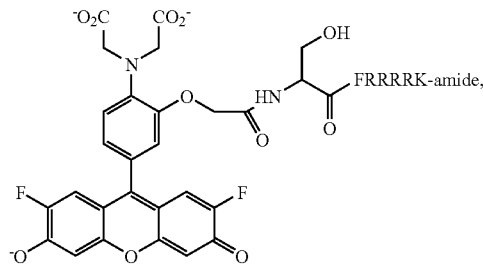

(SEQ ID NO: 3)

and

-continued

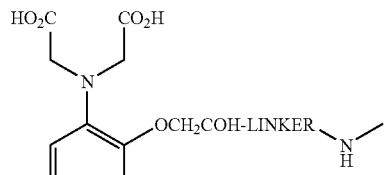

(SEQ ID NO: 1)

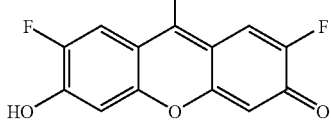

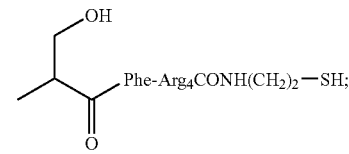

wherein F is phenylalanine, K is lysine, and R is arginine; and wherein the LINKER is selected from the group consisting of N-methyl glycine, L-proline, D-proline,

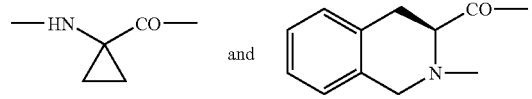 .

2. A composition comprising the substrate of claim 1, and a carrier.

3. The composition of claim 2, wherein the composition is a pharmaceutical composition and the carrier is a pharmaceutically acceptable carrier.

4. A substrate for a protein kinase or a precursor of the substrate, wherein the substrate or the precursor comprises:
   a peptide substrate for the protein kinase, wherein the peptide comprises a serine, a threonine, or a tyrosine on a terminal end of the peptide;
   at least one fluorophore, wherein a fluorophore is attached to the serine, the threonine, or the tyrosine on the terminal end of the peptide;
   wherein the fluorophore is attached to the peptide by a linker selected from the group consisting of

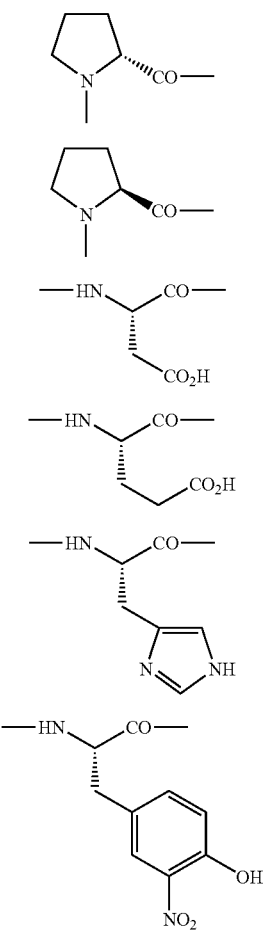

-continued

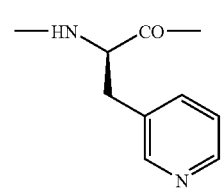 g

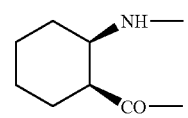 h

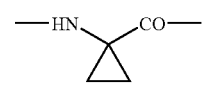 i

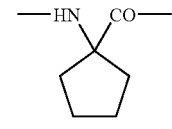 j

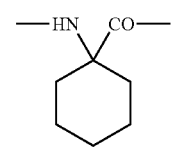 k

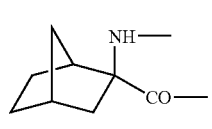 l

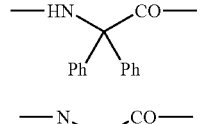 m

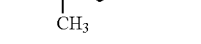 n

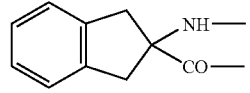 o

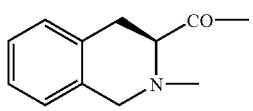 p

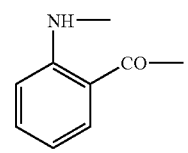 q

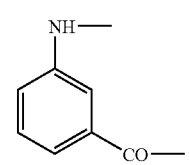 r

-continued

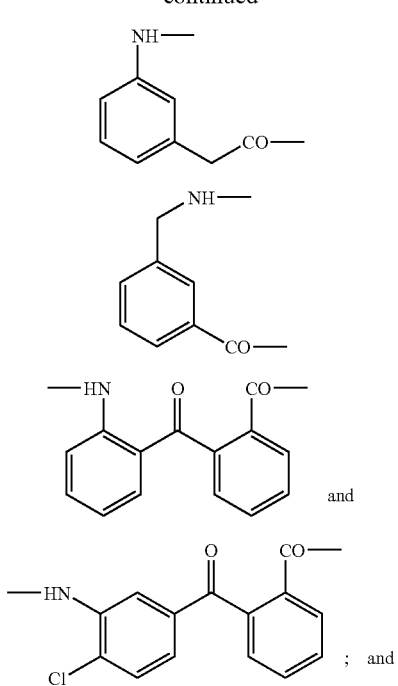

wherein
(i) the substrate is specific for a protein kinase subtype,
(ii) the fluorophore is attached to the C-terminal end of the peptide,
(iii) a fluorophore is attached to each terminal end of the peptide,
(iv) a first fluorophore is attached to a terminal end of the peptide and a second fluorophore, with photophysical properties distinct from the first fluorophore, is attached to any nonterminal site on the peptide,
(v) the fluorophore is a 7-nitrobenz-2-oxa-1,3-diazole derivative, and/or
(vi) the substrate further comprises a carbohydrate, a lipid or a nucleic acid.

5. The precursor of the substrate of claim 4, wherein the precursor of the substrate comprises a serine with a photolabile side chain that blocks phosphoryl transfer.

6. The substrate of claim 4, wherein the substrate is specific for a protein kinase subtype.

7. The substrate of claim 6, wherein the substrate is specific for protein kinase C.

8. The substrate of claim 7, wherein the substrate is specific for isoforms α, β, and γ of protein kinase C.

9. The substrate of claim 6, wherein the substrate is specific for protein kinase A, protein kinase B, protein kinase D, protein kinase G, Ca$^+$/calmodulin-dependent protein kinase, mitogen-activated protein kinase, protein kinase mos, protein kinase raf, protein tyrosine kinase, tyrosine kinase abl, tyrosine kinase src, tyrosine kinase yes, tyrosine kinase fps, tyrosine kinase met, cyclin-dependent protein kinase, or cdc2 kinase.

10. The substrate or the precursor of the substrate of claim 4, wherein the substrate further comprises a carbohydrate, a lipid or a nucleic acid.

11. The substrate or the precursor of the substrate of claim 4, wherein the fluorophore is attached to the C-terminal end of the peptide.

12. The substrate or the precursor of the substrate of claim 4, wherein the fluorophore is attached to the N-terminal end of the peptide.

13. The substrate or the precursor of the substrate of claim 4, wherein a fluorophore is attached to each terminal end of the peptide.

14. The substrate or the precursor of the substrate of claim 13, wherein fluorophores with distinct photophysical properties are attached to different terminal ends of the peptide.

15. The substrate or the precursor of the substrate of claim 4, wherein a first fluorophore is attached to a terminal end of the peptide and a second fluorophore, with photophysical properties distinct from the first fluorophore, is attached to any nonterminal site on the peptide.

16. The substrate or the precursor of the substrate of claim 4, wherein the fluorophore is a 7-nitrobenz-2-oxa-1,3-diazole derivative.

17. The substrate or the precursor of the substrate of claim 4, wherein the fluorophore comprises a fluorescein group.

18. The substrate or the precursor of the substrate of claim 4, wherein the fluorophore comprises a dansyl group, an acridine group, a rhodamine group, or a coumarin group.

19. The substrate or the precursor for the substrate of claim 4, wherein the fluorophore is attached to the peptide by a linker selected from the group consisting of N-methyl glycine, L-proline, D-proline,

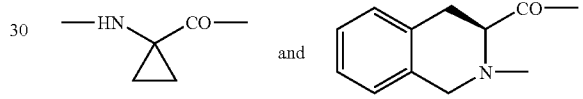

20. A composition comprising the substrate or the precursor for the substrate of claim 4, and a carrier.

21. The composition of claim 20, wherein the composition is a pharmaceutical composition and the carrier is a pharmaceutically acceptable carrier.

22. The precursor of a substrate for a protein kinase, where the precursor comprises SEQ ID NO:3 and has the structure

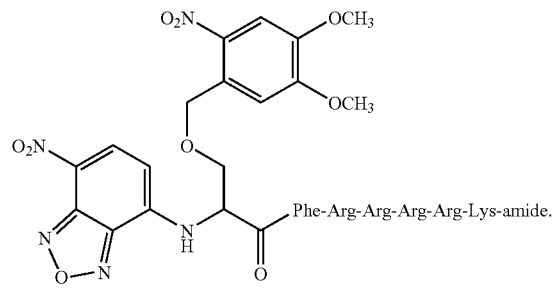

23. A composition comprising the precursor of a substrate for a protein kinase of claim 22, and a carrier.

24. The composition of claim 23, wherein the composition is a pharmaceutical composition and the carrier is a pharmaceutically acceptable carrier.

25. A precursor for a substrate for a protein kinase, wherein the precursor for the substrate comprises:
a peptide comprising a serine, a threonine, or a tyrosine on a terminal end of the peptide;
at least one fluorophore, wherein a fluorophore is attached to the serine, the threonine, or the tyrosine on the terminal end of the peptide; and a photolabile side chain attached to the serine, the threonine, or the tyrosine on the terminal end of the peptide, wherein the photolabile side chain blocks transfer of a phosphoryl group from adenosine triphosphate to a hydroxyl moiety of the serine, the threonine, or the tyrosine so that the substrate cannot be phosphorylated by a protein kinase until the photolabile side chain is removed from the substrate, and wherein the photolabile side chain comprises the structure

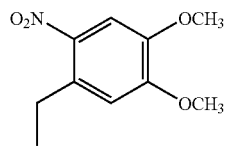

and wherein the fluorophore is attached to the peptide by a linker selected from the group consisting of a carboxamide linker, an aminobenzoic acid linker, a sulfonamide linker, a urea linker, a thiourea linker, an ester linker, a thioester linker, an alkylamine linker, an arylamine linker, an ether linker, and a thioether linker.

26. A composition comprising the substrate of claim 25, and a carrier.

27. The composition of claim 26, wherein the composition is a pharmaceutical composition and the carrier is a pharmaceutically acceptable carrier.

28. A chemical compound selected from the group of compounds consisting of:

Compound 1

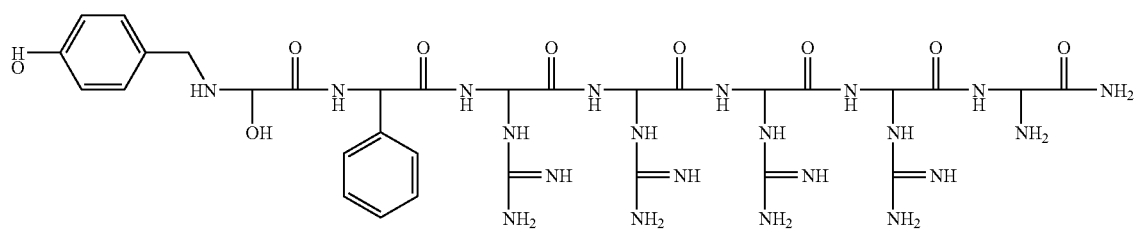

Compound 2

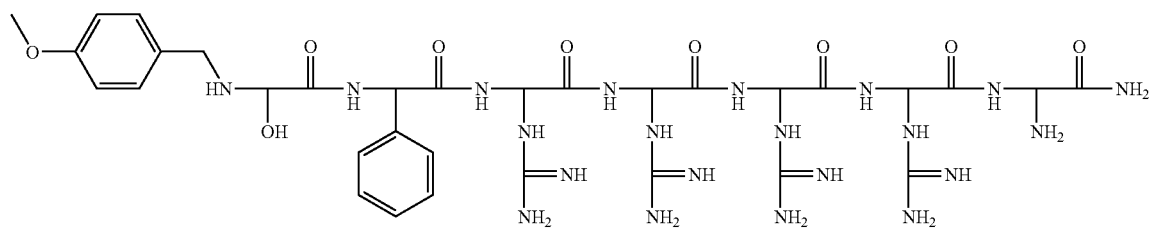

Compound 3

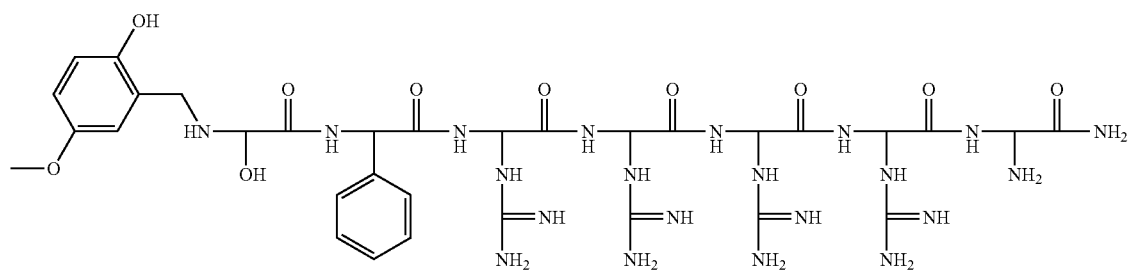

Compound 4

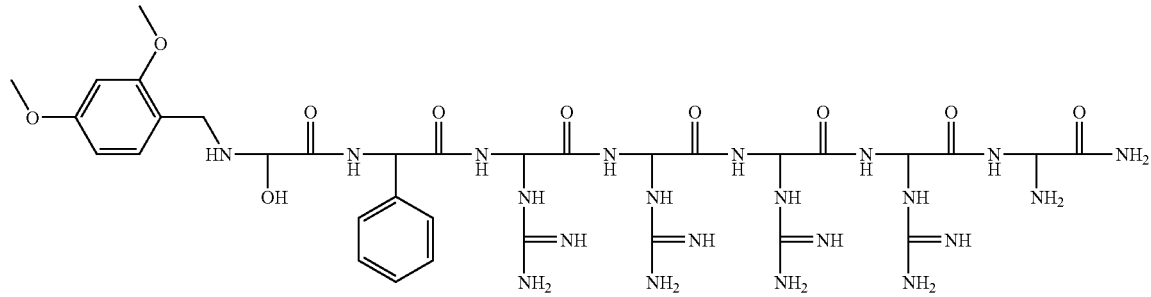

-continued
Compound 5
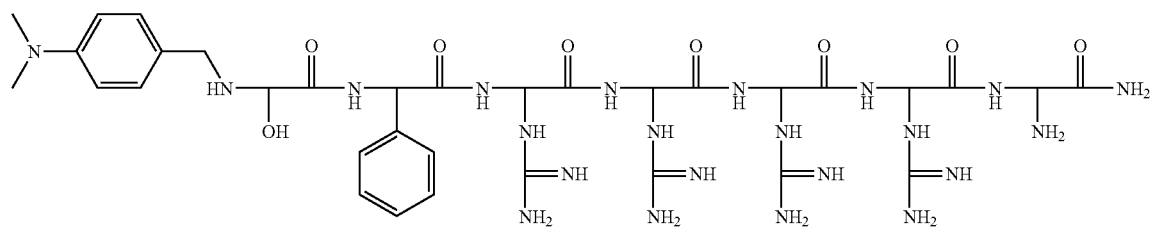
Compound 6
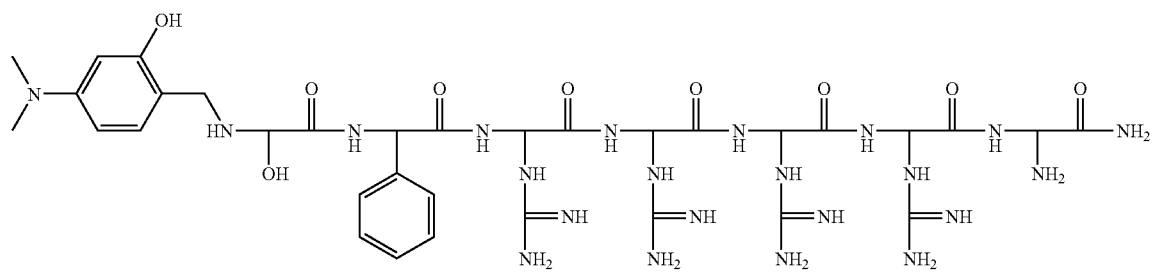
Compound 7
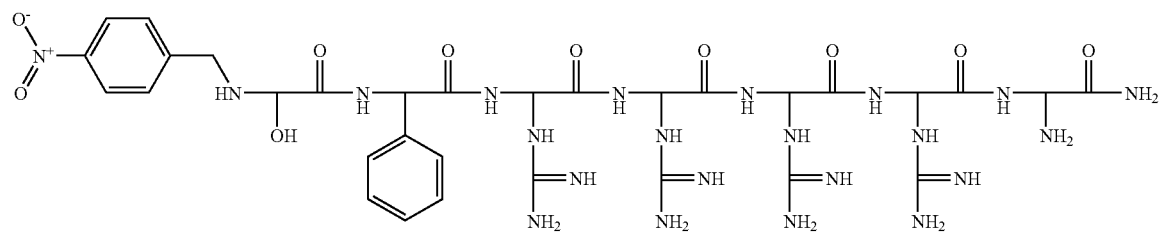
Compound 8
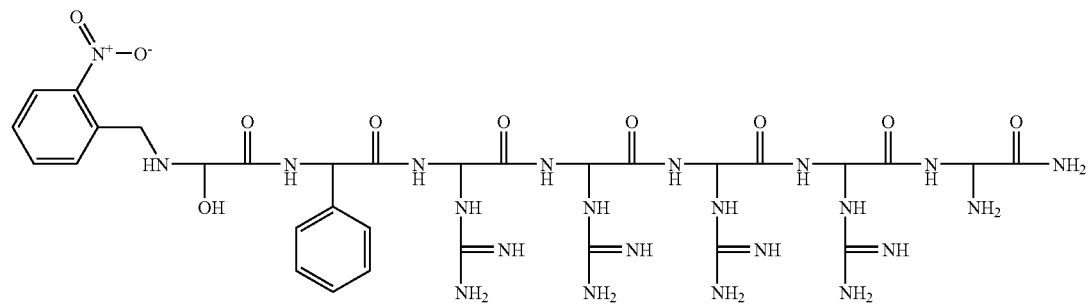
Compound 9
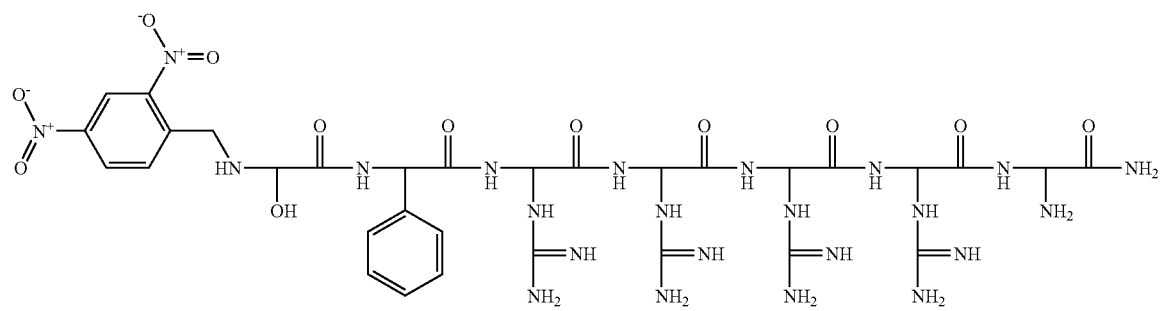

Compound 10
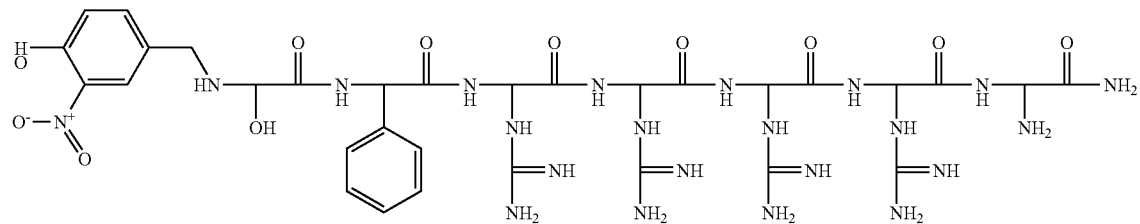
Compound 11
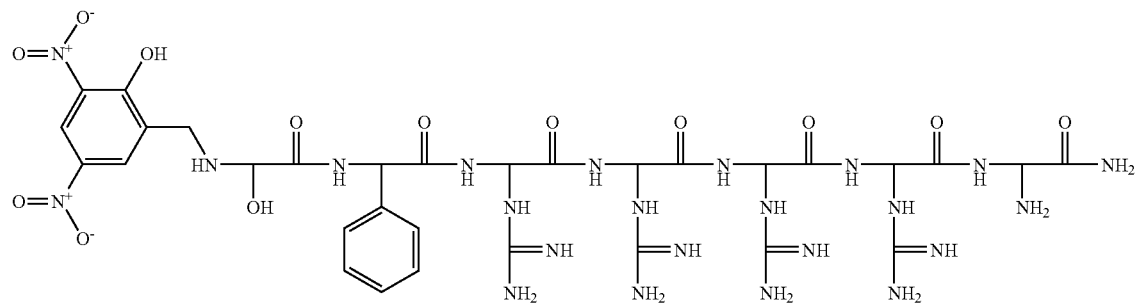
Compound 12
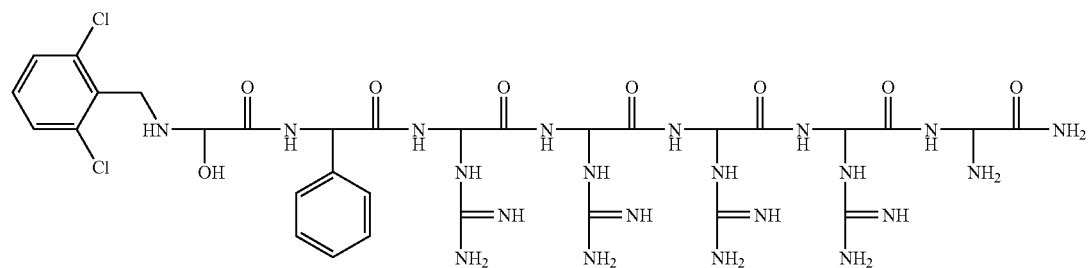
Compound 13
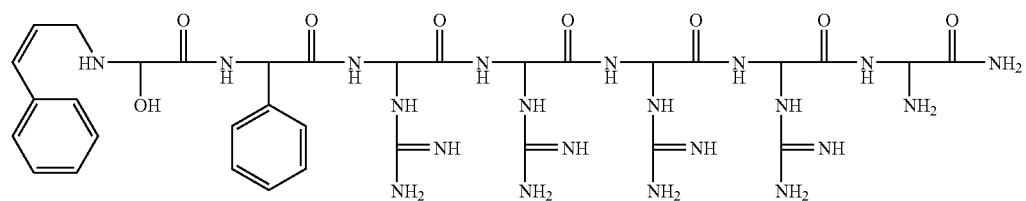
Compound 14
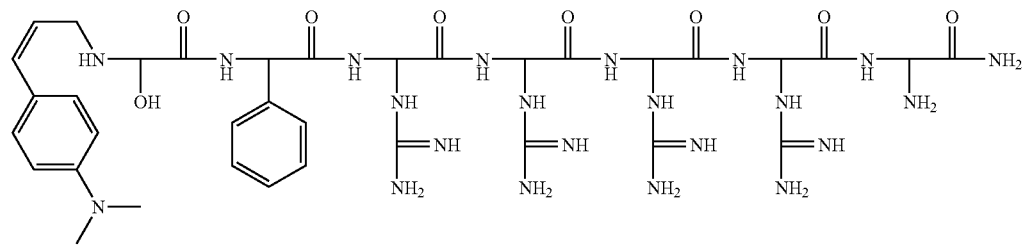
Compound 15
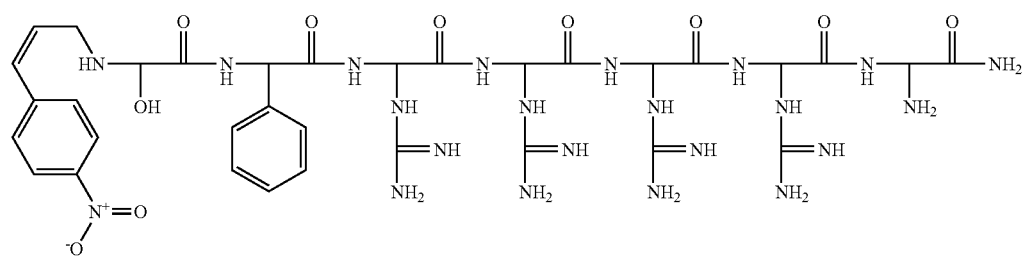

Compound 16
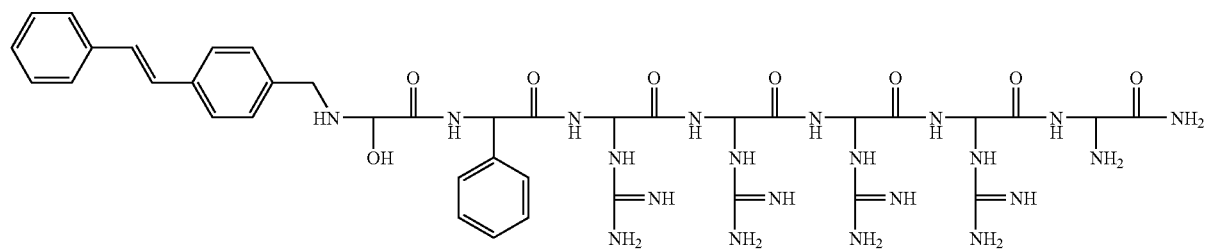
Compound 17
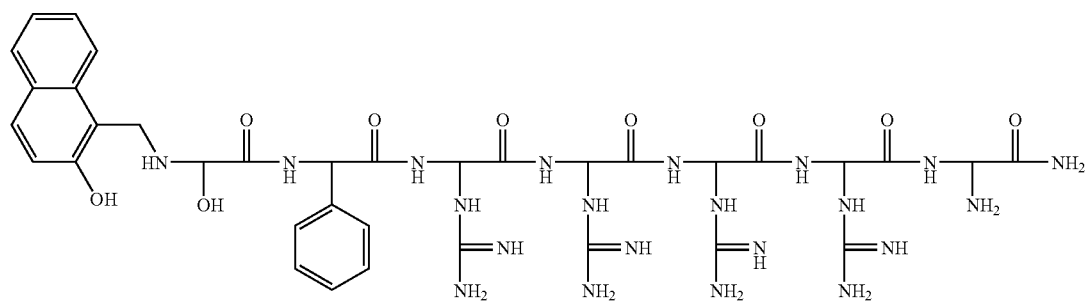
Compound 18
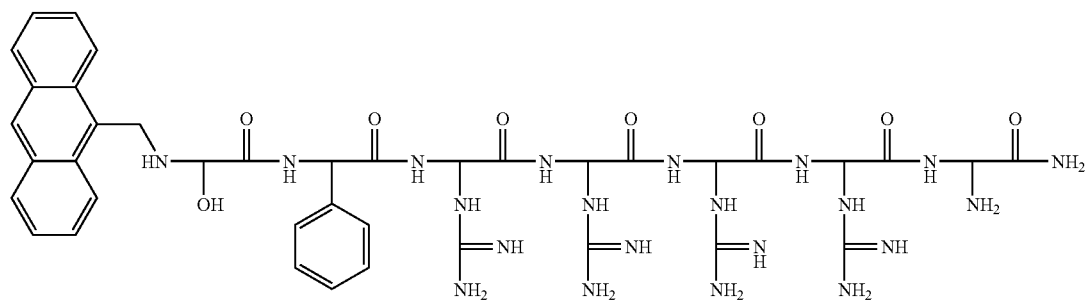
Compound 19
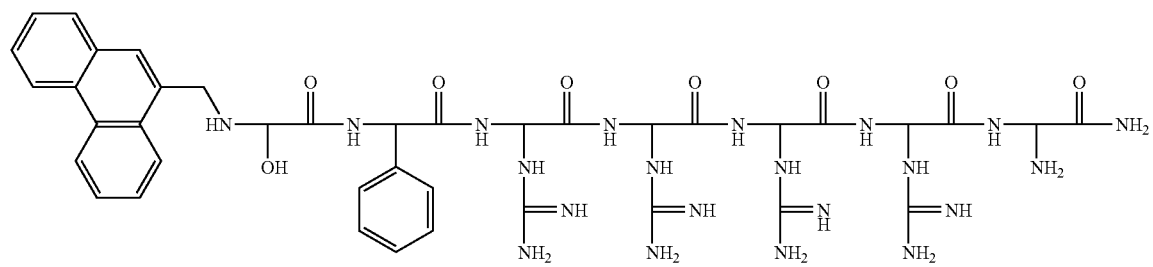
Compound 20
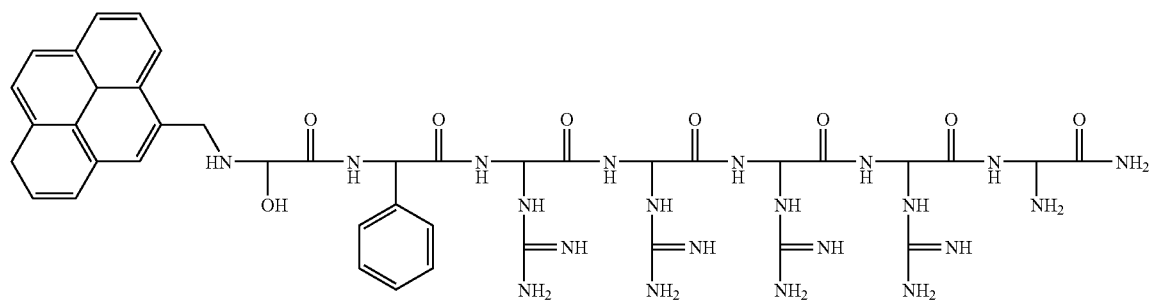

Compound 21
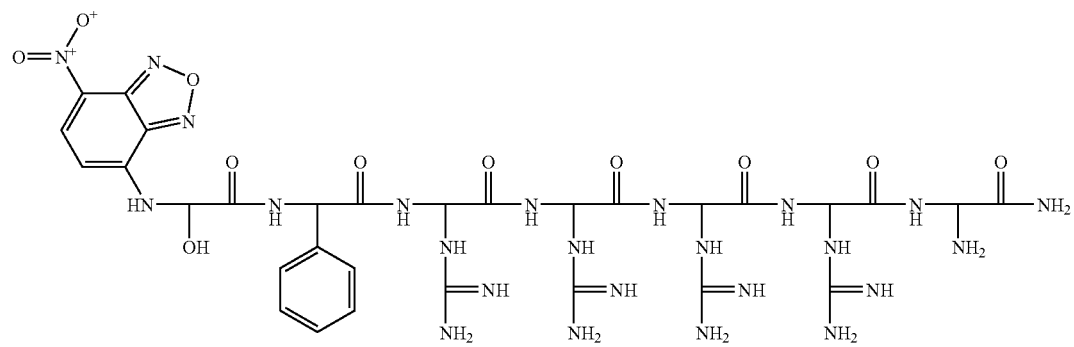
Compound 22
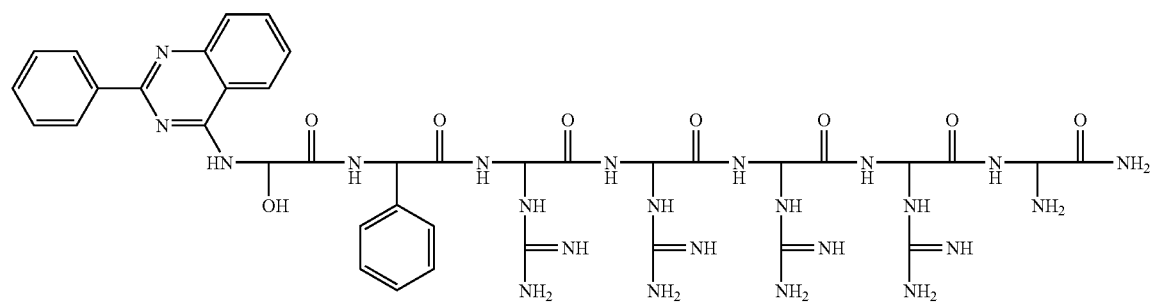
Compound 23
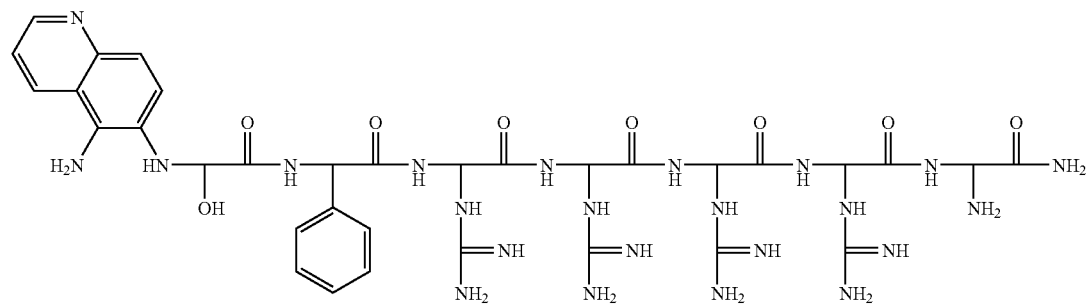
Compound 25
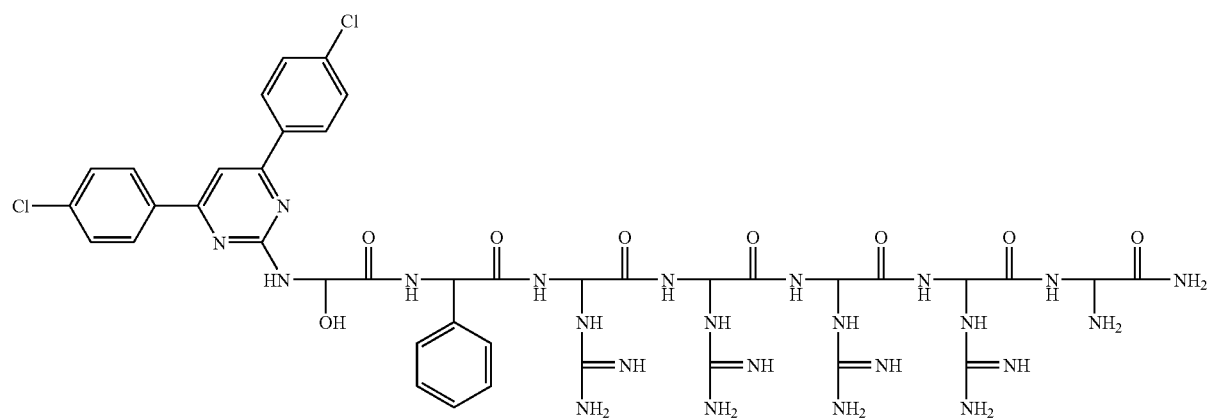

Compound 26
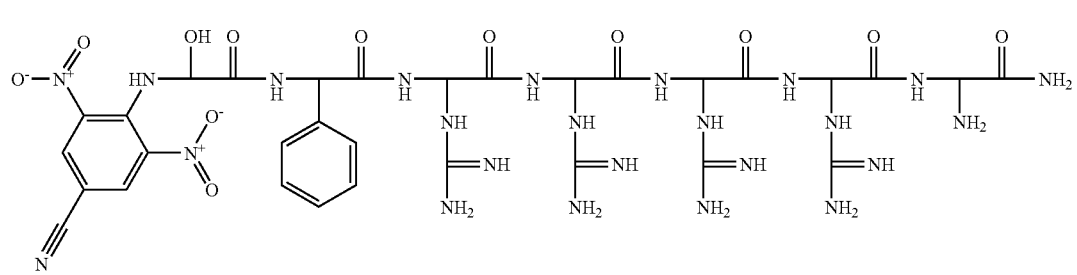
Compound 27
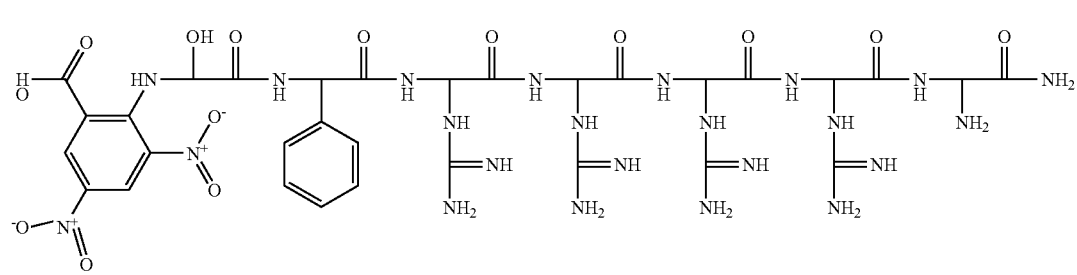
Compound 28
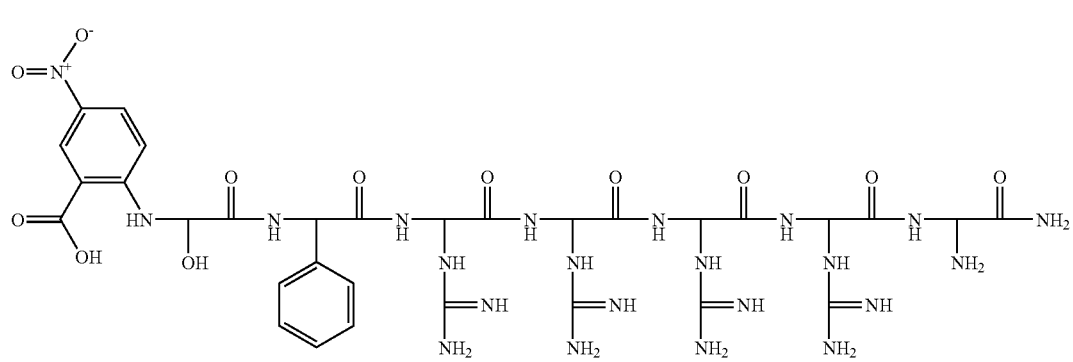
Compound 29
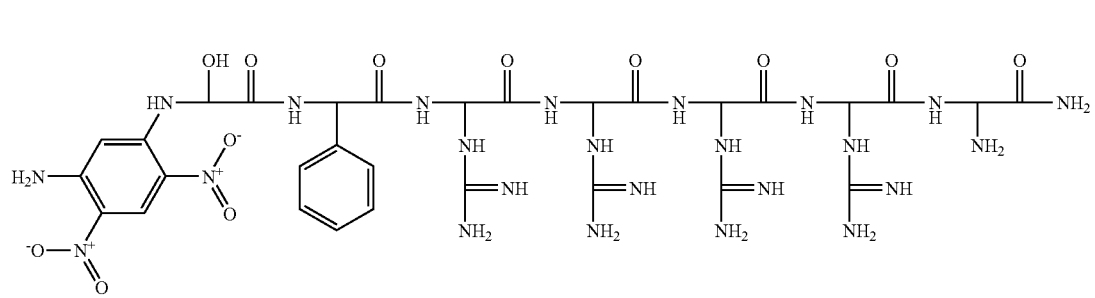
Compound 30
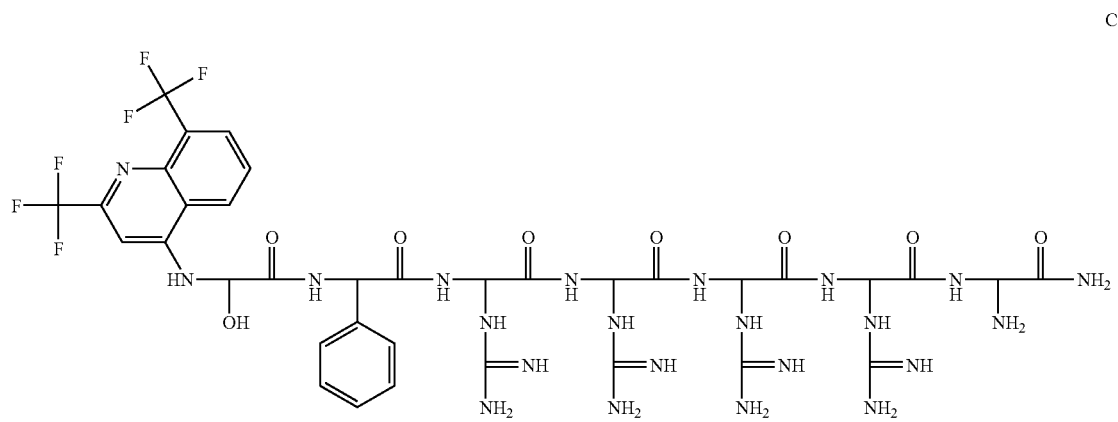

-continued
Compound 31
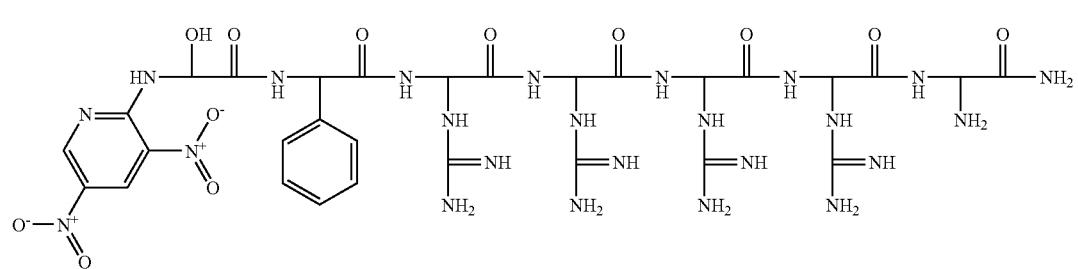
Compound 32
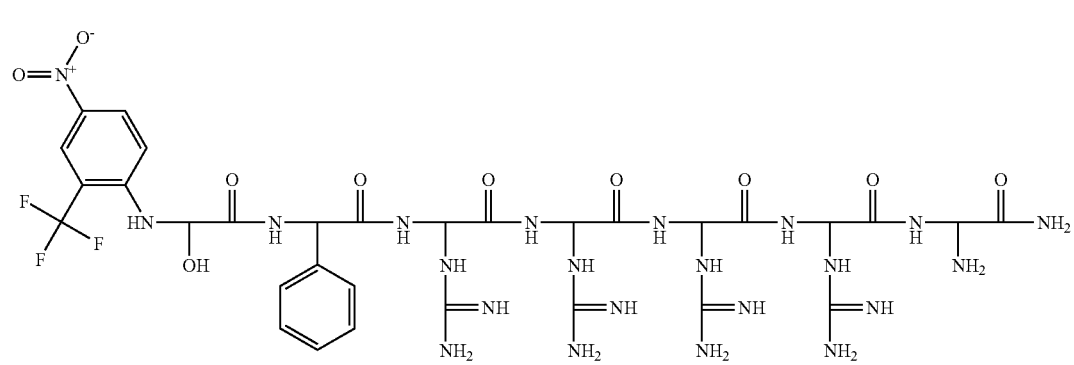
Compound 33
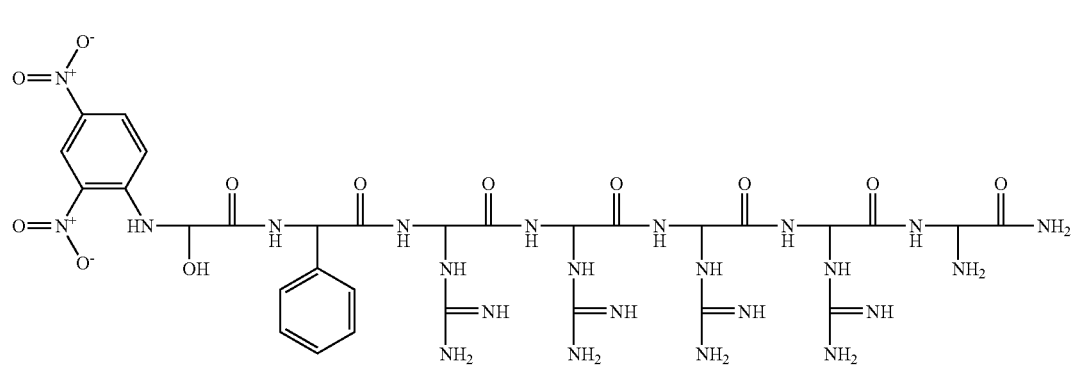
Compound 34
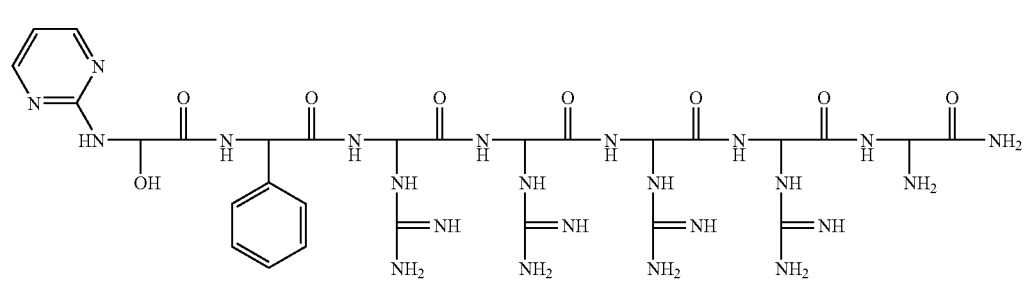
Compound 35
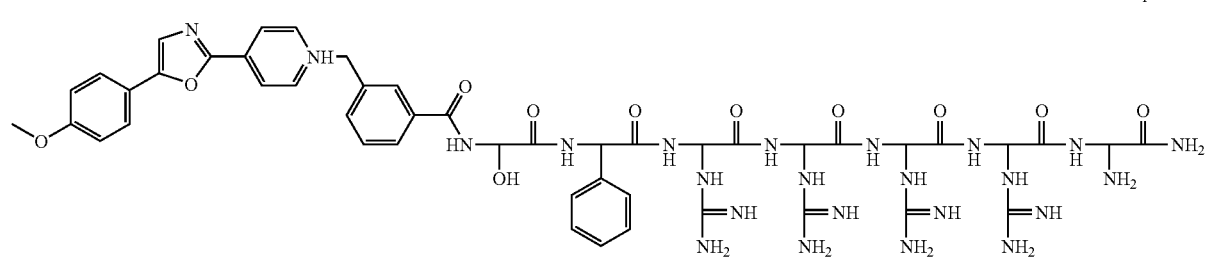

Compound 36
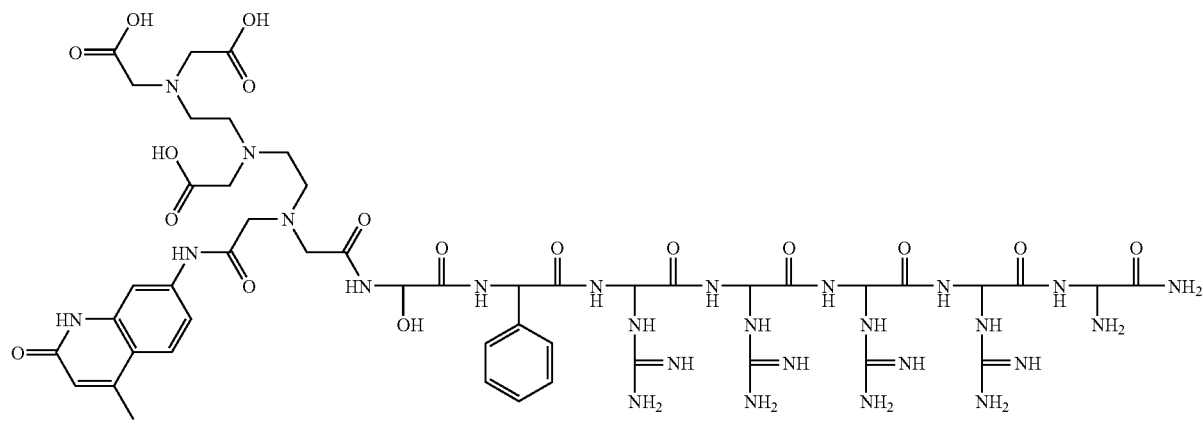
Compound 37
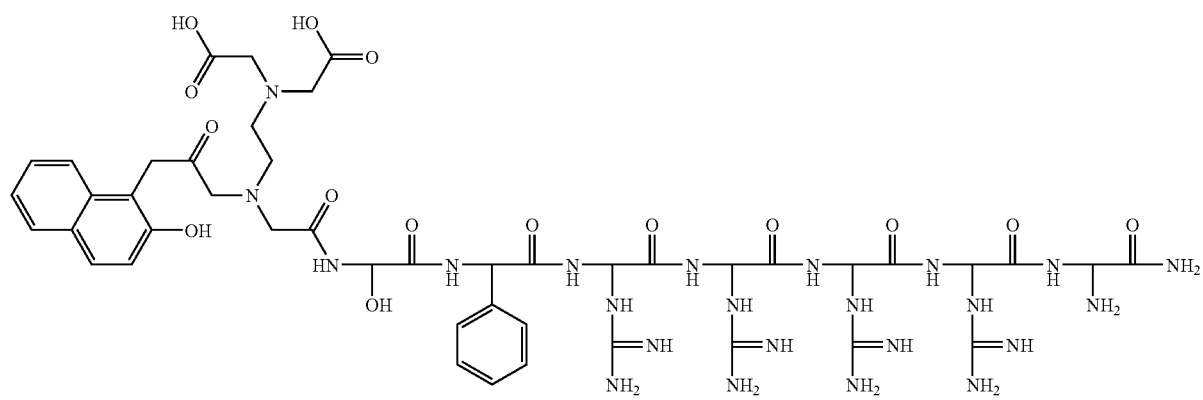
Compound 38
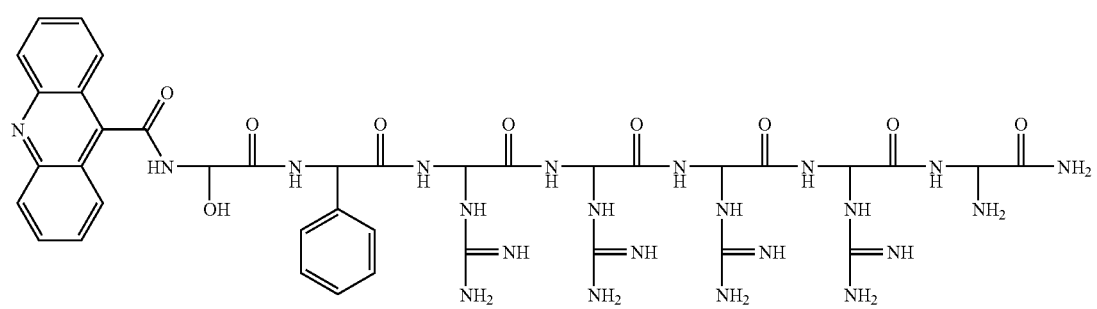
Compound 39
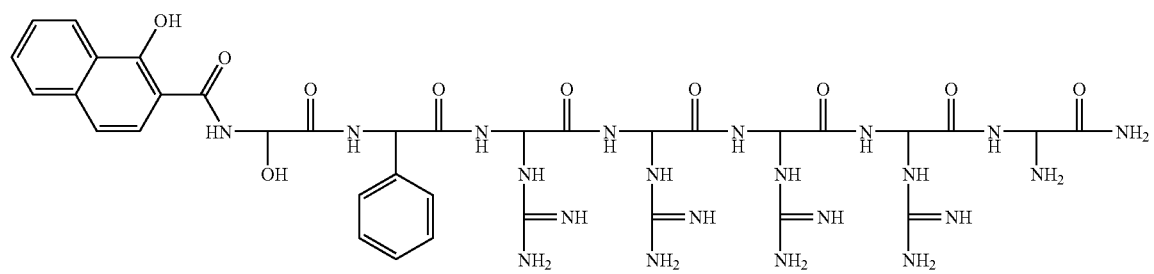

Compound 40
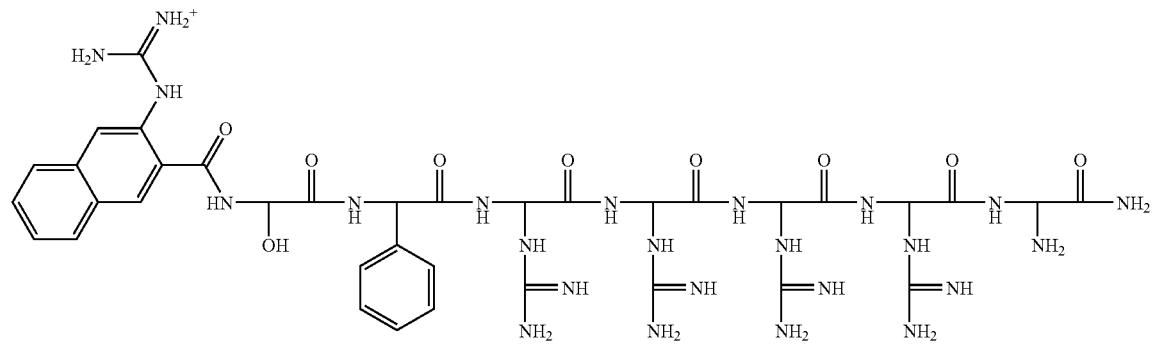
Compound 41
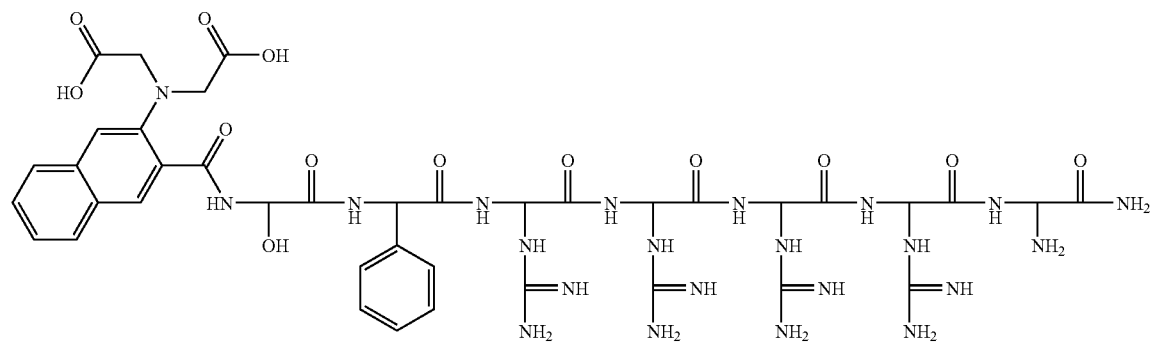
Compound 42
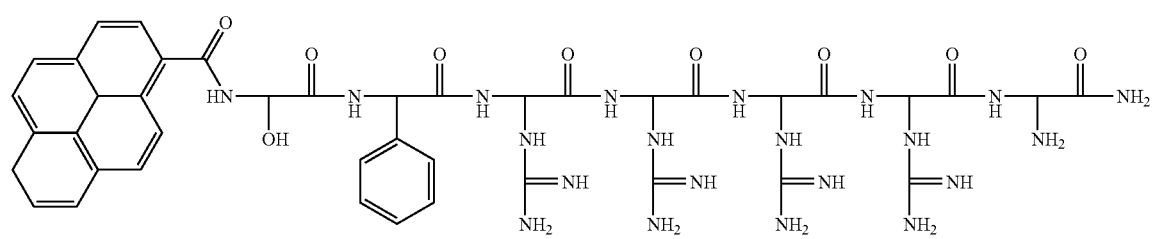
Compound 43
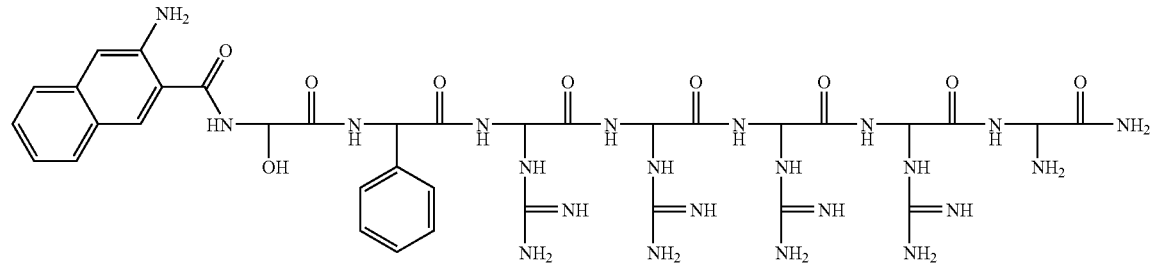

Compound 44
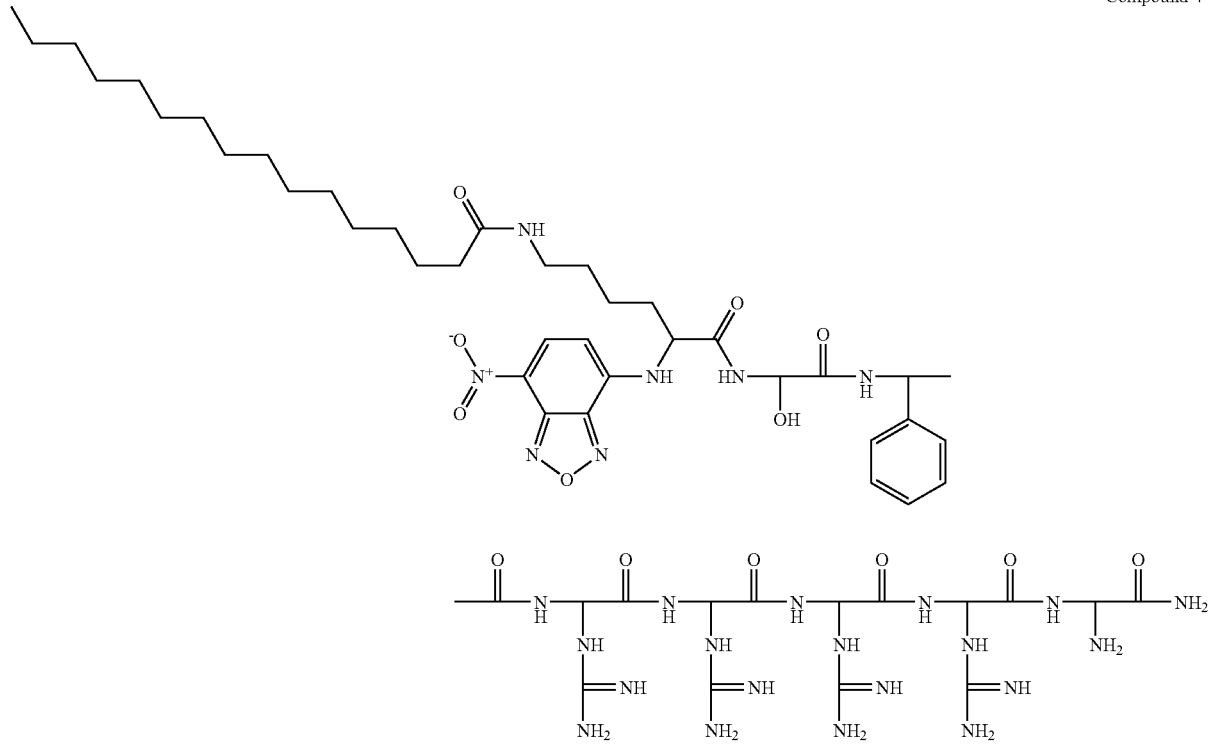
Compound 45
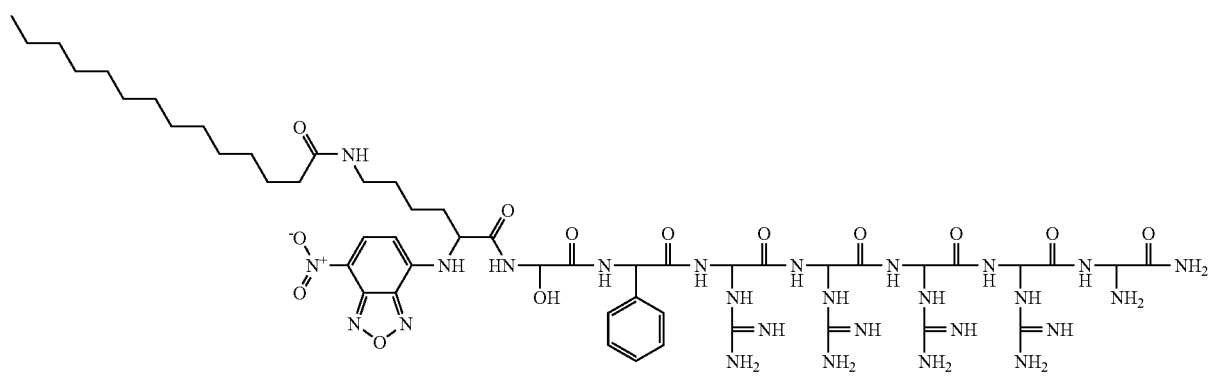
Compound 46
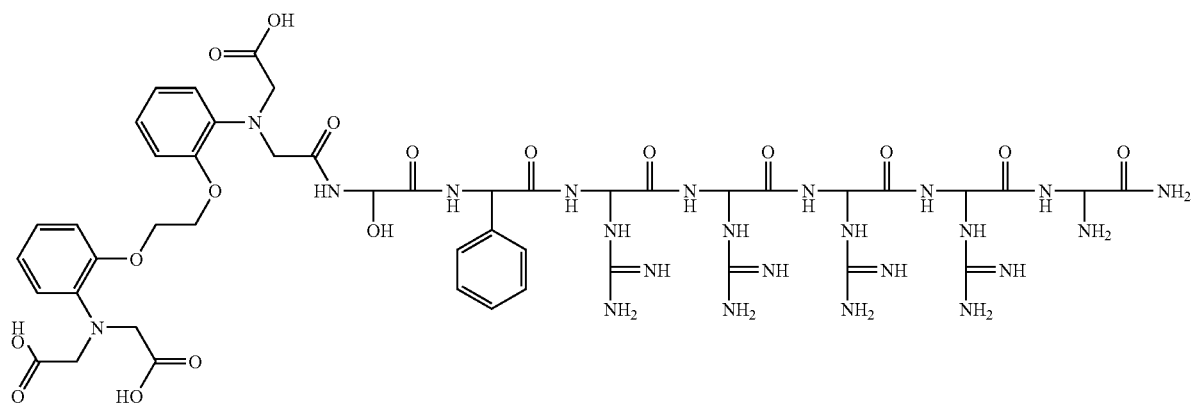

Compound 47
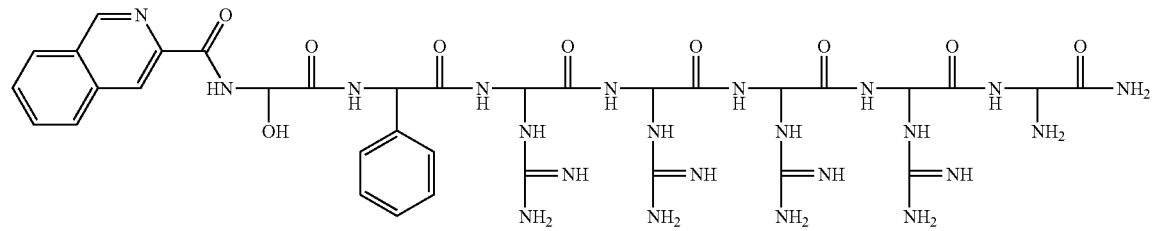
Compound 48
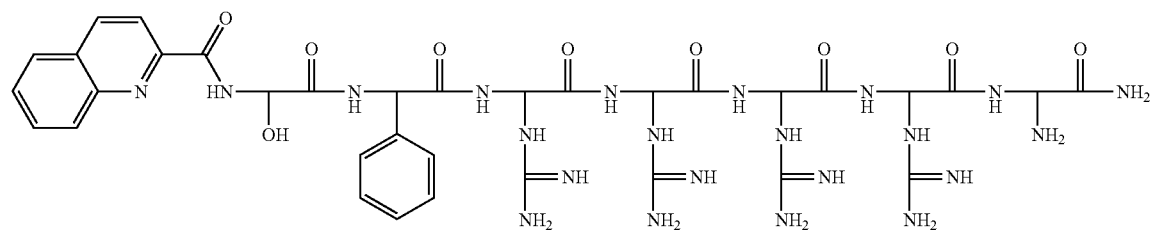
Compound 49
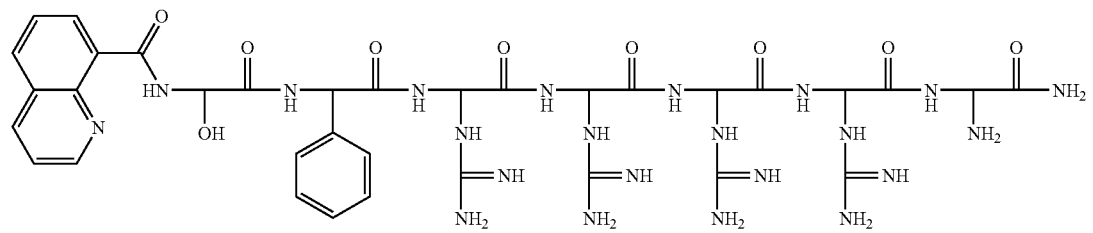
Compound 50
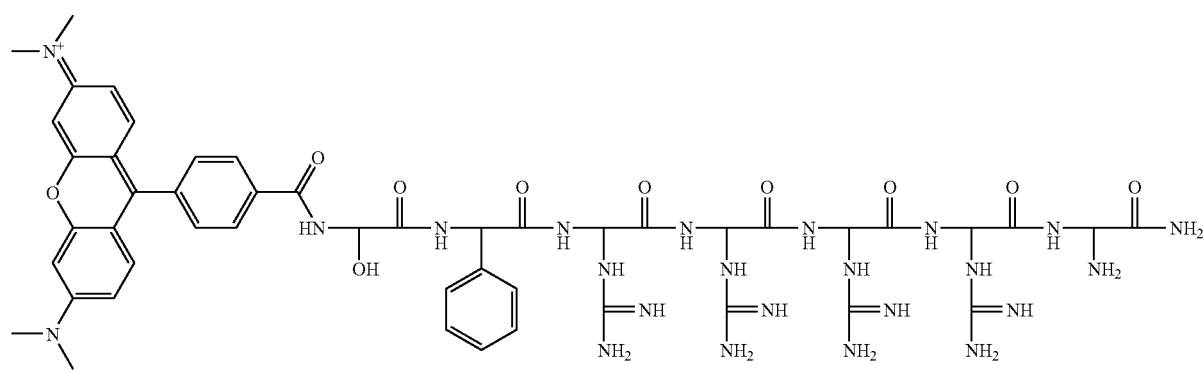
Compound 51
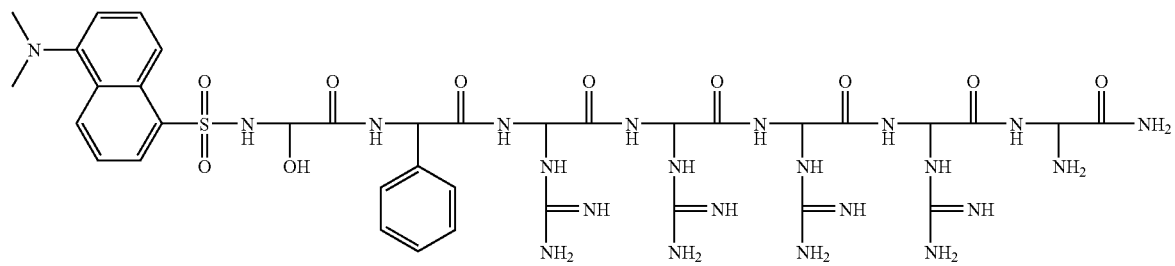

Compound 52
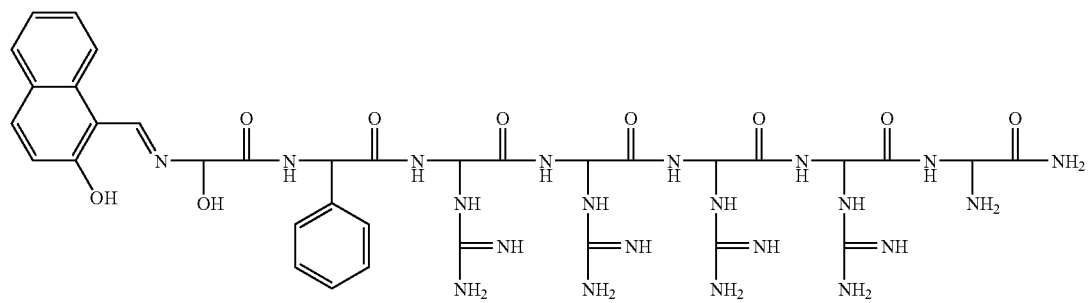
Compound 53
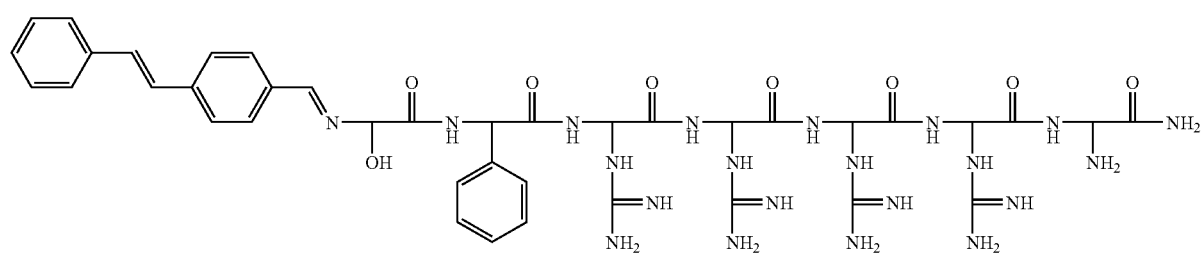
Compound 54
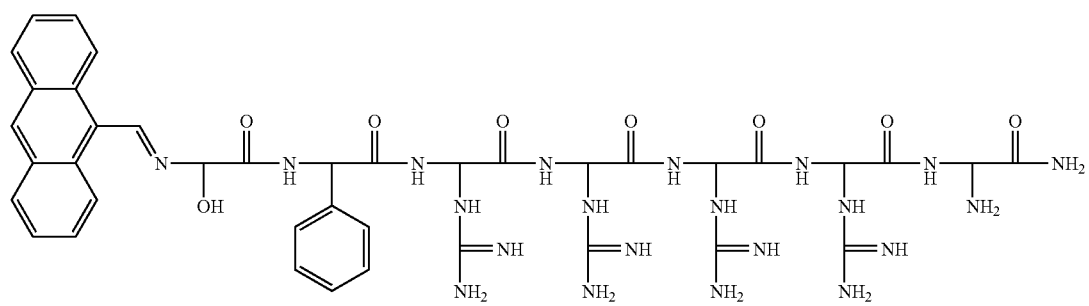
Compound 55
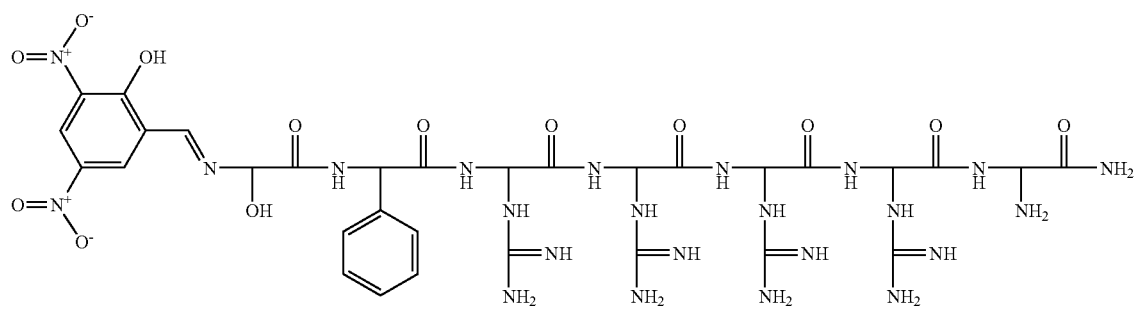
Compound 56
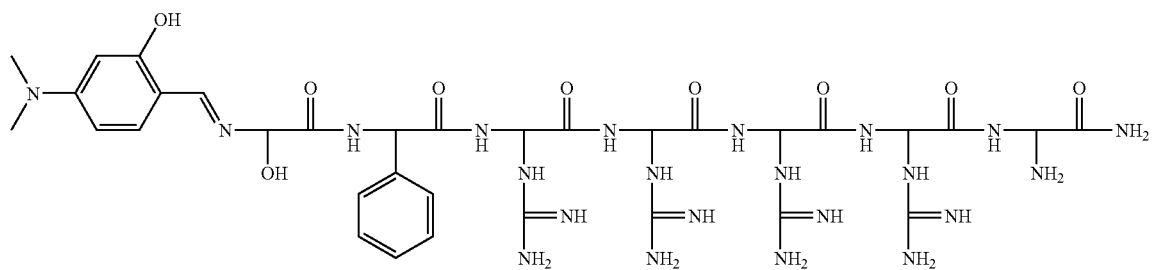

-continued
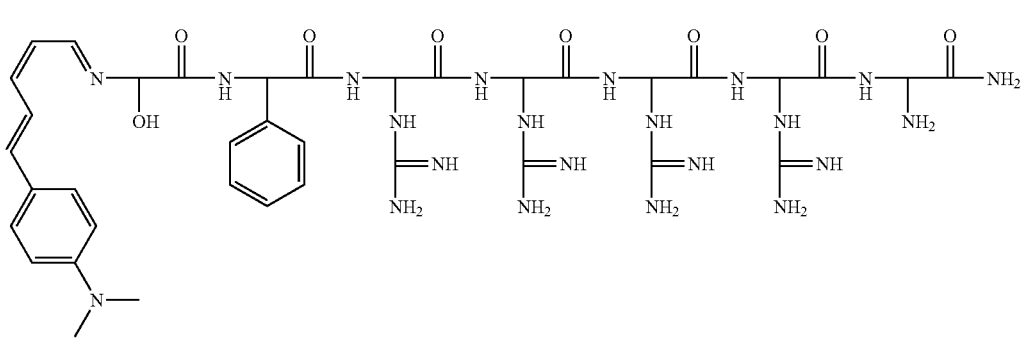
Compound 57
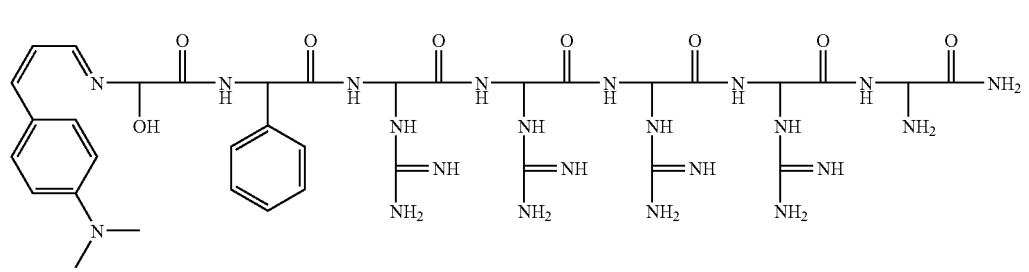
Compound 58
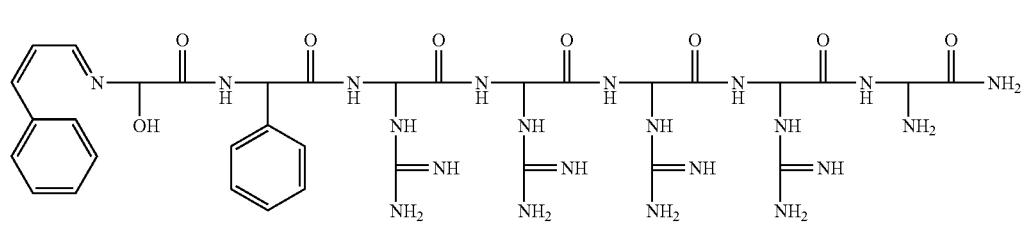
Compound 59
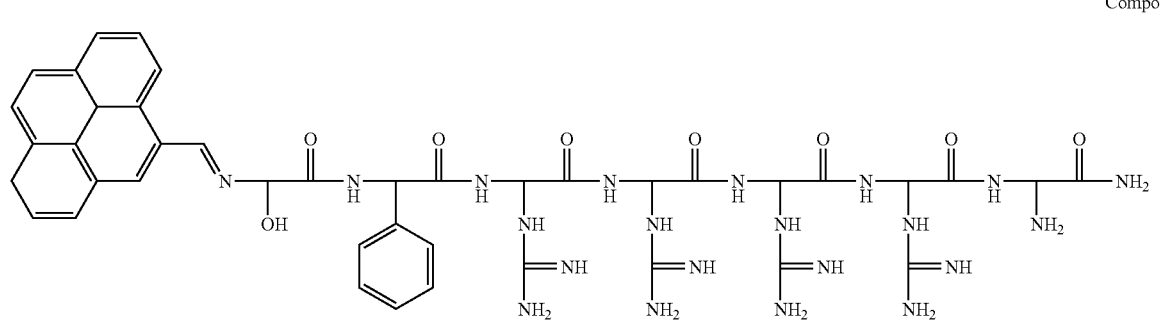
Compound 60
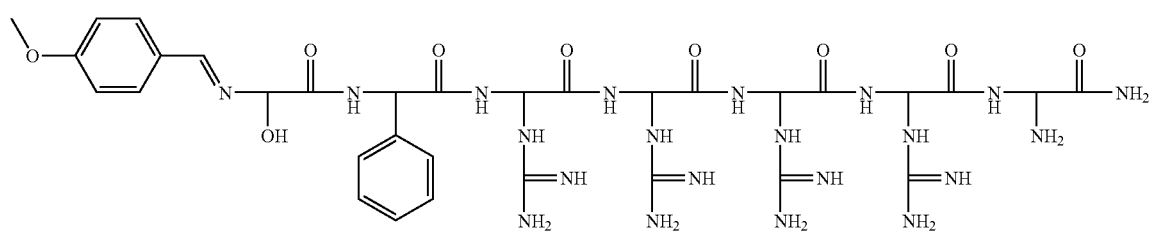
Compound 61

Compound 62
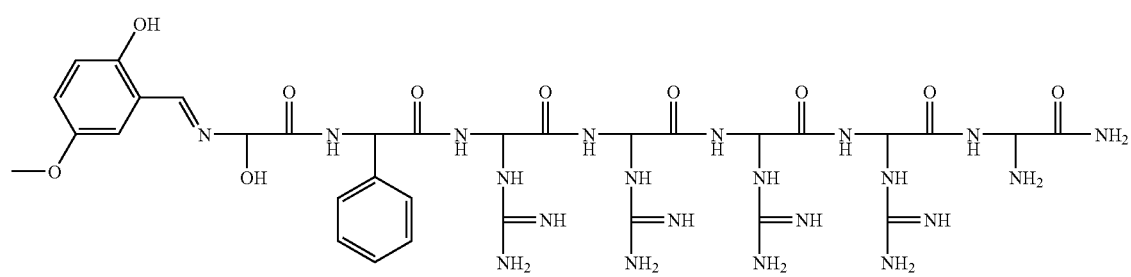
Compound 63
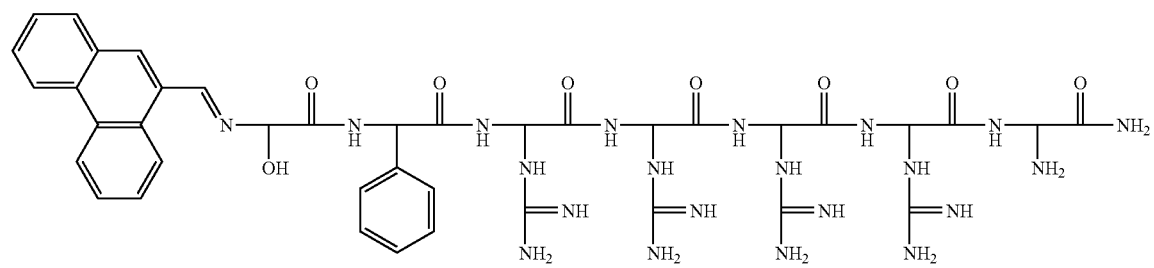
Compound 64
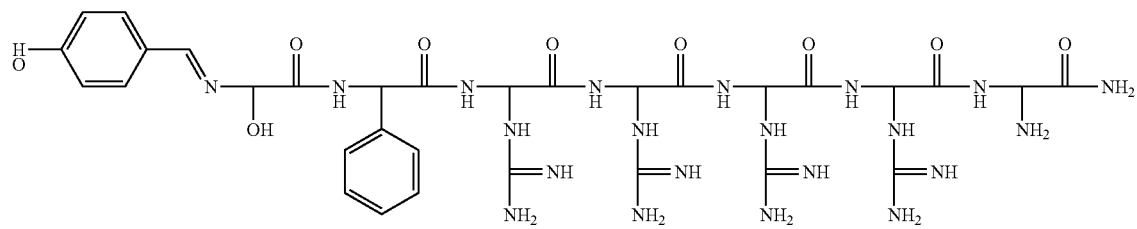
Compound 65
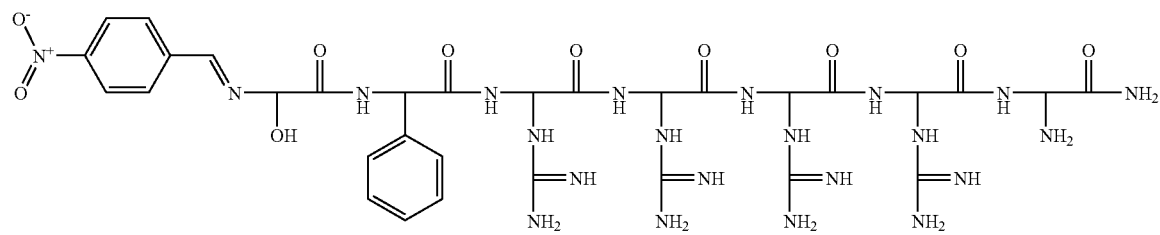
Compound 66
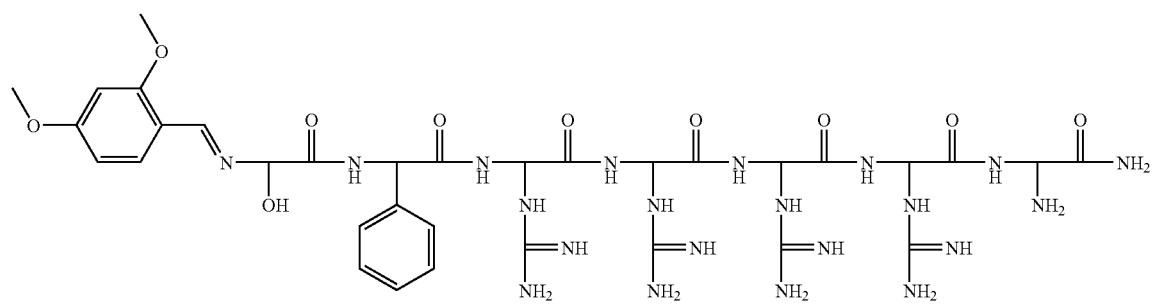

Compound 67
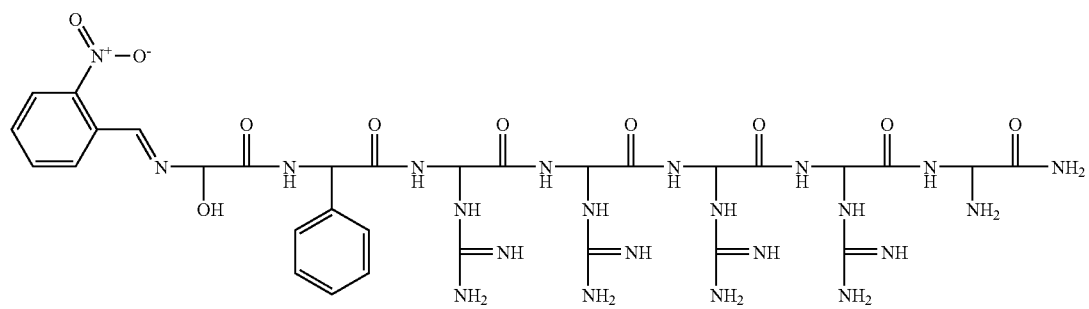
Compound 68
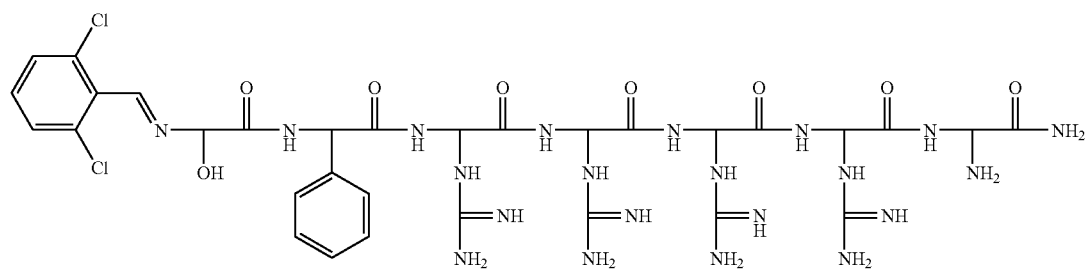
Compound 69
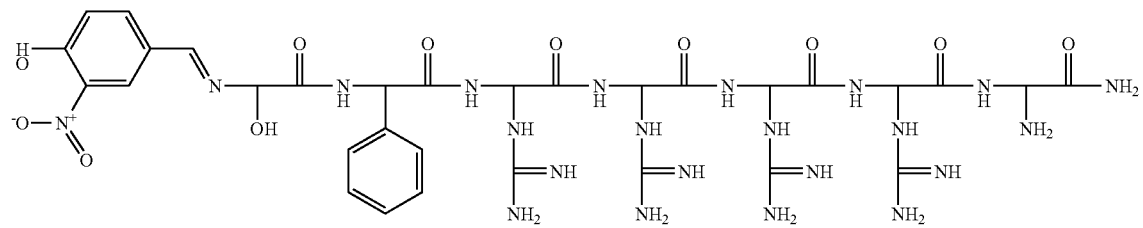
Compound 70
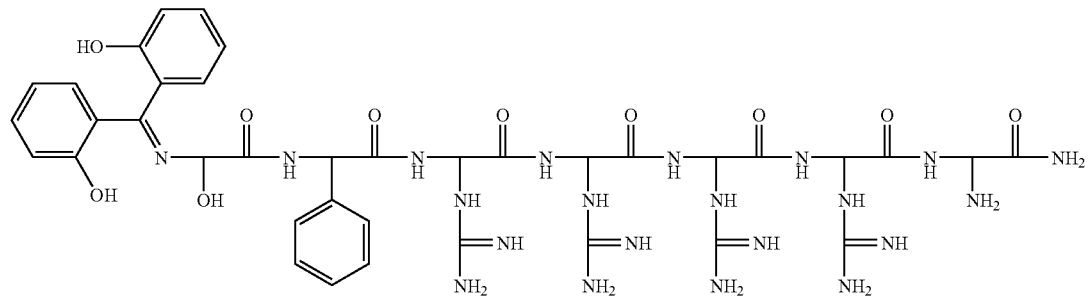
Compound 71
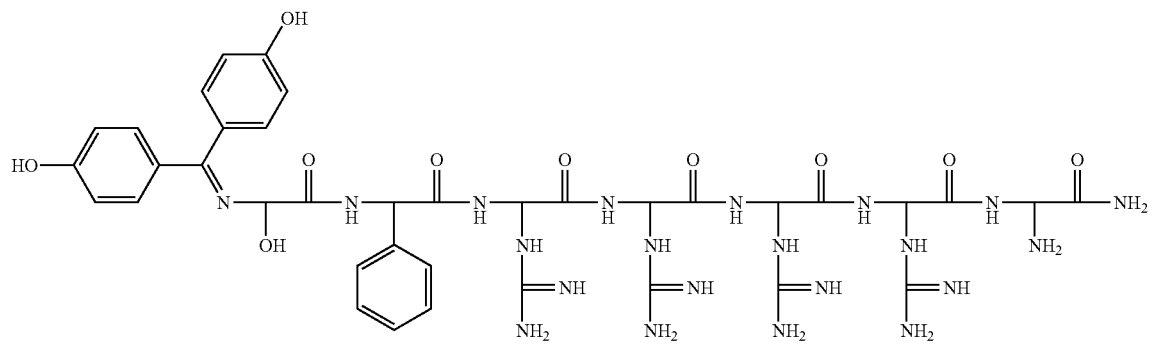

Compound 72
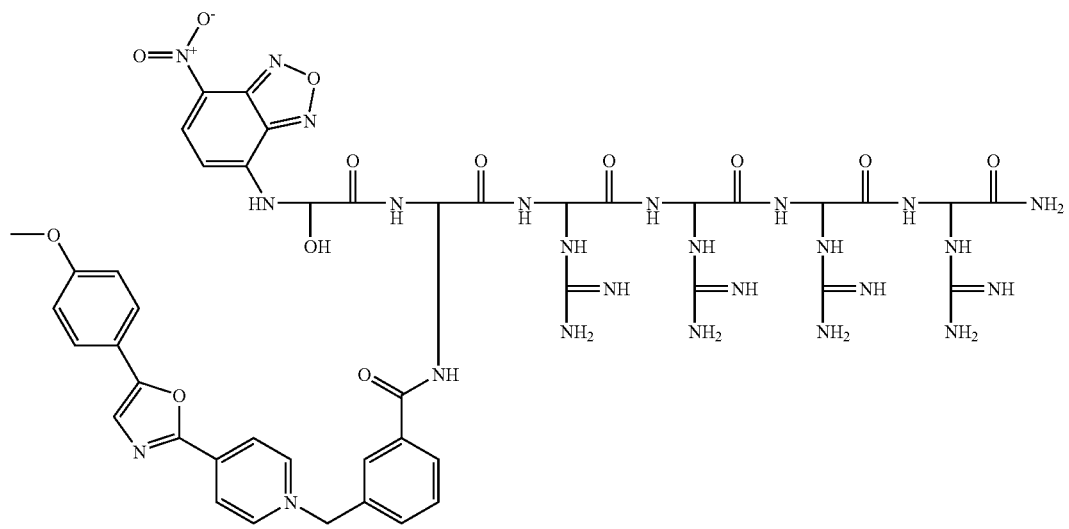
Compound 73
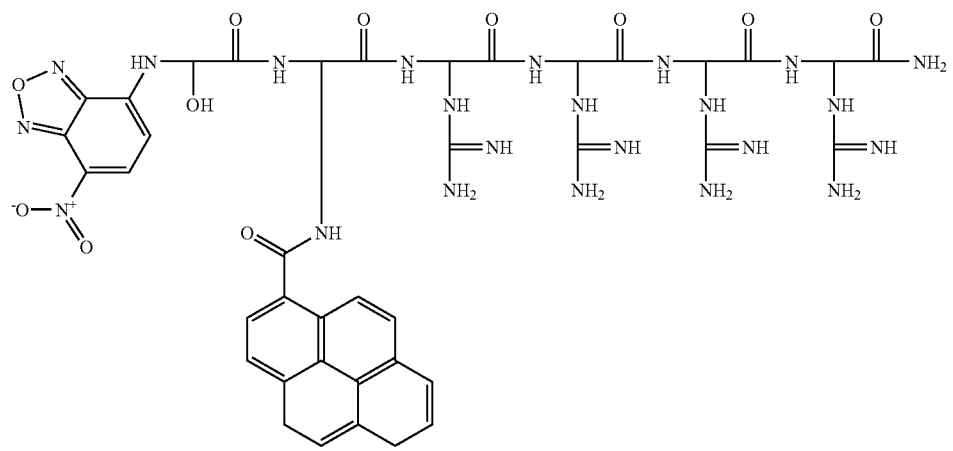
Compound 74
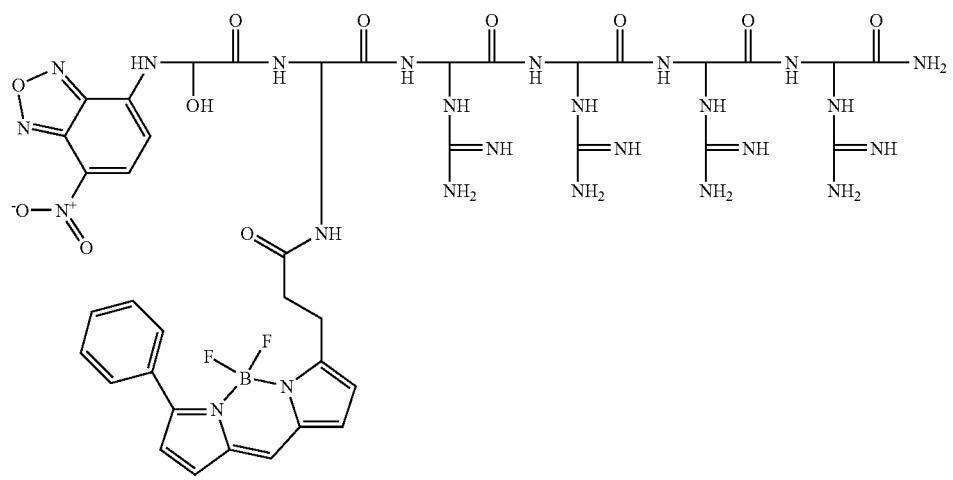

Compound 75
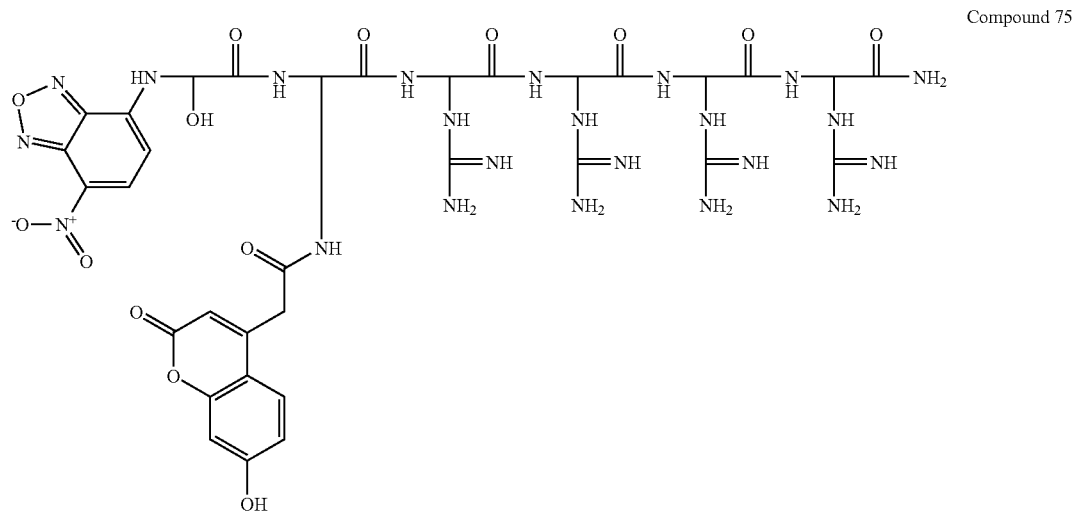
Compound 76
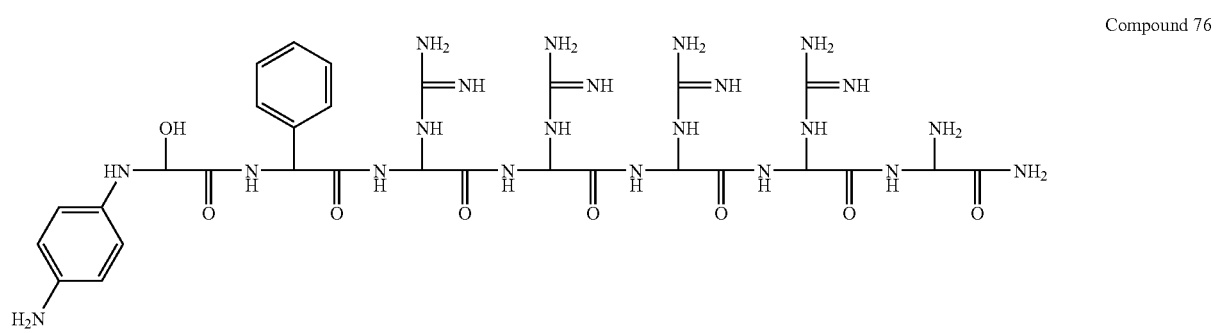
Compound 77
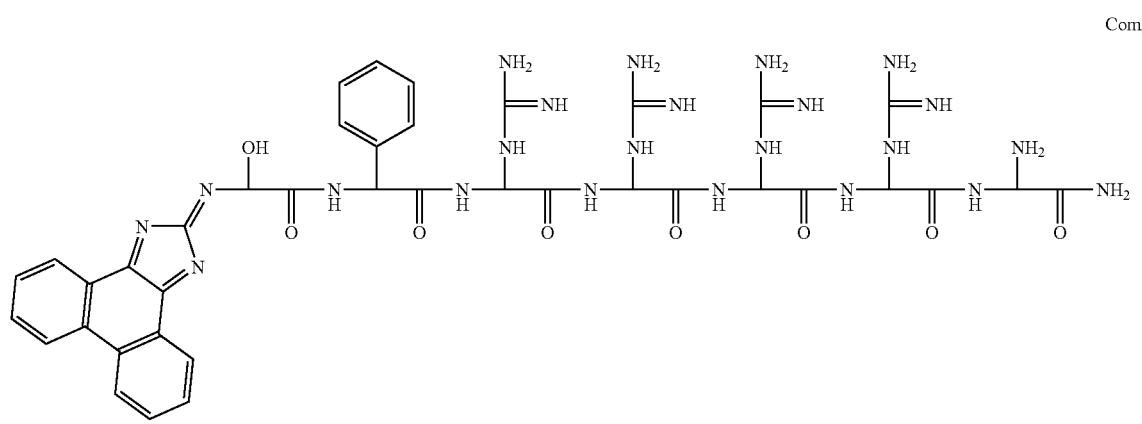
Compound 78
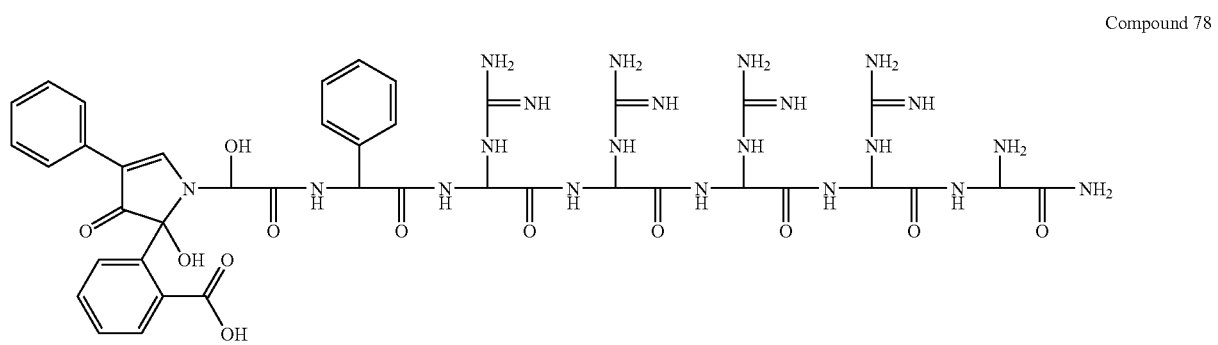

-continued
Compound 79
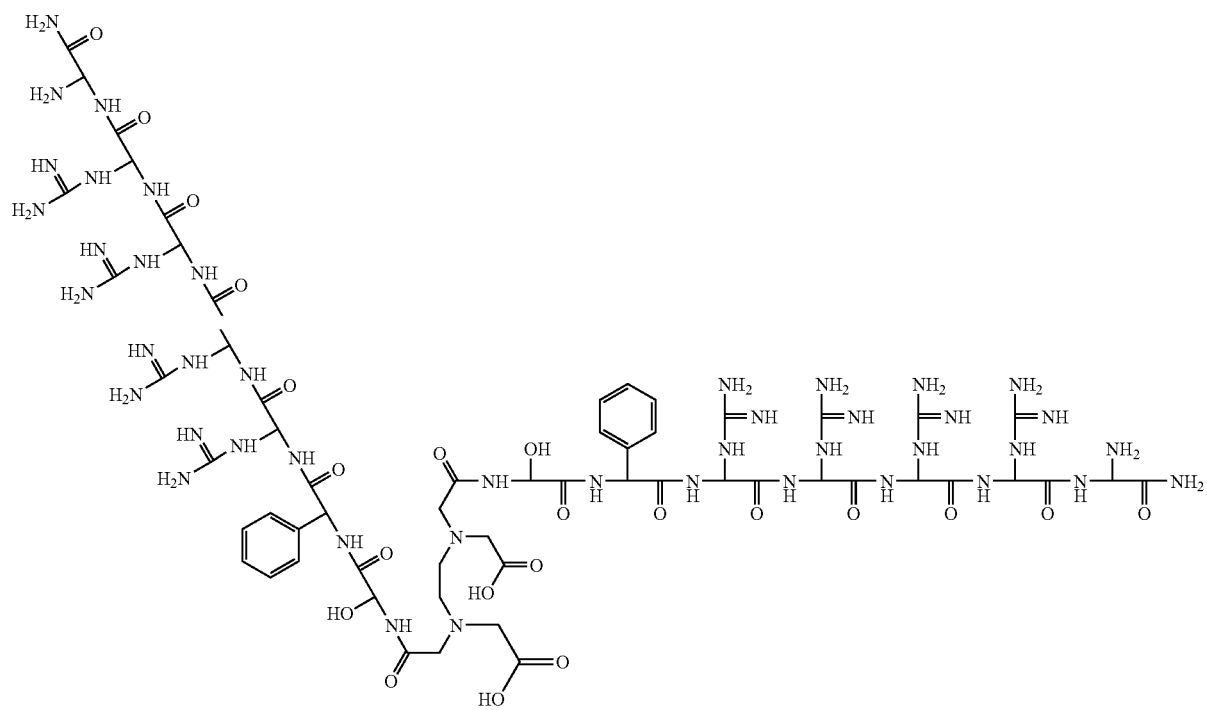
Compound 80
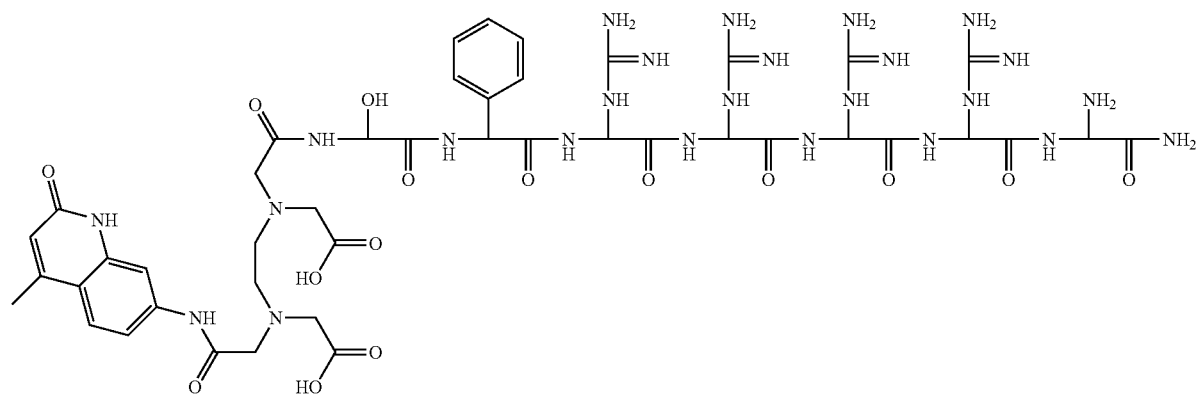
Compound 81
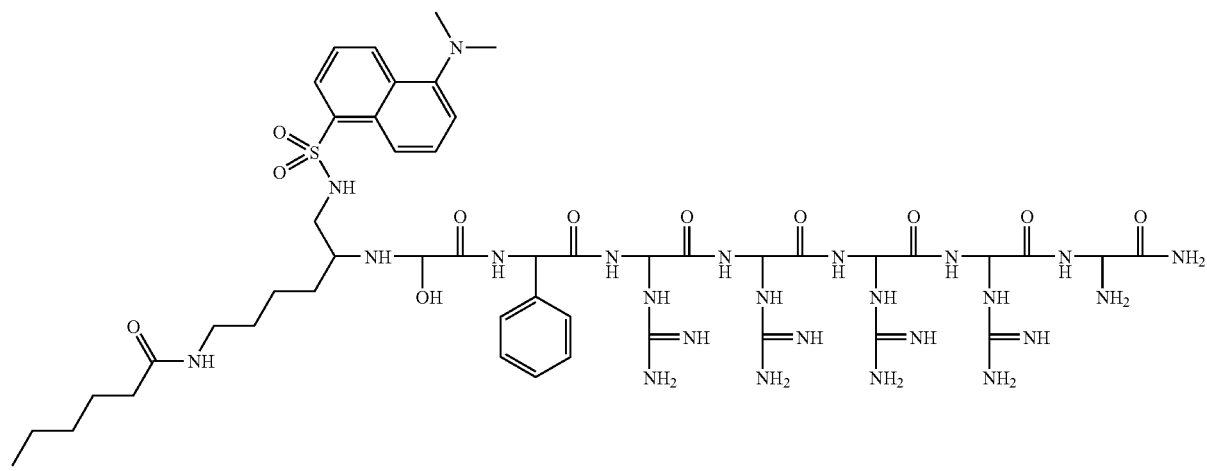

Compound 82
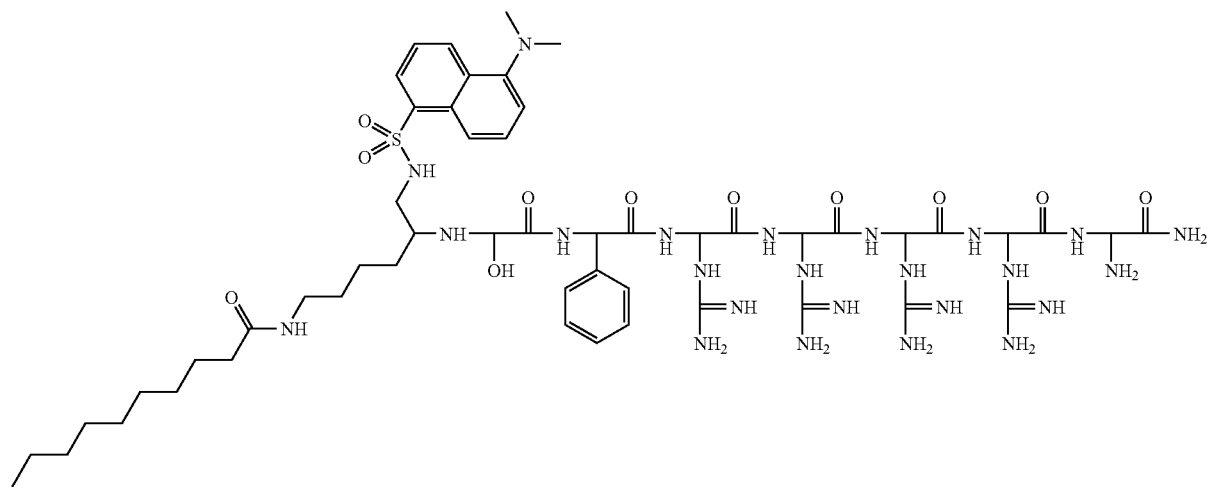
Compound 83
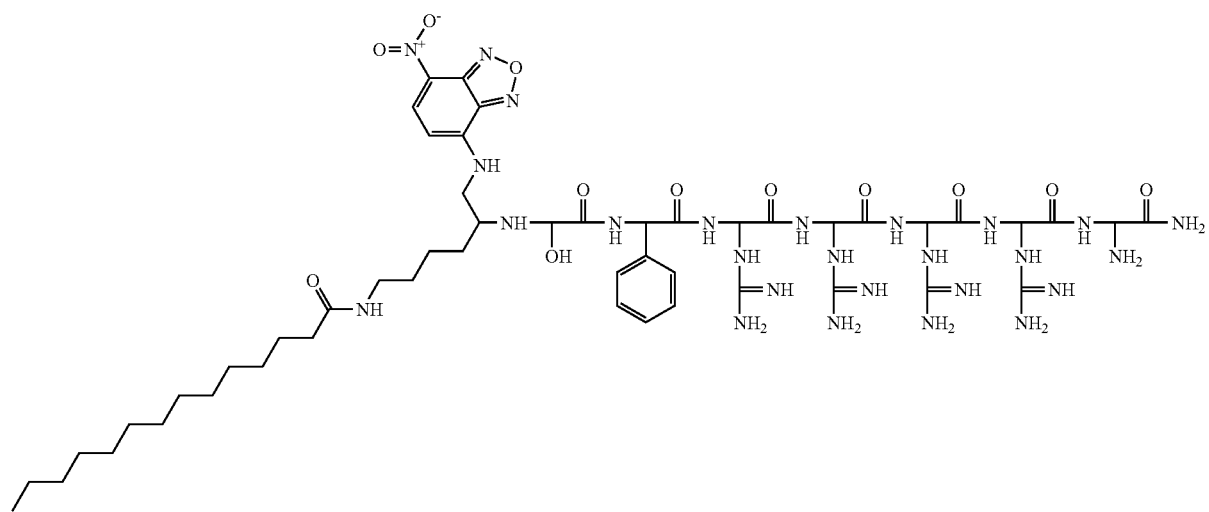
Compound 84
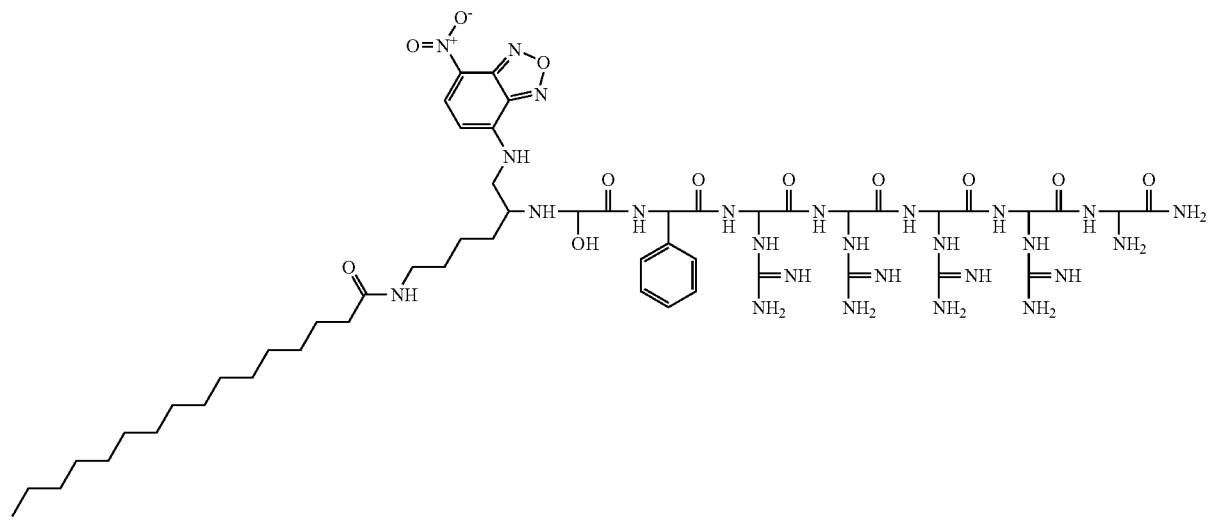

Compound 85
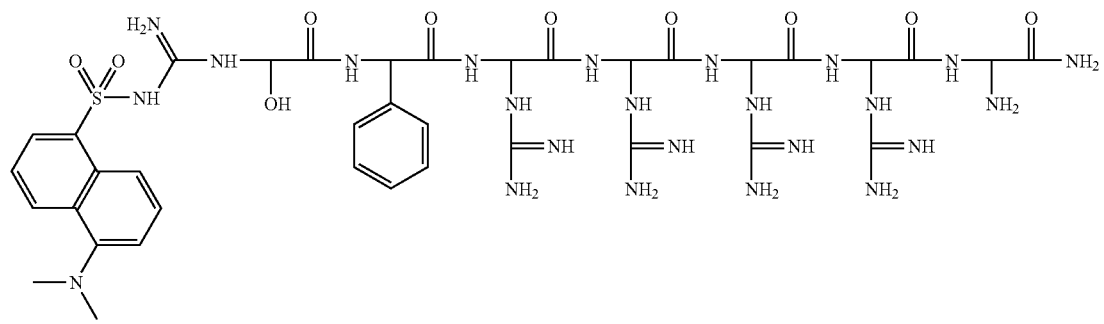
Compound 86
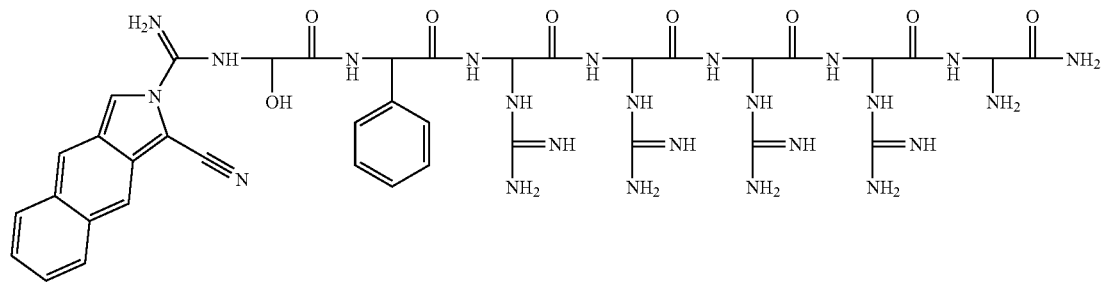
Compound 88
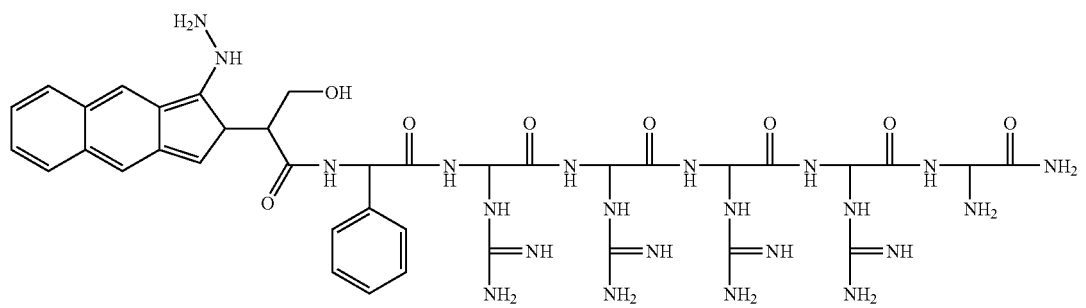
Compound 89
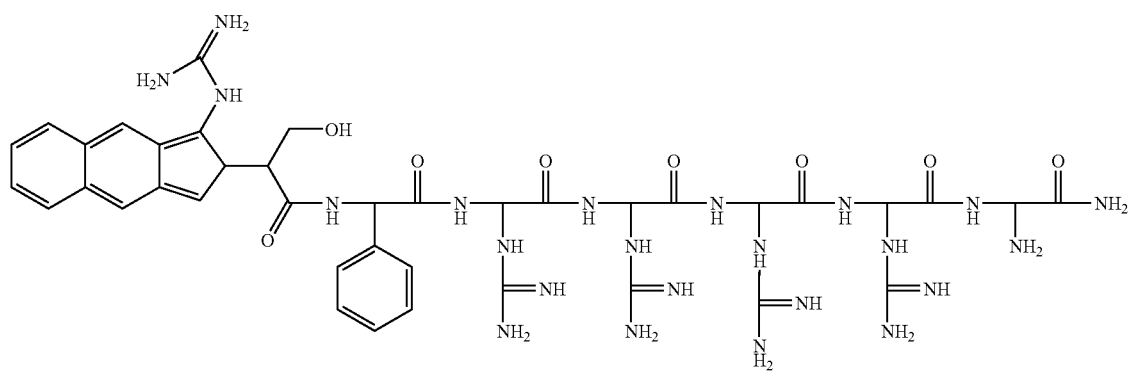

-continued
Compound 90
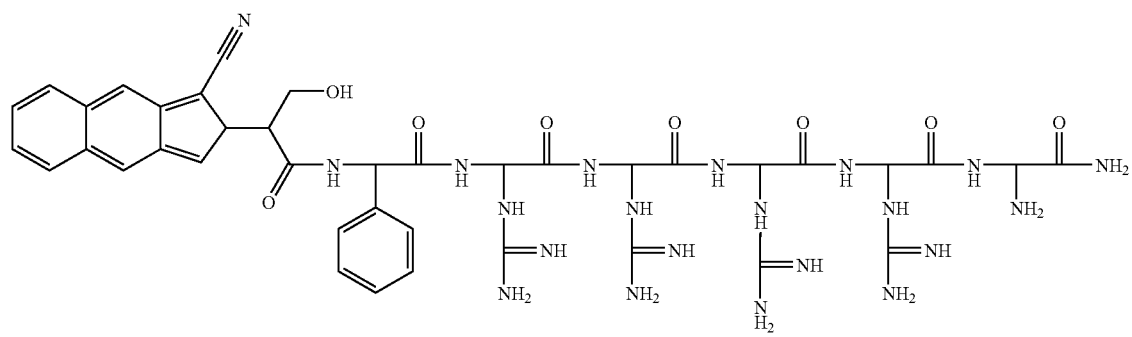
Compound 91
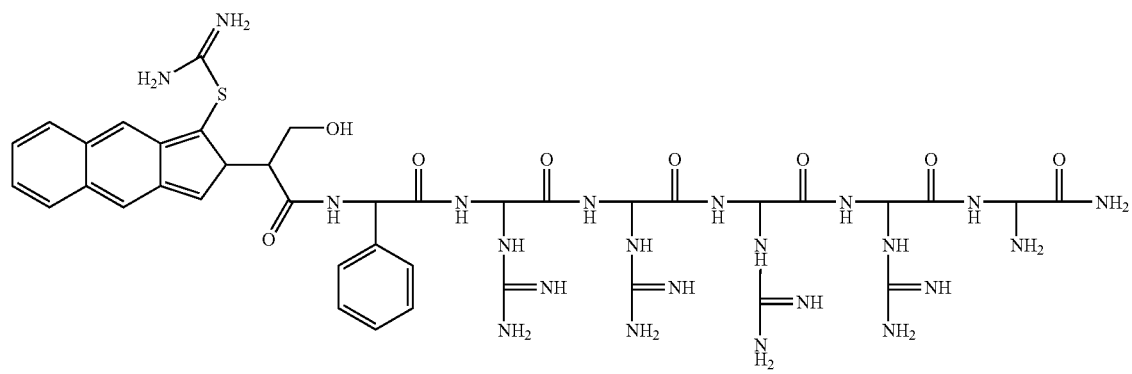
Compound 92
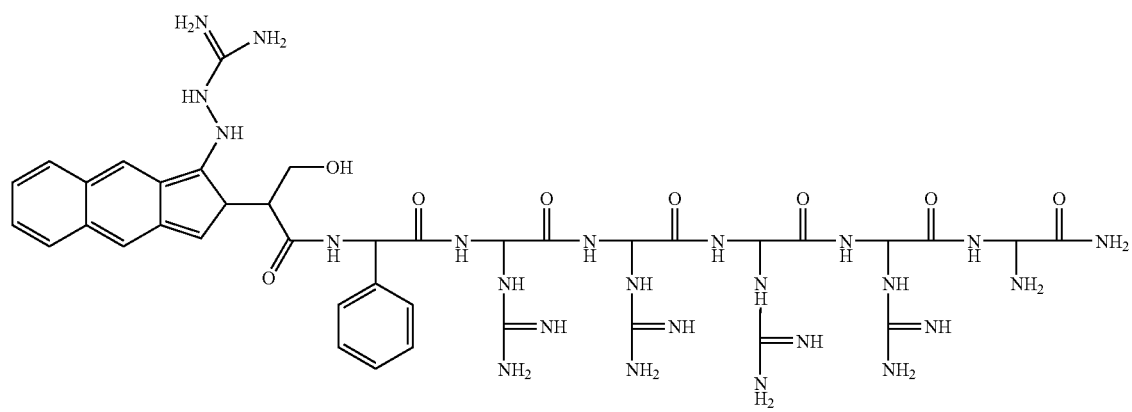
Compound 93
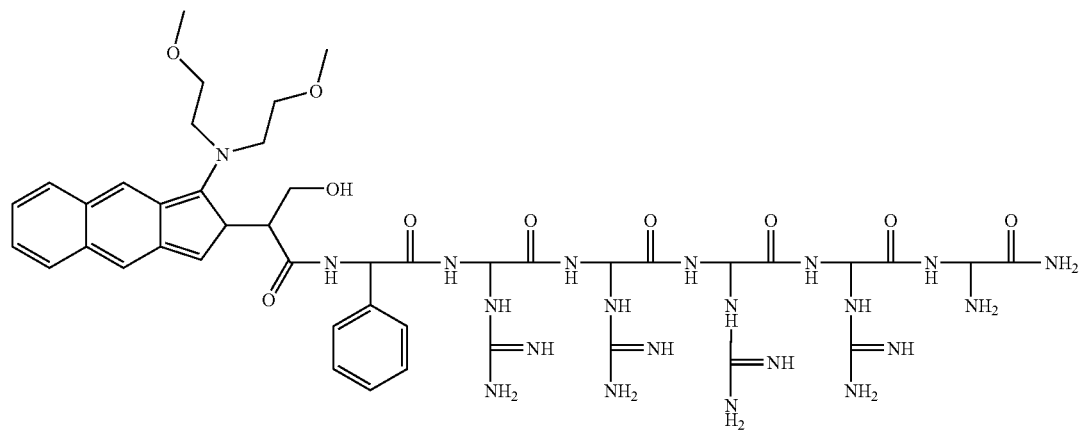

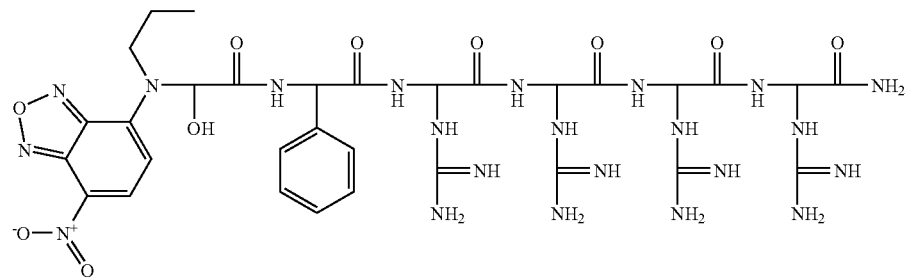
Compound 94
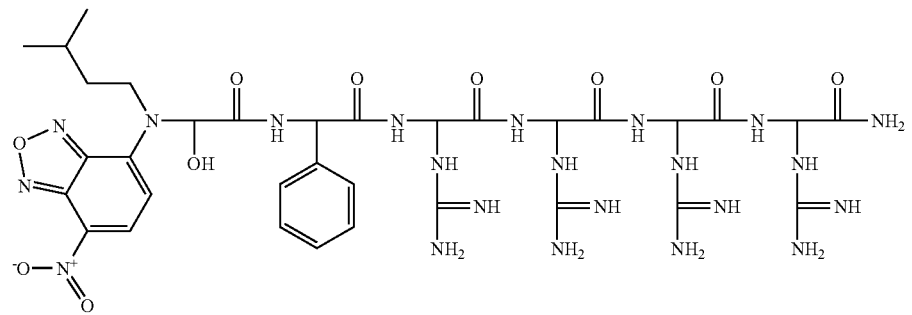
Compound 95
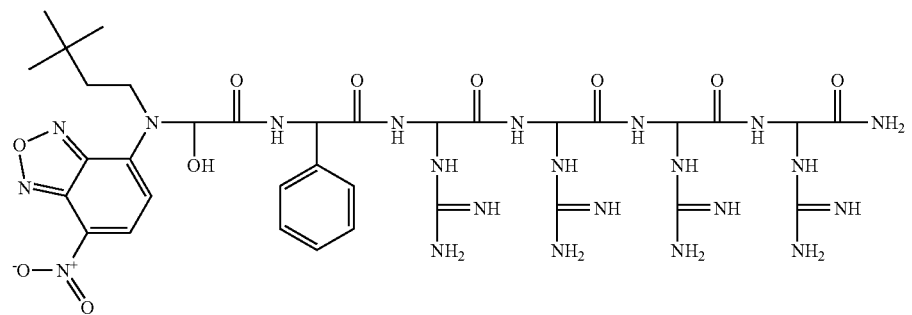
Compound 96
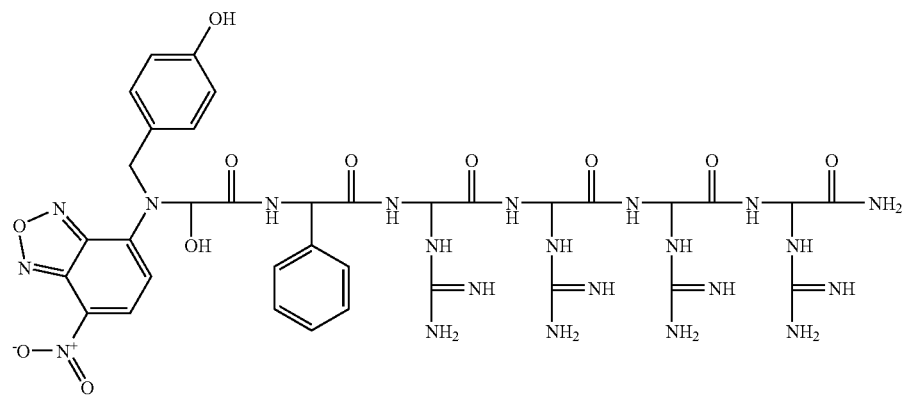
Compound 97

-continued
Compound 98
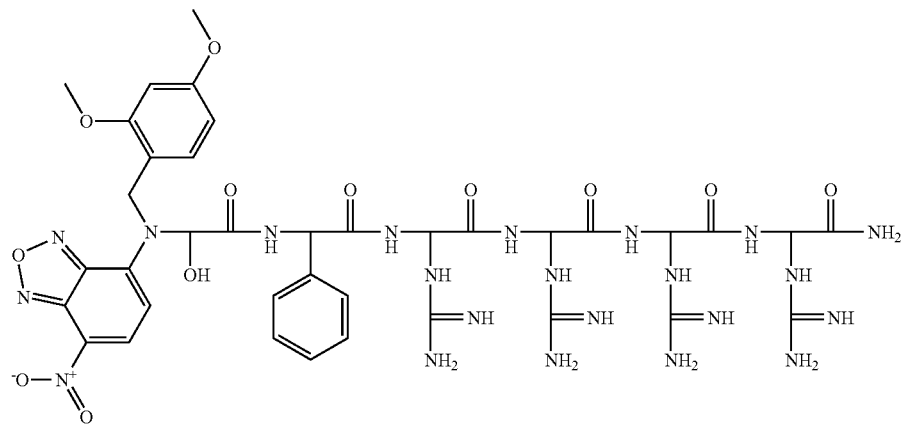
Compound 99
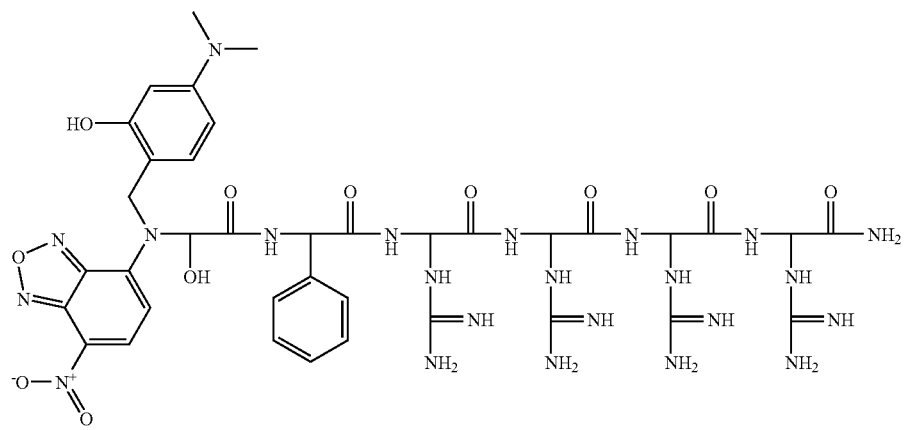
Compound 100
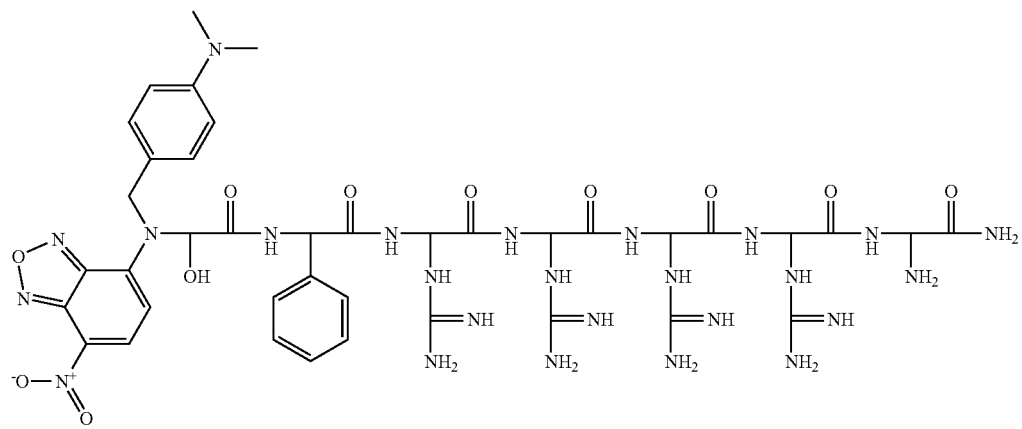
Compound 102
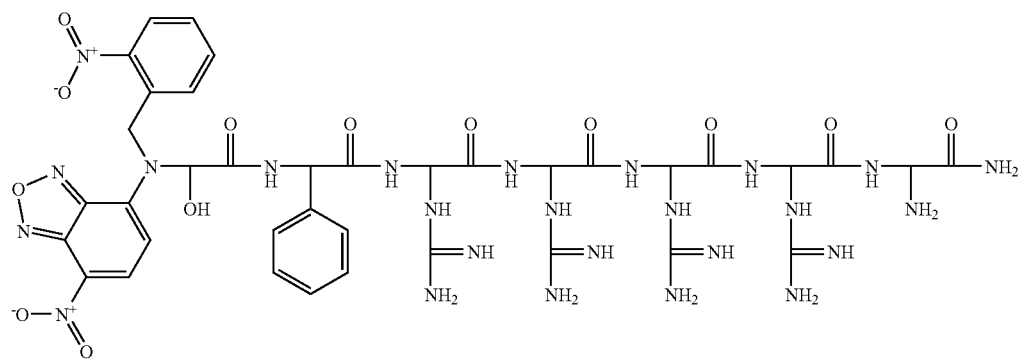

Compound 103
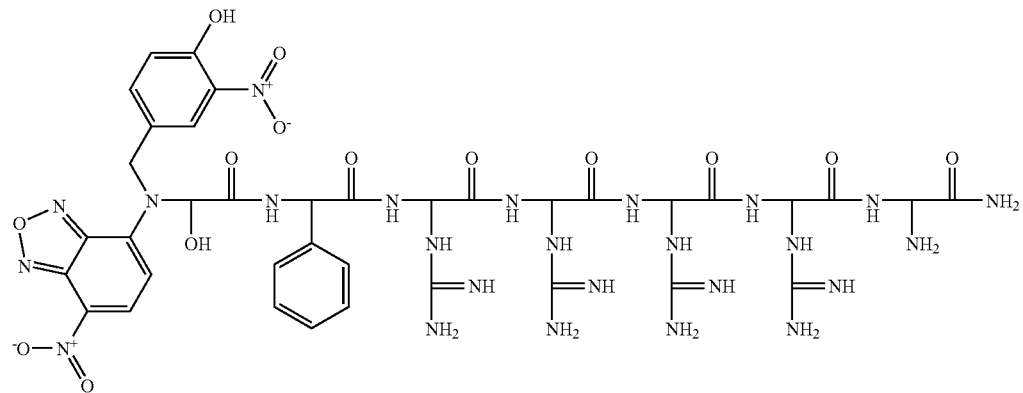
Compound 104
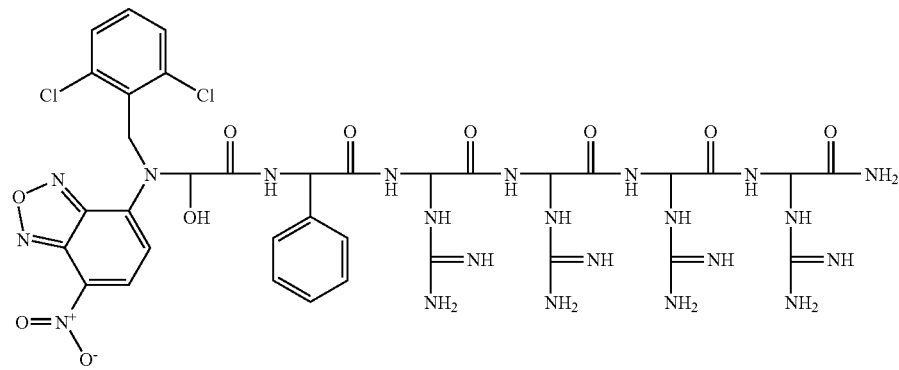
Compound 107
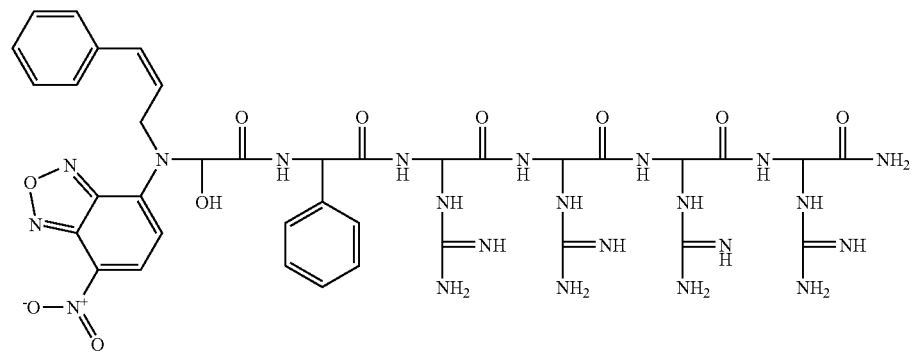
Compound 108
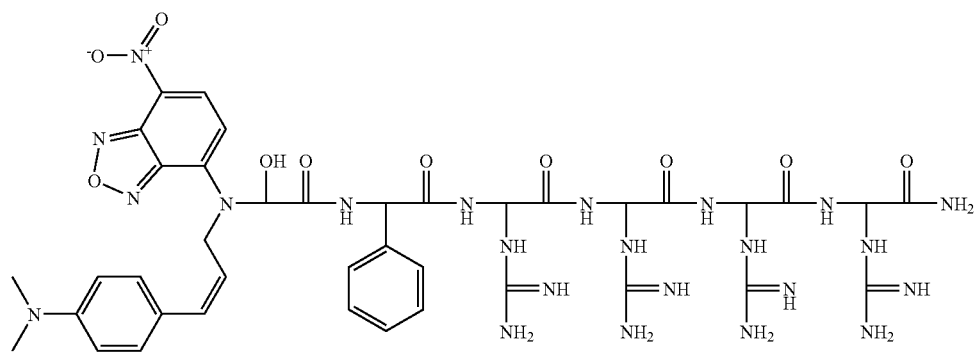

-continued
Compound 110
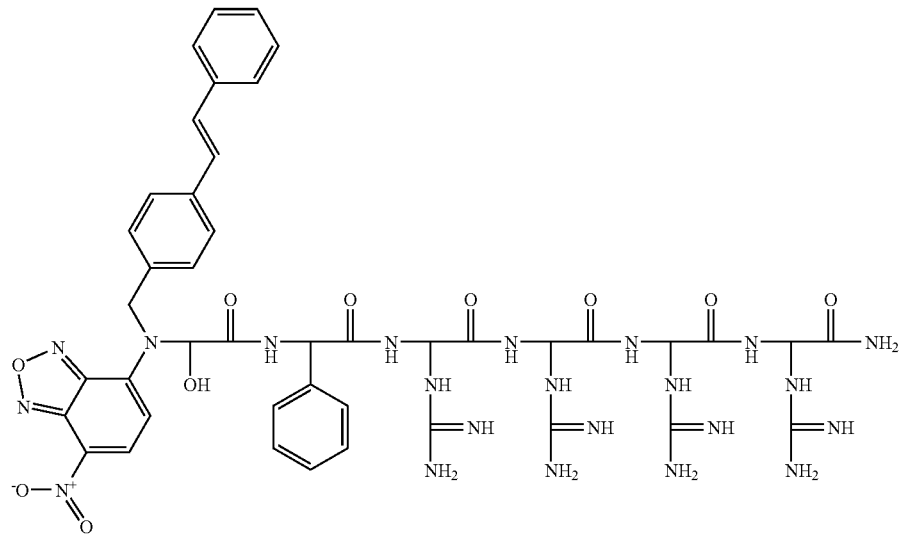
Compound 111
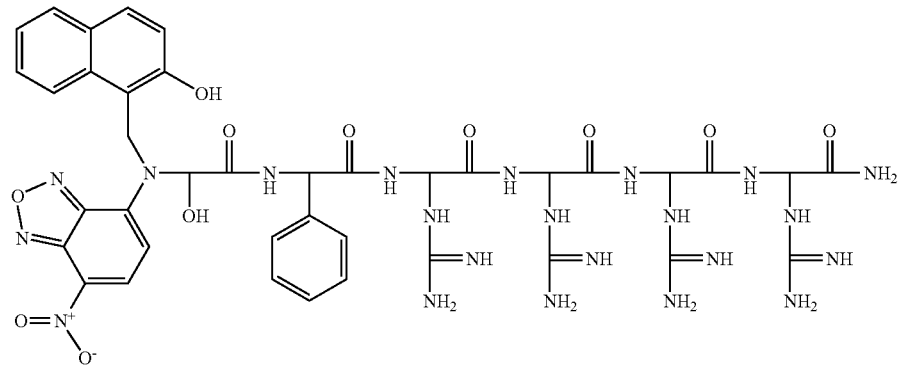
Compound 112
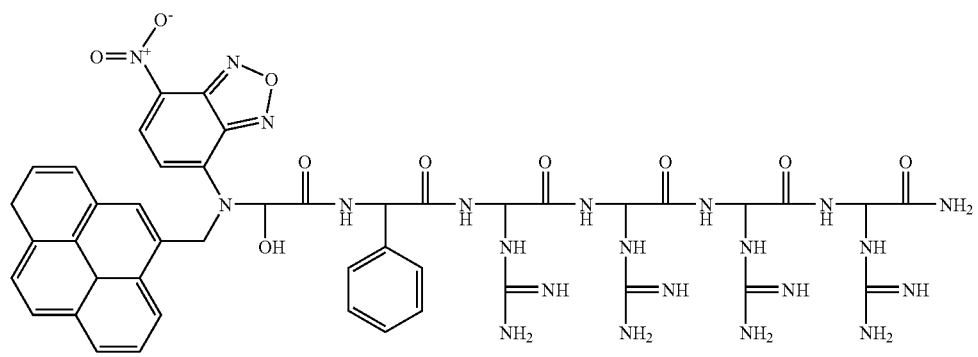
Compound 113
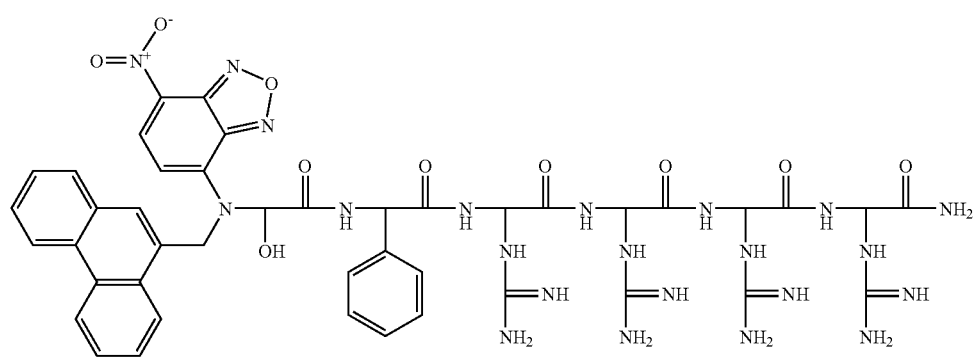

Compound 114
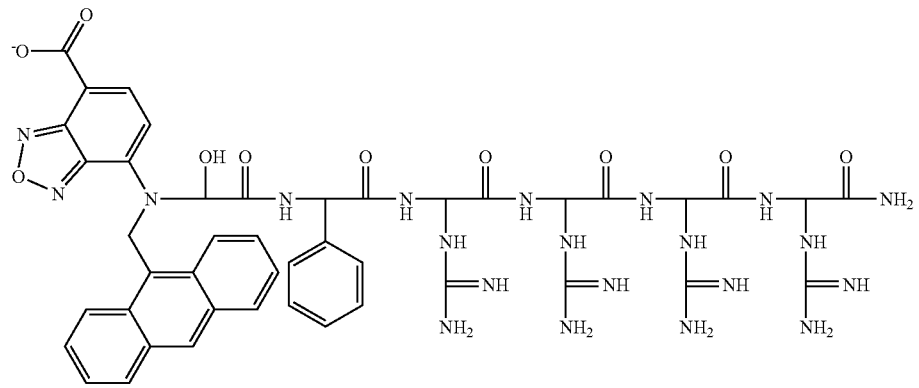
Compound 115
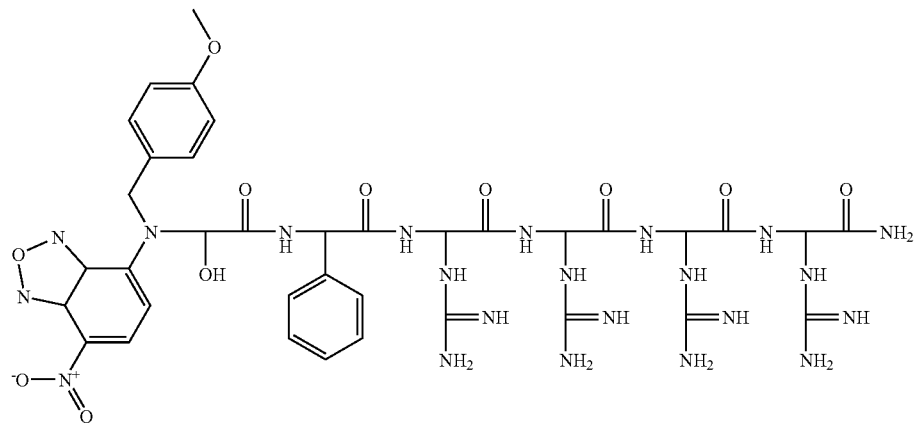
Compound 116
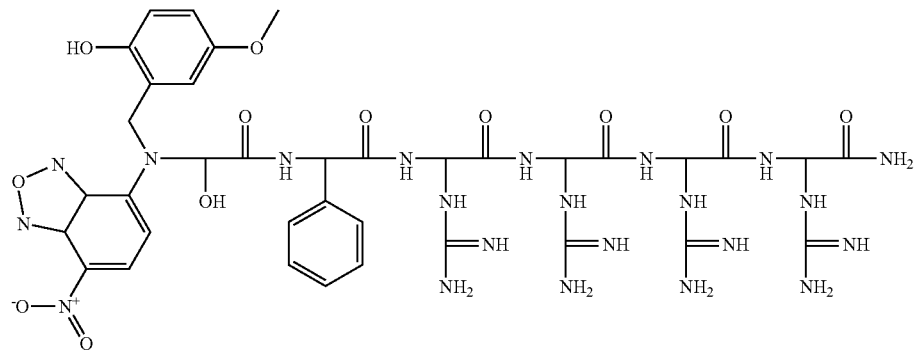
Compound 117
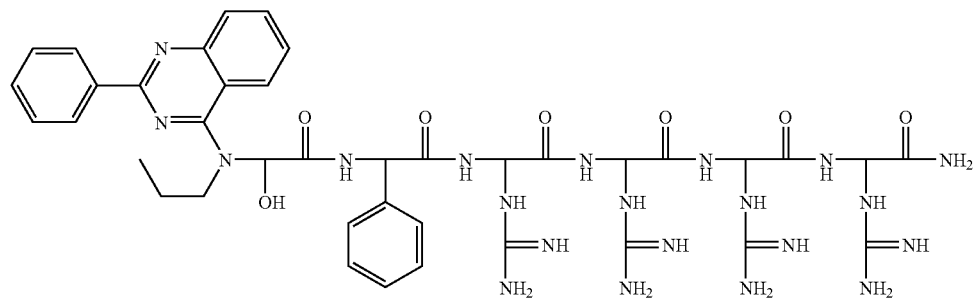

-continued
Compound 118
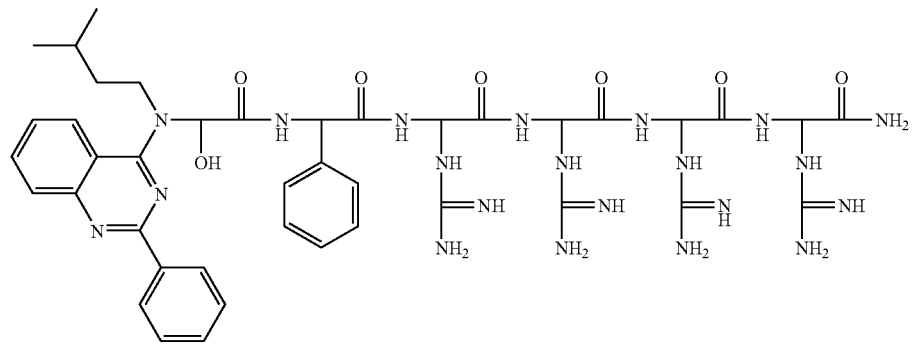
Compound 119
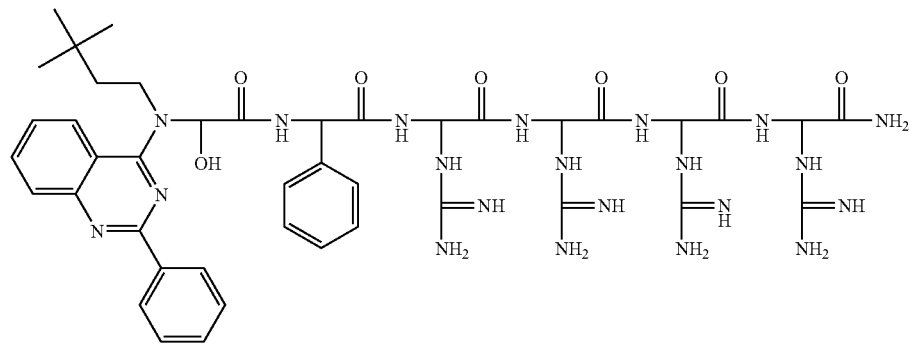
Compound 120
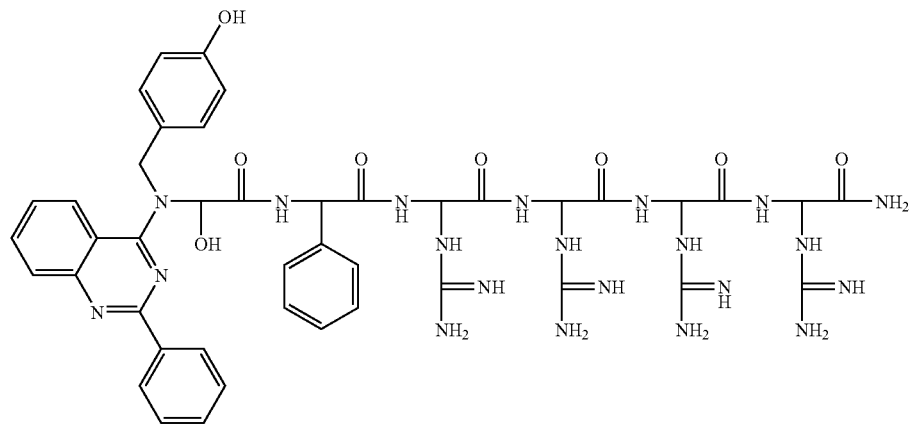
Compound 121
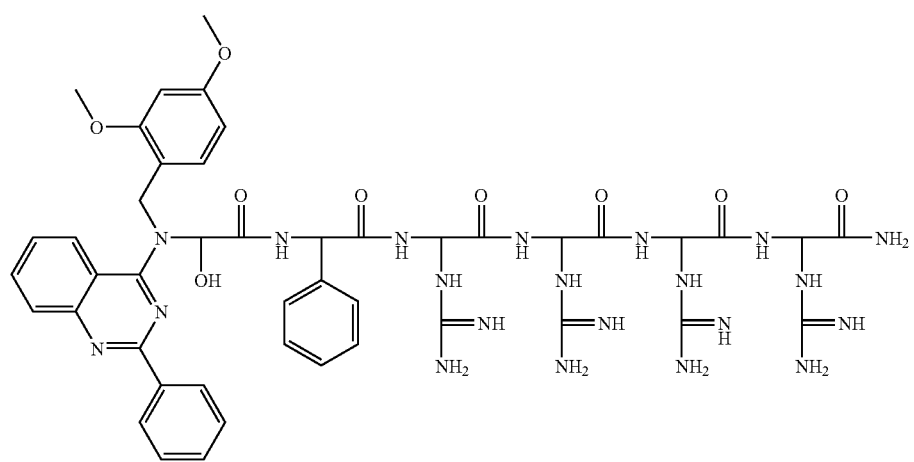

-continued
Compound 122
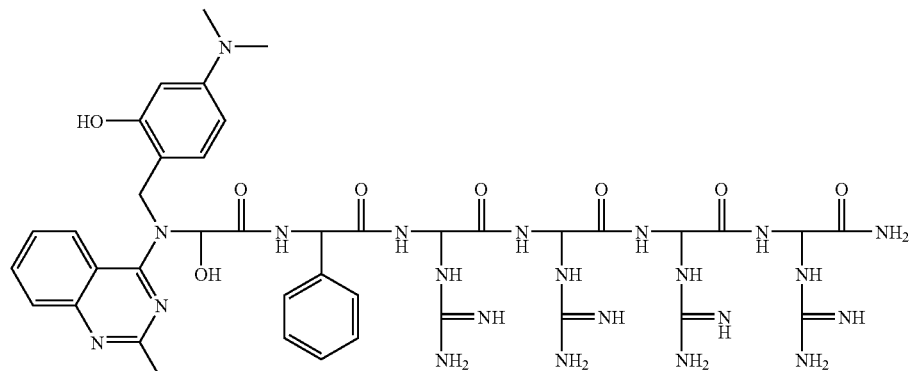
Compound 123
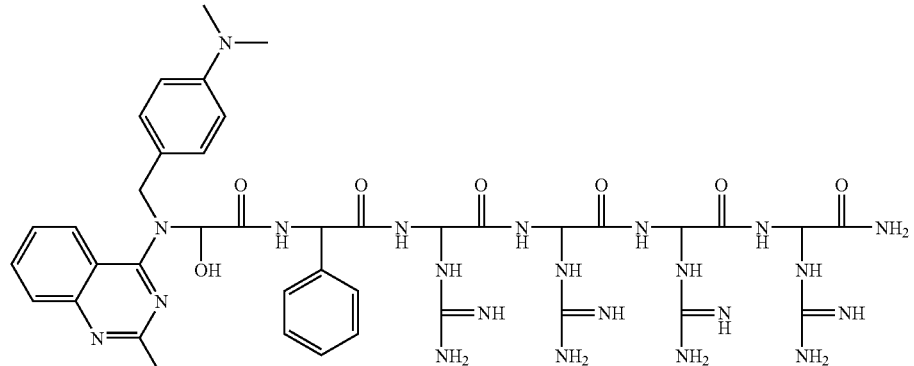
Compound 125
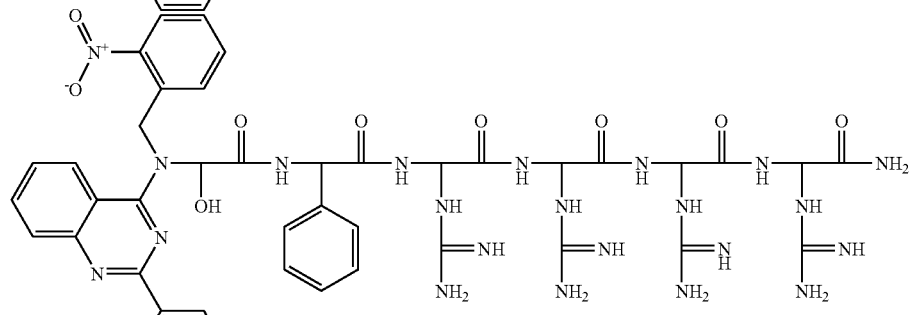
Compound 126
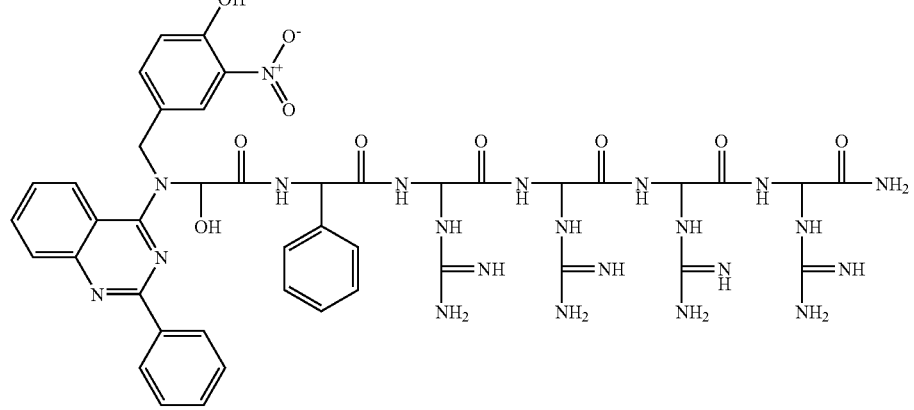

Compound 127
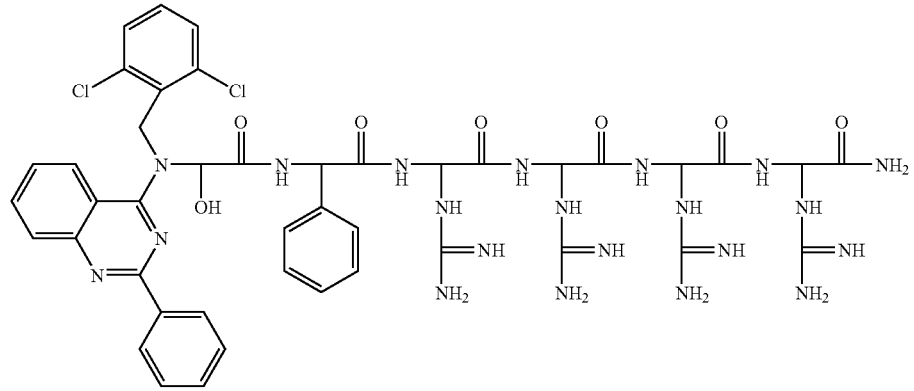
Compound 130
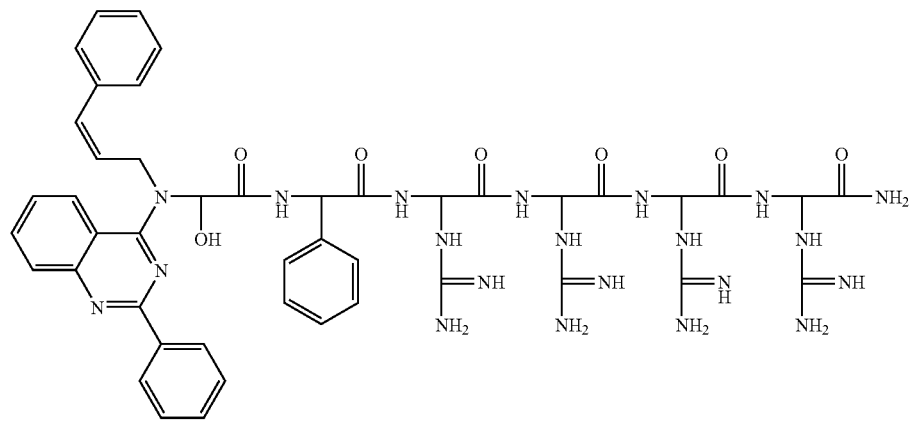
Compound 131
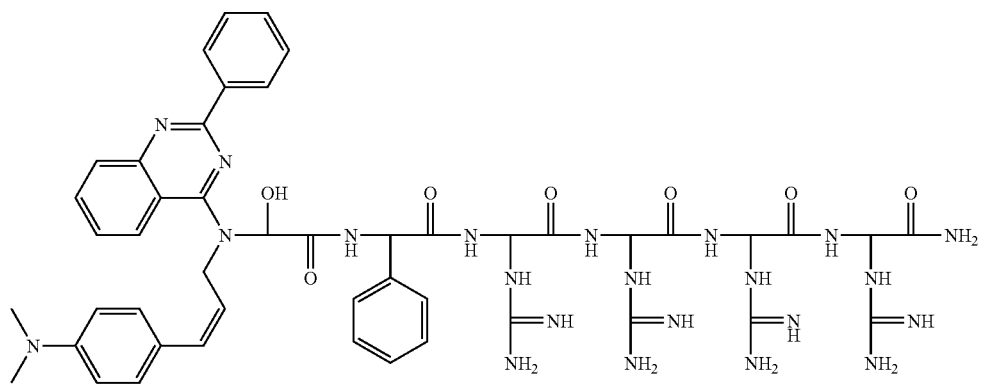

Compound 133
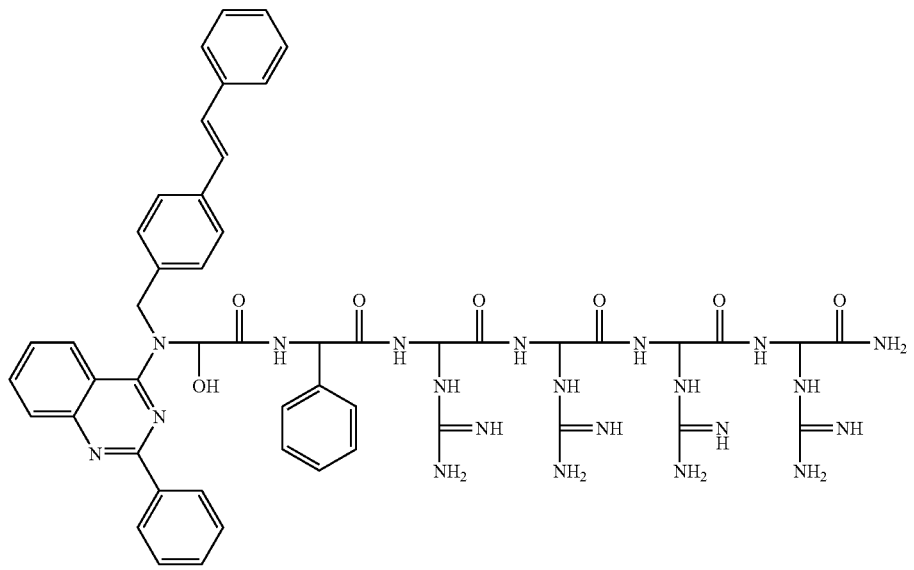
Compound 134
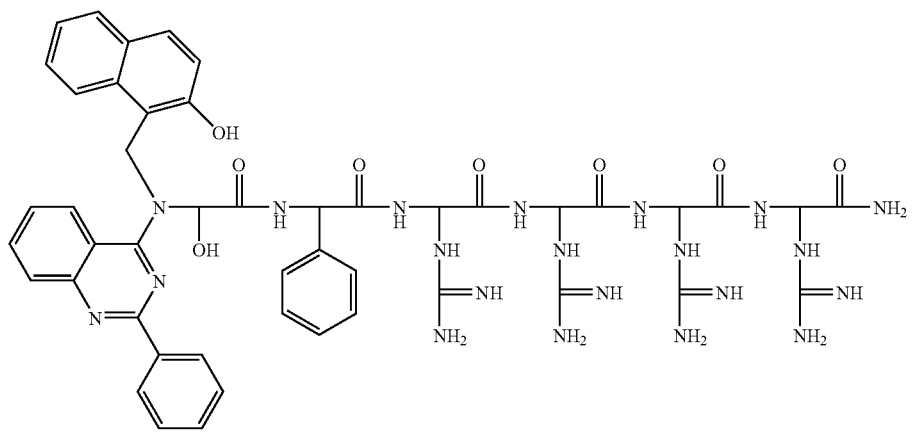
Compound 135
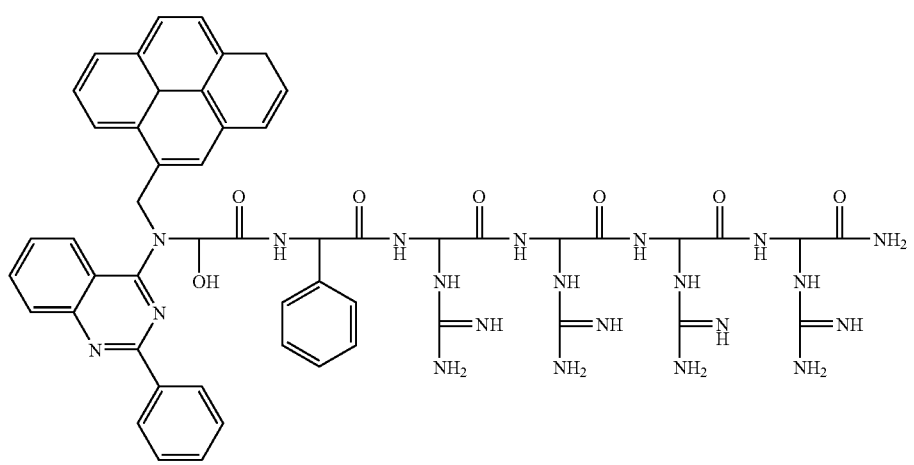

Compound 136
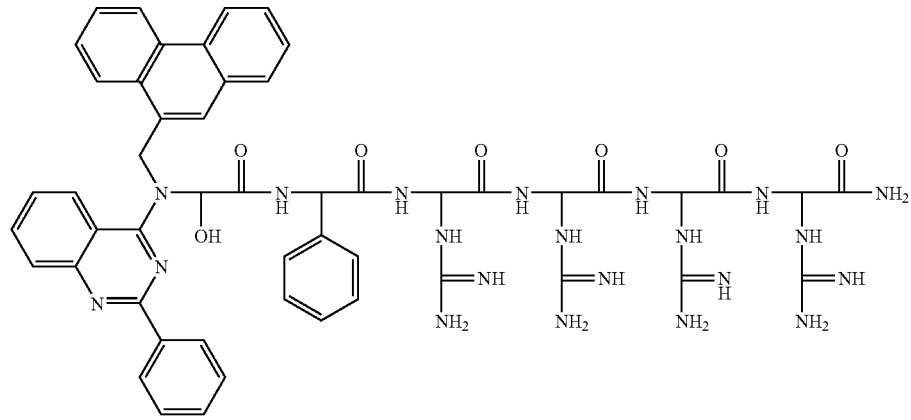
Compound 137
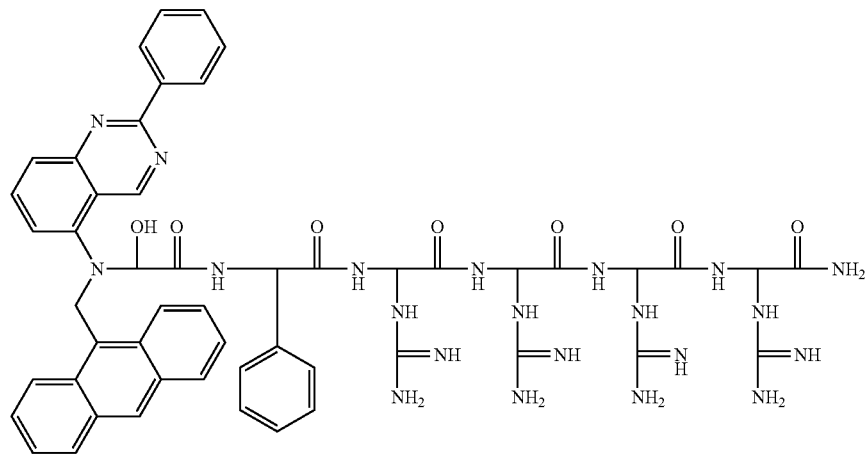
Compound 138
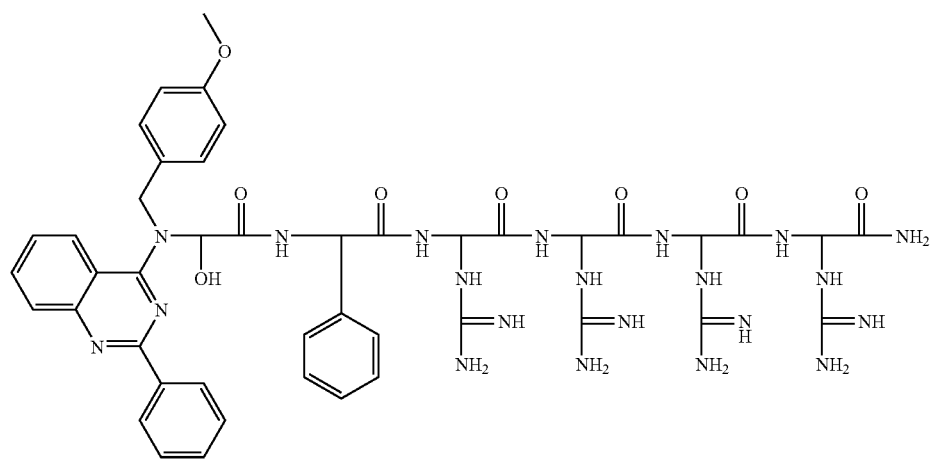

Compound 139
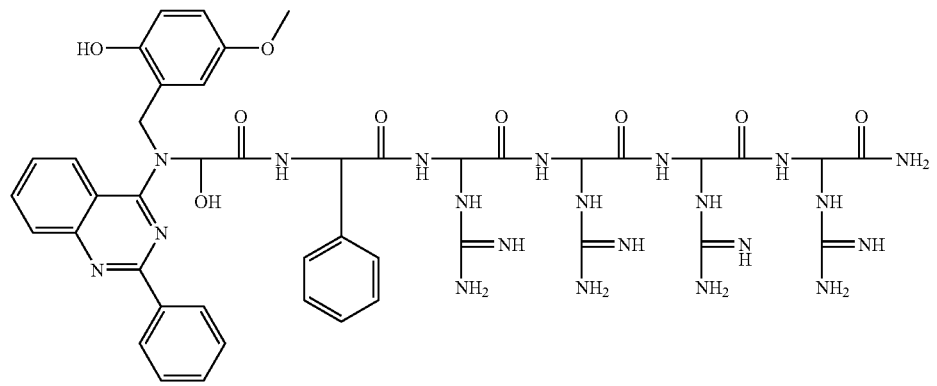
Compound 140
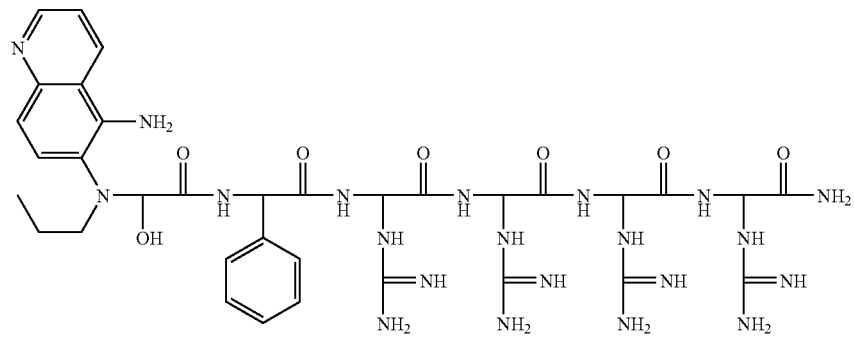
Compound 141
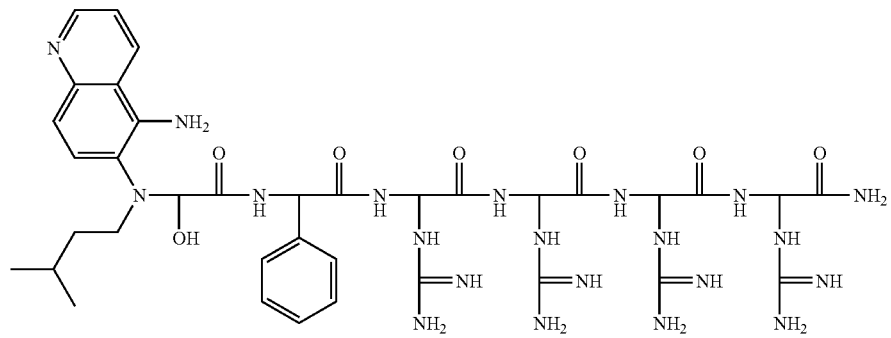
Compound 142
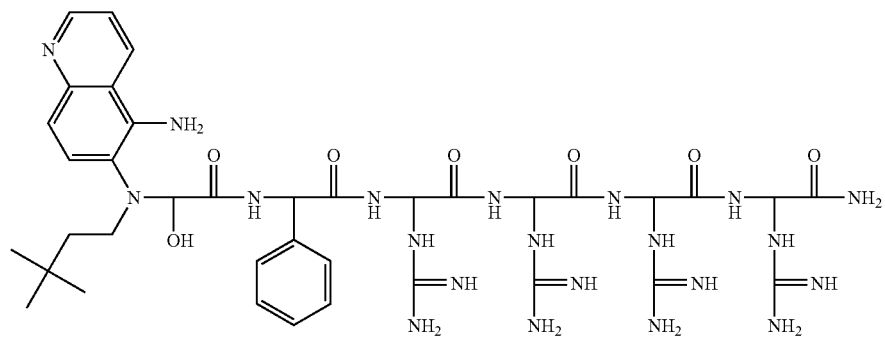

Compound 143
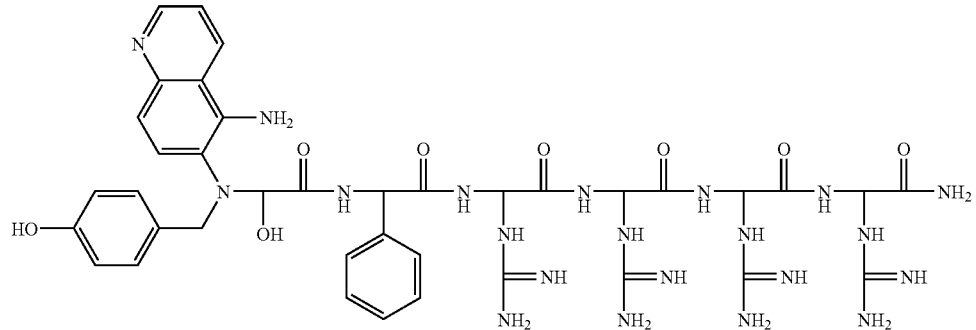
Compound 144
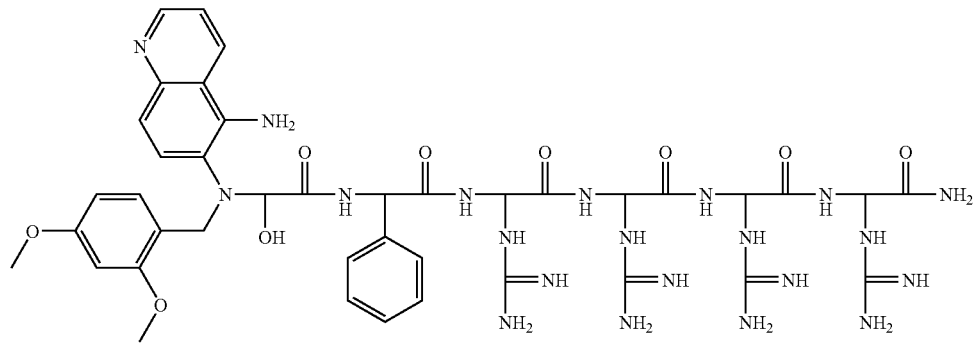
Compound 145
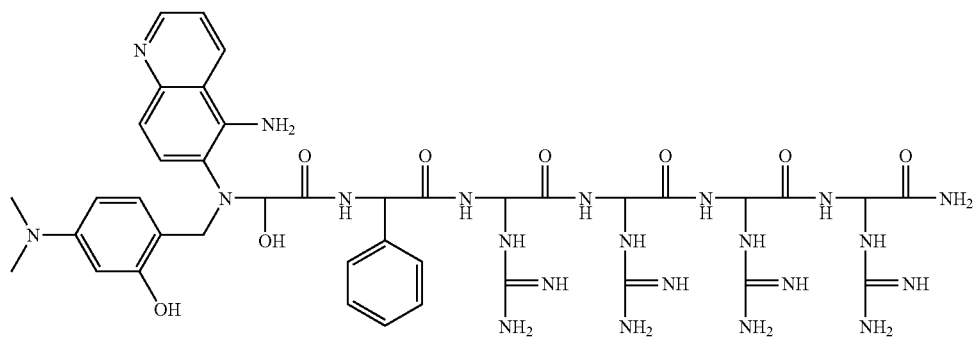
Compound 146
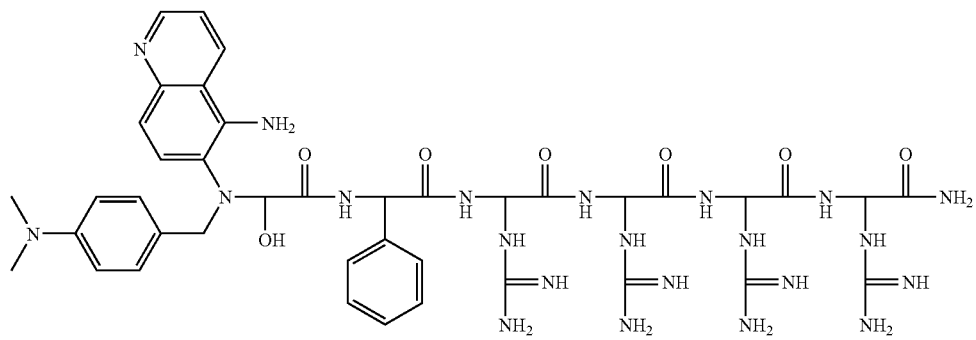

-continued
Compound 148
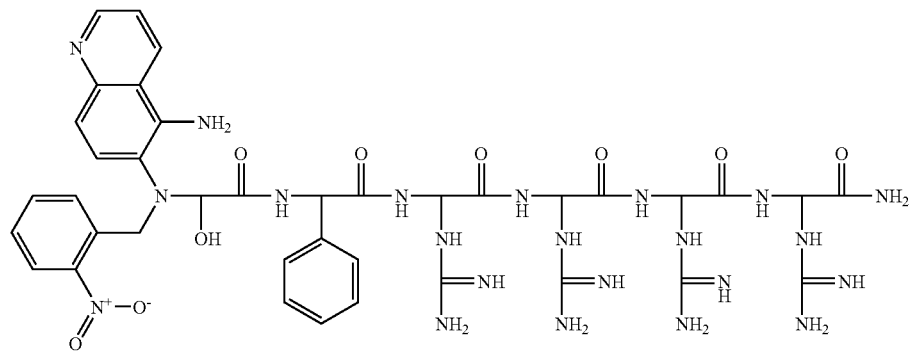
Compound 149
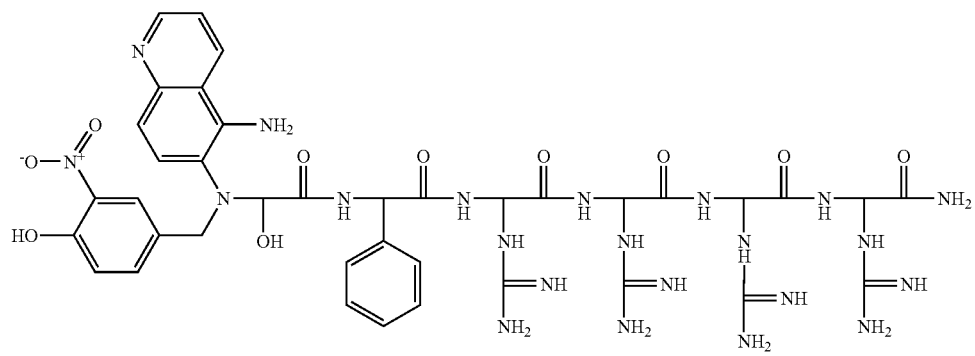
Compound 150
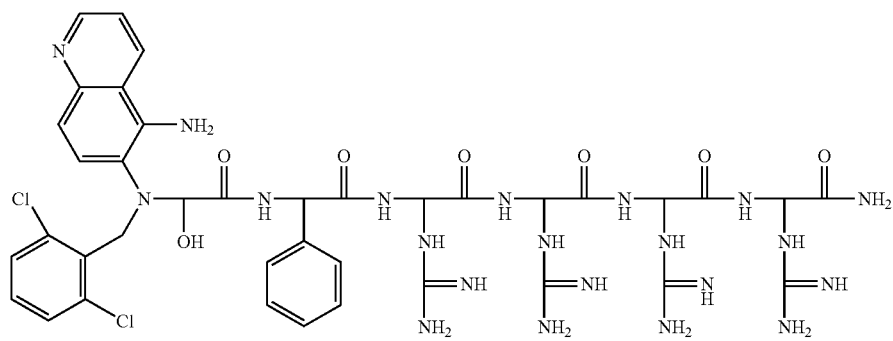
Compound 153
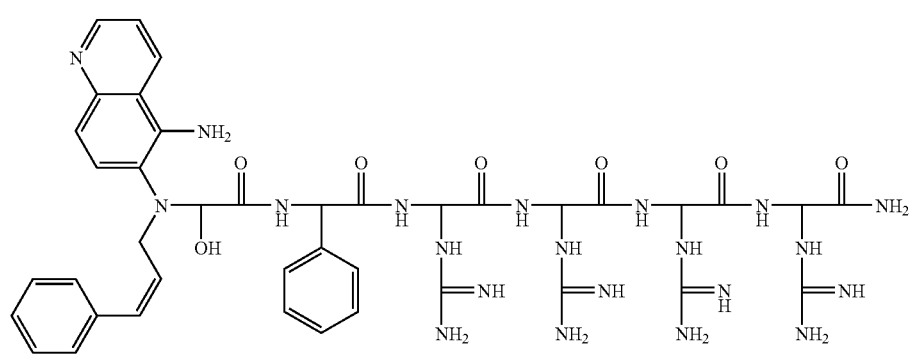

Compound 154
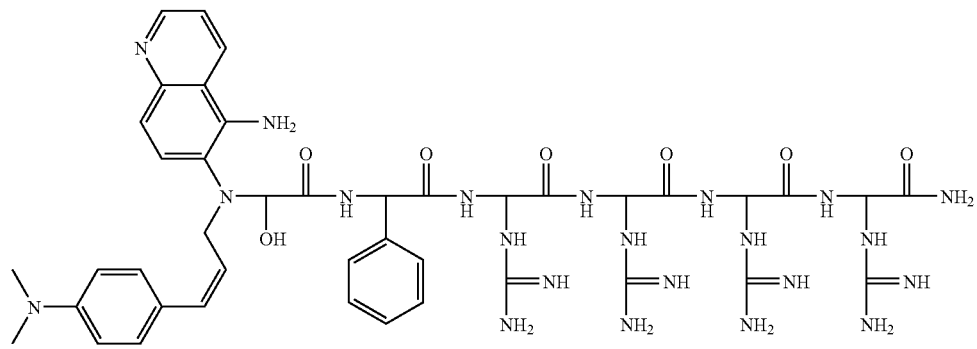
Compound 156
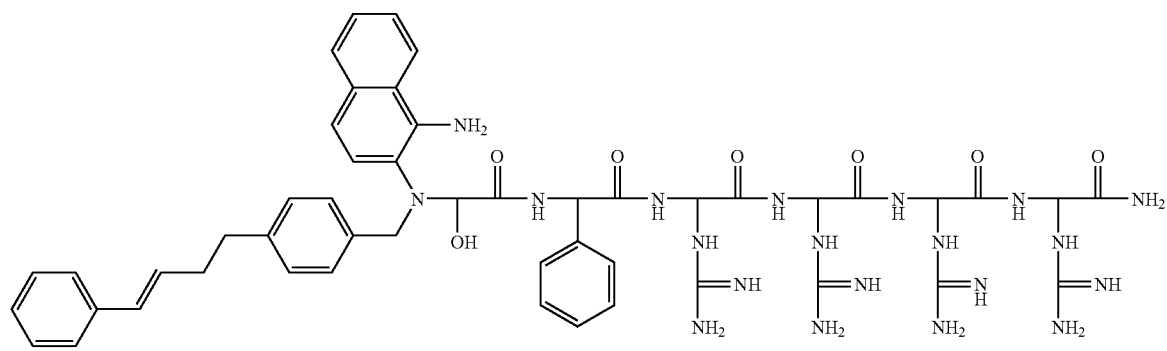
Compound 157
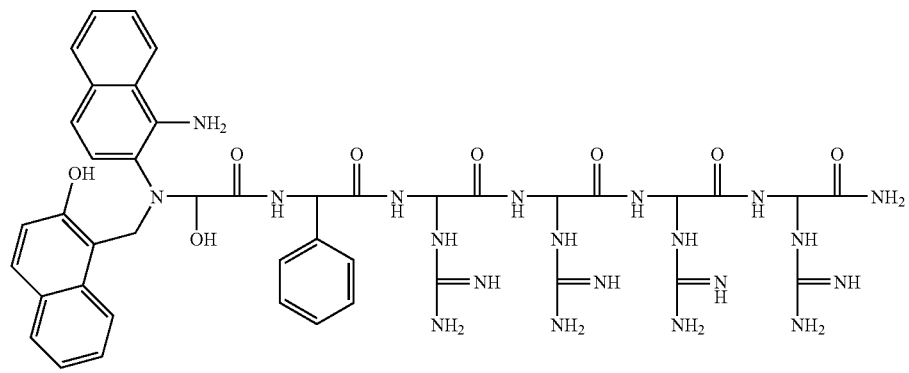
Compound 158
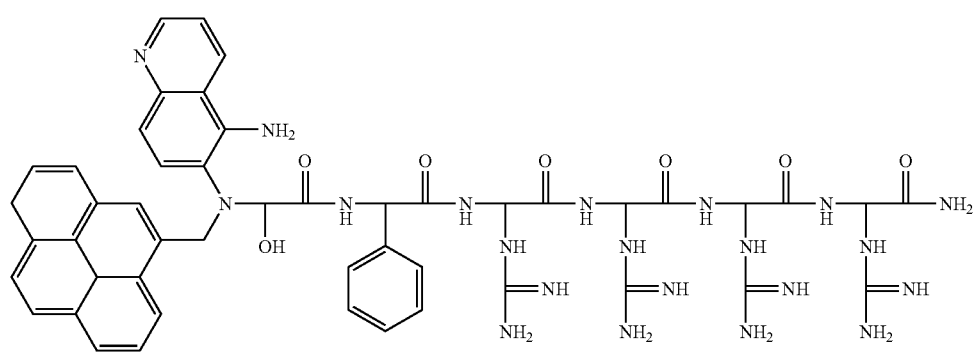

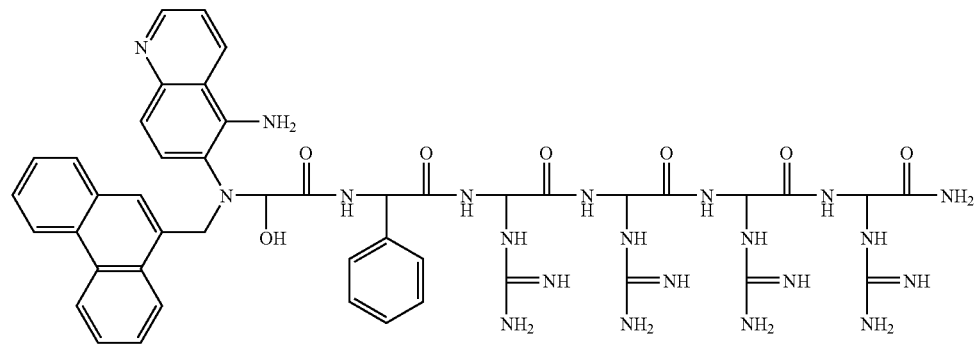
Compound 159
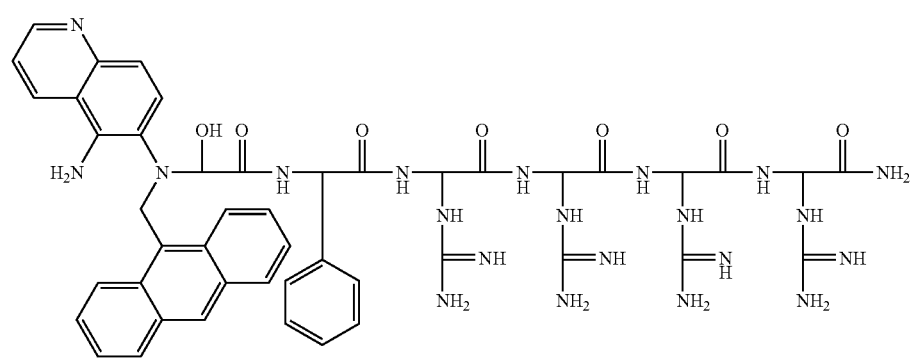
Compound 160
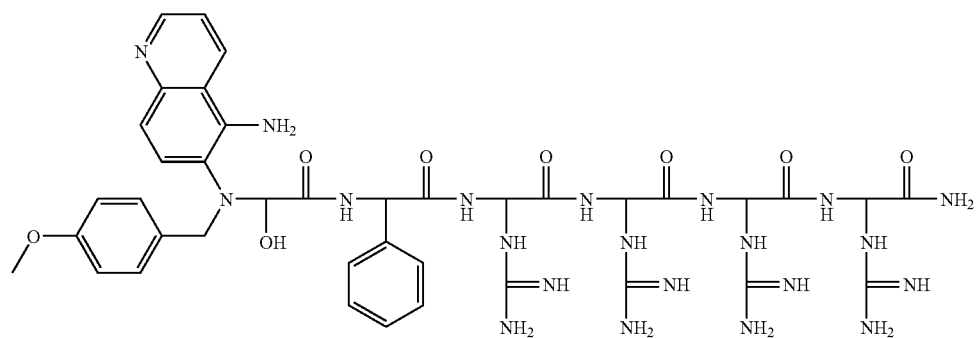
Compound 161
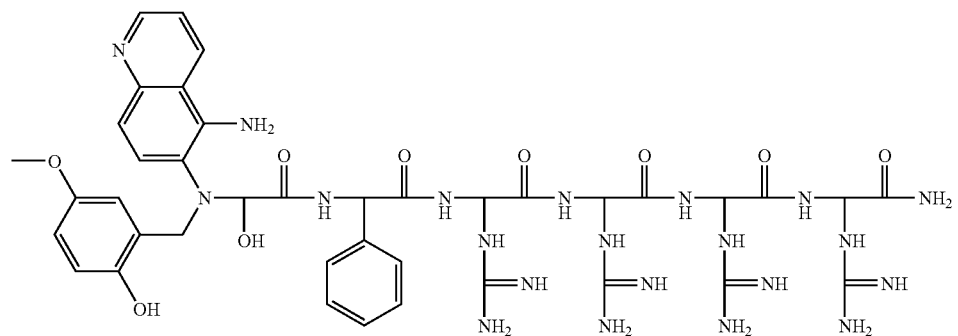
Compound 162

-continued
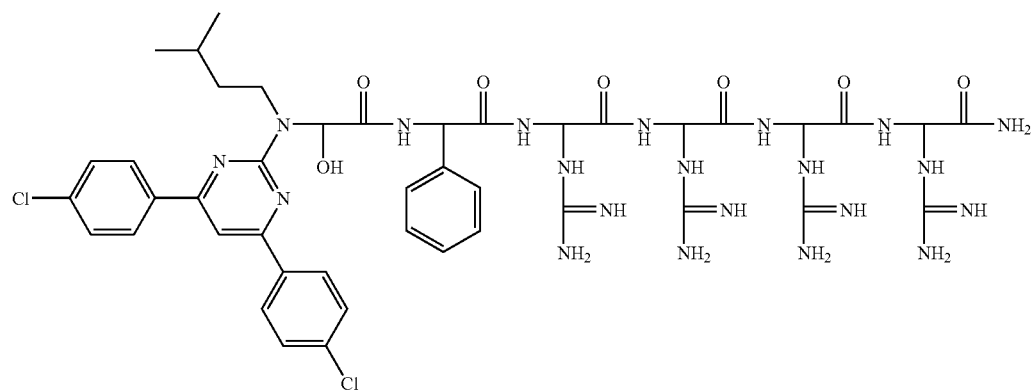
Compound 186
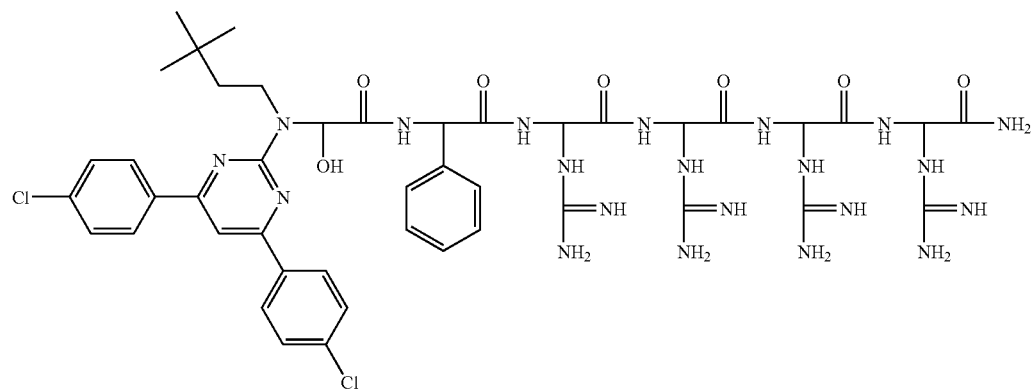
Compound 187
Compound 188
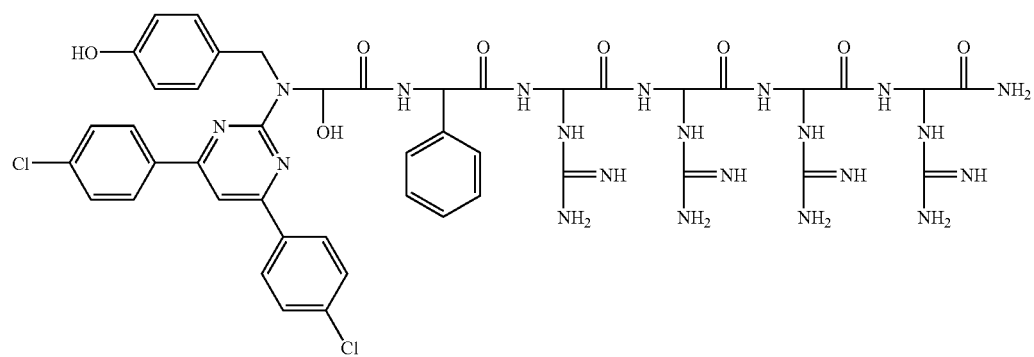
Compound 189

-continued
Compound 190
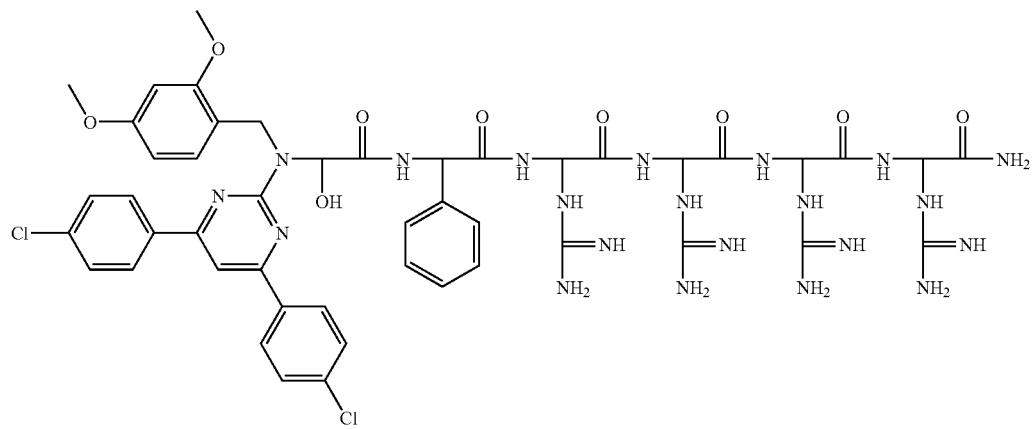
Compound 191
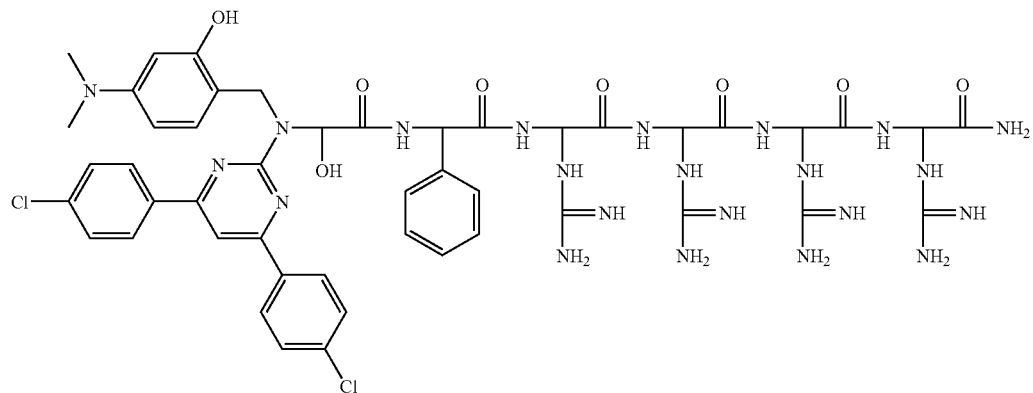
Compound 192
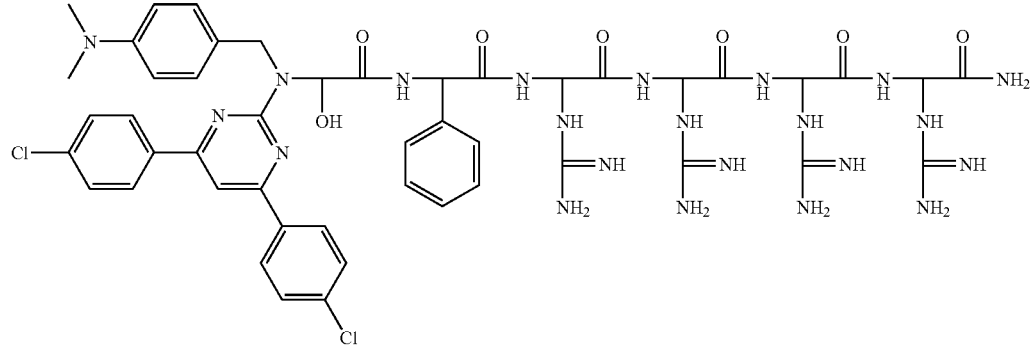
Compound 194
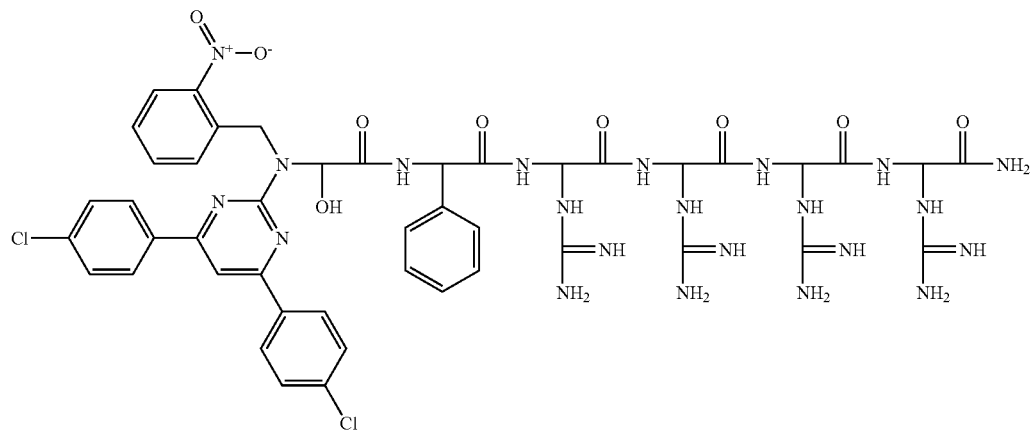

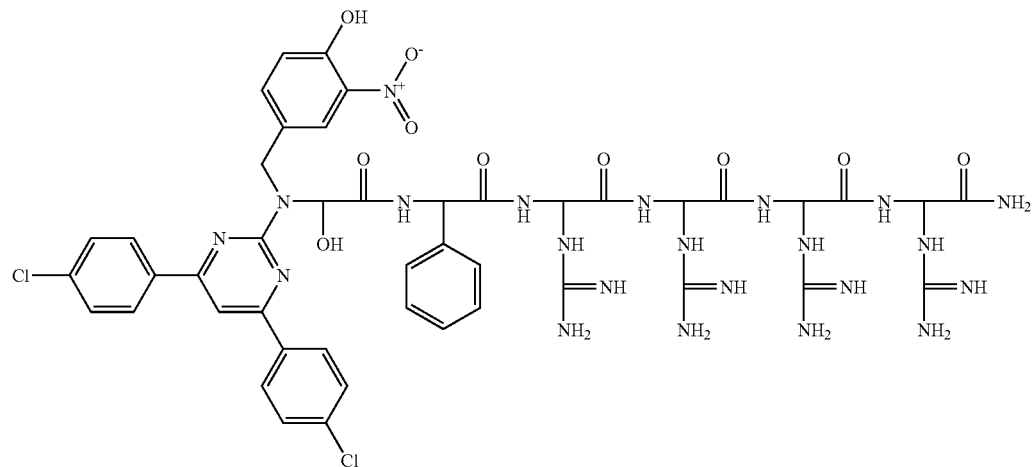
Compound 195
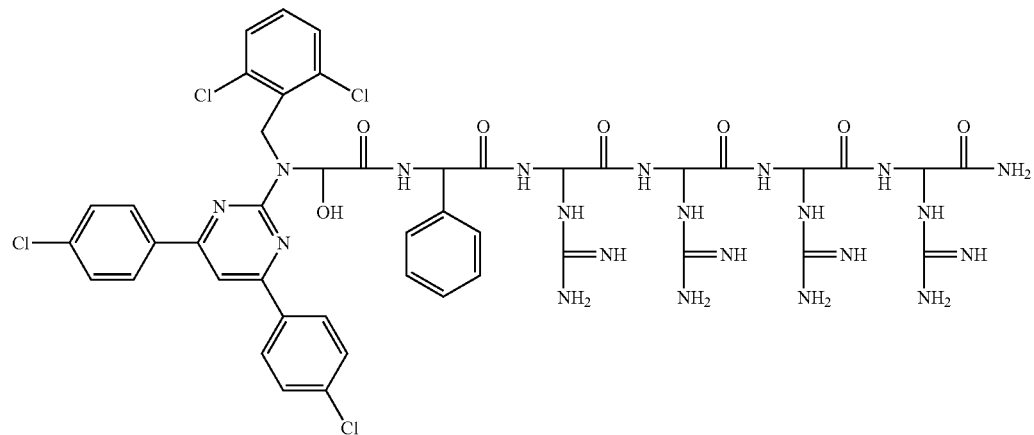
Compound 196
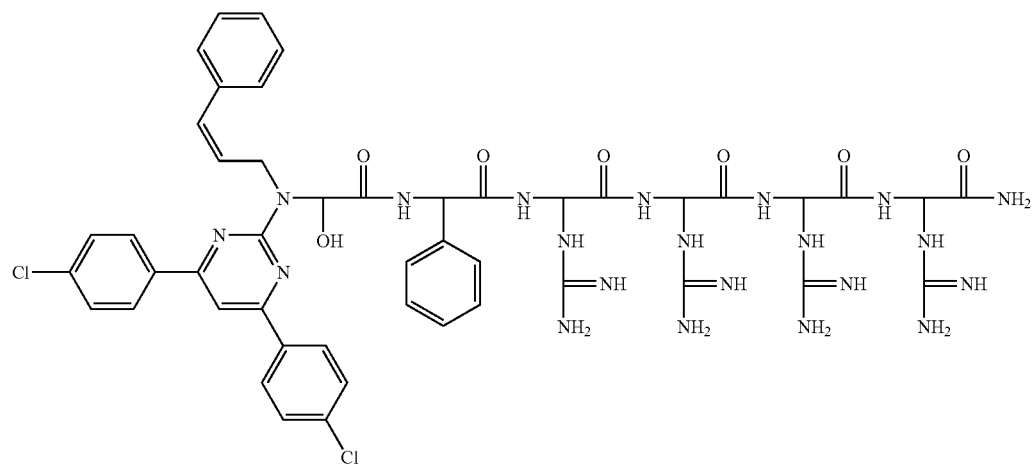
Compound 199

Compound 200
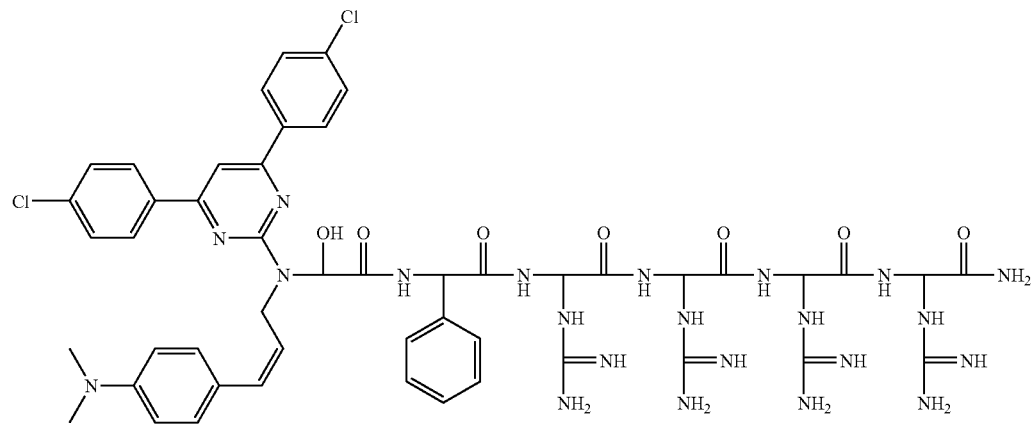
Compound 202
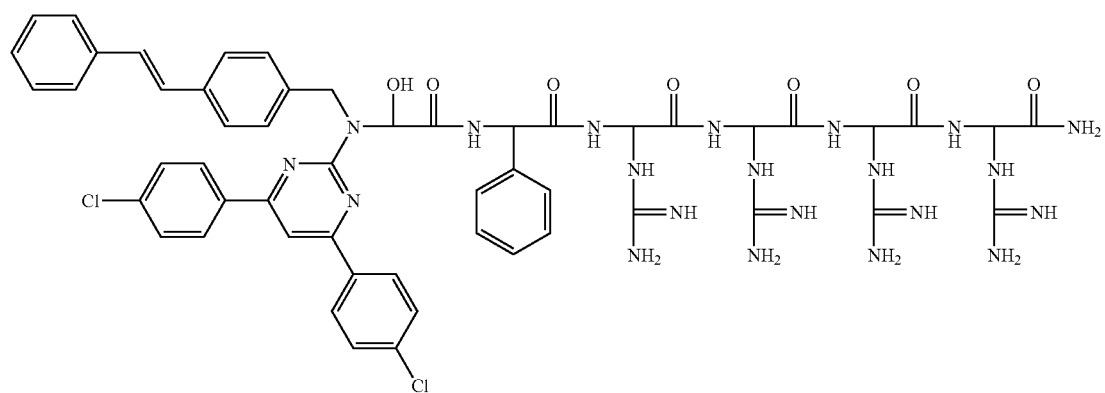
Compound 203
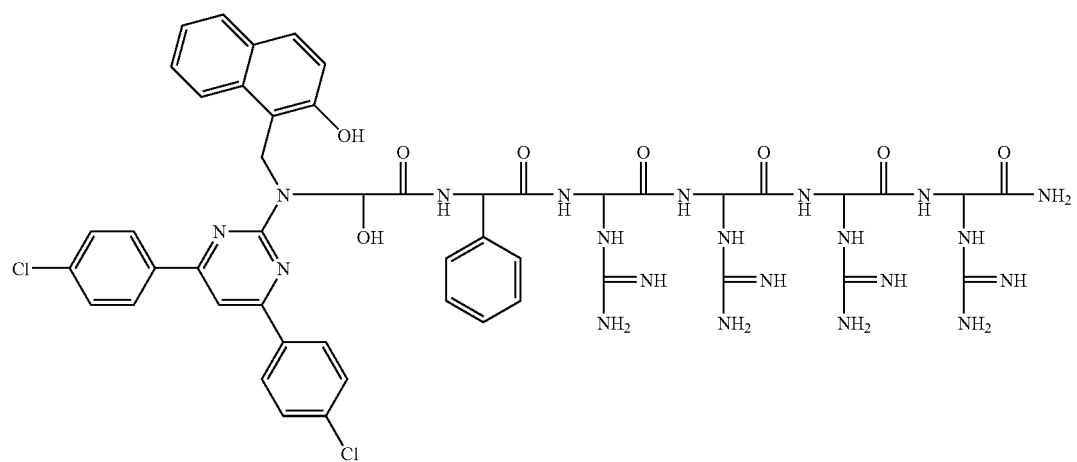

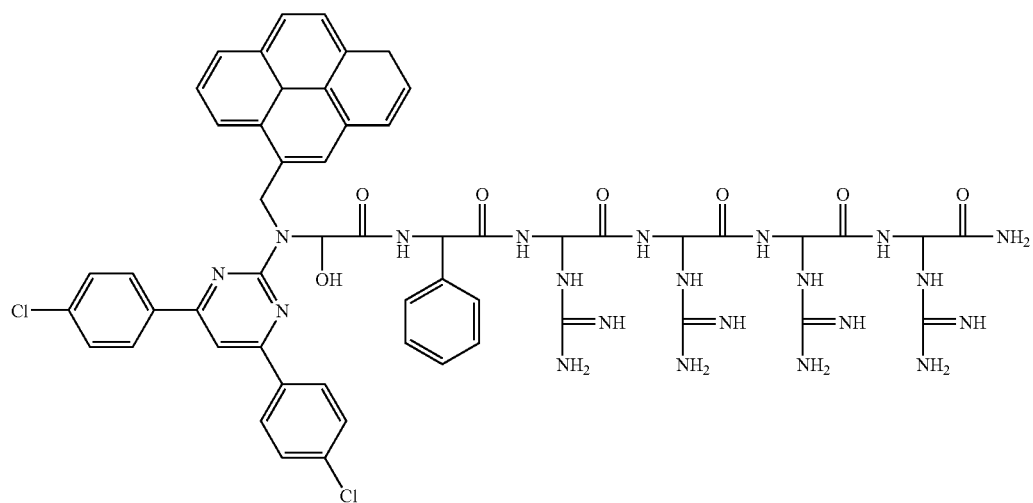
Compound 204
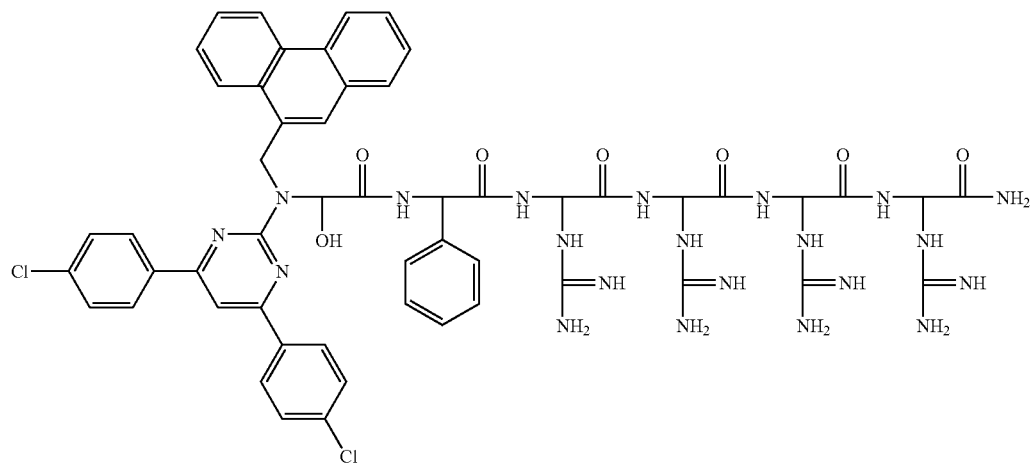
Compound 205
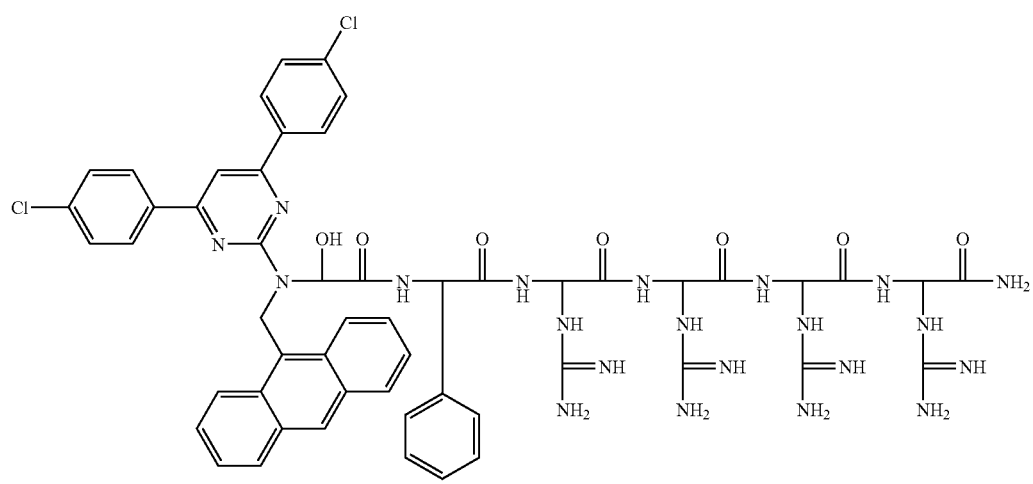
Compound 206

Compound 207
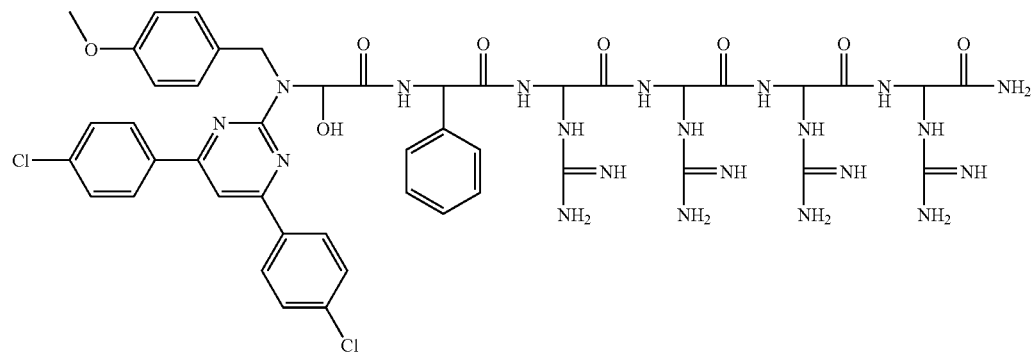
Compound 208
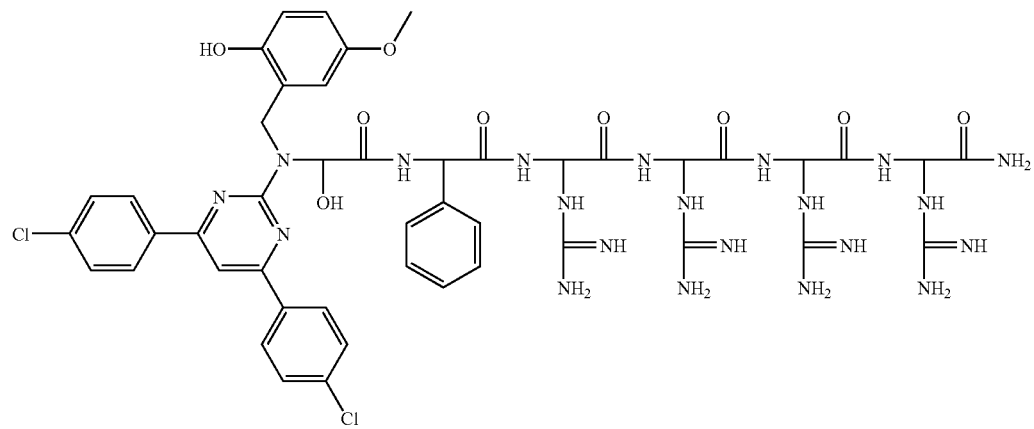
Compound 209
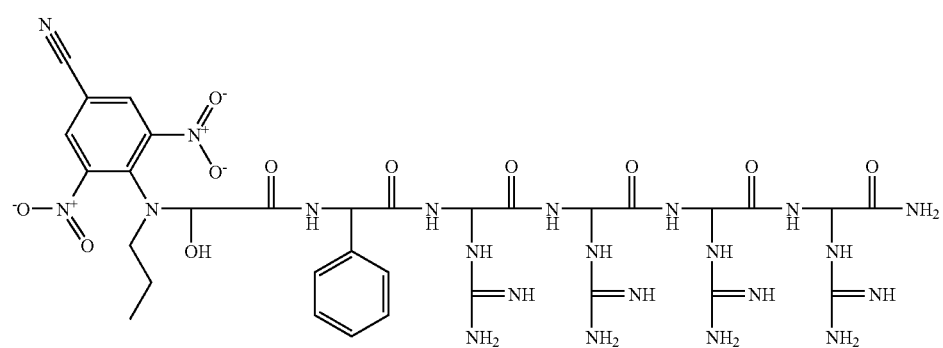
Compound 210
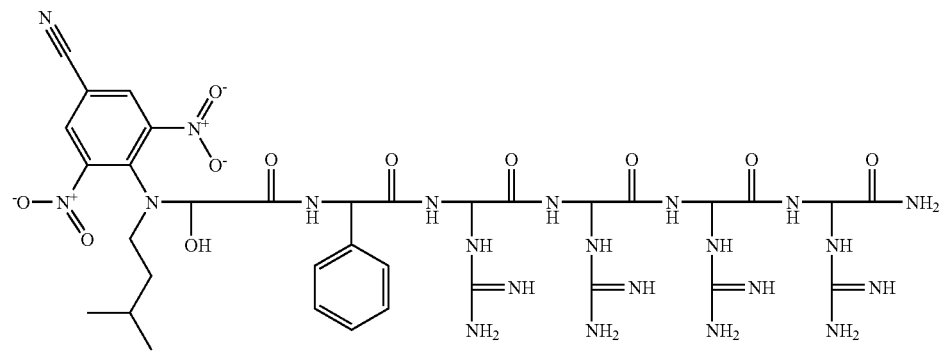

Compound 211
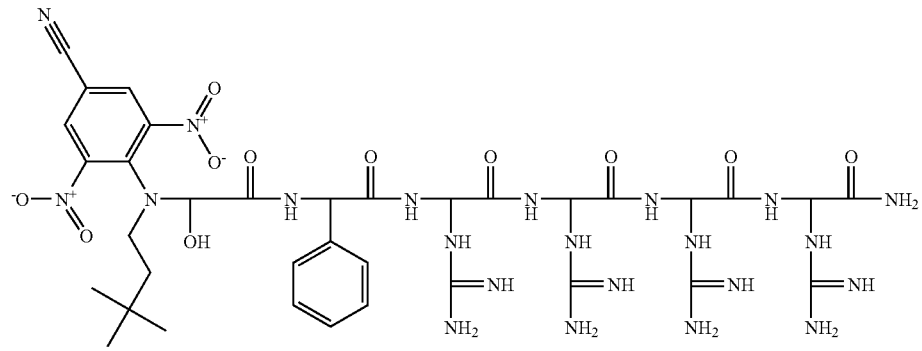
Compound 212
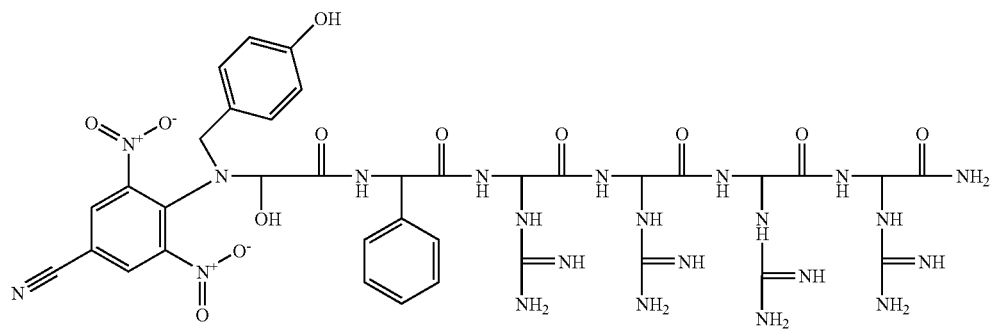
Compound 213
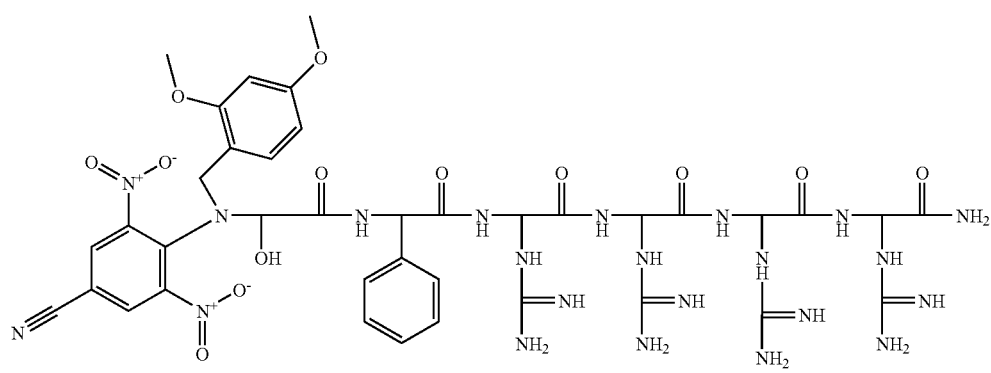
Compound 214
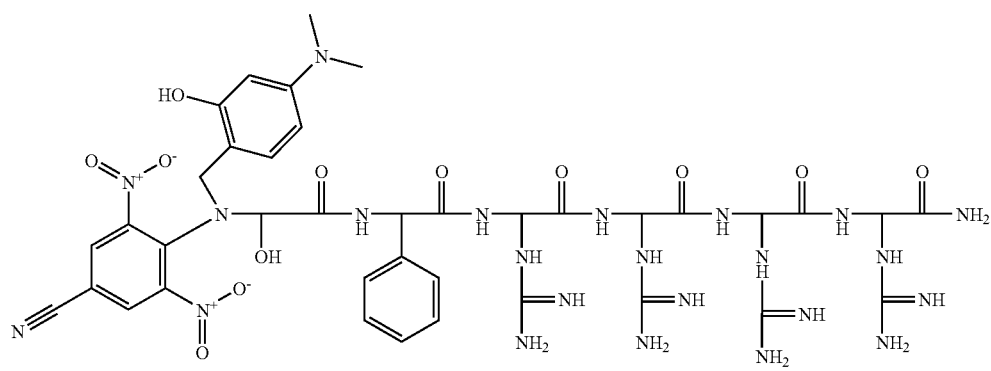

Compound 215
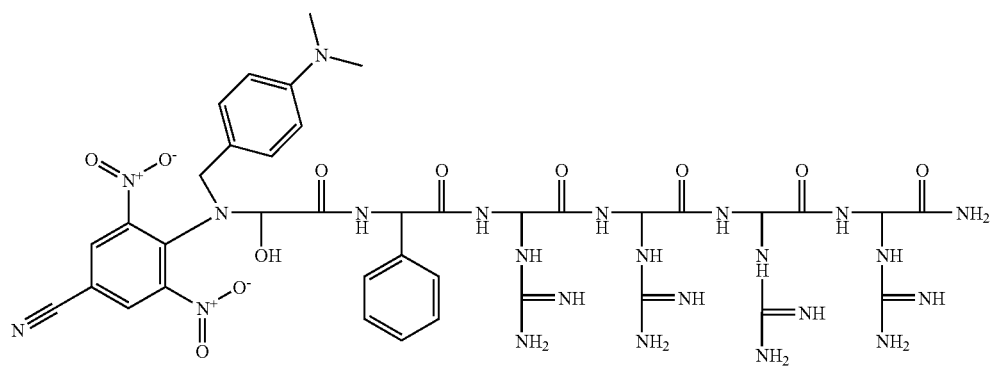
Compound 217
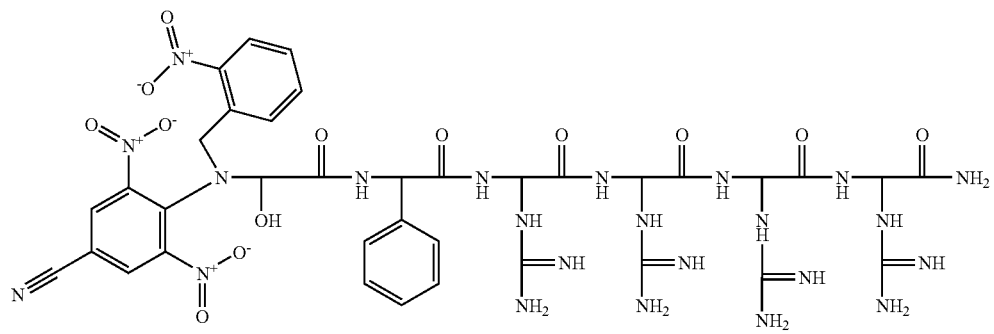
Compound 218
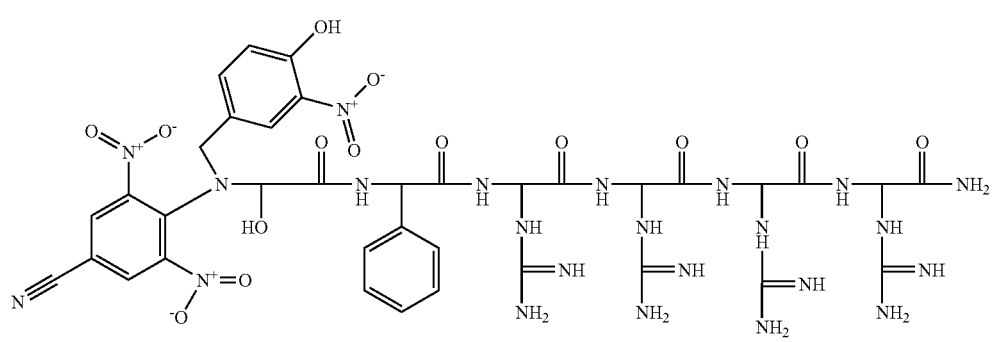
Compound 219
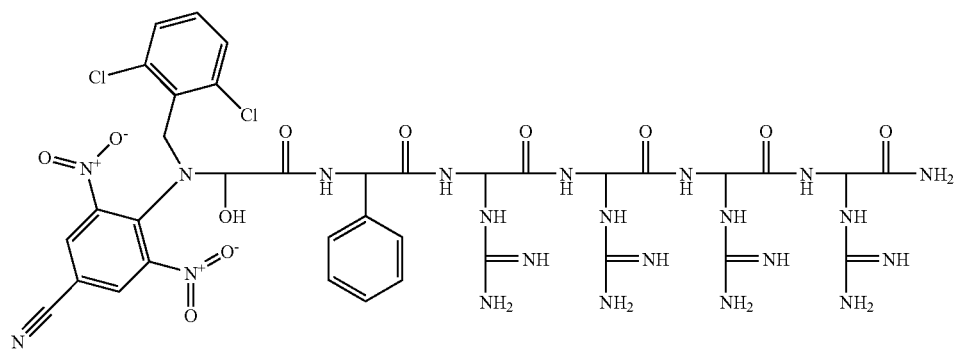

Compound 222
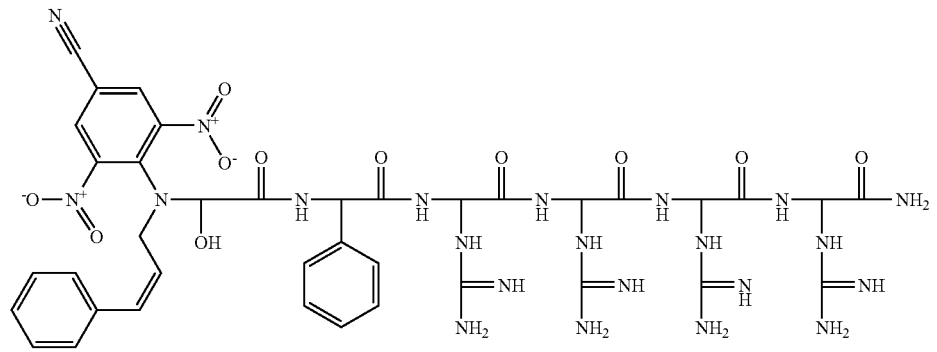
Compound 223
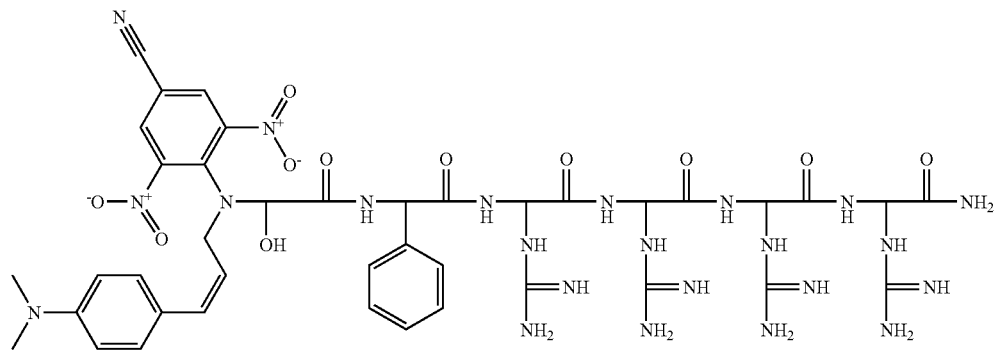
Compound 225
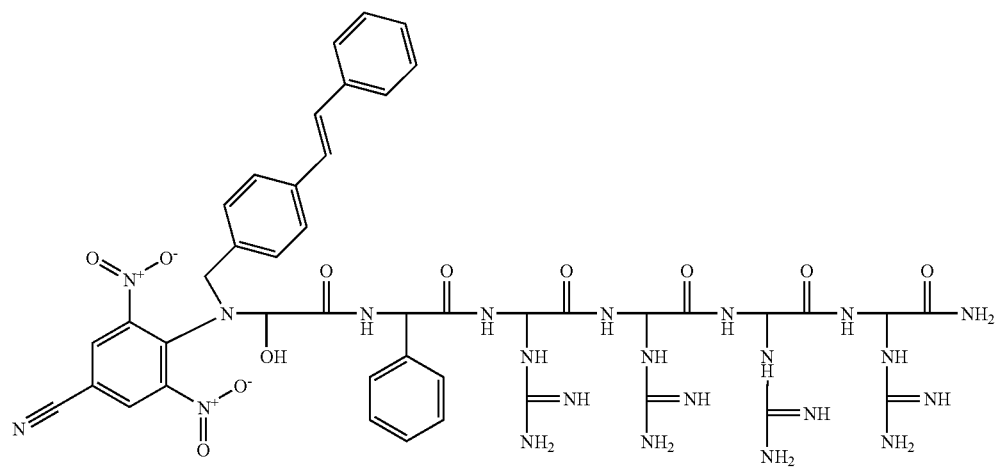
Compound 226
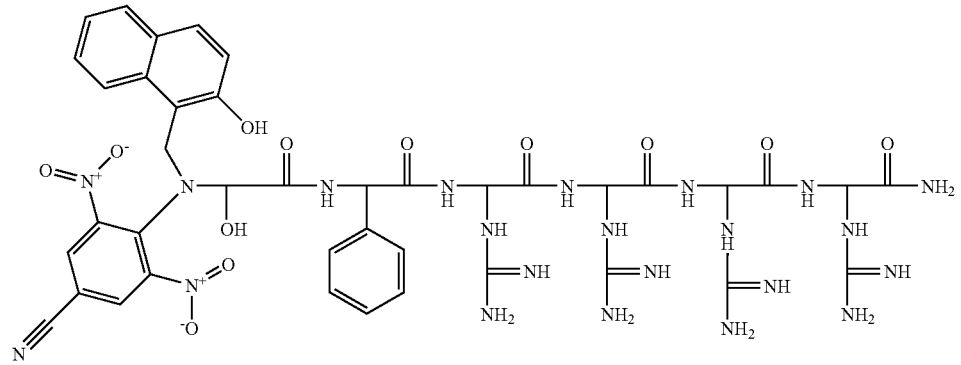

Compound 227
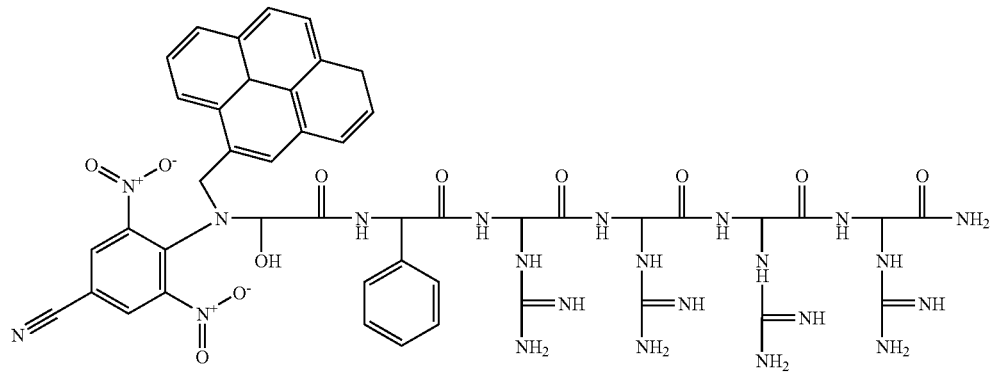
Compound 228
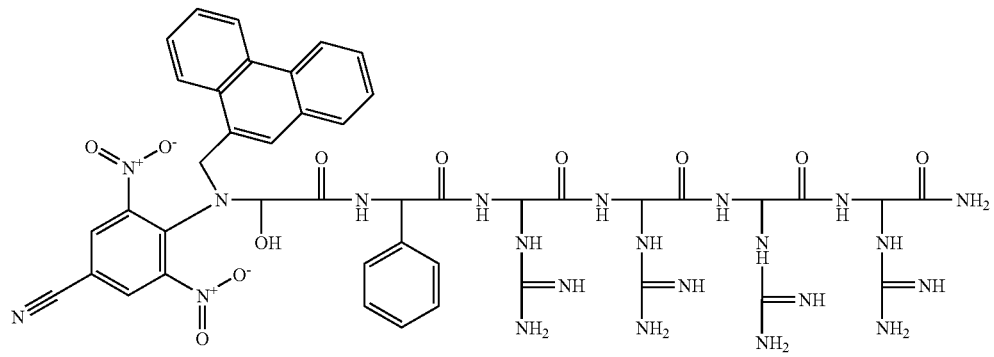
Compound 229
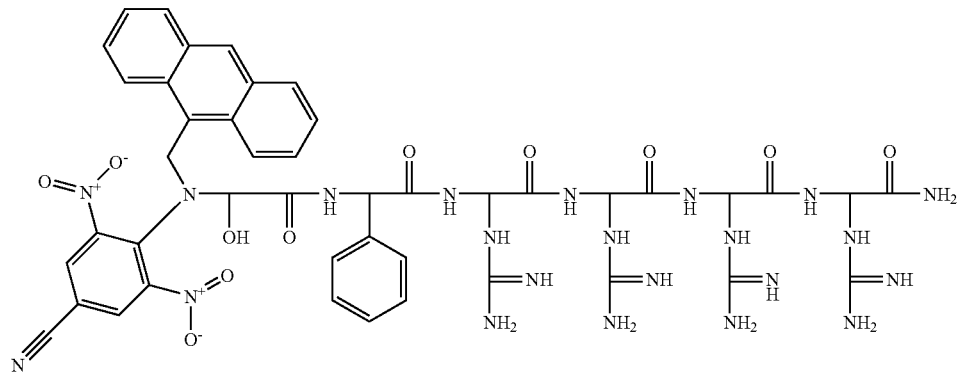
Compound 230
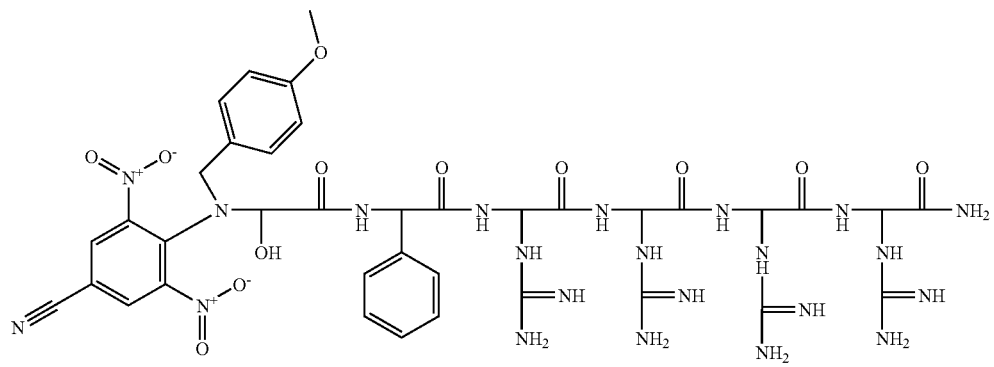

Compound 231
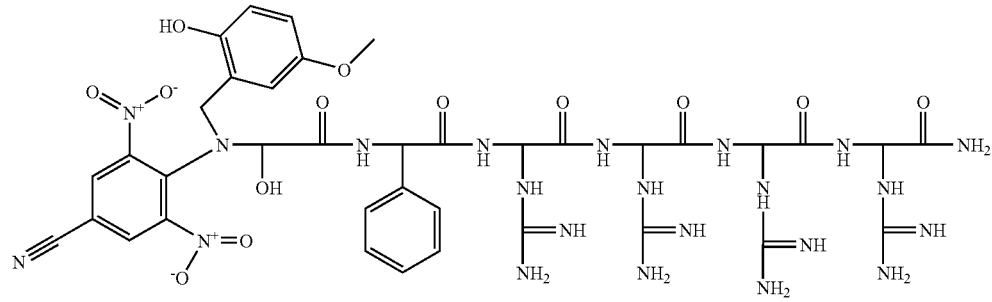
Compound 232
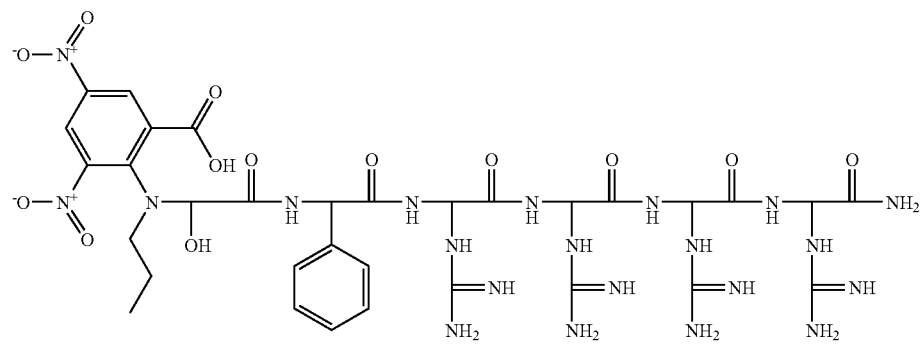
Compound 233
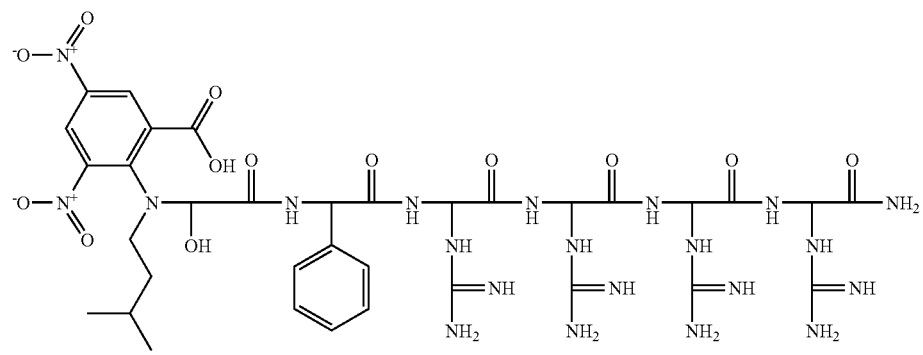
Compound 234
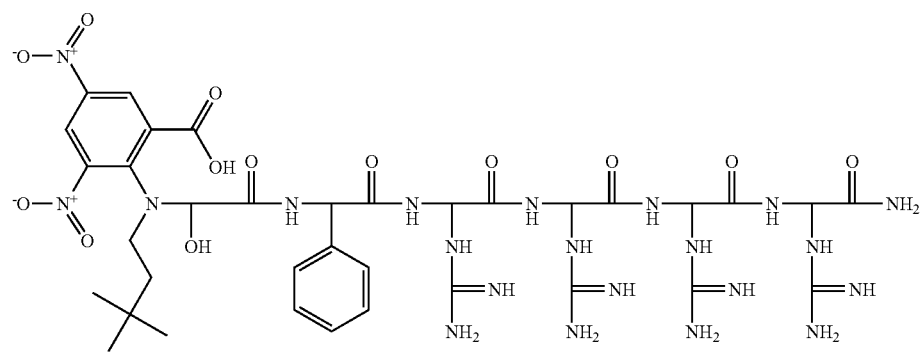

-continued
Compound 235
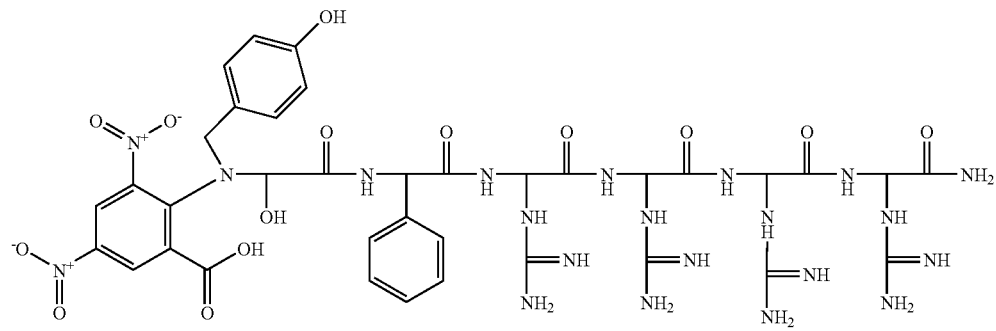
Compound 236
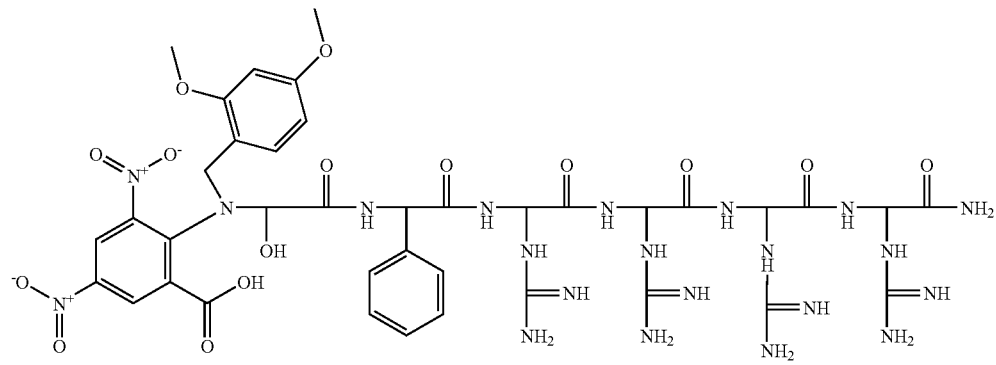
Compound 237
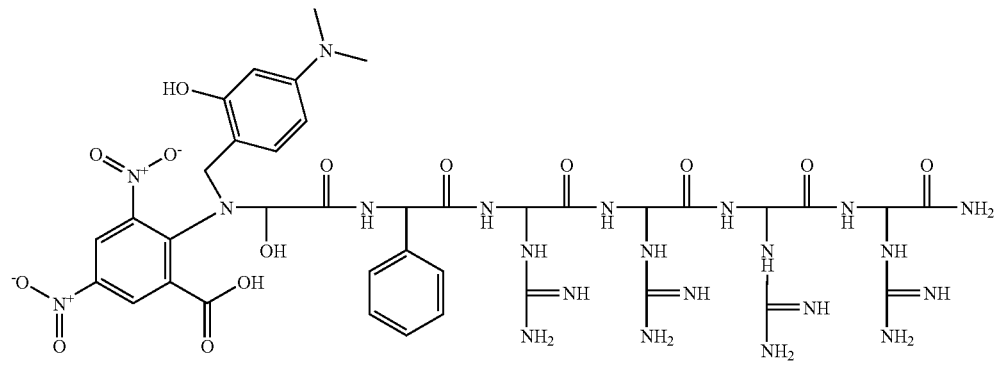
Compound 238
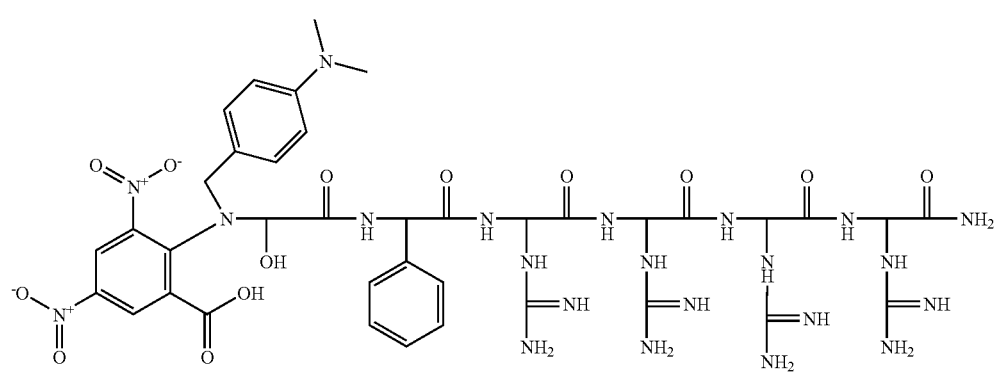

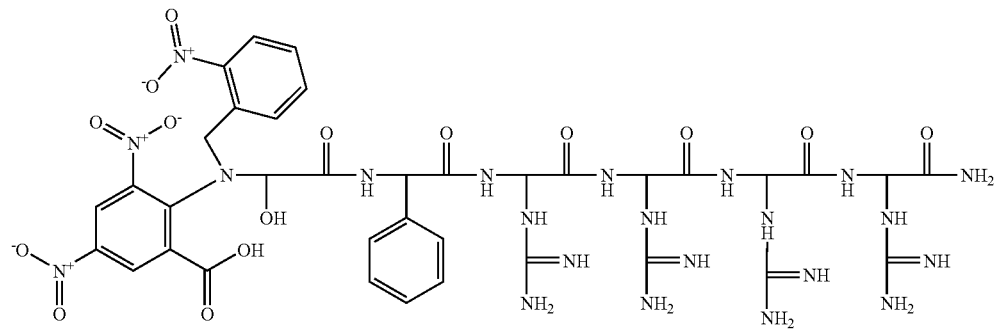
Compound 240
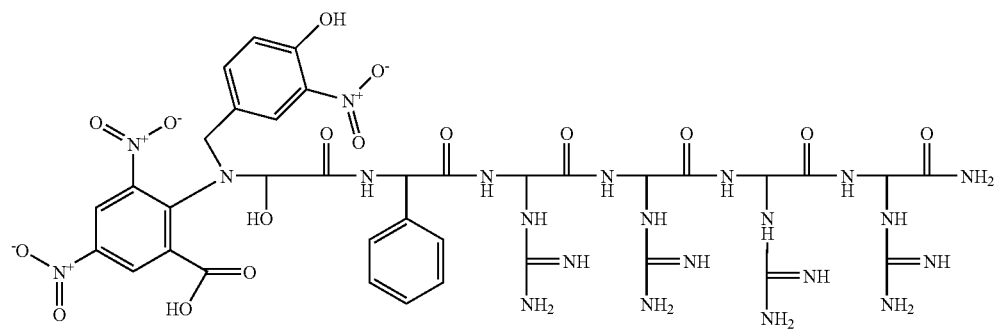
Compound 241
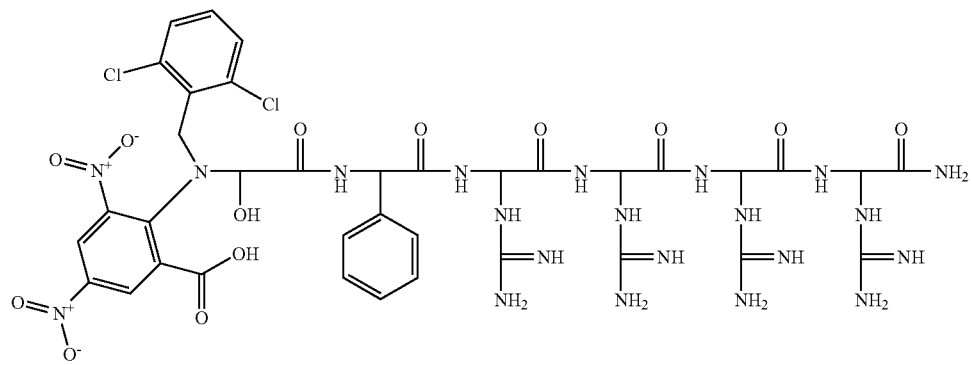
Compound 242
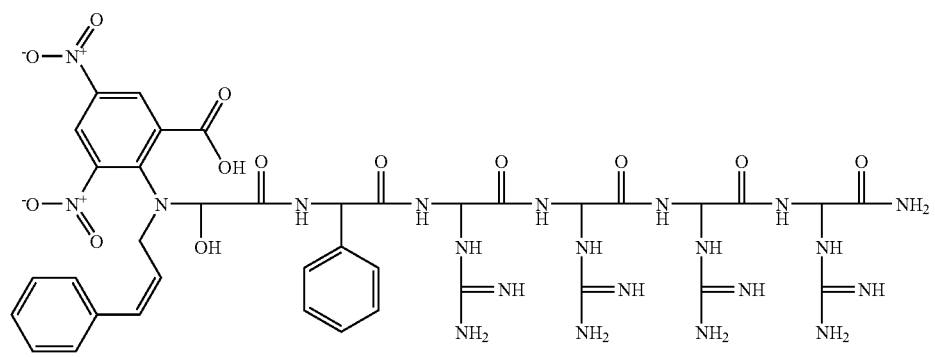
Compound 245

Compound 246
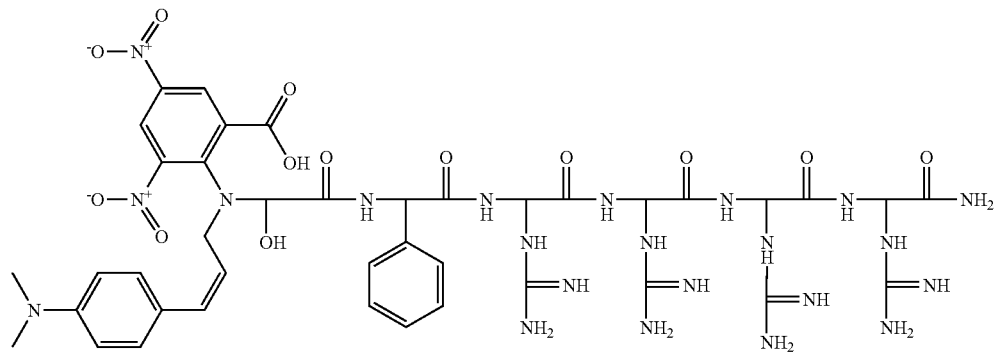
Compound 248
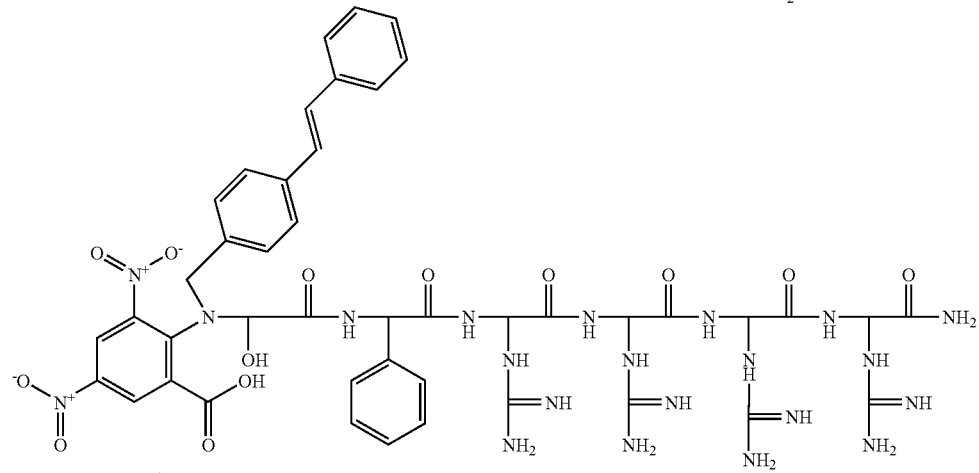
Compound 249
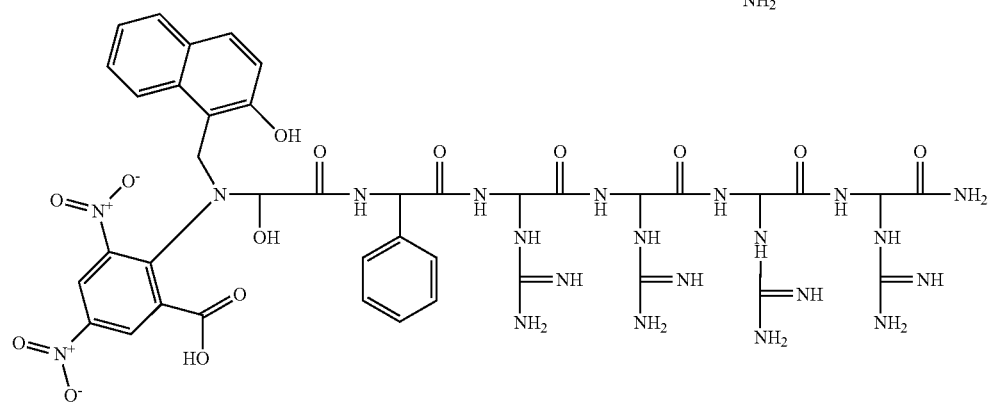
Compound 250
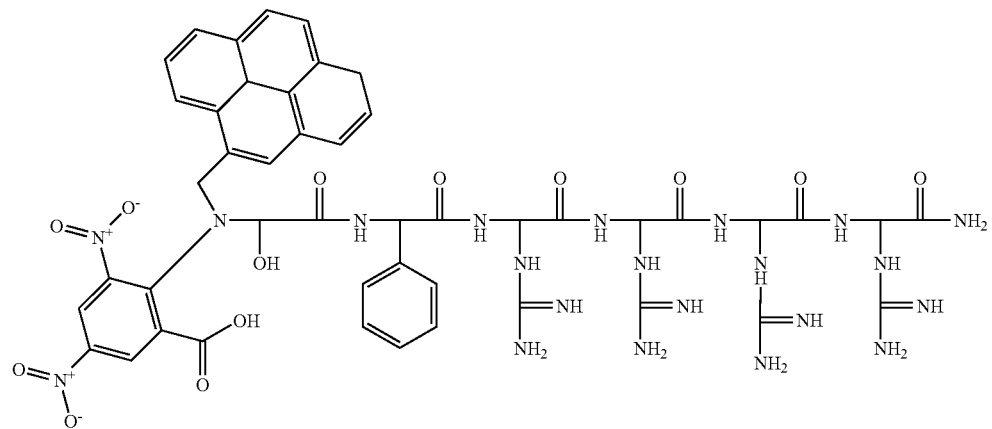

-continued
Compound 251
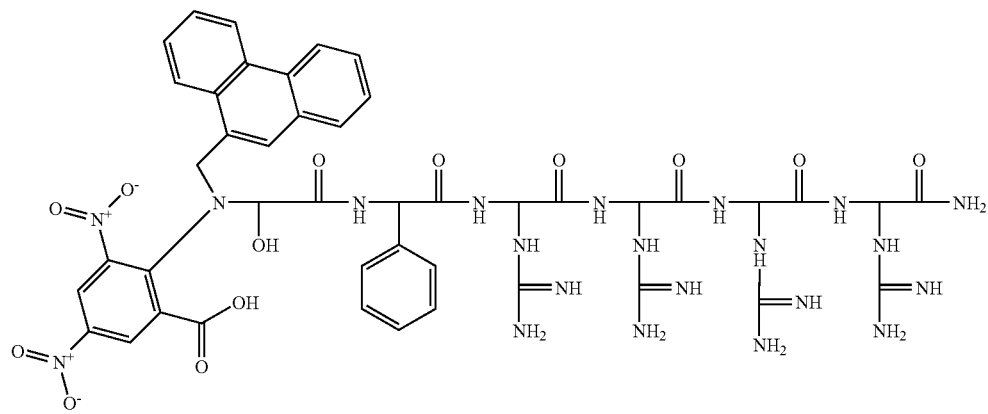
Compound 252
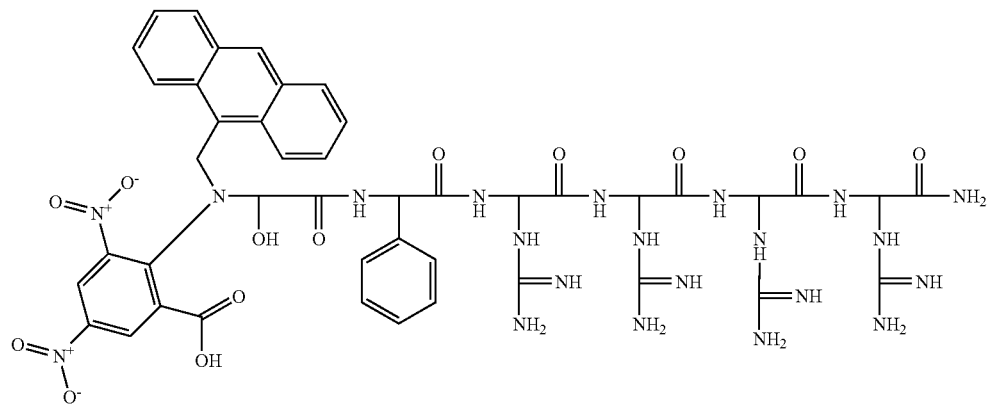
Compound 253
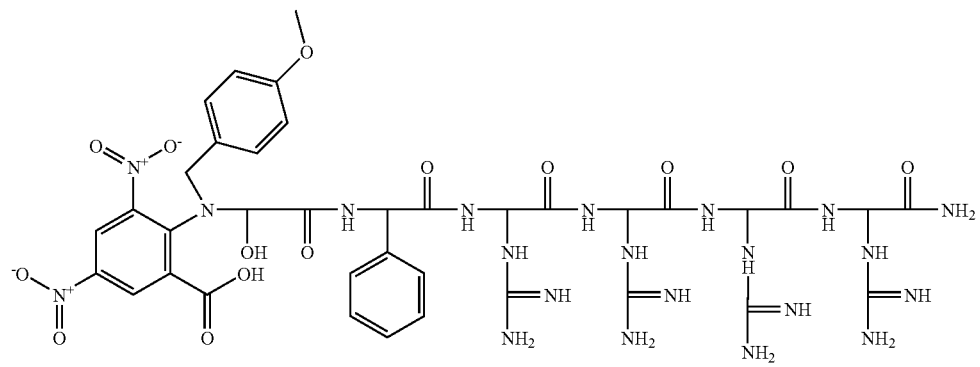
Compound 254
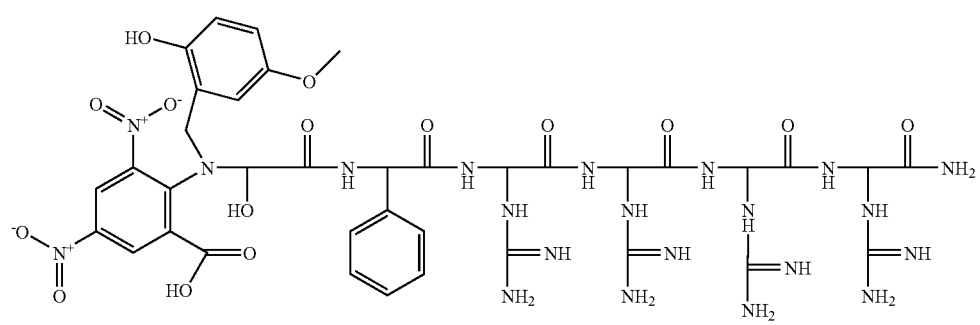

Compound 255
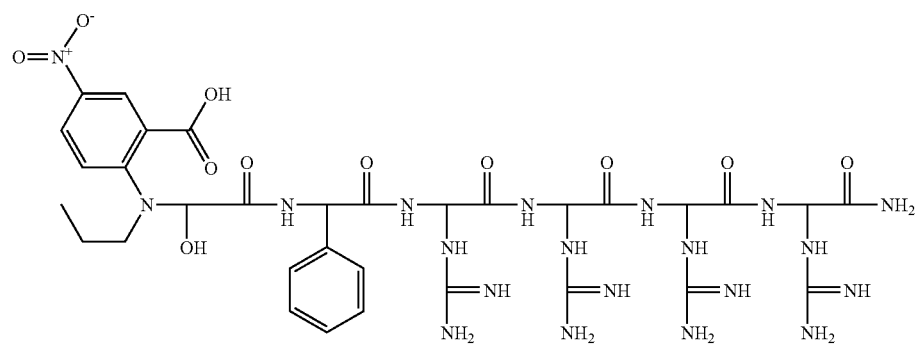
Compound 256
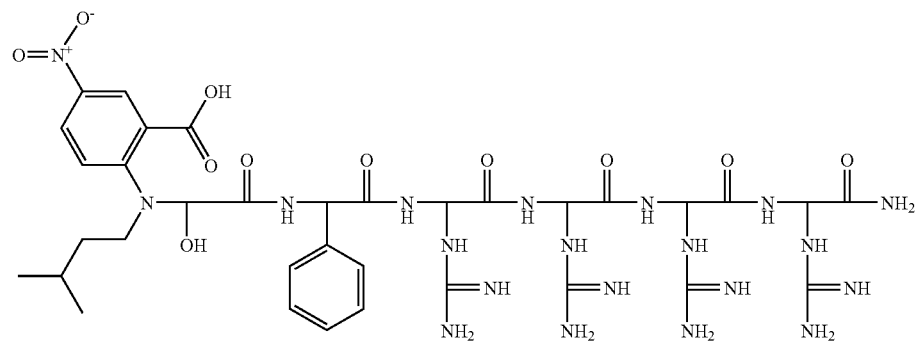
Compound 257
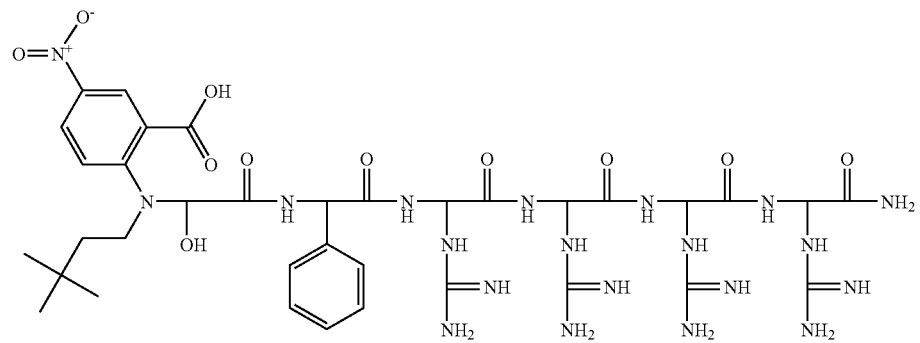
Compound 258
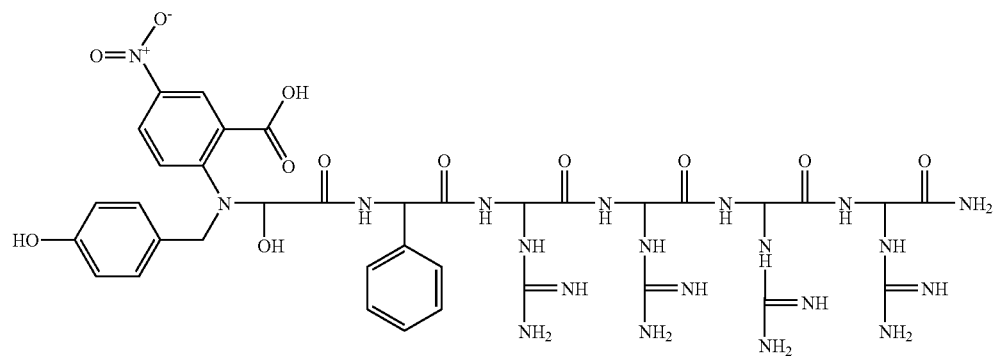

Compound 259
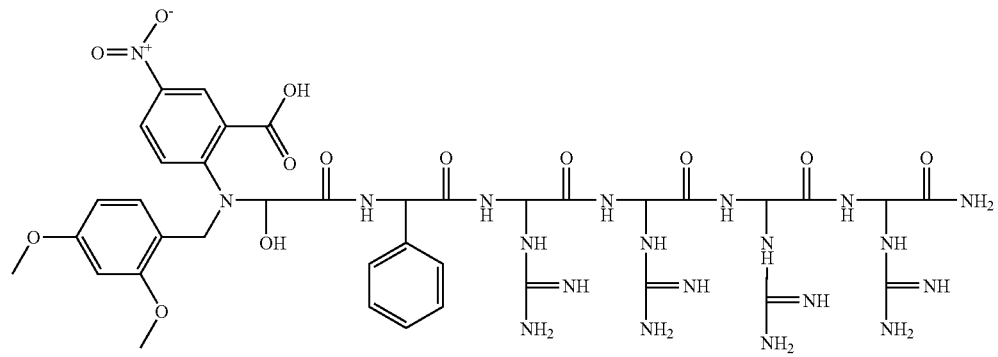
Compound 260
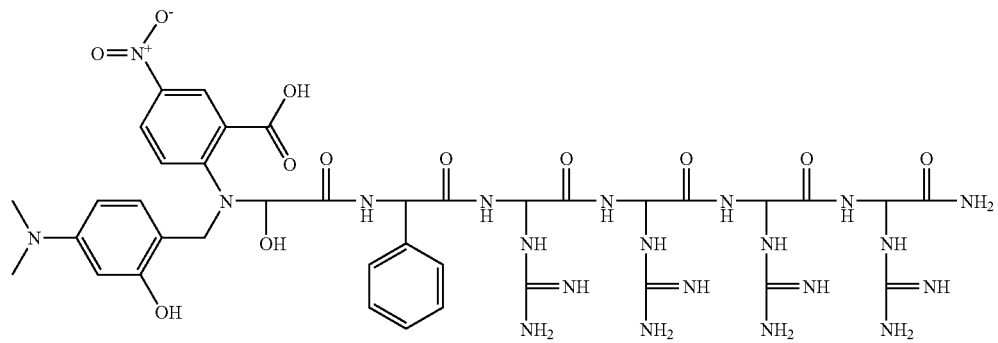
Compound 261
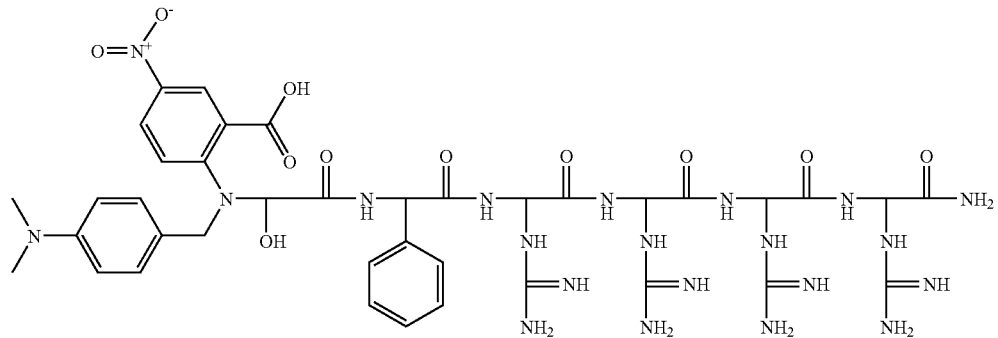
Compound 263
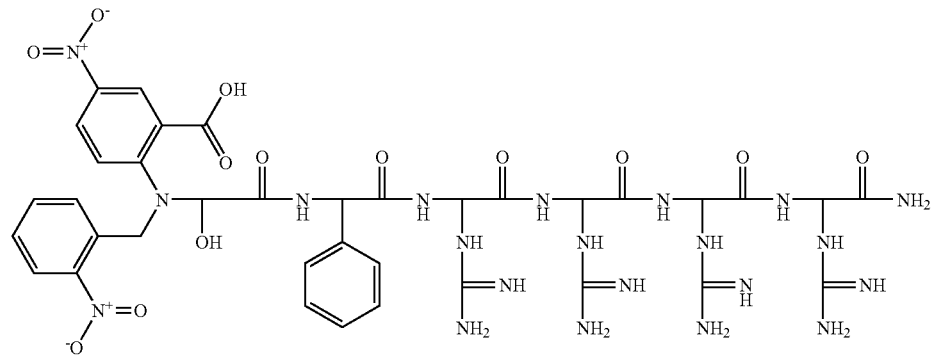

-continued
Compound 264
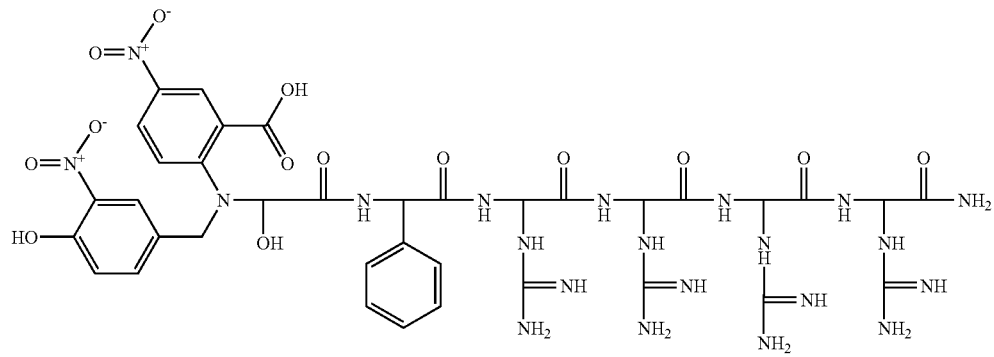
Compound 265
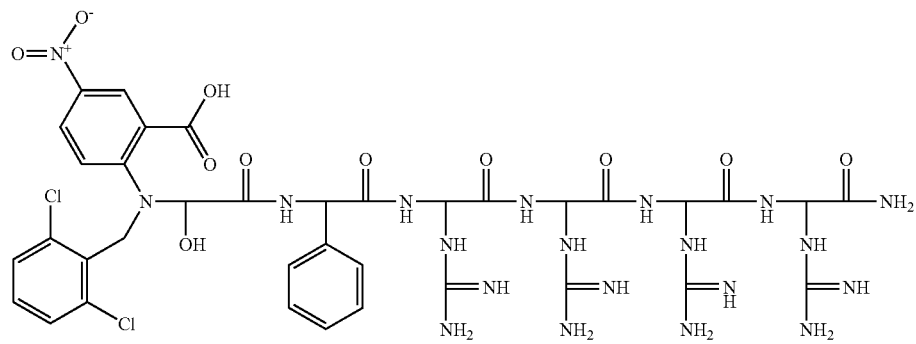
Compound 268
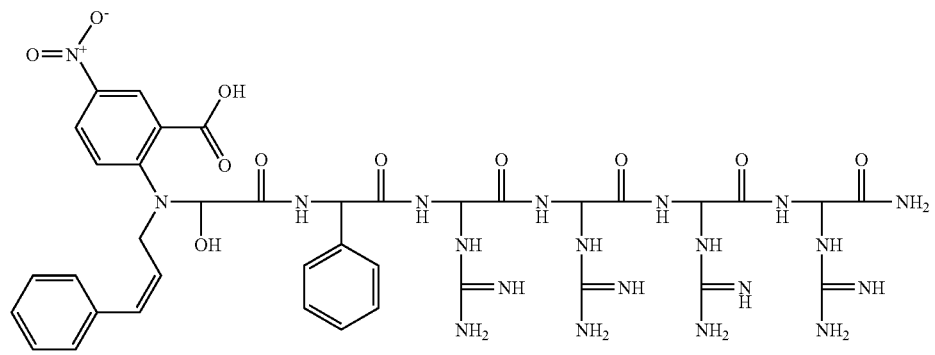
Compound 269
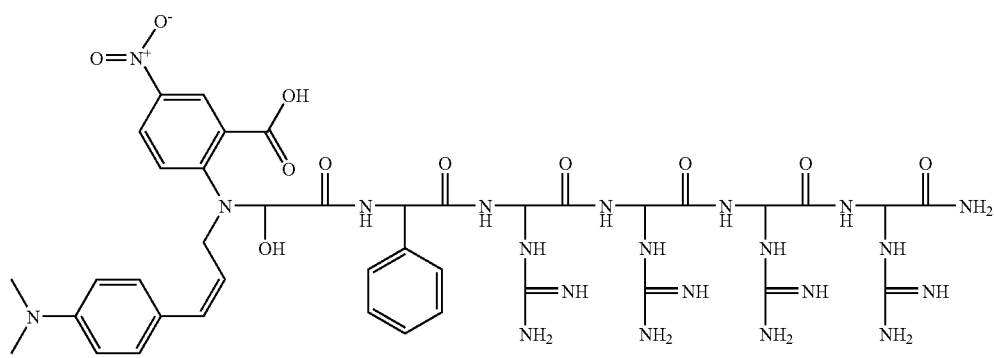

Compound 271
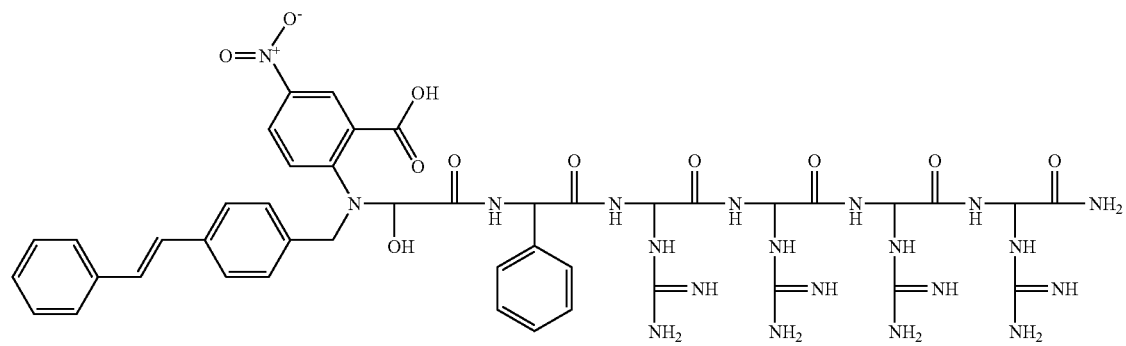
Compound 272
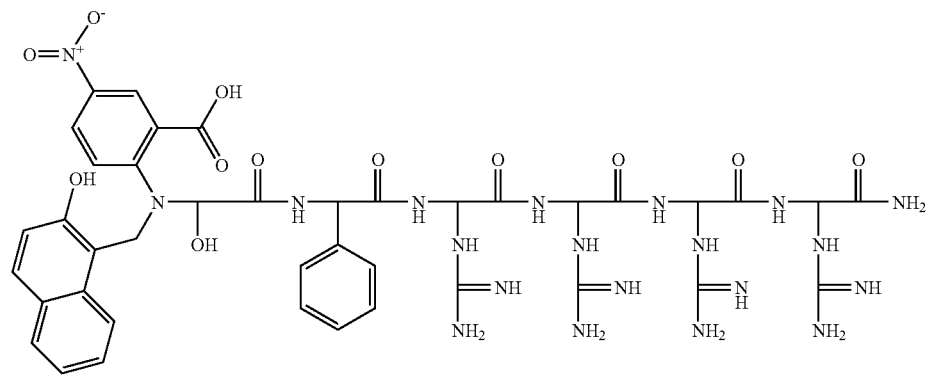
Compound 273
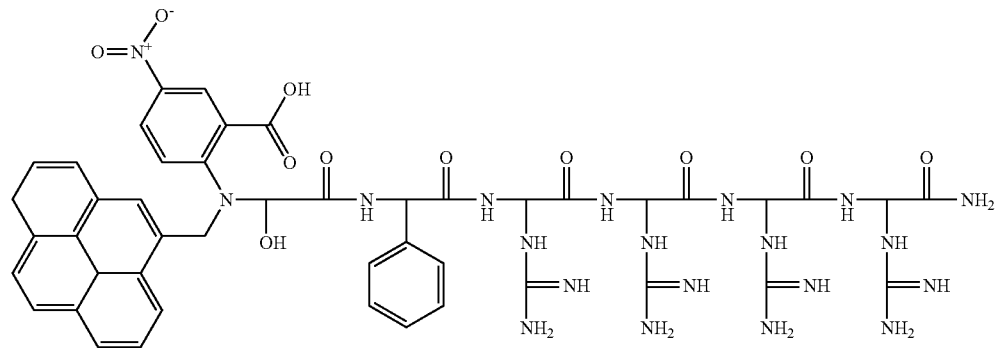
Compound 274
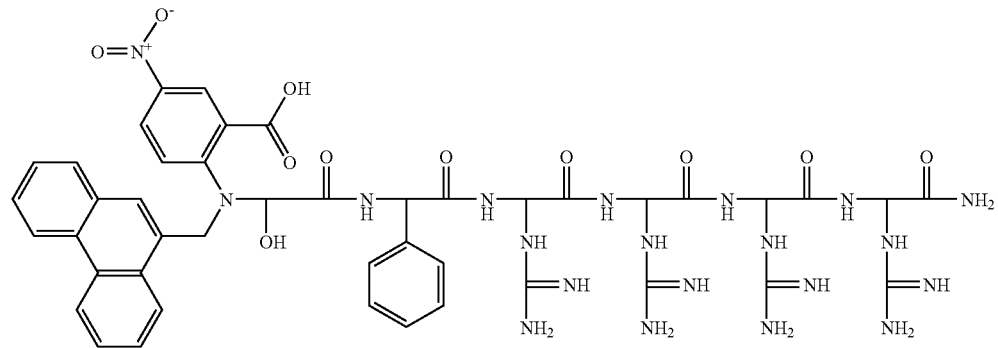

Compound 275
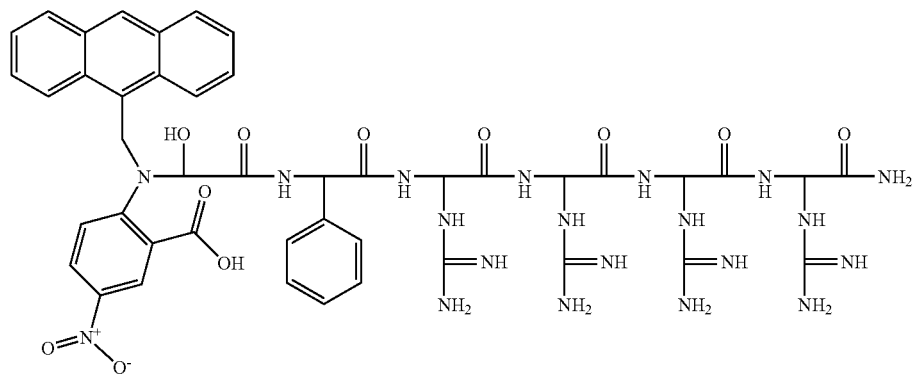
Compound 276
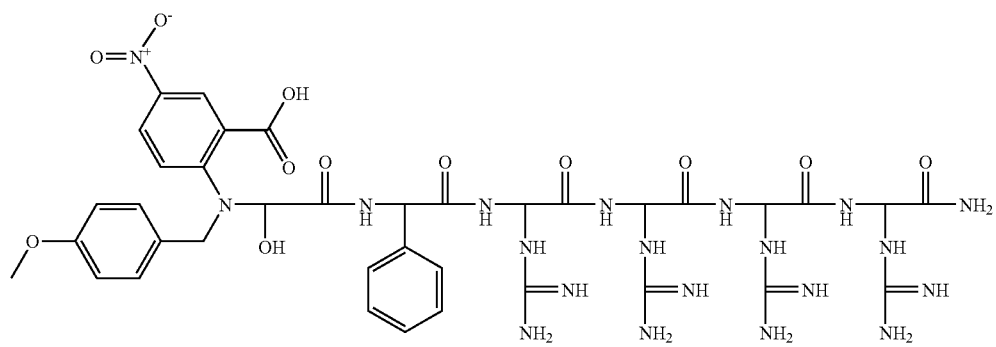
Compound 277
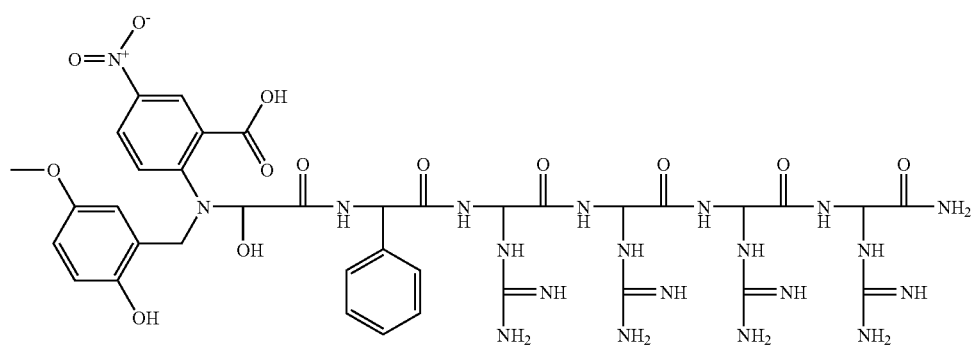
Compound 278
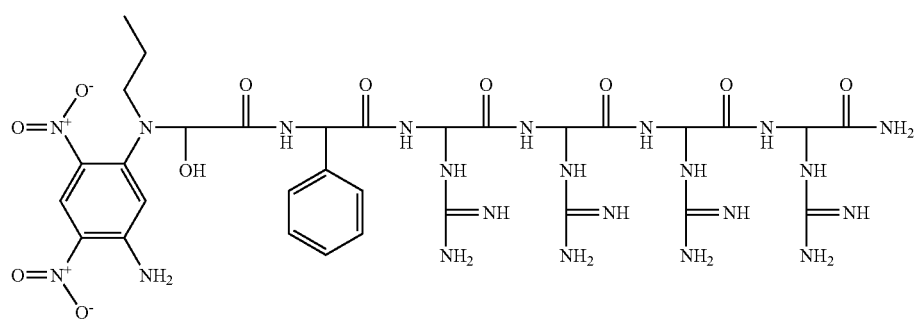

-continued
Compound 279
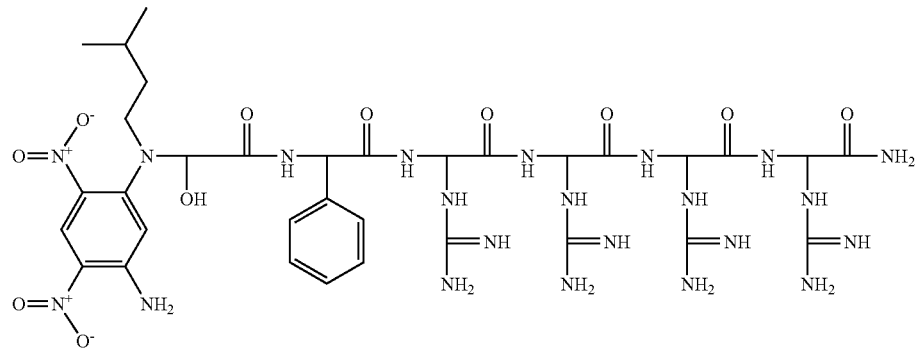
Compound 280
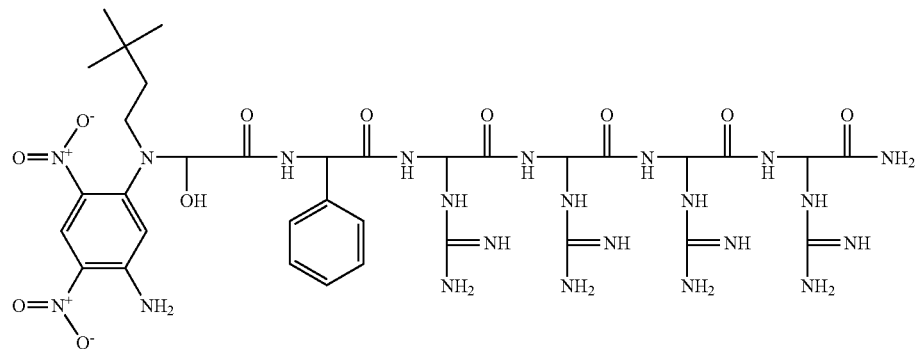
Compound 281
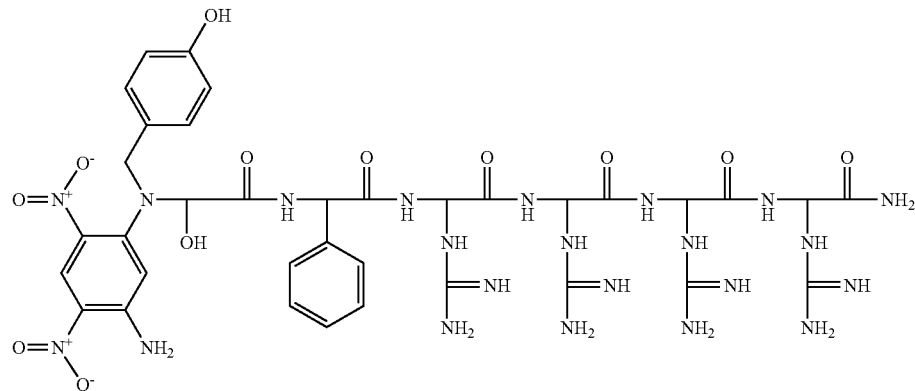
Compound 282
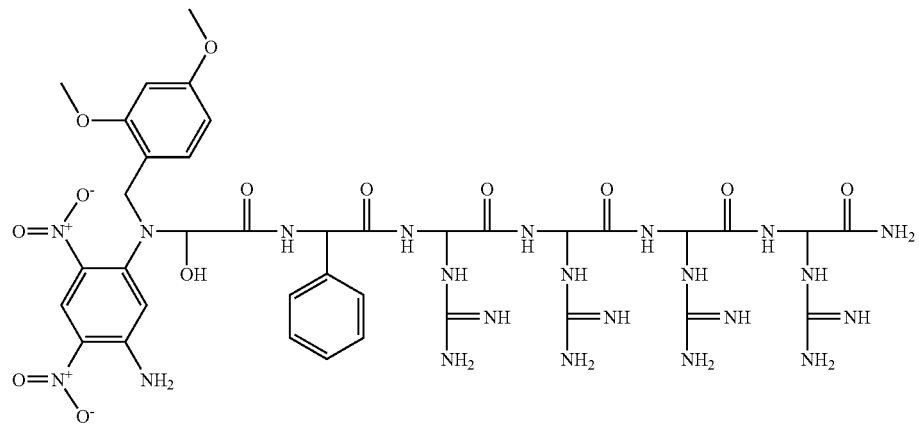

-continued
Compound 283
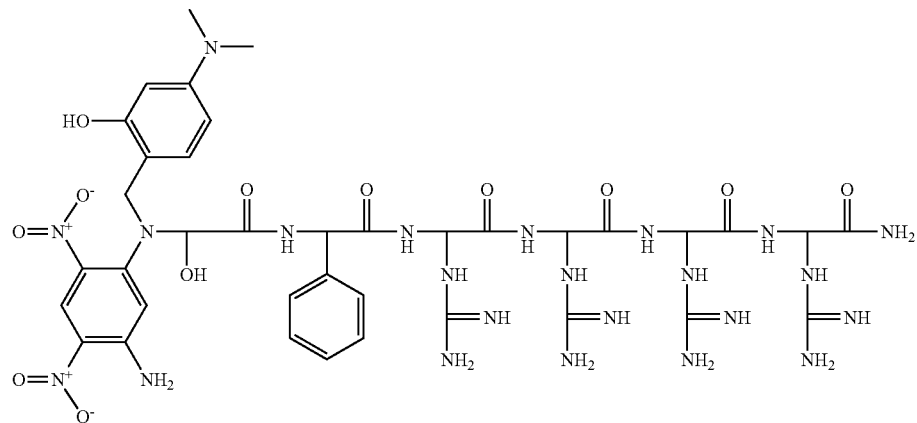
Compound 284
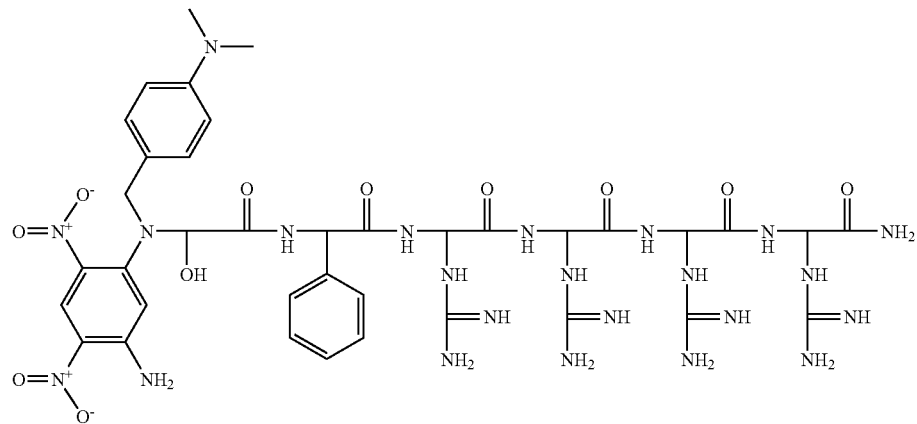
Compound 286
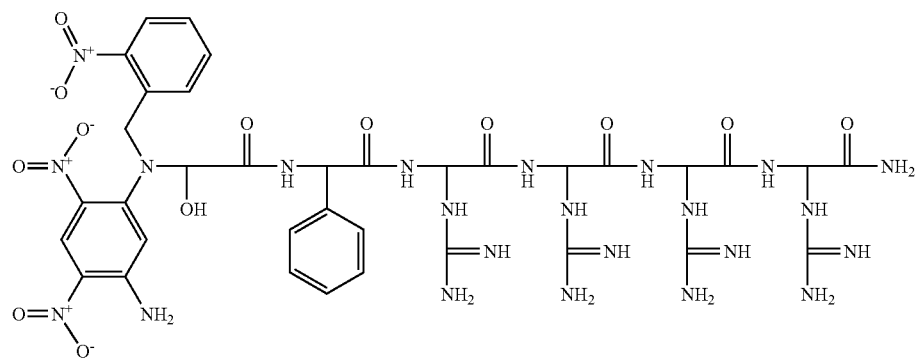
Compound 287
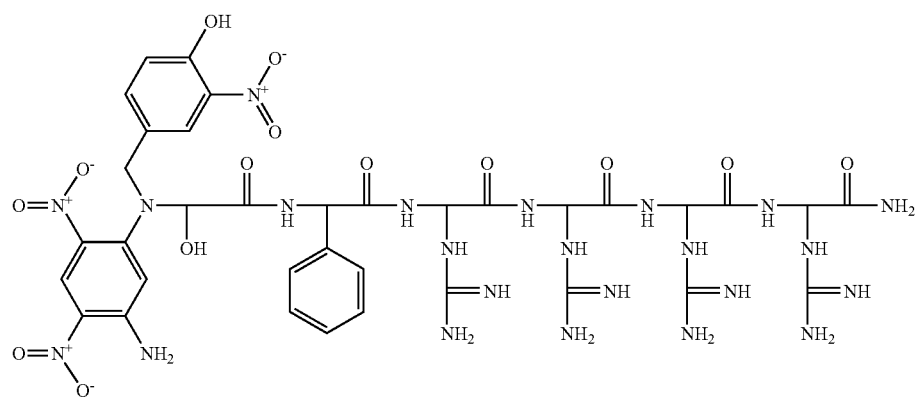

-continued
Compound 288
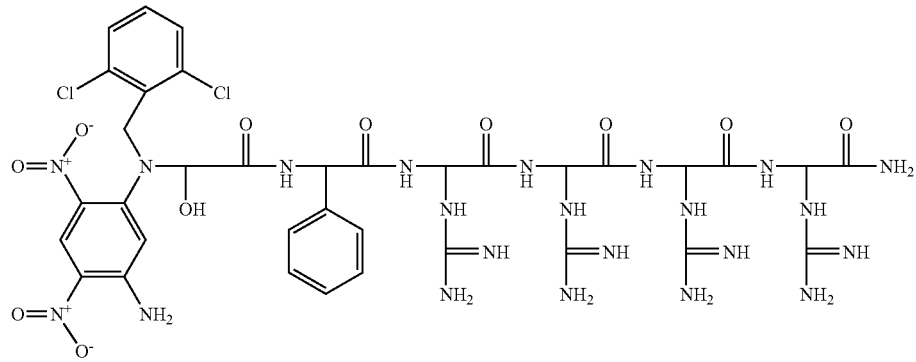
Compound 291
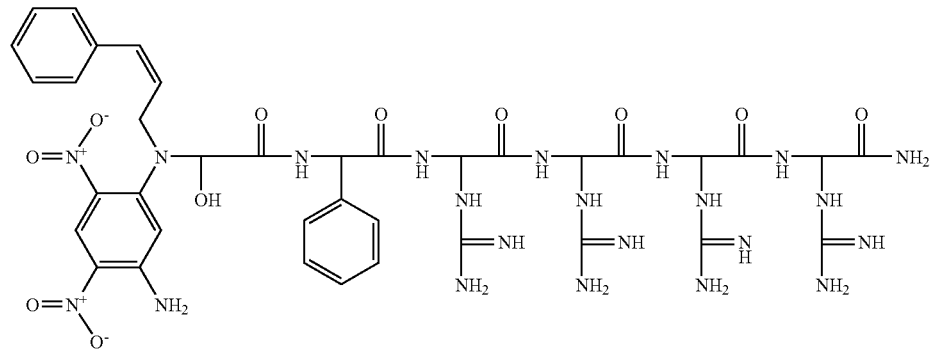
Compound 292
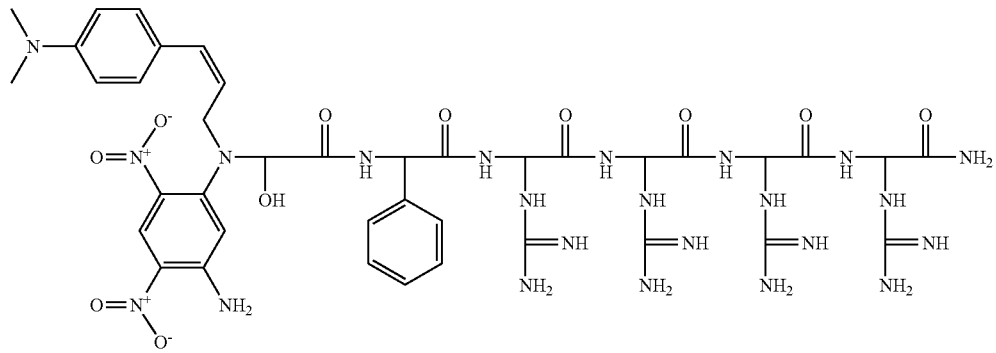
Compound 294
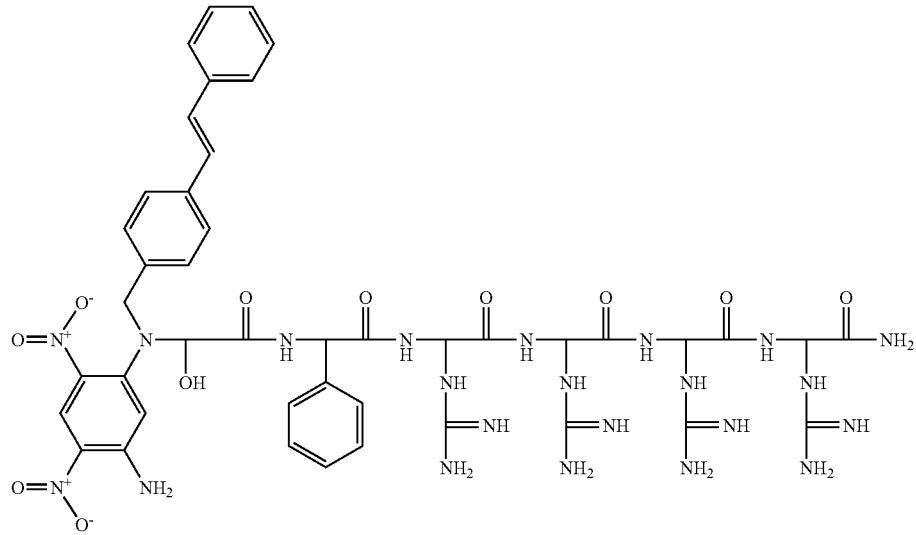

-continued
Compound 295
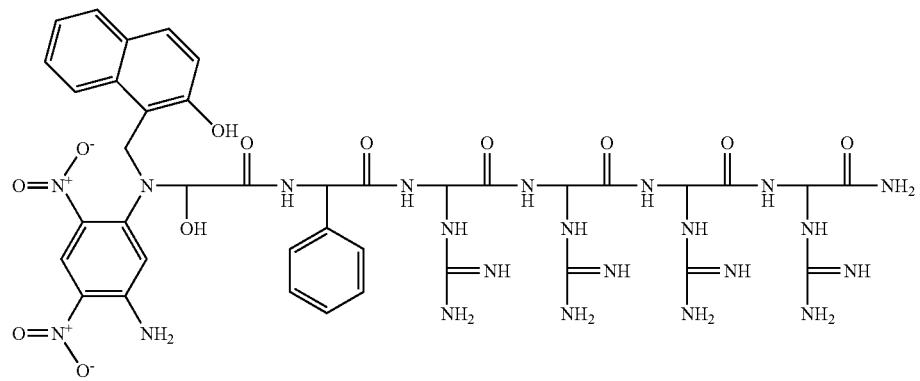
Compound 296
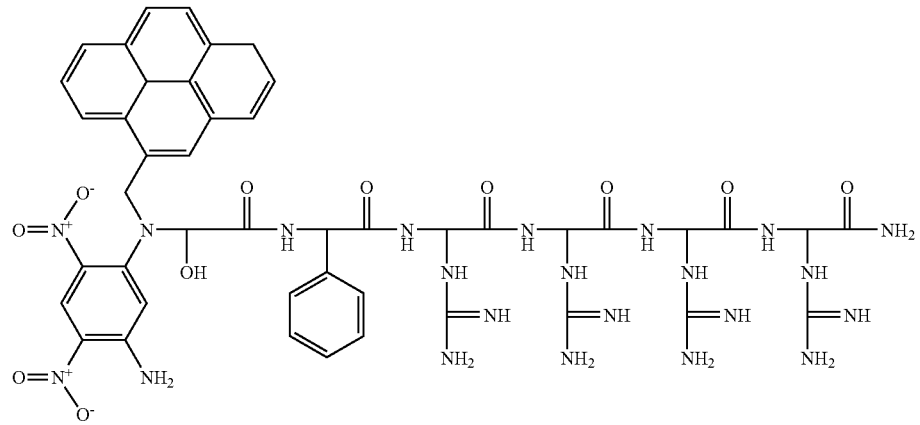
Compound 297
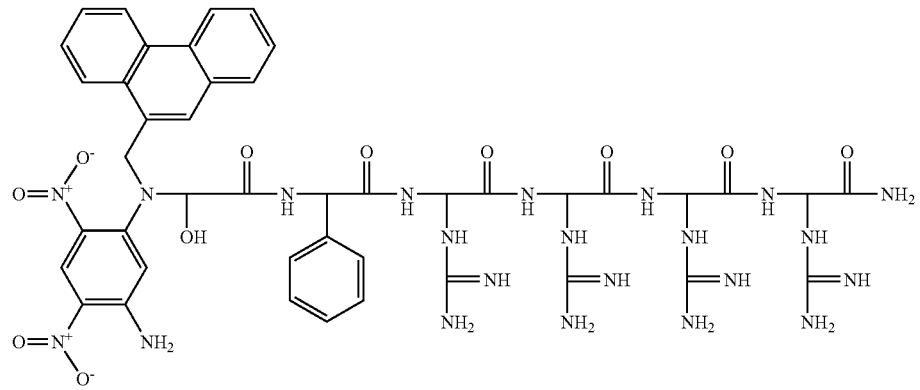
Compound 298
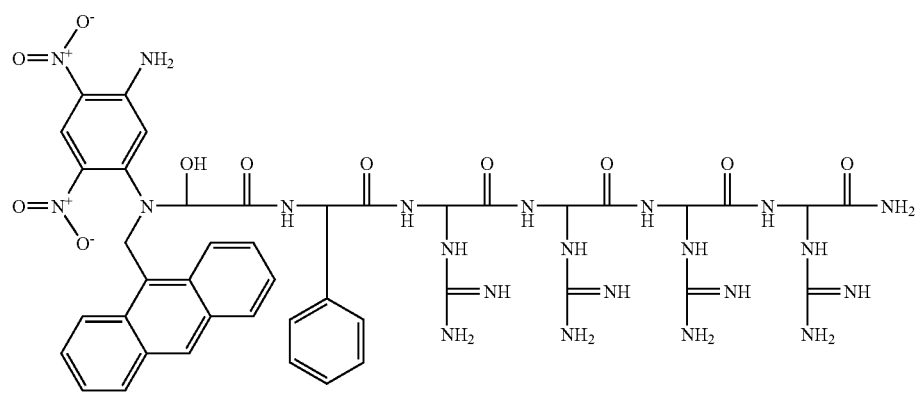

Compound 299
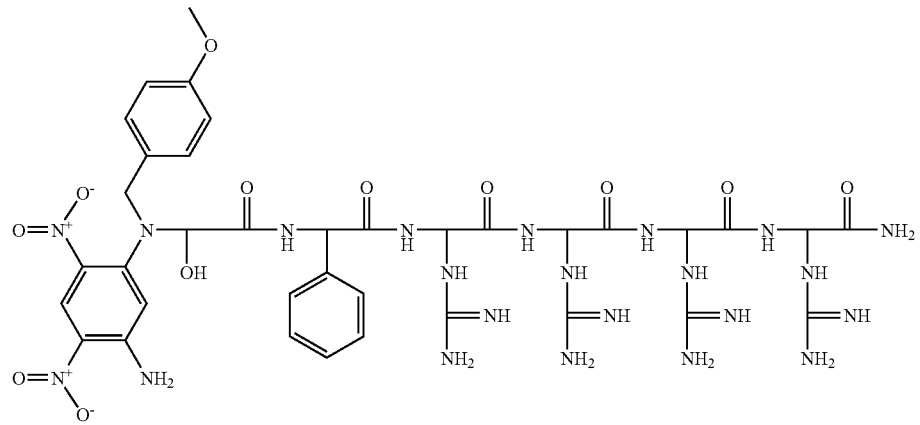
Compound 300
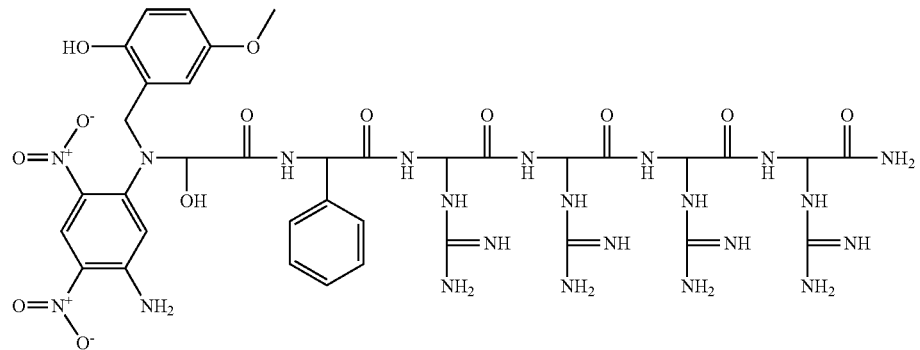
Compound 301
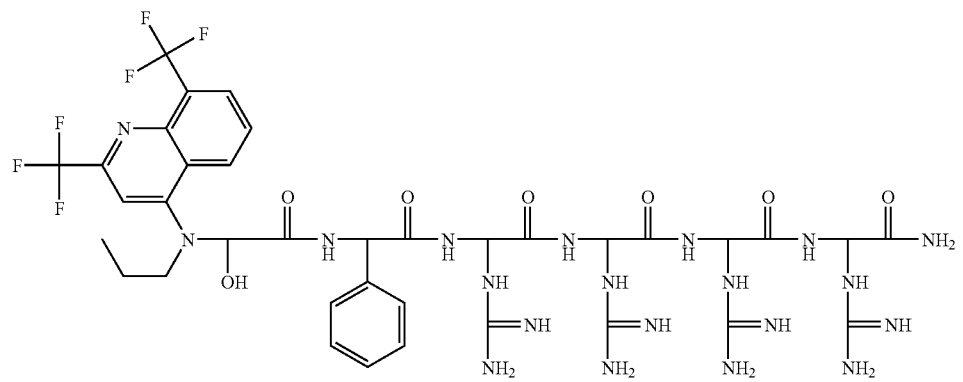
Compound 302
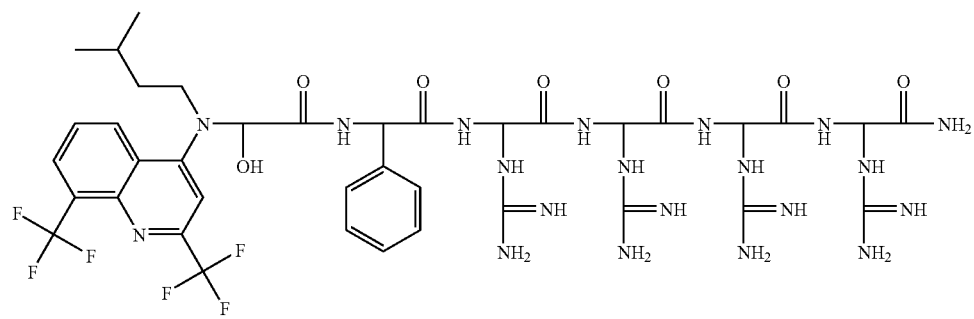

Compound 303
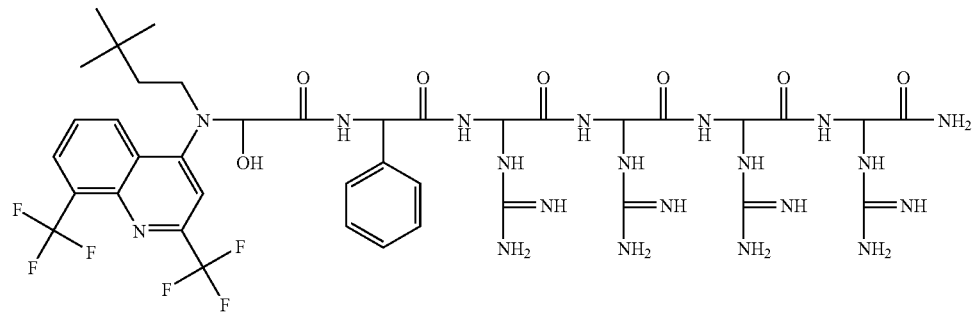
Compound 304
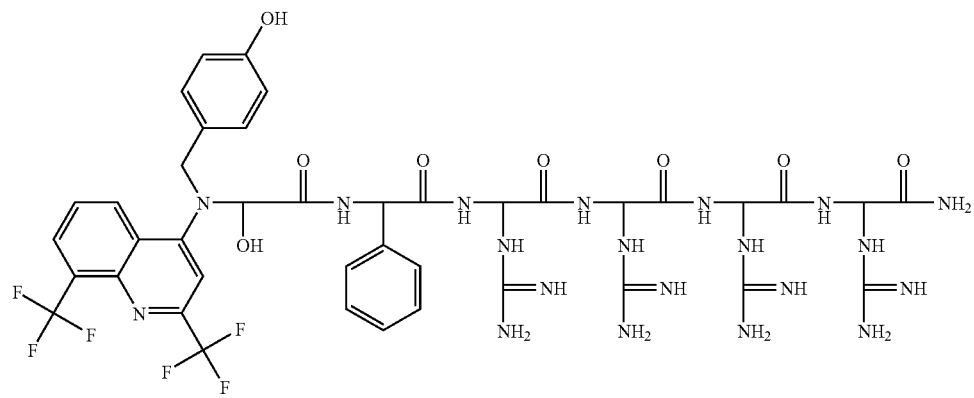
Compound 305
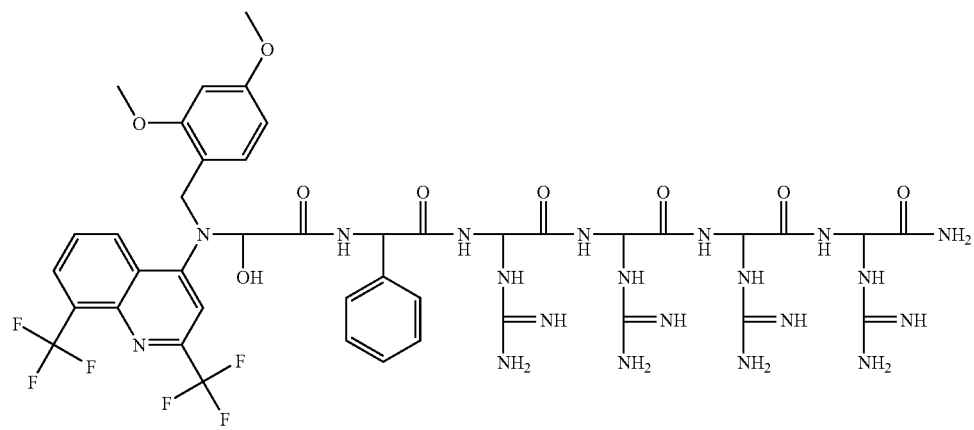
Compound 306
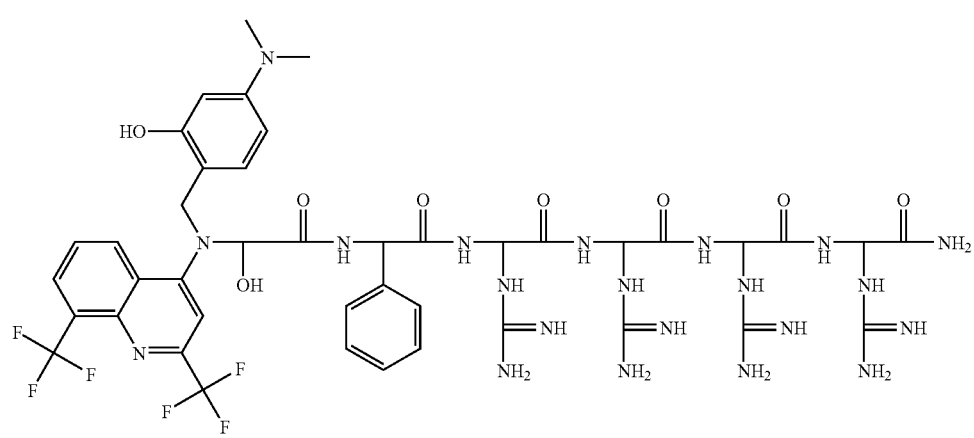

-continued
Compound 307
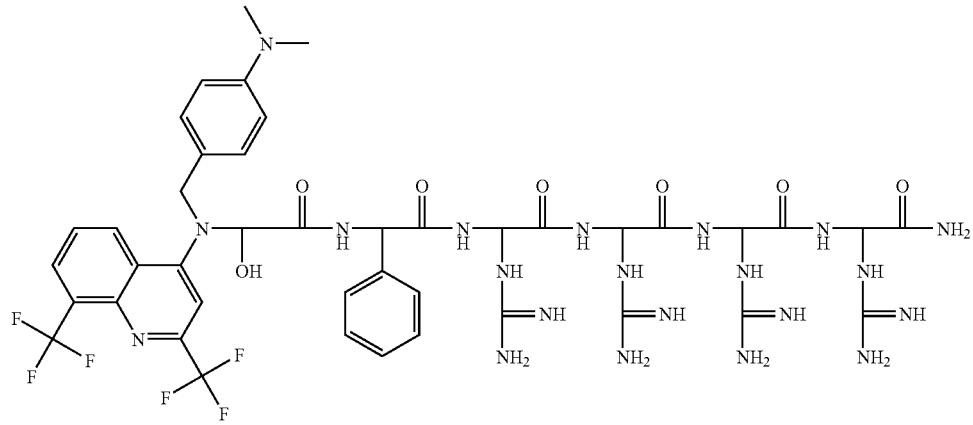
Compound 309
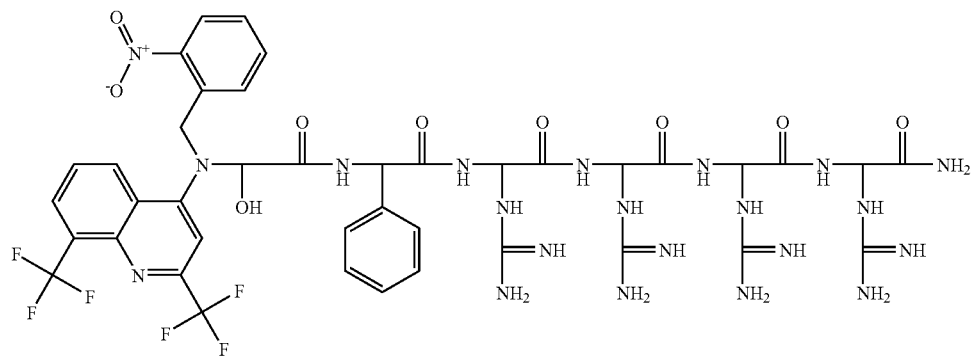
Compound 310
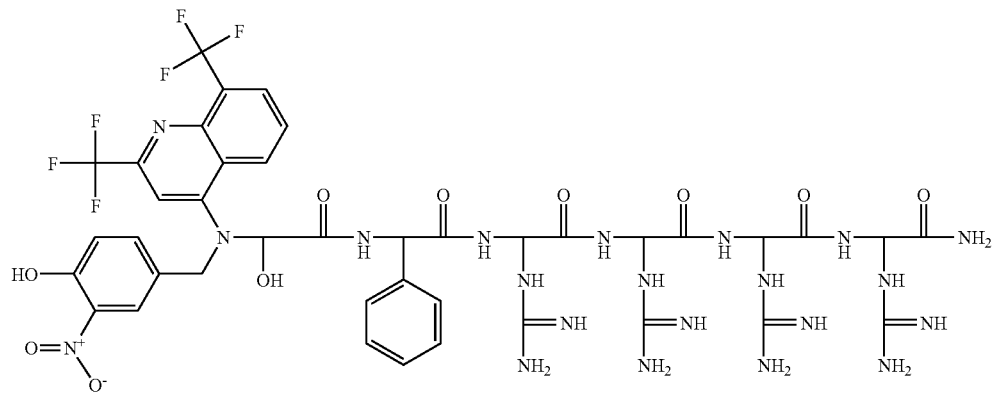
Compound 311
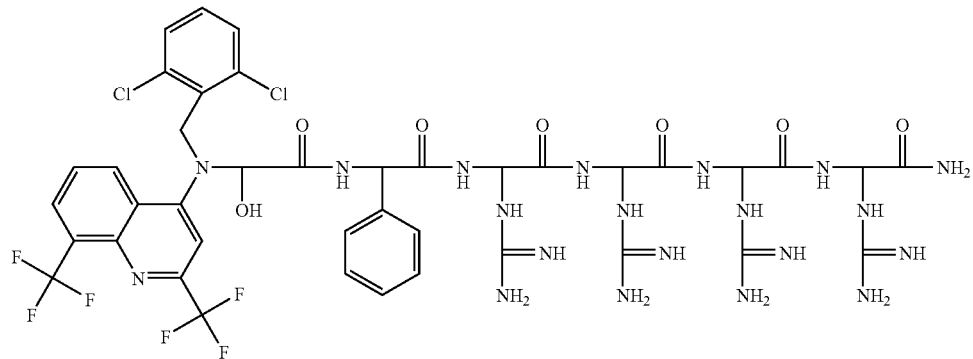

Compound 314
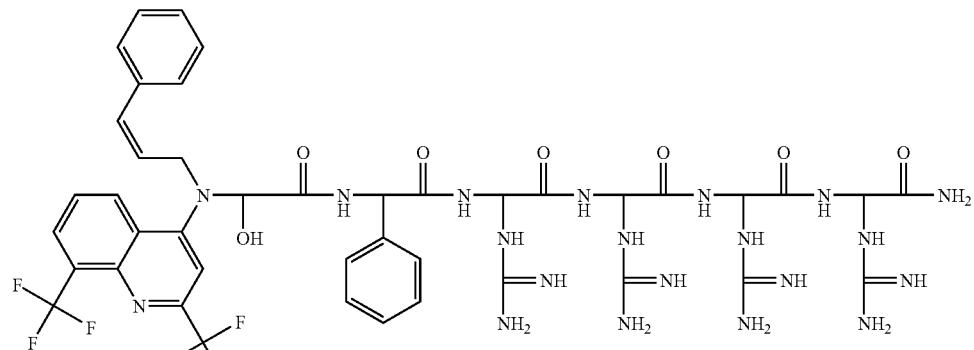
Compound 315
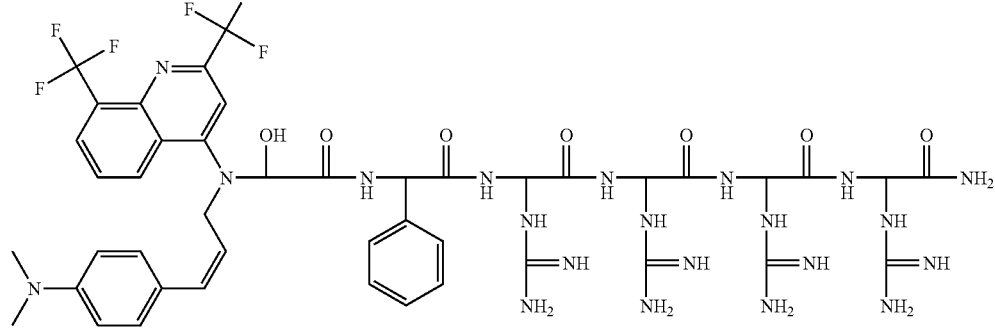
Compound 317
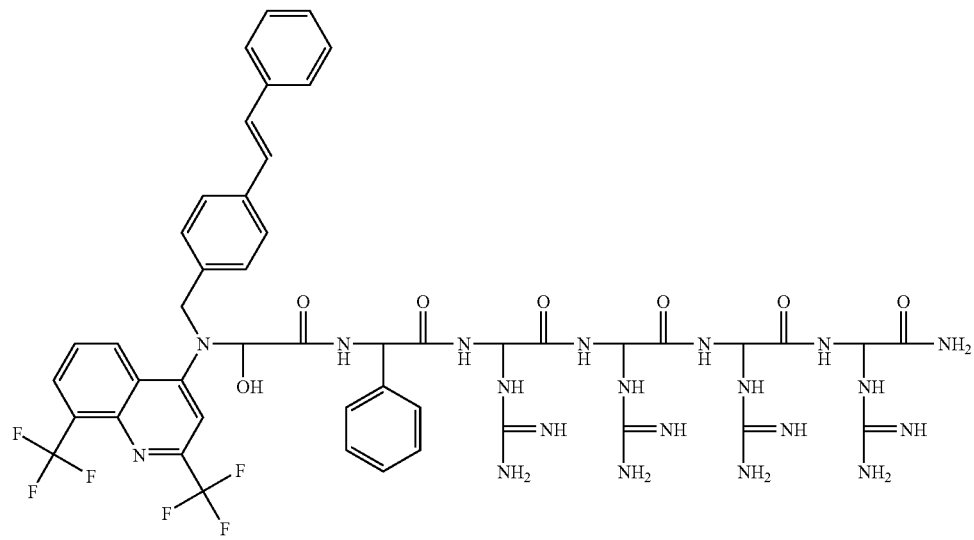
Compound 318
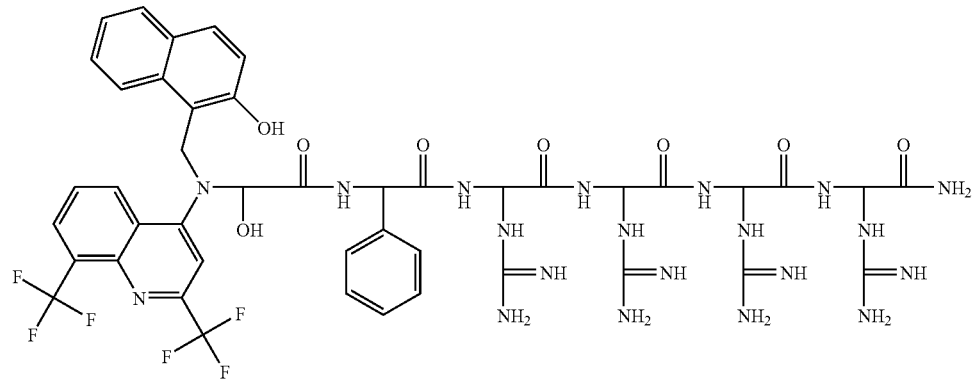

-continued
Compound 319
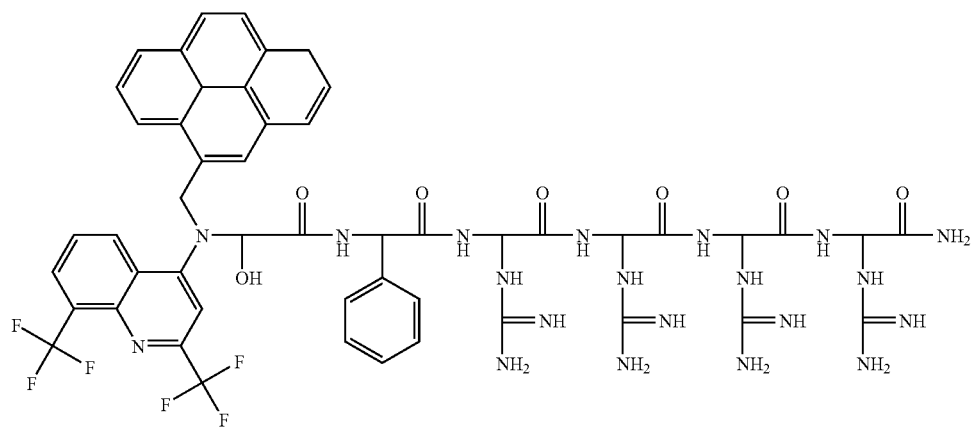
Compound 320
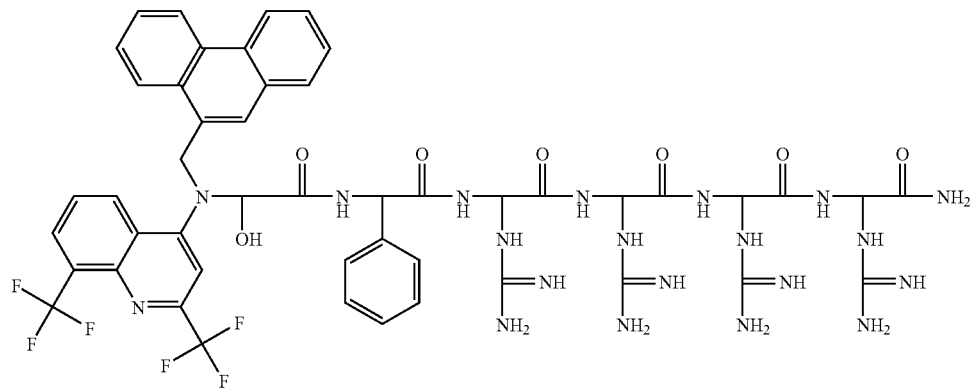
Compound 321
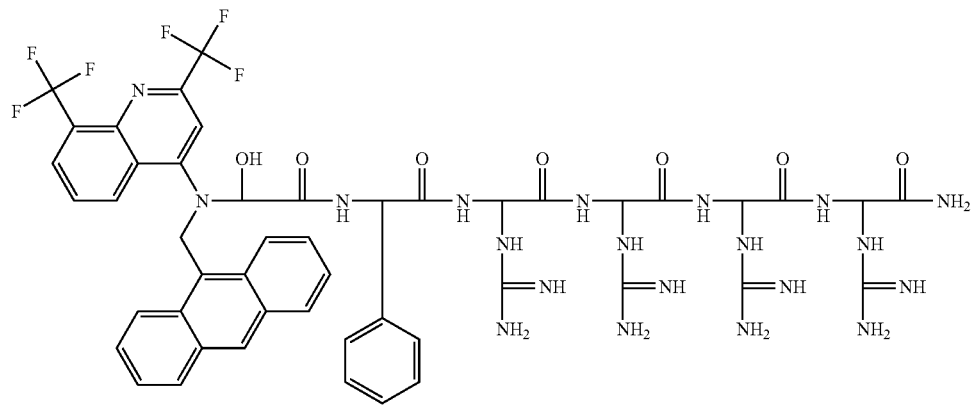
Compound 322
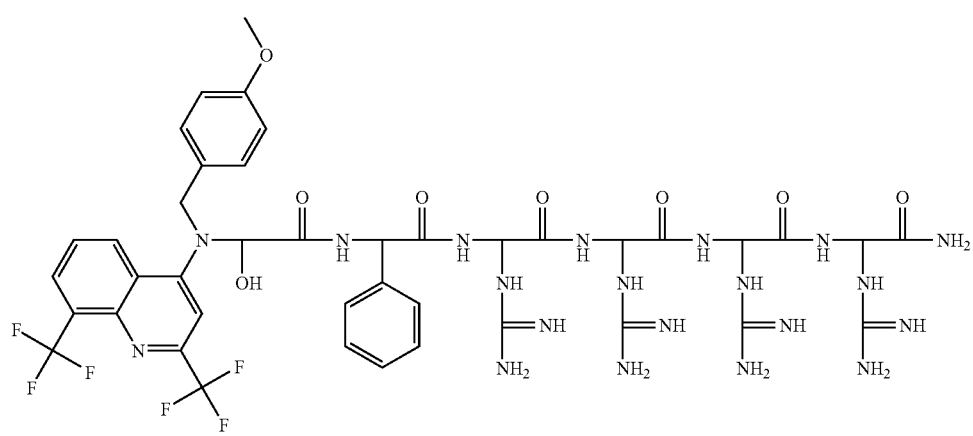

Compound 323
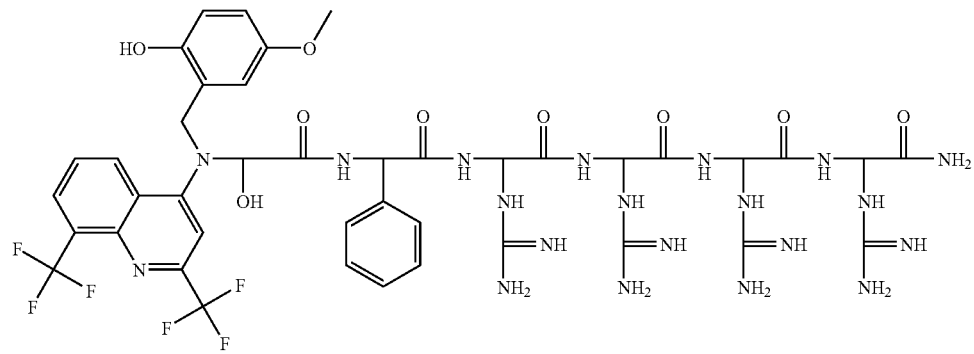
Compound 324
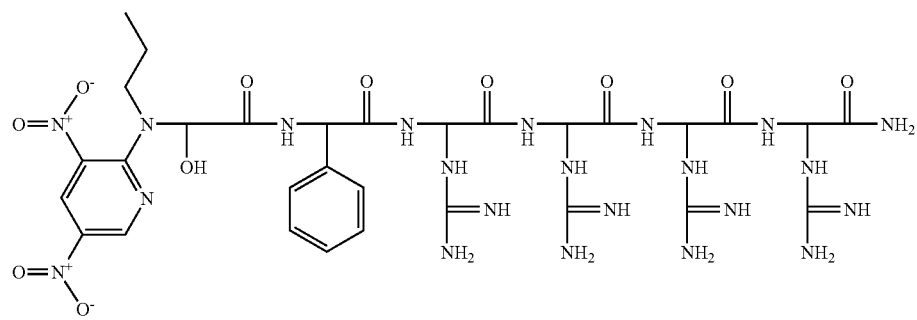
Compound 325
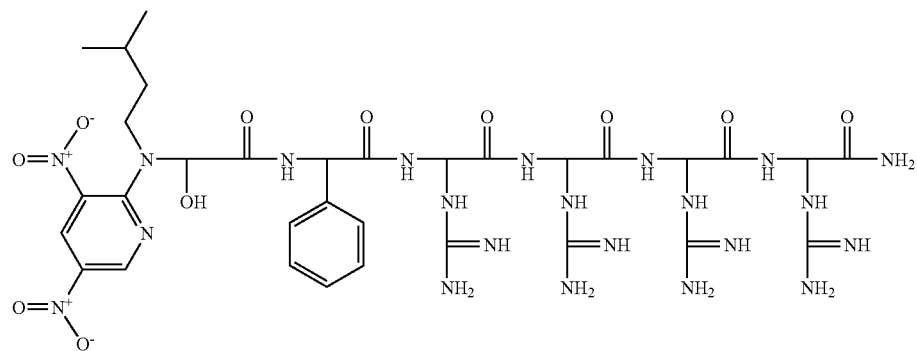
Compound 326
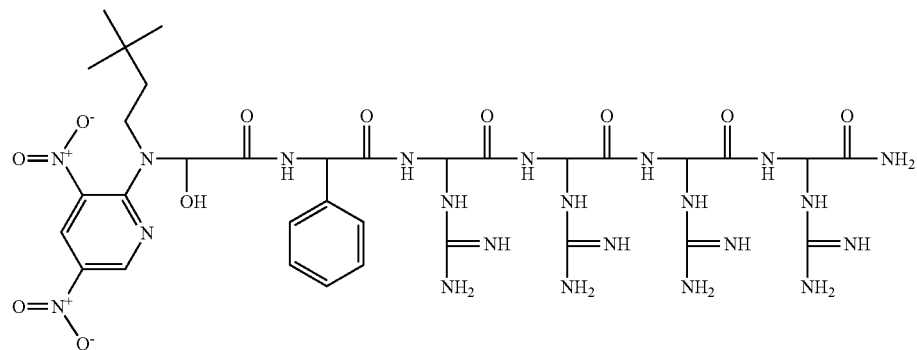

-continued
Compound 327
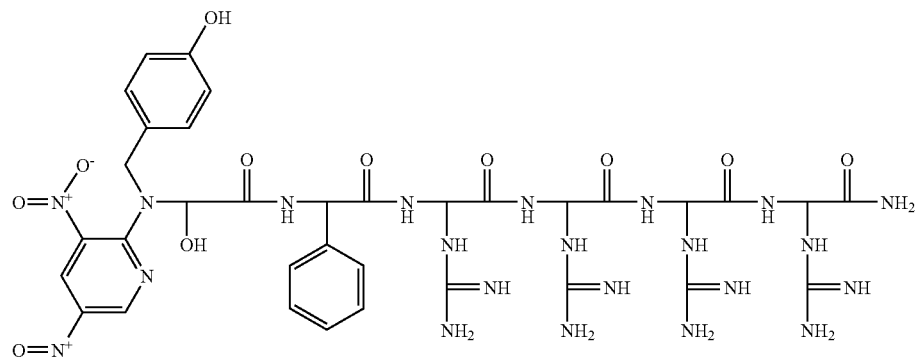
Compound 328
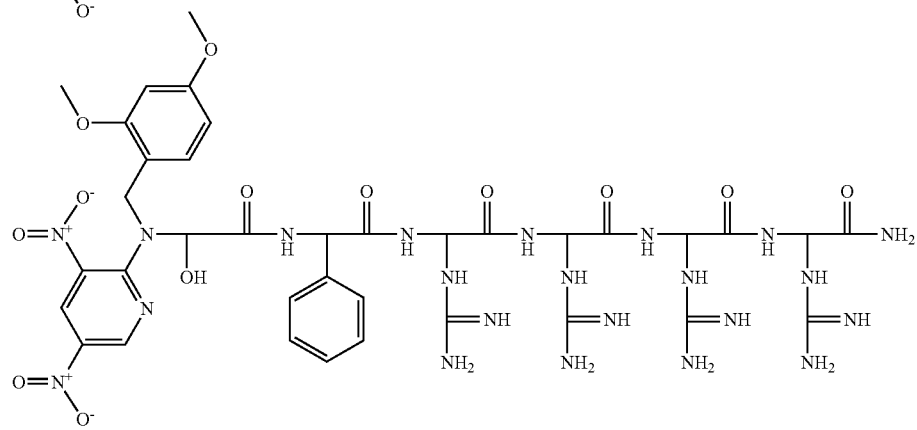
Compound 329
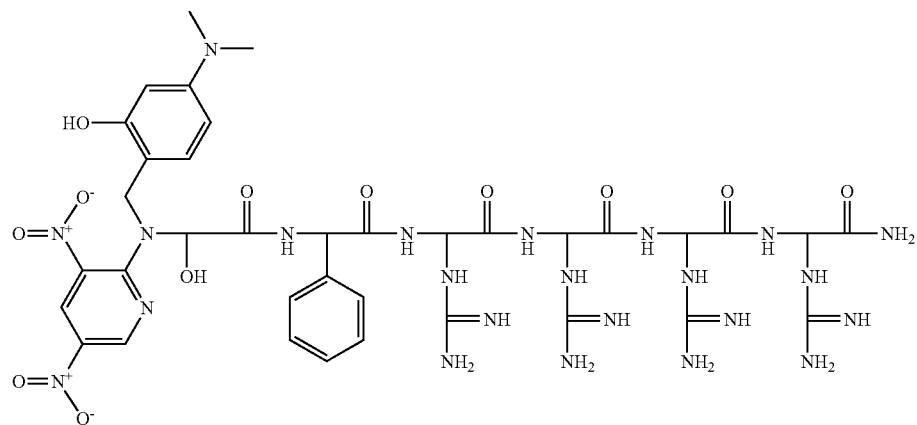
Compound 330
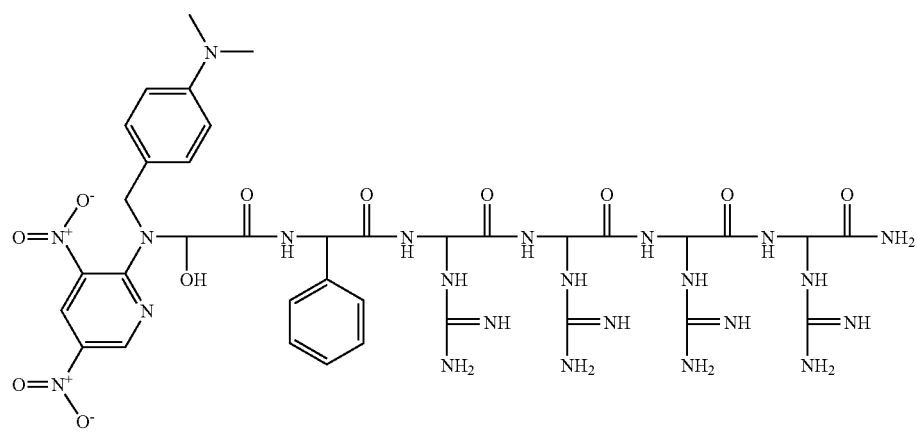

-continued
Compound 332
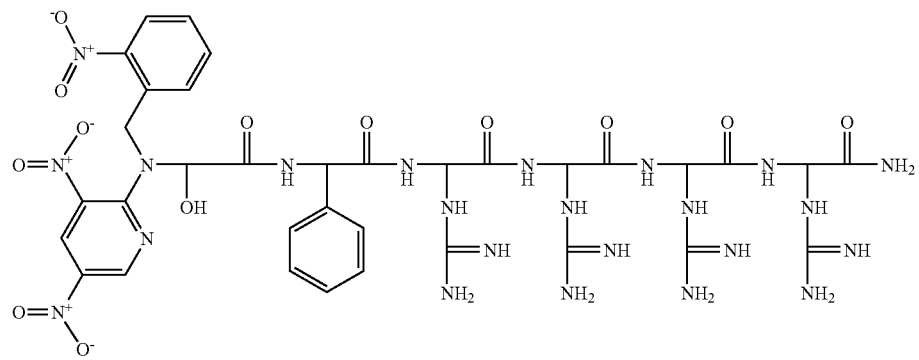
Compound 333
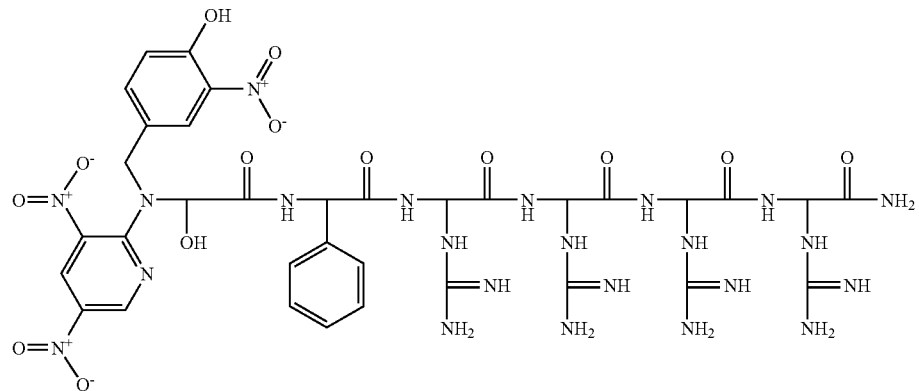
Compound 334
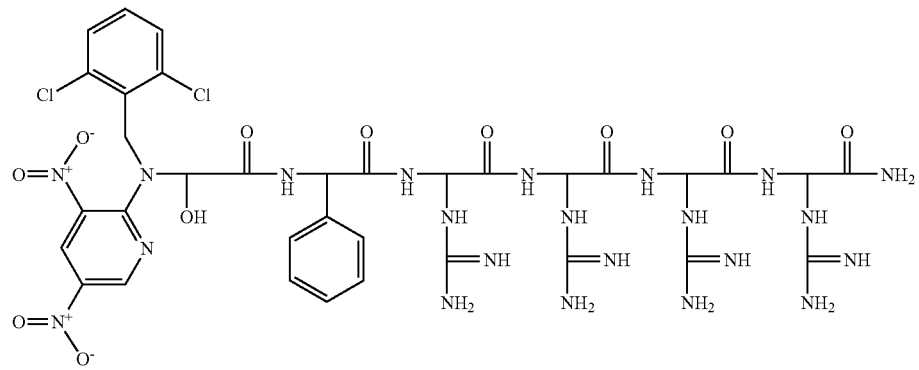
Compound 337
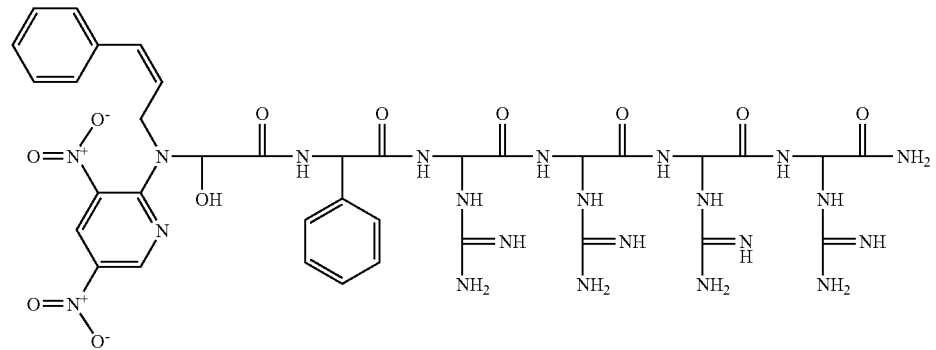

Compound 338
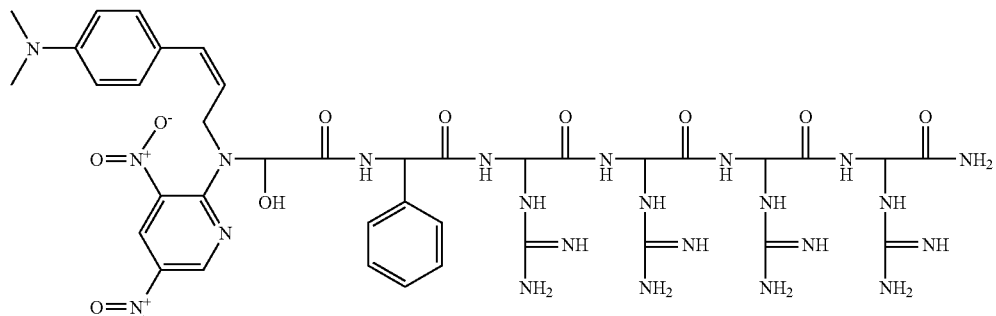
Compound 340
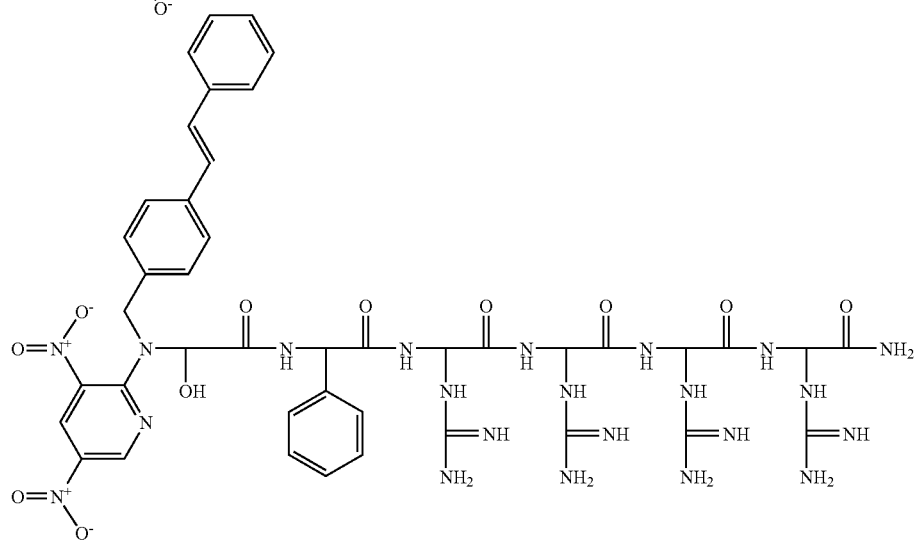
Compound 341
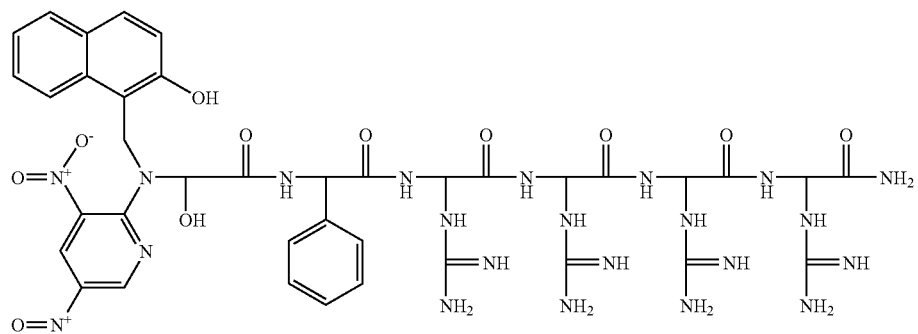
Compound 342
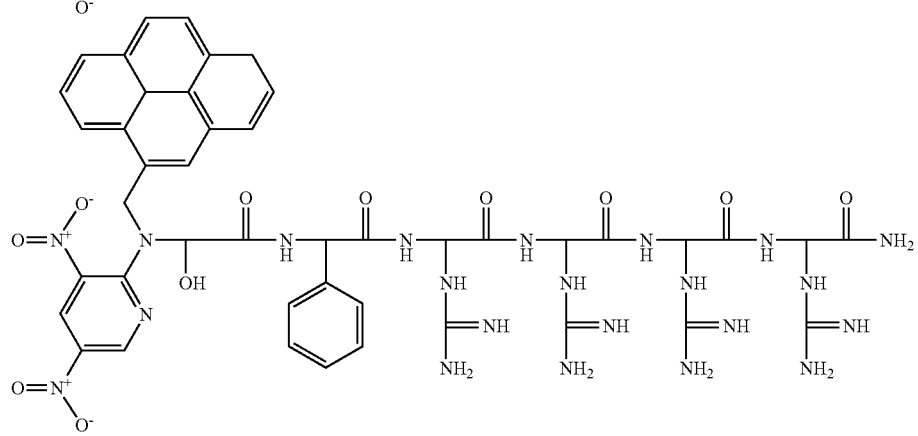

Compound 343
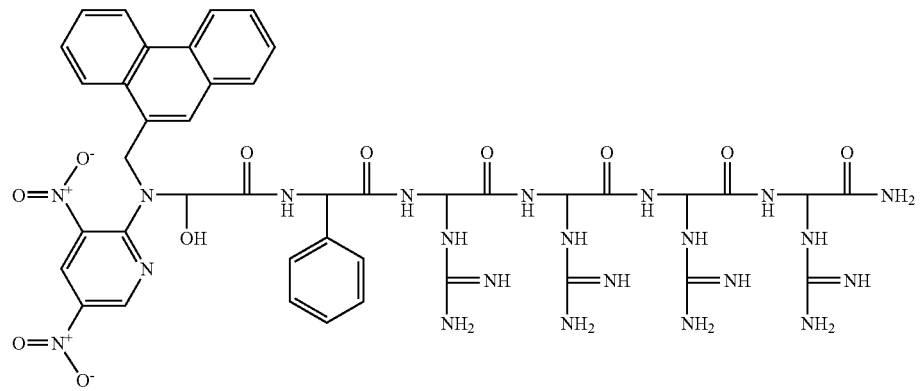
Compound 344
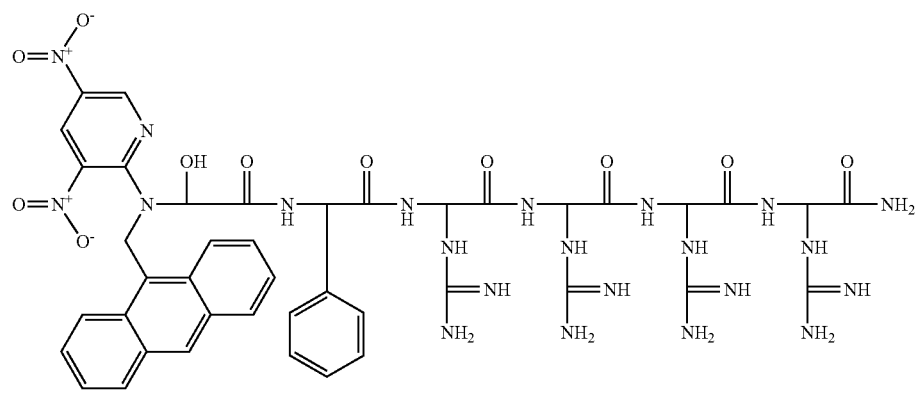
Compound 345
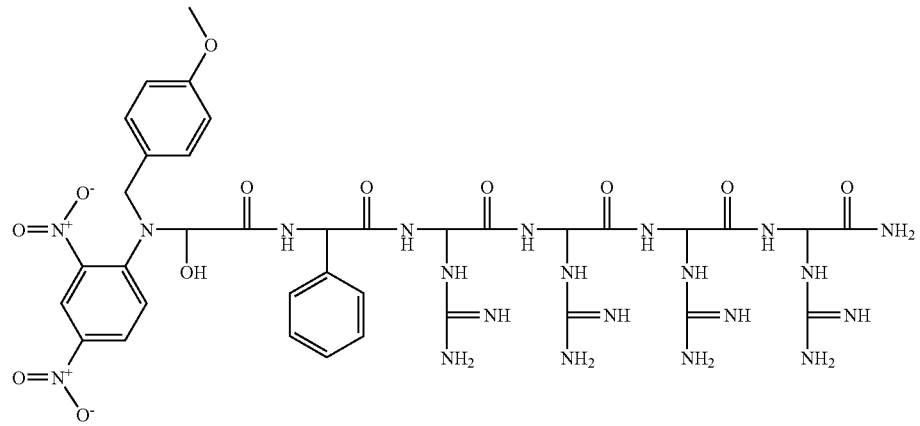
Compound 346
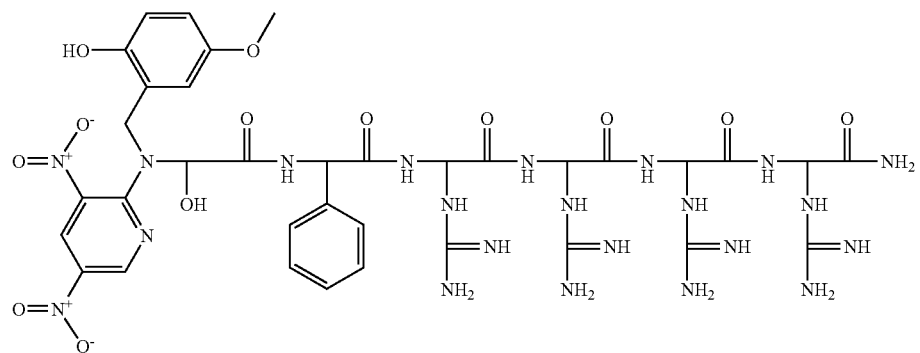

-continued
Compound 347
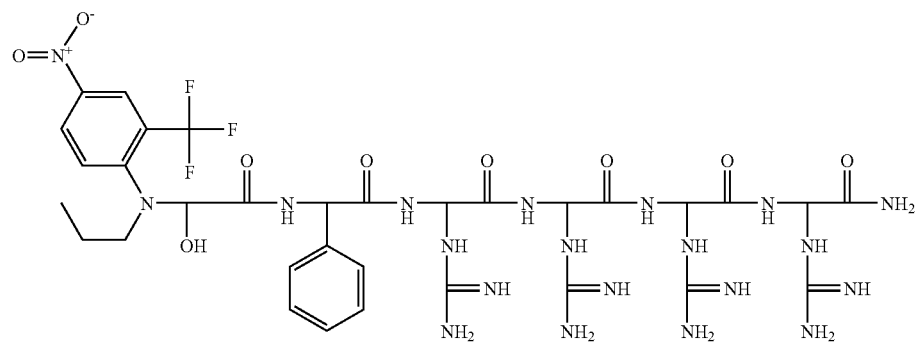
Compound 348
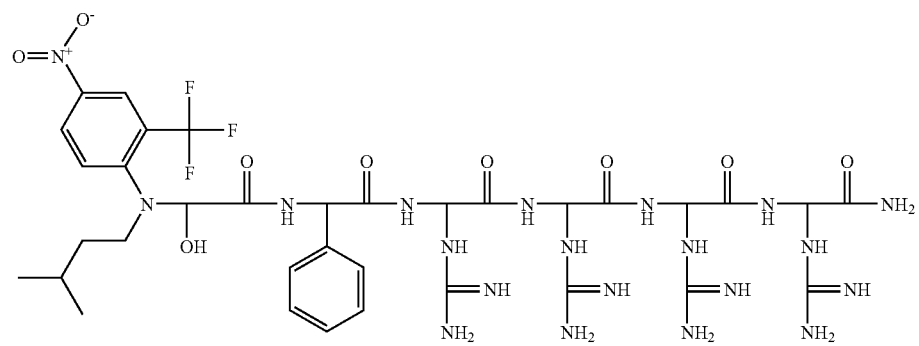
Compound 349
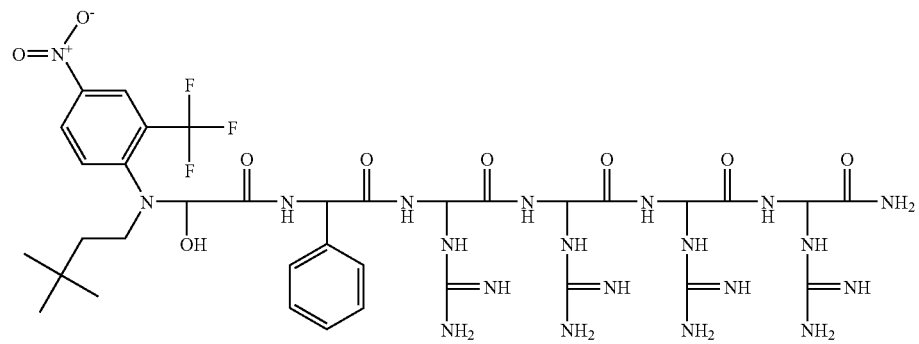
Compound 350
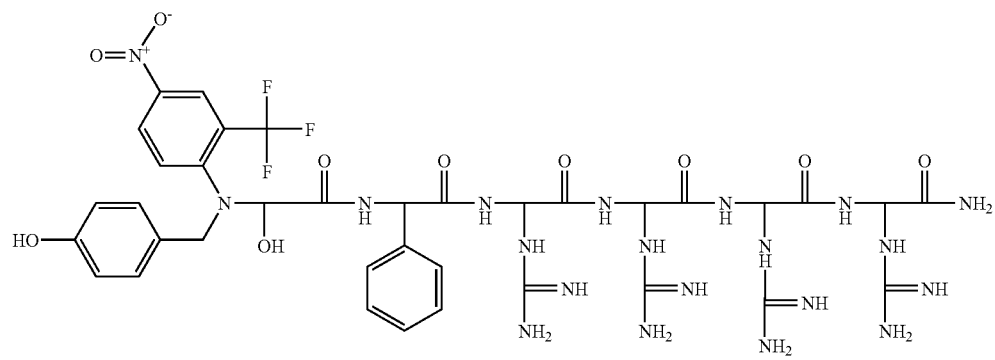

-continued
Compound 351
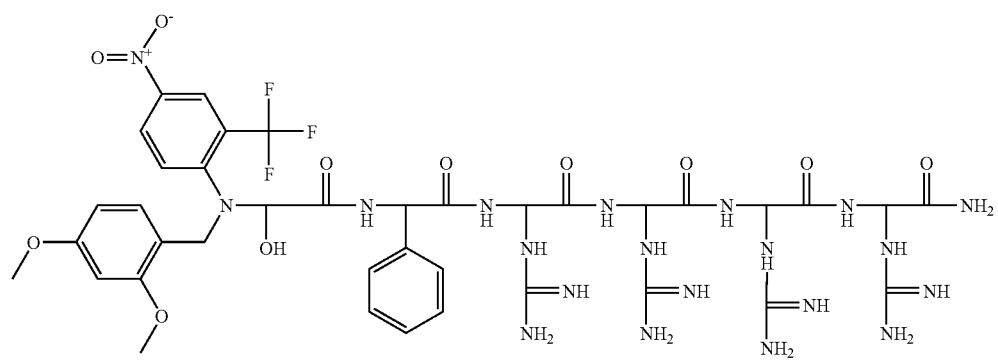
Compound 352
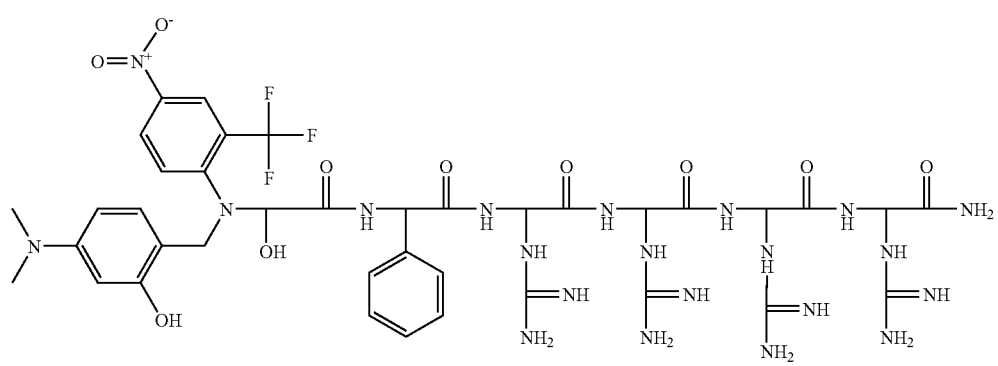
Compound 353
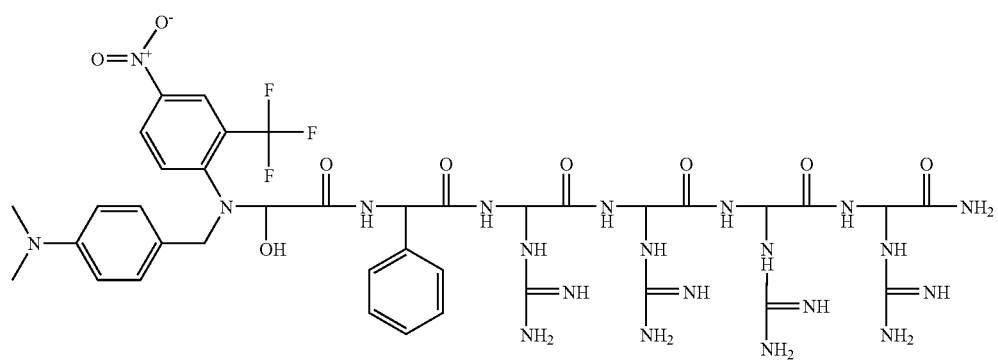
Compound 355
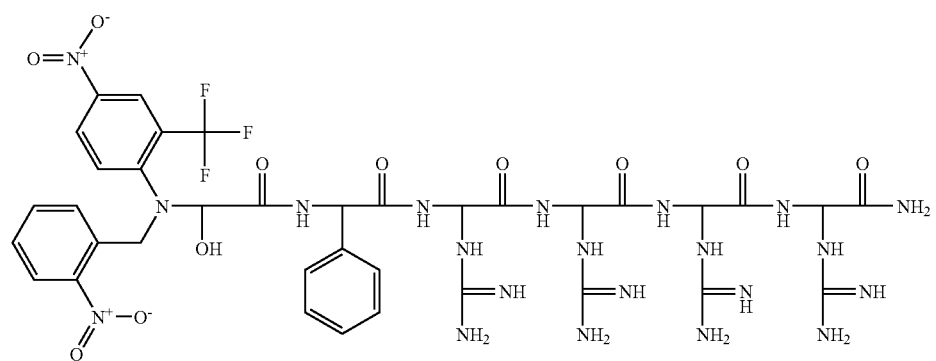

-continued
Compound 356
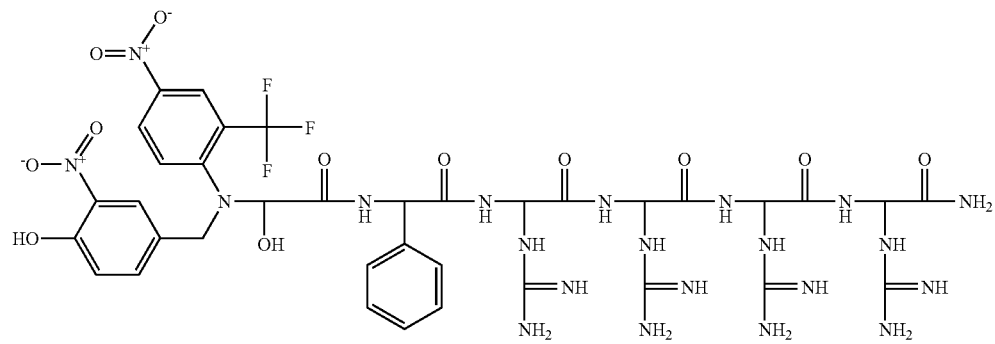
Compound 357
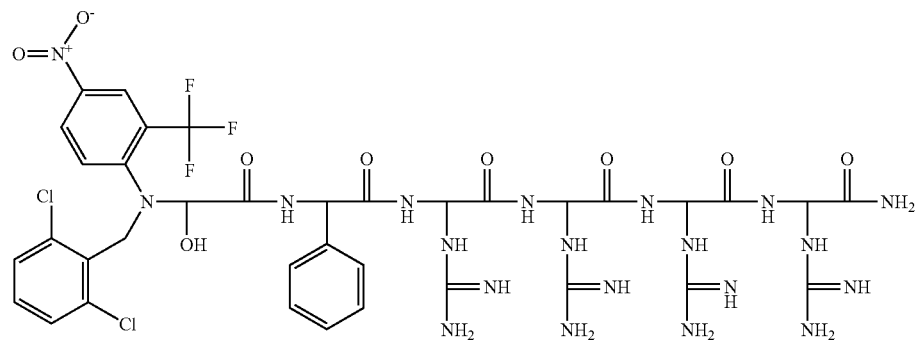
Compound 360
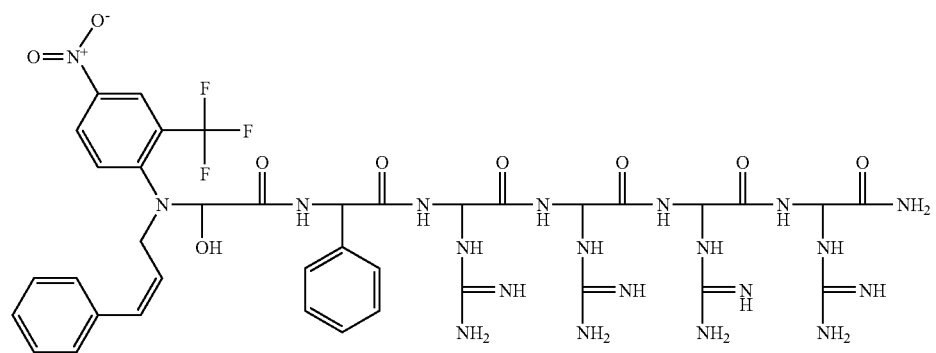
Compound 361
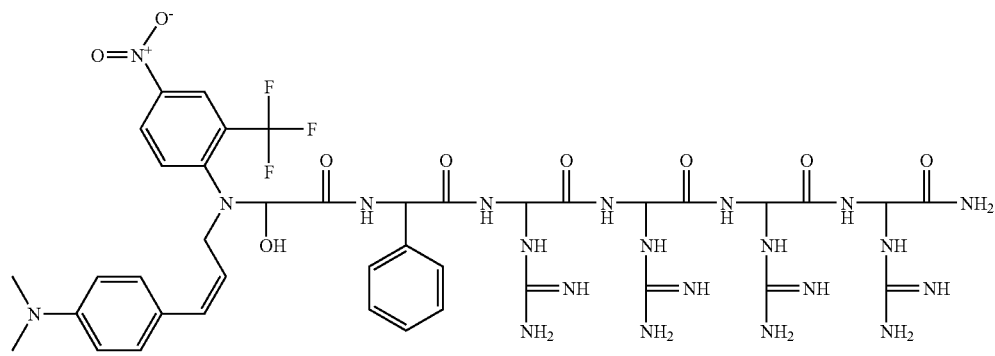

Compound 363
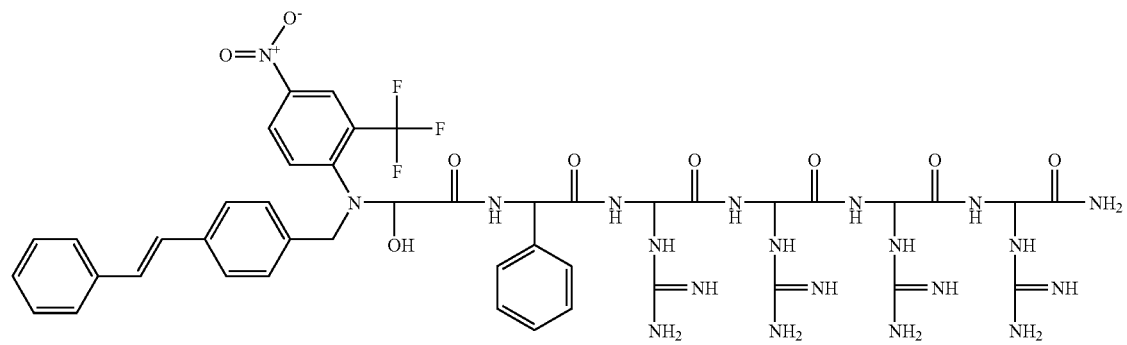
Compound 364
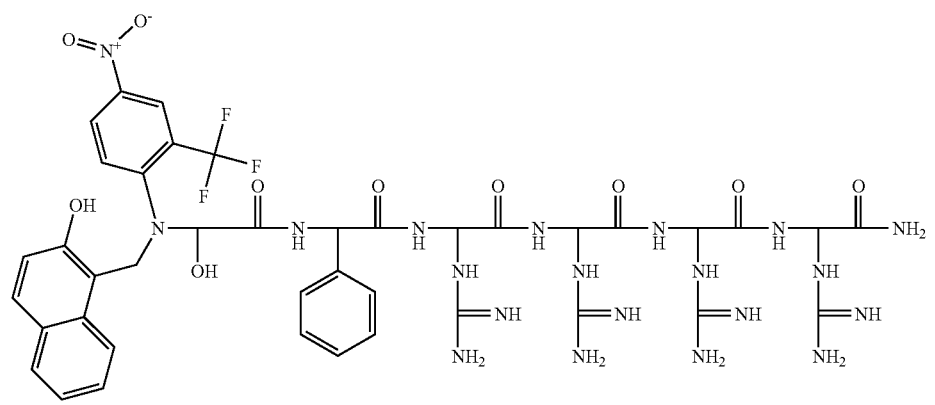
Compound 365
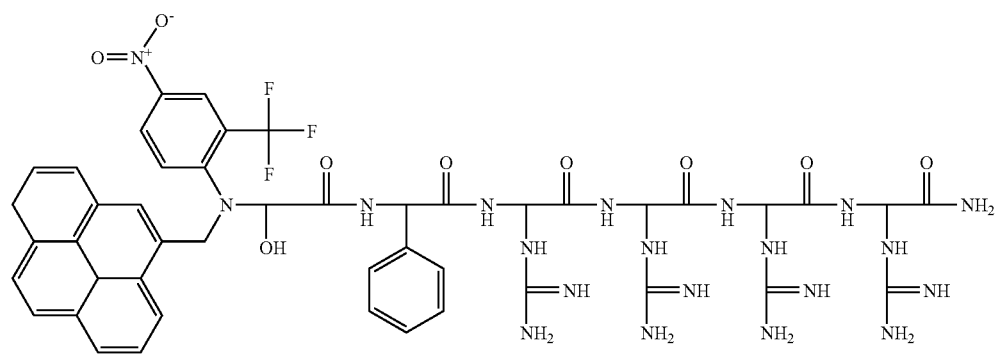
Compound 366
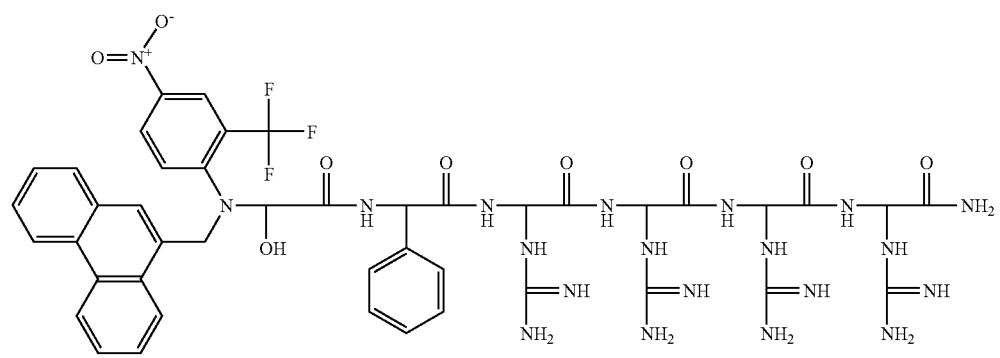

Compound 367
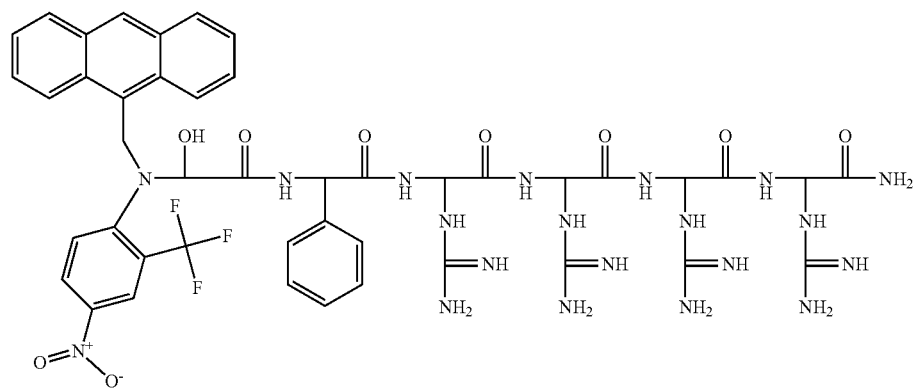
Compound 368
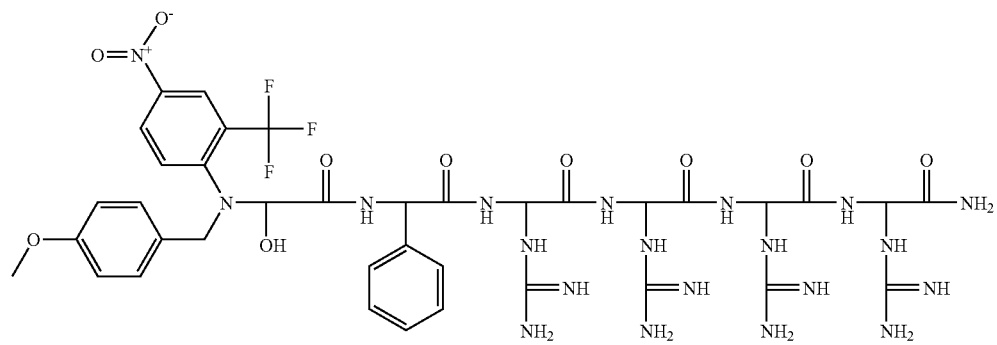
Compound 369
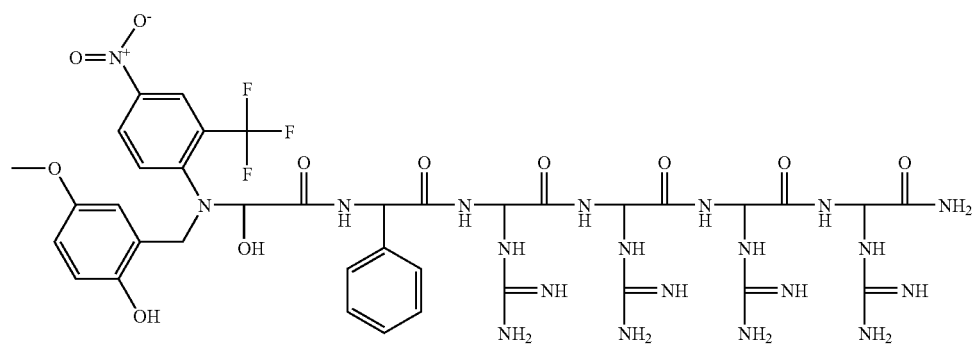
Compound 370
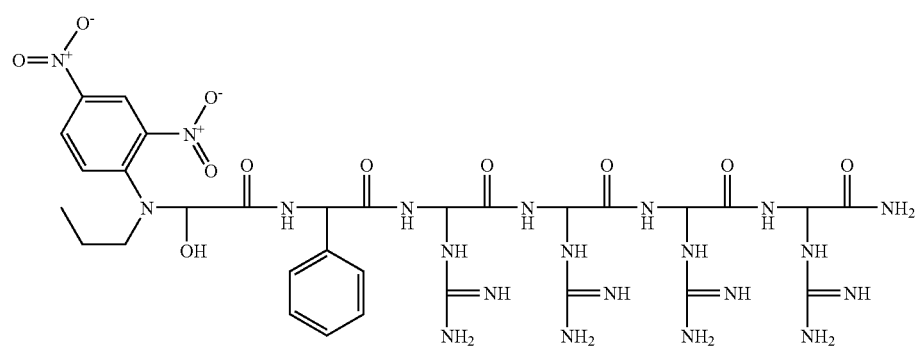

-continued
Compound 371
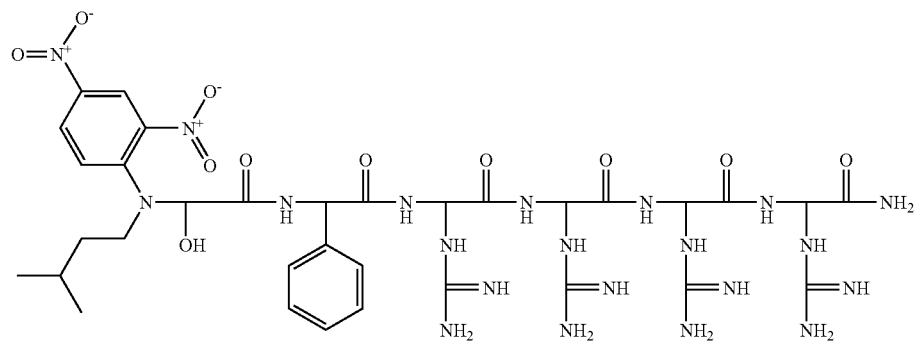
Compound 372
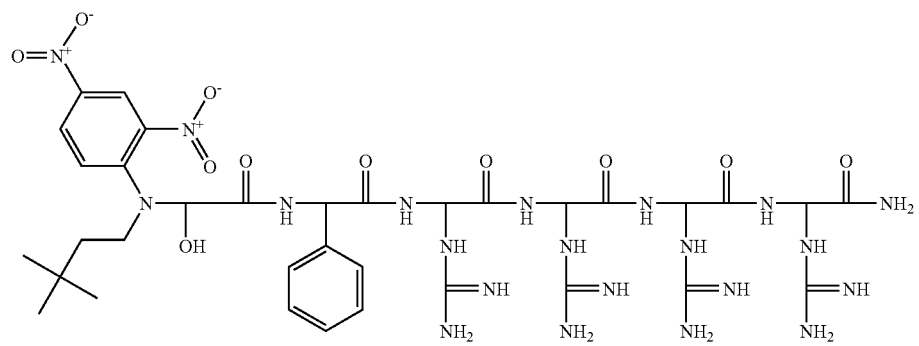
Compound 373
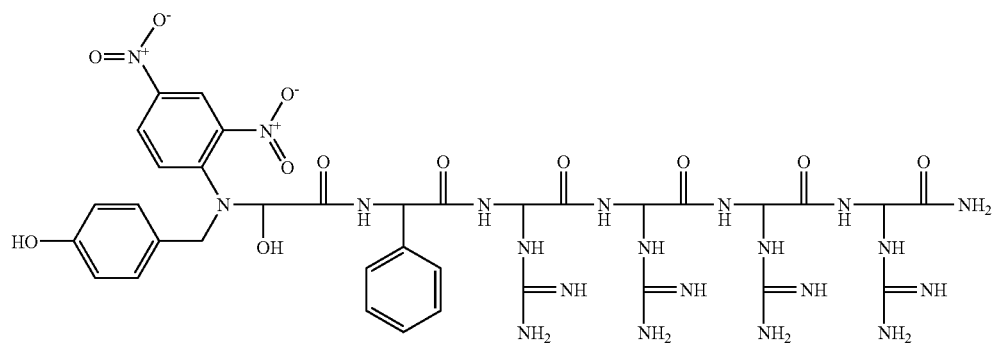
Compound 374
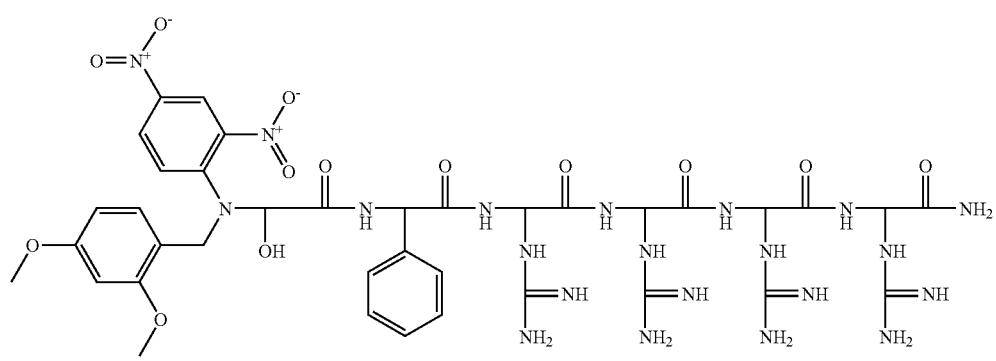

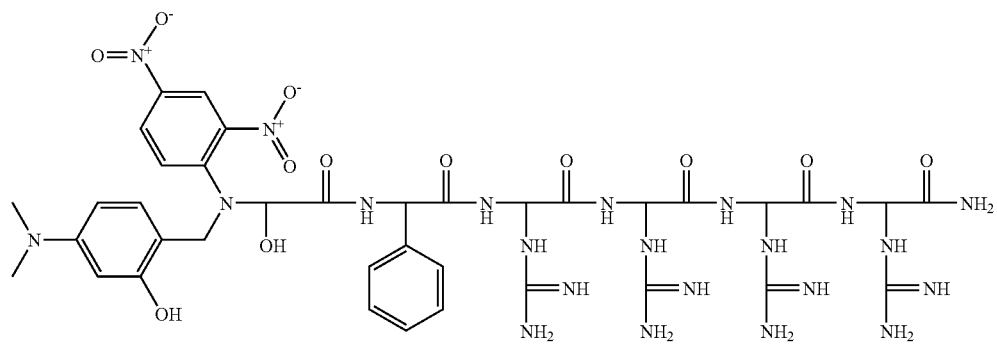
Compound 375
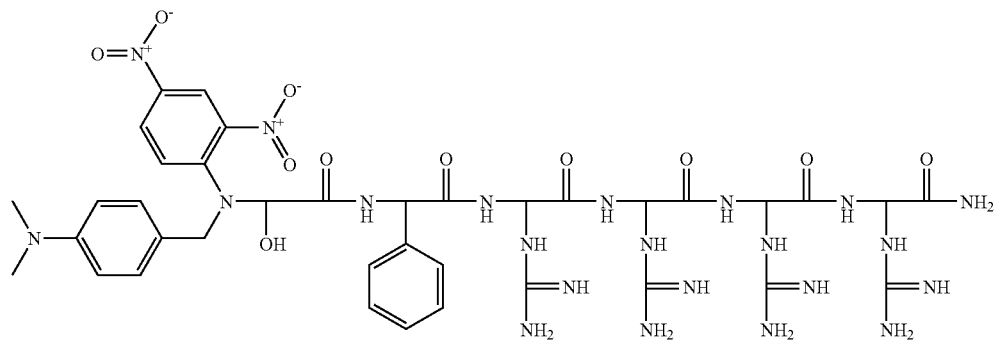
Compound 376
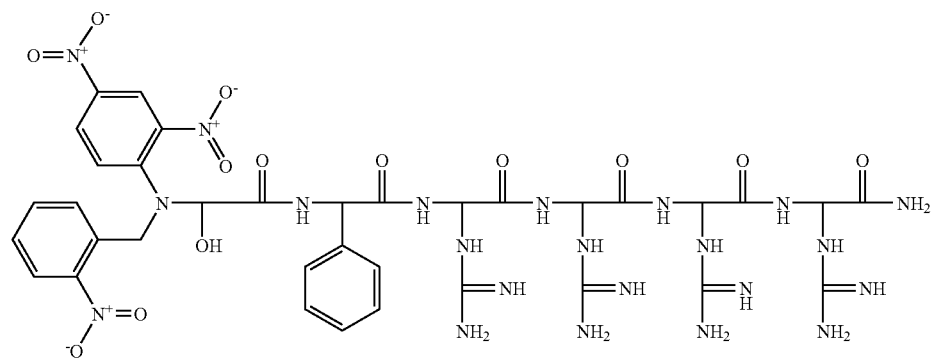
Compound 378
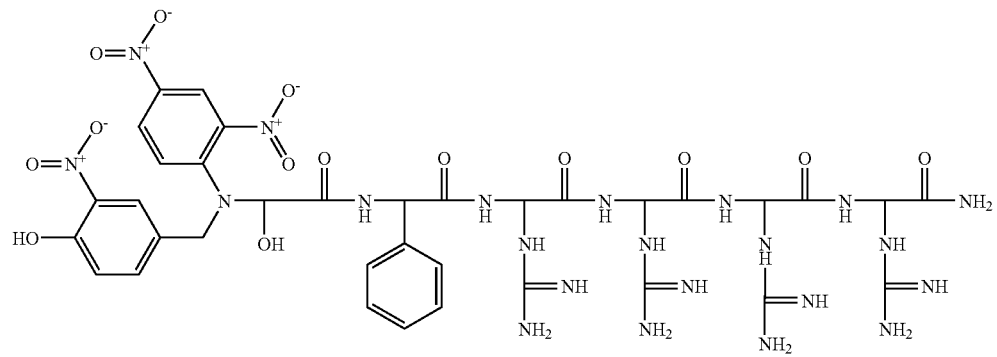
Compound 379

-continued
Compound 380
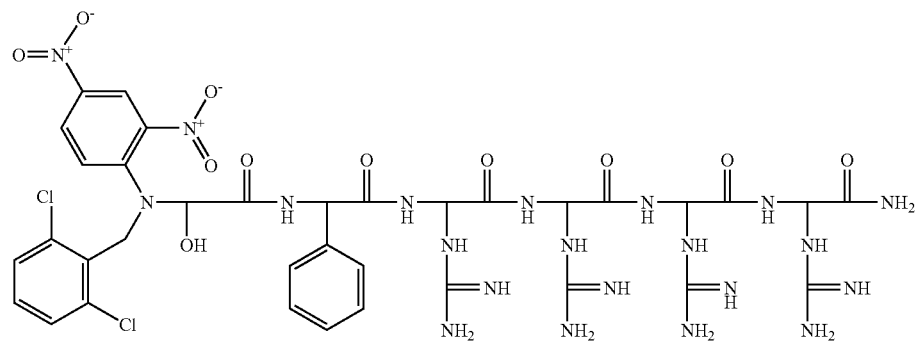
Compound 383
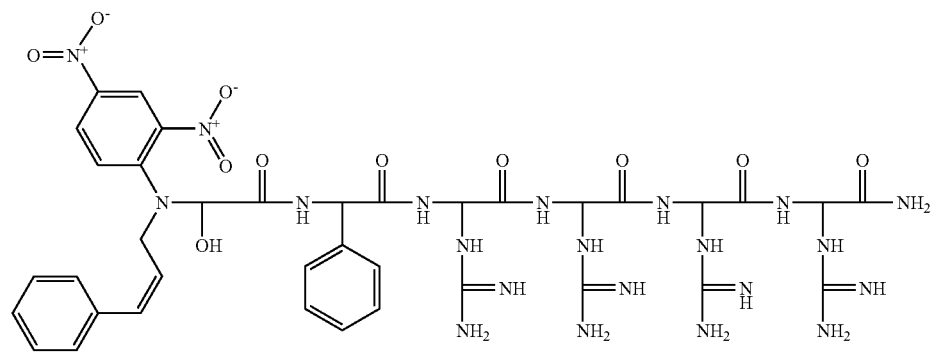
Compound 384
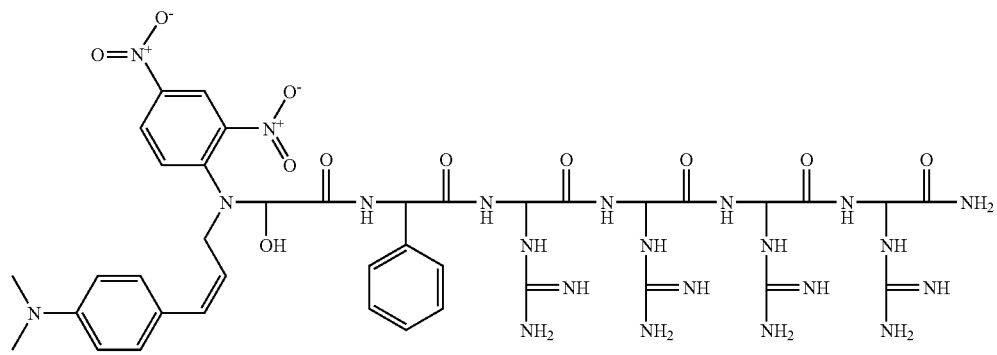
Compound 386
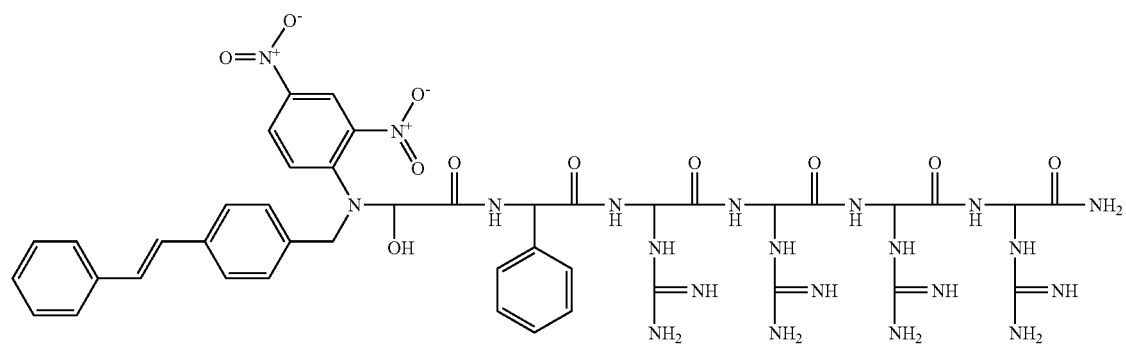

Compound 387
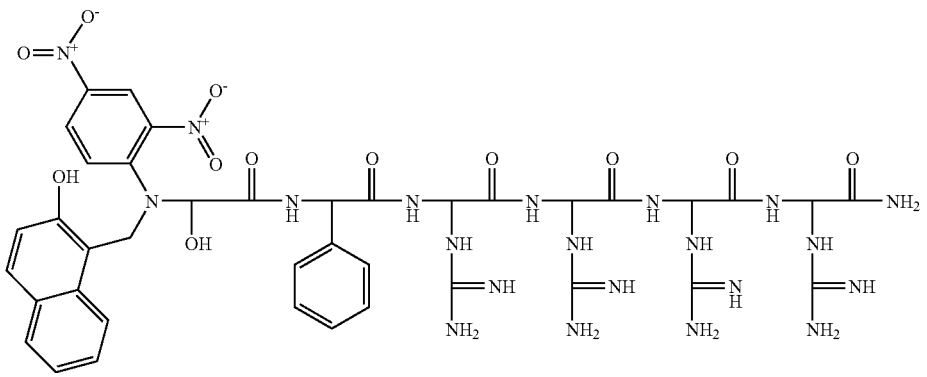
Compound 388
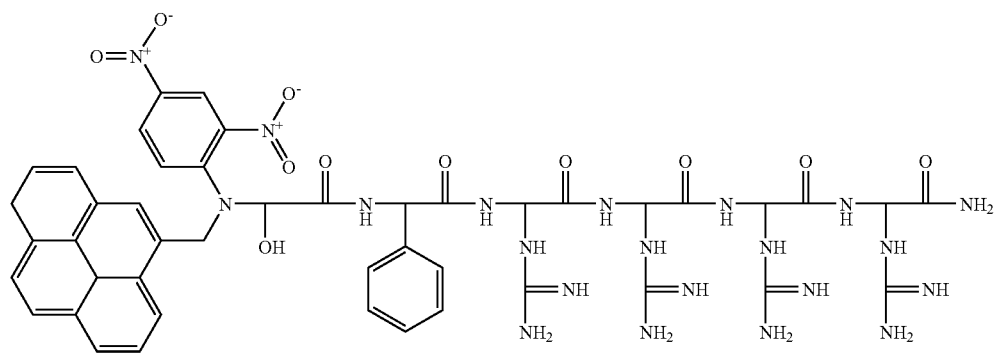
Compound 389
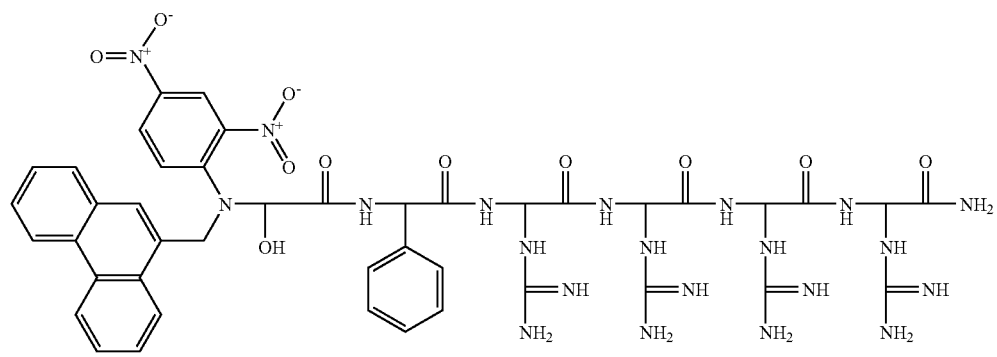
Compound 390
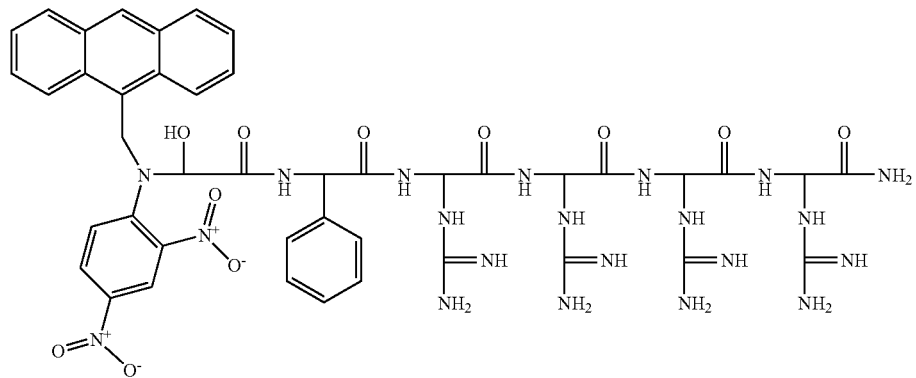

Compound 391
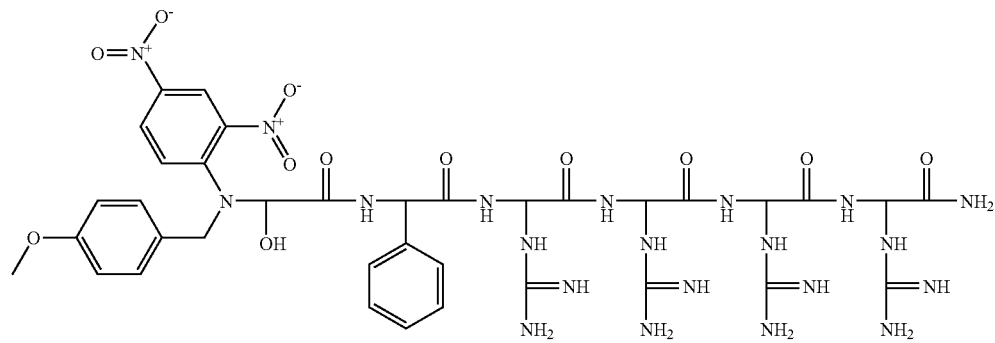
Compound 392
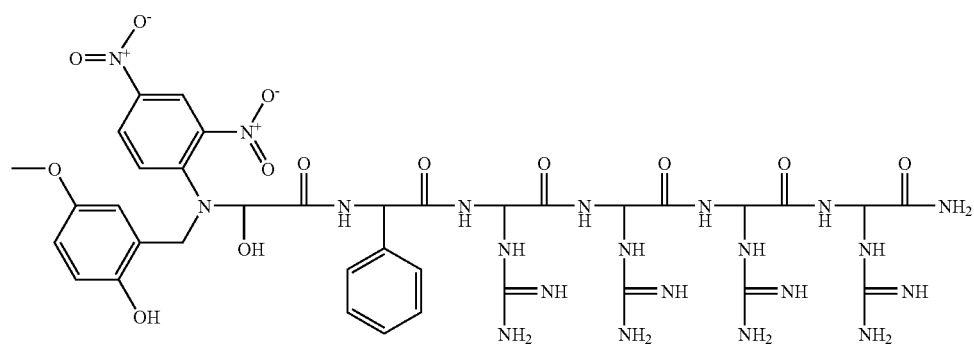
Compound 393
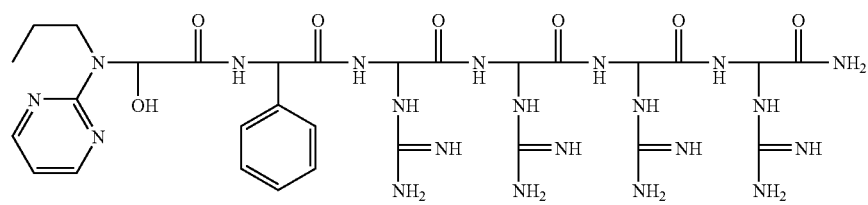
Compound 394
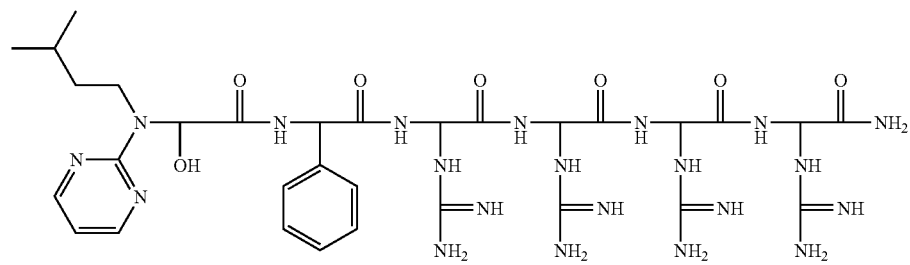
Compound 395
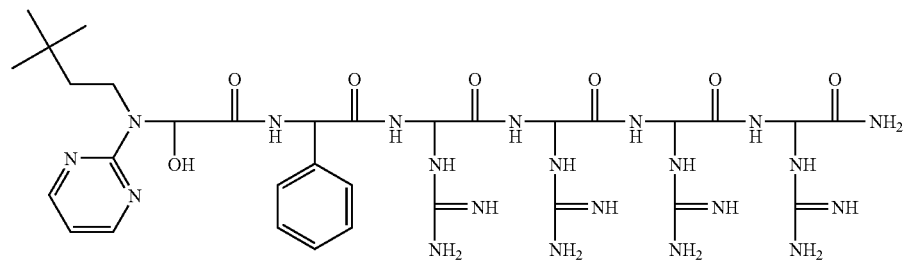

-continued
Compound 396
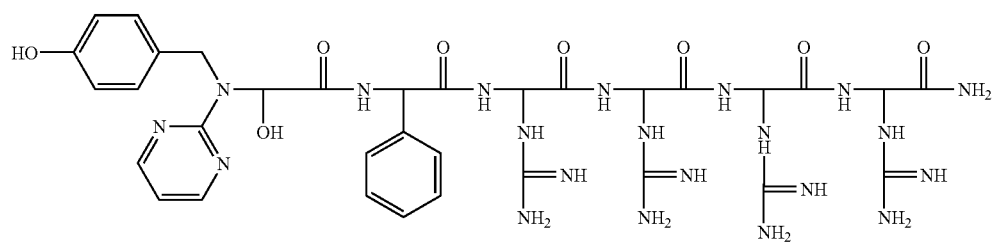
Compound 397
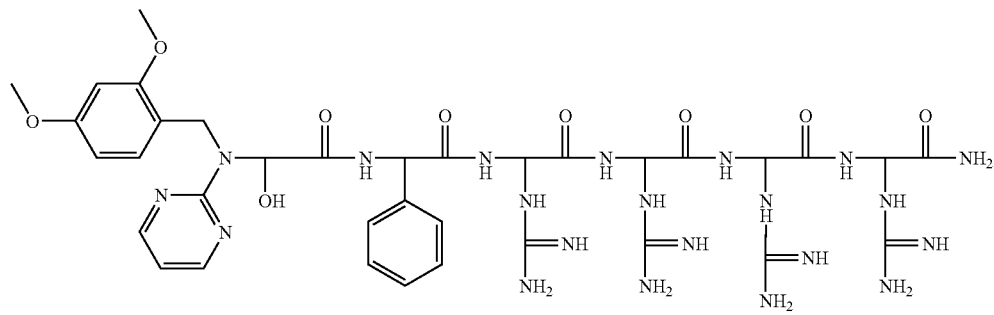
Compound 398
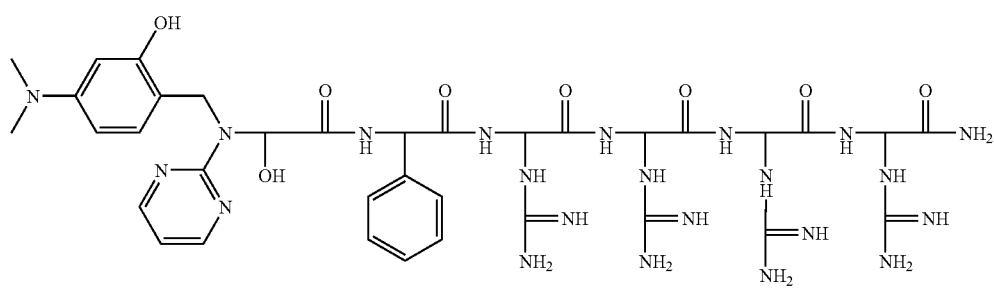
Compound 399
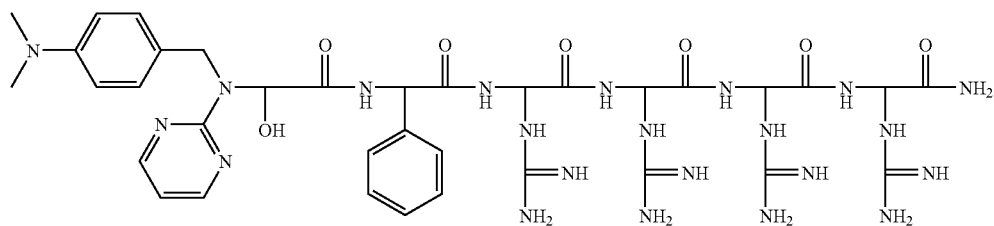
Compound 401
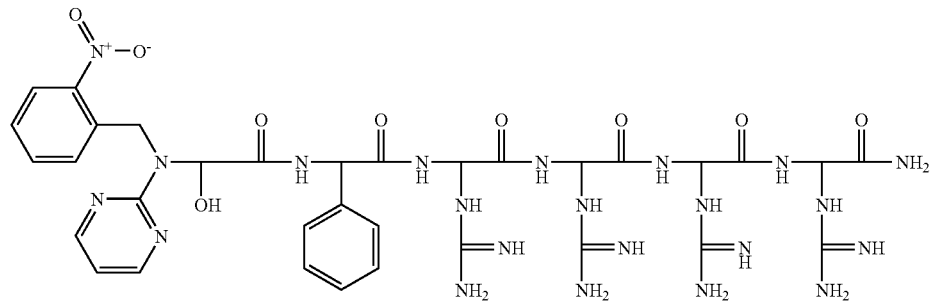
Compound 402
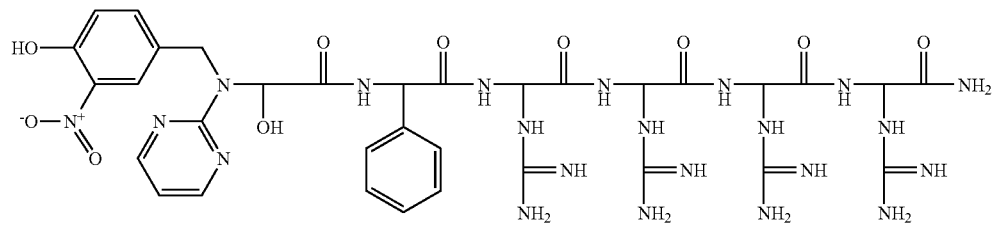

-continued
Compound 403
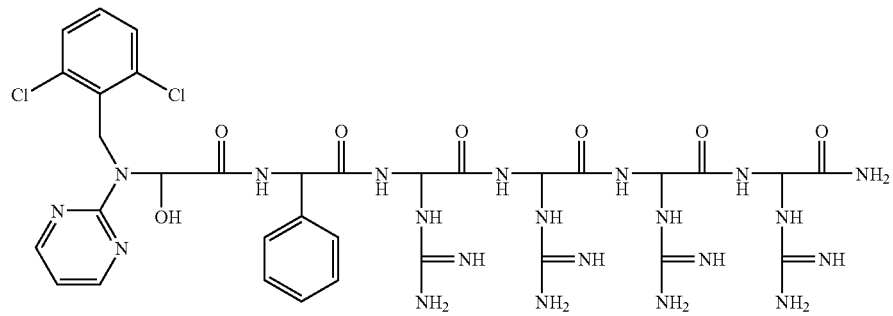
Compound 406
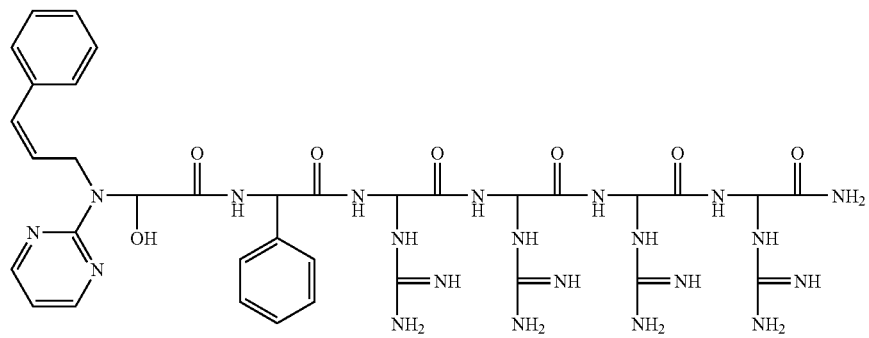
Compound 407
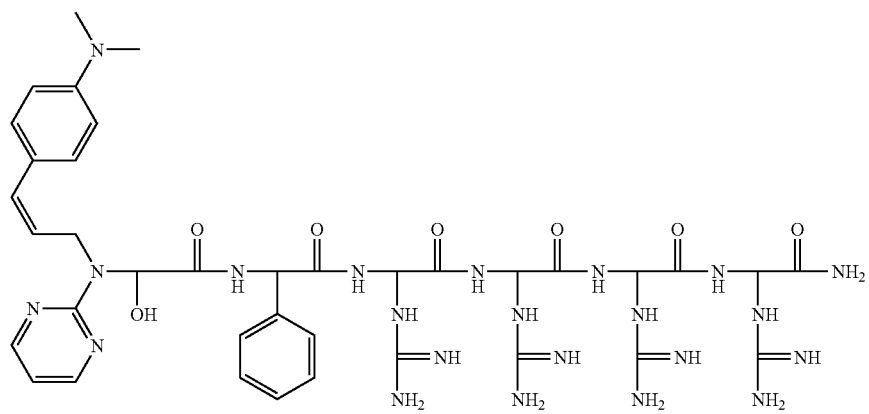
Compound 409
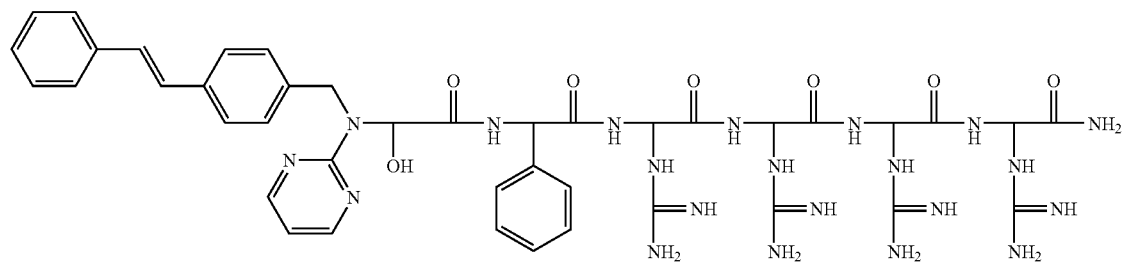

Compound 410
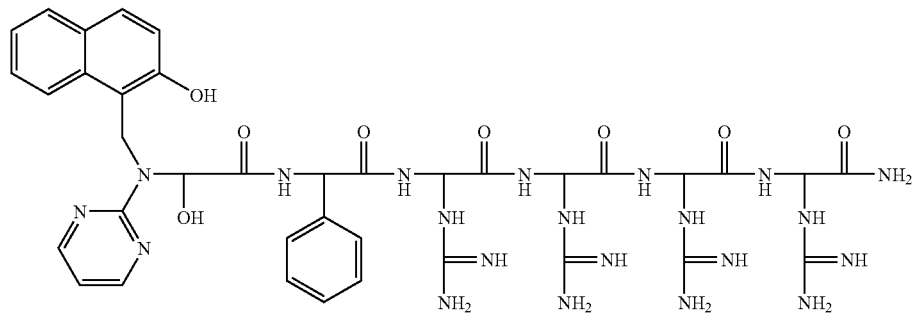
Compound 411
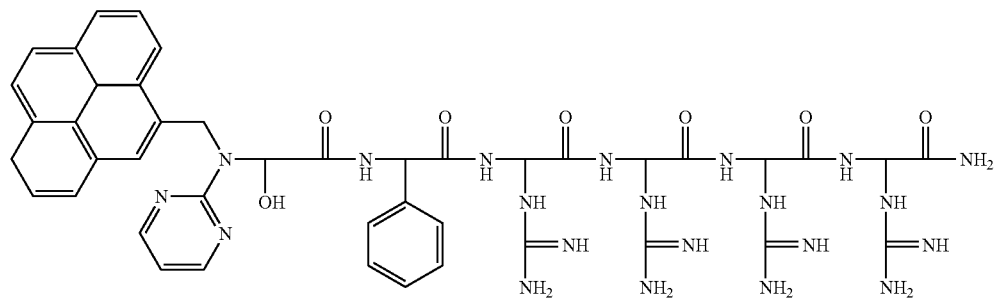
Compound 412
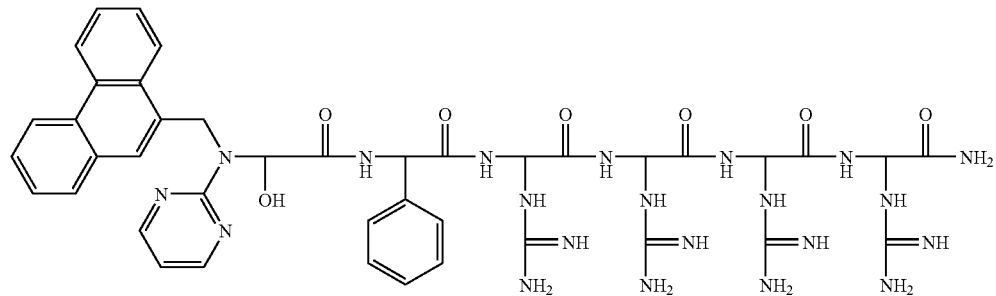
Compound 413
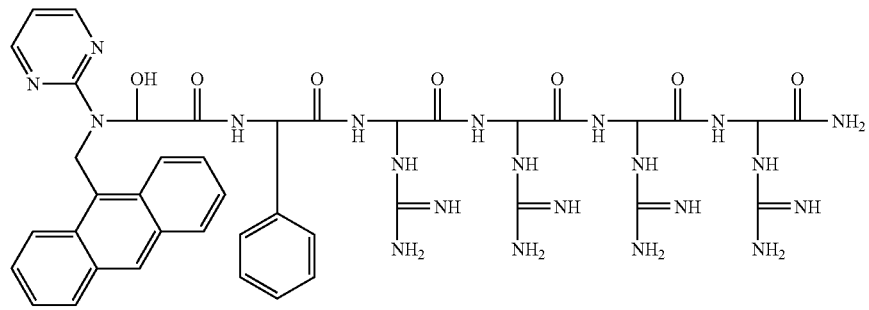
Compound 414
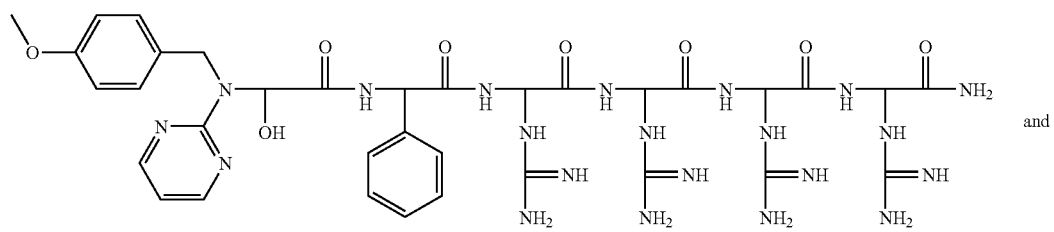
and Compound 415

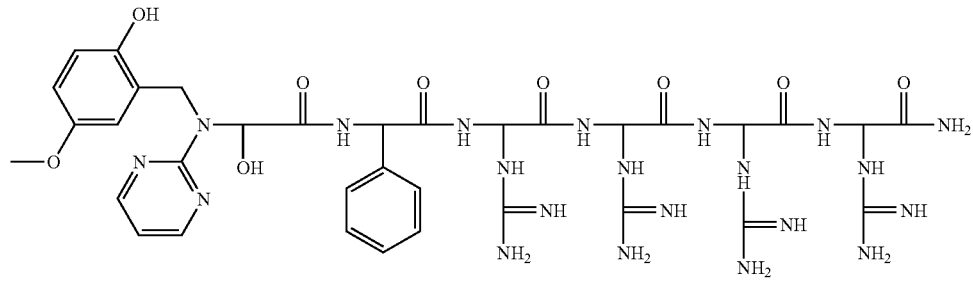

wherein amino acid chains are indicated as follows:
—OH represents serine,
—NH₂ represents lysine,

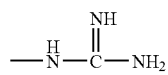

represents arginine, and

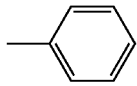

represents phenylalanine.

29. A composition comprising the compound of claim 28, and a carrier.

30. The composition of claim 29, wherein the composition is a pharmaceutical composition and the carrier is a pharmaceutically acceptable carrier.

31. A chemical compound comprising SEQ ID NO:1 having the structure:

wherein the LINKER is selected from the group consisting of the following:

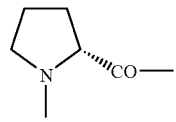

a

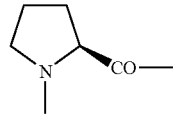

b

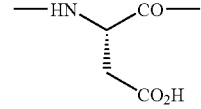

c

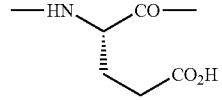

d

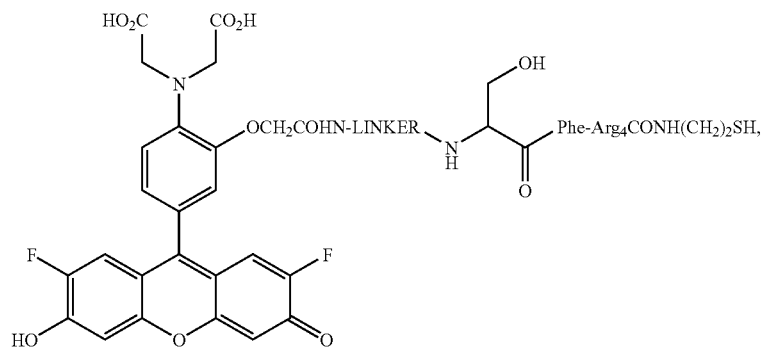

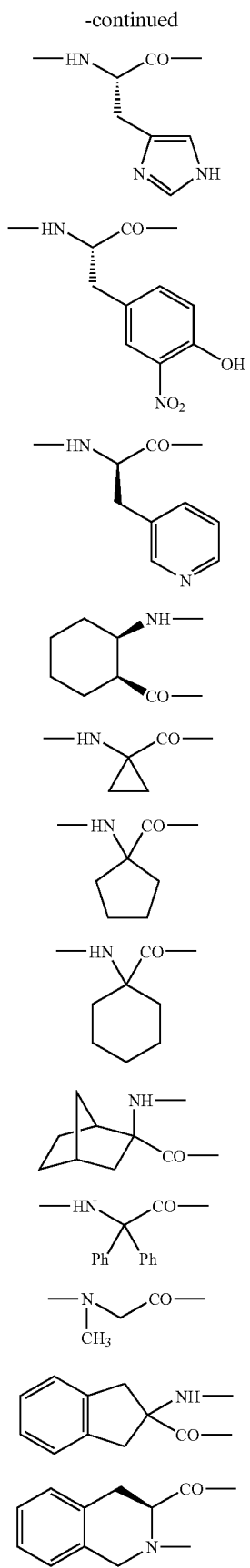

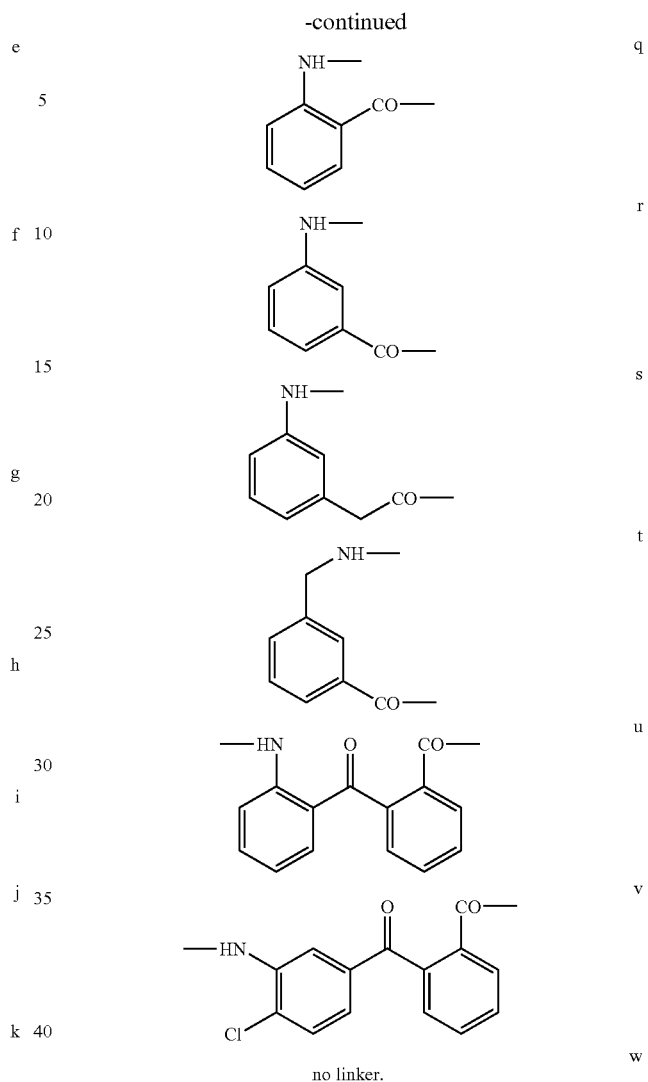

no linker.

32. A composition comprising a chemical compound of claim 31, and a carrier.

33. The composition of claim 32, wherein the composition is a pharmaceutical composition and the carrier is a pharmaceutically acceptable carrier.

34. The chemical compound of claim 31, wherein the linker comprises a turn to position the fluorophore in a location closer to the terminal serine, the terminal threonine or the terminal tyrosine than the location the fluorophore would occupy in the absence of a turn in the linker.

35. A chemical compound having the structure:
fluorophore-LINKER-X-FRRRRK-amide (SEQ ID NO:3); wherein F is phenylalanine; K is lysine; R is arginine; and X is serine, threonine, or tyrosine; wherein the linker is selected from the group consisting of a carboxamide linker, an aminobenzoic acid linker, a sulfonamide linker, a urea linker, a thiourea linker, an ester linker, a thioester linker, an alkylamine linker, an arylamine linker, an ether linker, and a thioether linker; and wherein the chemical compound is a substrate for a protein kinase or a precursor of a substrate for a protein kinase.

36. The chemical compound of claim 35, wherein the fluorophore is a 7-nitrobenz-2-oxa-1,3-diazole derivative.

37. The chemical compound of claim 35, wherein the fluorophore comprises a fluorescein group.

38. The chemical compound of claim 35, wherein the fluorophore comprises a dansyl group, an acridine group, a rhodamine group, or a coumarin group.

39. The chemical compound of claim 35, wherein the chemical compound is specific for protein kinase C.

40. The chemical compound of claim 39, wherein the chemical compound is specific for isoforms α, β, and γ of protein kinase C.

41. The chemical compound of claim 35, the chemical compound is specific for protein kinase A, protein kinase B, protein kinase D, protein kinase G, $Ca^+$/calmodulin-dependent protein kinase, mitogen-activated protein kinase, protein kinase mos, protein kinase raf, protein tyrosine kinase, tyrosine kinase abl, tyrosine kinase src, tyrosine kinase yes, tyrosine kinase fps, tyrosine kinase met, cyclin-dependent protein kinase, or cdc2 kinase.

42. The chemical compound of claim 35, wherein the chemical compound further comprises a carbohydrate, a lipid or a nucleic acid.

43. The chemical compound of claim 35, wherein the chemical compound comprises a metal ion chelator and the metal ion chelator induces a change in fluorescence intensity.

44. The chemical compound of claim 43, wherein the metal ion is a magnesium ion or a calcium ion.

45. The chemical compound of claim 43, wherein the change in fluorescence intensity is at least a 20% change in fluorescence intensity.

46. The chemical compound of claim 35, wherein the linker comprises a turn to position the fluorophore in a location closer to the serine, the threonine or the tyrosine than the location the fluorophore would occupy in the absence of a turn in the linker.

47. A composition comprising the compound of claim 35, and a carrier.

48. The composition of claim 47, wherein the composition is a pharmaceutical composition and the carrier is a pharmaceutically acceptable carrier.

49. A chemical compound having the structure:
fluorophore-LINKER-X-FRRRRK-amide (SEQ ID NO:3);
wherein F is phenylalanine; K is lysine; R is arginine; and X is serine, threonine, or tyrosine, wherein the linker is selected from the group consisting of N-methyl glycine, L-proline, D-proline,

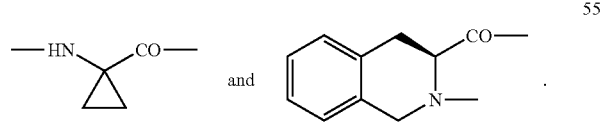

and

50. A chemical compound having the structure:
fluorophore-LINKER-X-FRRRRK-amide (SEQ ID NO:3);
wherein F is phenylalanine; K is lysine; R is arginine; and X is serine, threonine, or tyrosine, wherein the linker is selected from the group consisting of the following:

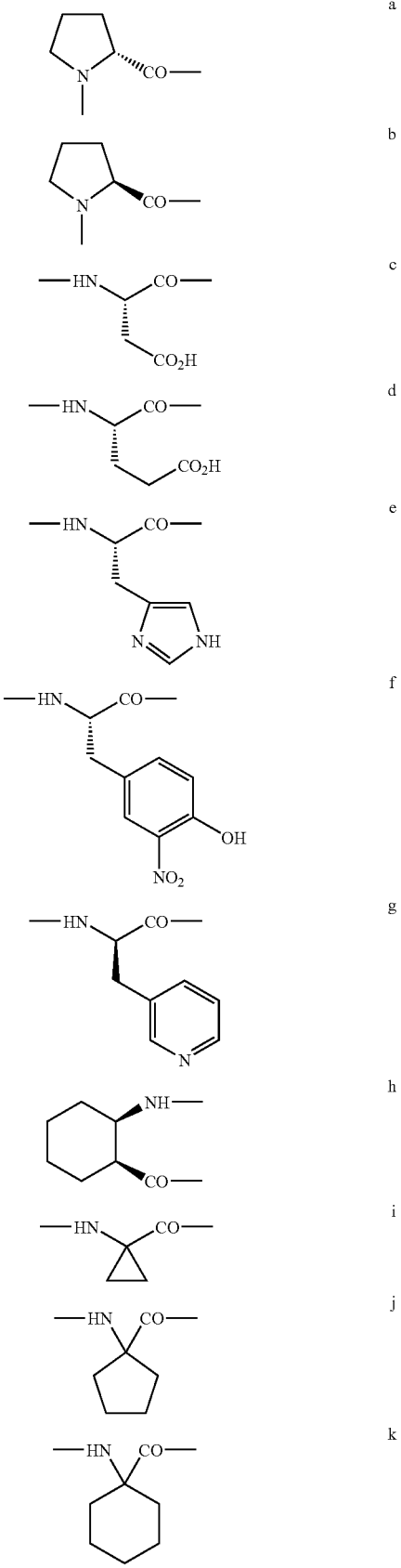

-continued

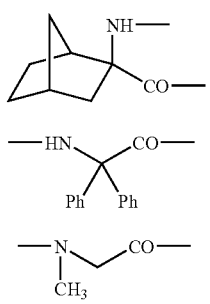
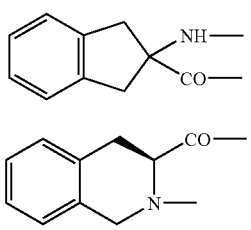
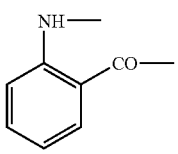
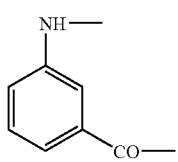
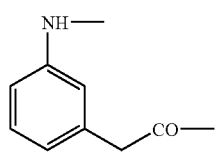
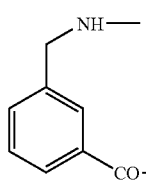
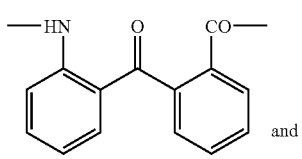
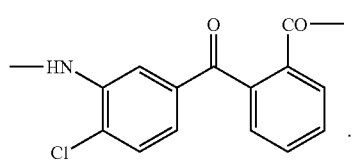

and

51. A chemical compound comprising SEQ ID NO:3 having the structure

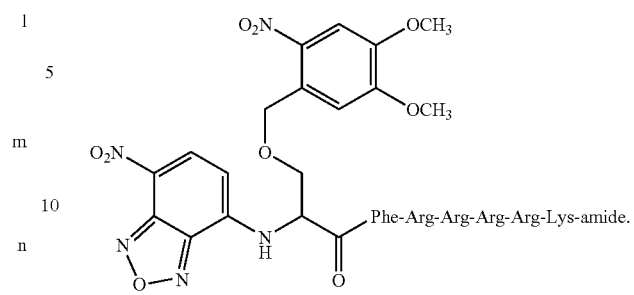

52. A composition comprising the compound of claim 51, and a carrier.

53. The composition of claim 52, wherein the composition is a pharmaceutical composition and the carrier is a pharmaceutically acceptable carrier.

54. A precursor of a substrate for a protein kinase, wherein the precursor comprises:

a peptide substrate for the protein kinase, wherein the peptide comprises a serine, a threonine, or a tyrosine on a terminal end of the peptide;

at least one fluorophore, wherein a fluorophore is attached to the serine, the threonine, or the tyrosine on the terminal end of the peptide;

wherein the fluorophore is attached directly to the peptide or the fluorophore is attached to the peptide by a linker selected from the group consisting of

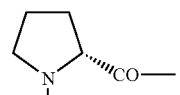

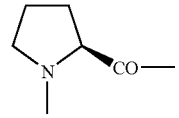

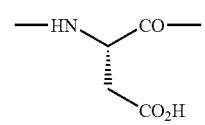

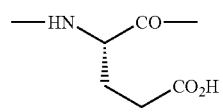

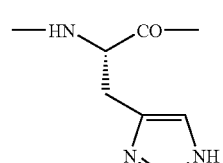

-continued

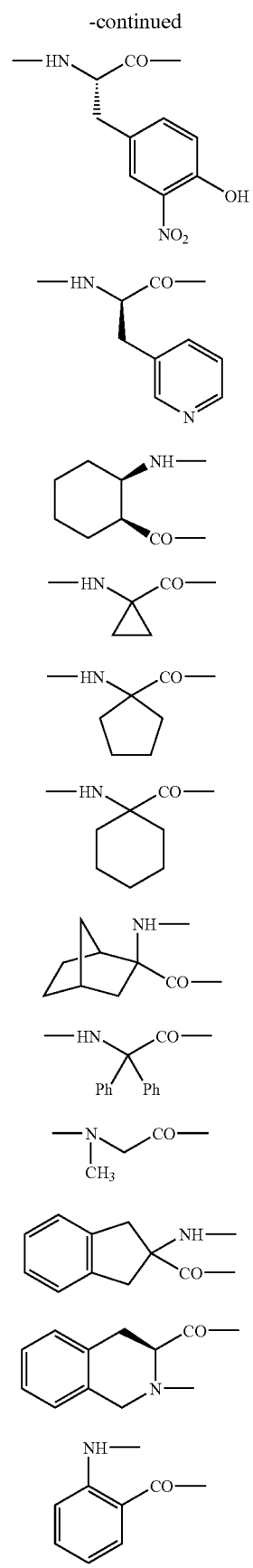

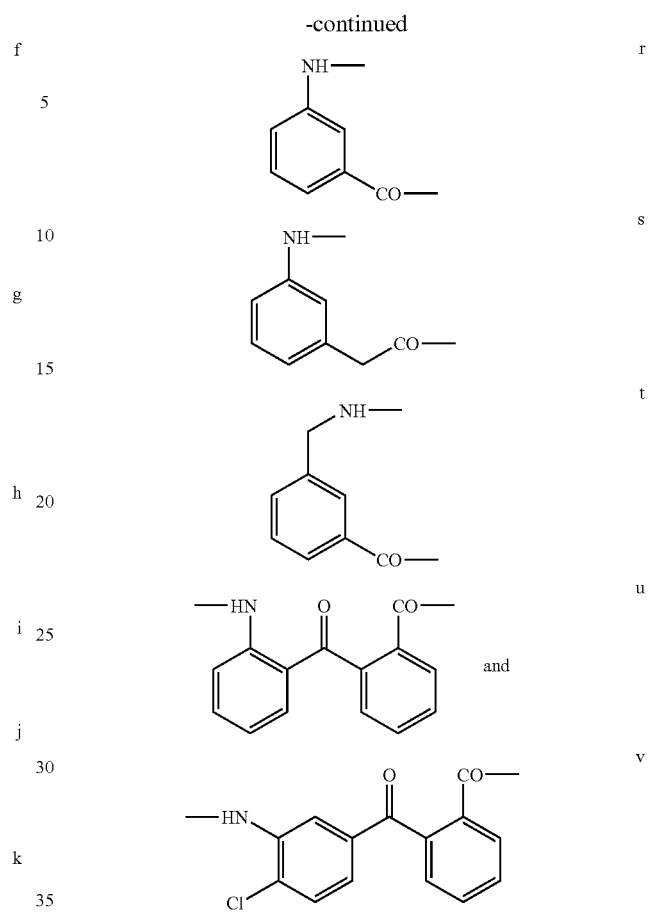

wherein a photolabile side chain is attached to the serine, the threonine, or the tyrosine on the terminal end of the peptide, and wherein the photolabile side chain blocks transfer of a phosphoryl group from adenosine triphosphate to a hydroxyl moiety of the serine, the threonine, or the tyrosine so that the precursor cannot be phosphorylated by a protein kinase until the photolabile side chain is removed from the precursor.

55. The precursor of the substrate of claim 54, wherein the photolabile side chain comprises the structure

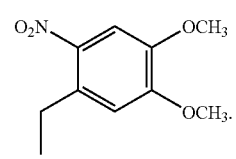

56. The precursor of a substrate for a protein kinase of claim 54, wherein after removal of the photolabile side chain, phosphorylation by a protein kinase of the terminal serine, the terminal threonine, or the terminal tyrosine to which the fluorophore is attached produces at least a 20% change in fluorescence intensity.

57. The precursor of a substrate for a protein kinase of claim 56, wherein phosphorylation by the protein kinase produces at least a 70% change in fluorescence intensity.

58. The precursor of a substrate for a protein kinase substrate of claim 57, wherein phosphorylation of the substrate by the protein kinase produces at least a 100% change in fluorescence intensity.

59. The precursor of a substrate for a protein kinase substrate of claim 58, wherein phosphorylation of the substrate by the protein kinase produces at least a 150% change in fluorescence intensity.

60. The precursor of a substrate for a protein kinase substrate of claim 59, wherein phosphorylation by the protein kinase produces at least a 250% change in fluorescence intensity.

61. The precursor of a substrate for a protein kinase of claim 56, wherein the substrate comprises a metal ion chelator.

62. The precursor of a substrate for a protein kinase of claim 61, wherein the metal ion is a magnesium ion or a calcium ion.

63. The precursor of a substrate for a protein kinase of claim 54, wherein after removal of the photolabile side chain, phosphorylation by a protein kinase of the terminal serine, the terminal threonine, or the terminal tyrosine to which the fluorophore is attached produces at least a 20% increase in fluorescence intensity.

64. The precursor of a substrate for a protein kinase of claim 54, wherein after removal of the photolabile side chain, phosphorylation by a protein kinase of the terminal serine, the terminal threonine, or the terminal tyrosine to which the fluorophore is attached produces at least a 20% decrease in fluorescence intensity.

65. A composition comprising the precursor of a substrate for a protein kinase of claim 54, and a carrier.

66. The composition of claim 65, wherein the composition is a pharmaceutical composition and the carrier is a pharmaceutically acceptable carrier.

* * * * *